(12) United States Patent
Mantlo et al.

(10) Patent No.: US 6,458,813 B1
(45) Date of Patent: Oct. 1, 2002

(54) SUBSTITUTED PYRIDINE COMPOUNDS AND METHODS OF USE

(75) Inventors: Nathan B. Mantlo, Lafayette; Stephen T. Schlachter, Boulder; John A. Josey, Longmont, all of CO (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/932,281

(22) Filed: Aug. 17, 2001

Related U.S. Application Data

(62) Division of application No. 09/642,860, filed on Aug. 21, 2000, now Pat. No. 6,333,341, which is a division of application No. 09/431,410, filed on Nov. 1, 1999, now Pat. No. 6,184,237, which is a division of application No. 09/185,119, filed on Nov. 3, 1998, now Pat. No. 6,022,884.

(60) Provisional application No. 60/064,953, filed on Nov. 7, 1997.

(51) Int. Cl.$^7$ .................... A61K 31/444; C07D 401/12
(52) U.S. Cl. .............. 514/335; 546/261; 546/262; 546/268.1; 544/238; 514/336; 514/340; 514/341; 514/342
(58) Field of Search .................. 514/335, 336, 514/340, 341, 342, 252; 546/261, 262, 268.1; 544/238

(56) References Cited

U.S. PATENT DOCUMENTS

| | | |
|---|---|---|
| 3,375,257 A | 3/1968 | Thiele et al. |
| 3,513,171 A | 5/1970 | Thiele et al. |
| 3,539,639 A | 11/1970 | Mrozik et al. |
| 3,712,900 A | 1/1973 | Thiele et al. |
| 3,819,639 A | 6/1974 | Delarge et al. |
| 3,929,807 A | 12/1975 | Fitzi |
| 3,980,652 A | 9/1976 | Delarge et al. |
| 3,991,057 A | 11/1976 | Delarge et al. |
| 4,002,629 A | 1/1977 | Delarge et al. |
| 4,094,982 A | 6/1978 | Morisawa et al. |
| 4,149,872 A | 4/1979 | Pilgram |
| 4,241,068 A | 12/1980 | Schromm et al. |
| 4,888,047 A | 12/1989 | Milano et al. |
| 4,983,600 A | 1/1991 | Ward et al. |
| 5,236,948 A | 8/1993 | Waterson |
| 5,312,820 A | 5/1994 | Ashton et al. |
| 5,380,734 A | 1/1995 | Hsu et al. |
| 5,593,992 A | 1/1997 | Adams et al. |
| 5,596,008 A | 1/1997 | Lee |
| 5,610,320 A | 3/1997 | Yoshino et al. |
| 5,665,724 A | 9/1997 | Sanfilippo et al. |
| 5,990,133 A | 11/1999 | Gaster et al. |

FOREIGN PATENT DOCUMENTS

| | | | |
|---|---|---|---|
| CA | 2052894 | 4/1992 | |
| DE | 1810162 | 11/1968 | |
| DE | 2655144 | 6/1978 | |
| DE | 3633485 | 4/1988 | |
| DE | 3737748 | 5/1989 | |
| DE | 3804346 | 8/1989 | |
| DE | 38 04 346 A 1 | 8/1989 | |
| EP | 039051 | 11/1981 | |
| EP | 0283762 | 9/1988 | |
| EP | 0424848 | 5/1991 | |
| EP | 0480258 | 4/1992 | |
| EP | 573883 | * 6/1993 | ................ 546/255 |
| EP | 0799825 | 10/1997 | |
| GB | 1189188 | 4/1970 | |
| JP | 4-364168 | 12/1992 | |
| JP | 6-135934 | 5/1994 | |
| JP | 7-285962 | 10/1995 | |
| JP | 8-175993 | 7/1996 | |
| JP | 8-175995 | 7/1996 | |
| WO | WO 91/04027 | 4/1991 | |
| WO | WO 93/14081 | 7/1993 | |
| WO | WO 95/26957 | 10/1995 | |
| WO | WO 96/03387 | 2/1996 | |
| WO | WO 96/11930 | 4/1996 | |
| WO | WO 96/18616 | 6/1996 | |
| WO | WO 96/18617 | 6/1996 | |
| WO | WO 96/18626 | 6/1996 | |
| WO | WO 96/21452 | 7/1996 | |
| WO | WO 96/21654 | 7/1996 | |
| WO | 96/23783 | * 8/1996 | ................ 546/256 |
| WO | WO 96/24584 | 8/1996 | |
| WO | WO 96/40143 | 12/1996 | |
| WO | WO 96/41795 | 12/1996 | |
| WO | WO 97/05877 | 2/1997 | |
| WO | WO 97/05878 | 2/1997 | |
| WO | WO 97/09315 | 3/1997 | |
| WO | WO 97/16426 | 5/1997 | |
| WO | WO 97/16441 | 5/1997 | |
| WO | WO 97/16442 | 5/1997 | |
| WO | WO 97/18626 | 5/1997 | |

OTHER PUBLICATIONS

Baracos, et al., "Stimulation of Muscle Protein Degradation and Prostaglandin $E_2$ Release by Leukocytic Pyrogen (Interleukin–1)", The New England Journal of Medicine, vol. 308, p. 553 (1983).

Berge et al., "Pharmaceutical Salts", Journal of Pharmaceutical Sciences, vol. 66, No. 1, pp. 1–19(1977).

Beutler et al., "Recombinant Interleukin 1 Suppresses Lipoprotein Lipase Activity in 3T3–L1 Cells", Journal of Immunology, vol. 135, p. 3969–3971 (1985).

(List continued on next page.)

Primary Examiner—Charanjit S. Aulakh
(74) Attorney, Agent, or Firm—Richard V. Person; Frank S. Ungemach; Steven M. Odre

(57) ABSTRACT

Selected novel substituted pyridine compounds are effective for prophylaxis and treatment of diseases, such as TNF-α, IL-1β, IL-6 and/or IL-8 mediated diseases, and other maladies, such as pain and diabetes. The invention encompasses novel compounds, analogs, prodrugs and pharmaceutically acceptable salts thereof, pharmaceutical compositions and methods for prophylaxis and treatment of diseases and other maladies or conditions involving inflammation, pain, diabetes, cancer and the like. The subject invention also relates to processes for making such compounds as well as to intermediates useful in such processes.

17 Claims, No Drawings

OTHER PUBLICATIONS

Brahn et al., "Effect of Tumor Necrosis Factor Alpha (TNF–α) on Collagen Arthritis", Lymphokine and Cytokine Research, vol.11, pp. 253–256 (1992).

Brunner et al., "Synthesis and antitumor activity of platinum (II) complexes containing substituted ethylenediamine ligands", Eur. J. Med. Chem., vol. 25, pp. 35–44 (1990).

Bundgaard et al., "A Novel Solution–Stable, Water–Soluble Prodrug Type for Drugs Containing a Hydroxyl or an NH–Acidic Group", J. Med. Chem., vol. 32, pp. 2503–2507 (1989).

Chandrasekhar et al., "Arthritis Induced by Interleukin–1 is Dependent on the Site and Frequency of Intraarticular Injection", Clinical Immunology and Immunopathology, vol. 55, pp. 382–400 (1990).

Clouse et al., "Monokine Regulation of Human Immmunodeficiency Virus–1 Expression in a Chronically Infected Human T Cell Clone", Journal of Immunology, vol. 142 pp. 431–438 (1989).

Colbry et al., Synthesis and Antimalarial Properties of 2,4–Diamino–6–[(aryl)thio, sulfinyl, and sulfonyl]pyrido[3,2–d]pyrimidines [1,2], J. Heterocyclic Chem., vol. 21, pp. 1521–1525 (1984).

Cooper et al., "Acceleration of onset of collagen–induced arthritis by intra–articular injection of tumor necrosis factor or transforming growth factor–beta", Clin. Exp. Immunol., vol. 89, pp. 244–250 (1992).

Courtenay et al., "Immunisation against heterologous type II collagen induces arthritis in mice", Nature, vol. 283, pp. 666–668 (1980).

Davies et al., "Asymmetric Syntheses of β–Phenylalanine, α–Methyl–β–phenylalanines and Derivatives", J. Chem. Soc., Chem. Commun., pp. 1153–1155 (1993).

Dinarello, "The Biological Properties of Interleukin–1", Eur. Cytokine Netw., vol. 5, pp. 517–531 (1994).

Dornow et al., "Über die Reduktion substituierter Cyanessigsäure–äthylester", Chem. Ber 87, pp. 985–990 (1954).

Firestein et al., "Stromelysin and Tissue Inhibitor of Metalloproteinases Gene Expression in Rheumatoid Arthritis Synovium", American Journal of Pathology, vol. 140, p. 1309–1314 (1992).

Folks et al., "Susceptibility of Normal Human Lymphocytes to Infection with HTLV–III/LAV", Journal of Immunology, vol. 136, pp. 4049–4053 (1986).

Freifelder et al., "Synthesis of Primary 1,2–Diamines by Hydrogenation of α–Aminonitriles", J. Am. Chem. Soc., vol. 82, pp. 696–698 (1959).

Grussenmeyer et al., "Complexes of polyoma virus medium T antigen and cellular proteins", PNAS USA, vol. 82, pp. 7952–7954 (1985).

Kaiser, "Lateral Metallation of Methylated Nitrogenous Heterocycles" Tetrahedron, vol. 39, pp. 2055–2064 (1983).

Kojima et al., "Preparation and Spectroscopic Studies of Steroisomers of the Tris[(S)–1–phenyl–1,3–propanediamine]cobalt(III) Complex", Bull. Chem. Soc. Jpn., vol. 55, pp. 1454–1459 (1982).

Lahdevirta et al., "Elevated Levels of Circulating Cachectin/Tumor Necrosis Factor in Patients with Acquired Immunodeficiency Syndrome", The American Journal of Medicine, vol. 85, p. 289–291 (1988).

Lang et al., "Tumor Necrosis Factor Impairs Insulin Action on Peripheral Glucose Disposal And Hepatic Glucose Output", Endocrinology, vol. 130, p. 43–52 (1992).

Liu et al., "Tumor Necrosis Factor–α Expression in Ischemic Neurons", Stroke, vol. 25, p. 1481–1488 (1994).

Maini et al., "Monoclonal anit–TNFα Antibody as a Probe of Pathogenesis and Therapy of Rheumatoid Disease", Immunological Reviews, vol. 144, p. 195–223 (1995).

Matsumoto et al., "Synthesis of Fluorinated Pyridines by the Balz–Schiemann Reaction. An Alternative Route to Enoxacin, A New Antibacterial Pyridonecarboxylic Acid [1]", J. Heterocyclic Chem., vol. 21, pp. 673–679 (1984).

Nishigaki et al., "Synthesis of 1–Substituted 1,4–Dihydro–7–[2–(5–nitro–2–furyl)vinyl]–4–oxo–1,8–naphthyridine Derivatives", Chem. Pharm. Bull, vol. 17:9, pp. 1827–1831 (1969).

Shohami et al., "Closed Head Injury Triggers Early Production of TNFα and IL–6 by Brain Tissue", J. Cereb. Blood Flow Metab., vol. 14, No. 4, p. 615–619 (1994).

Svensson et al., "The Design and Bioactivation of Presystemically Stable Prodrugs", Drug Metabolism Reviews, vol. 19(2), pp. 165–194 (1988).

Swingle, "Evaluation of Antiinflammatory Activity", *Antiinflammatory Agents*, Edited by Robert Scherrer and Michael Whitehouse, vol. II, Ch. 2, pp. 33–122 (1974).

Szalkowski et al., "Antidiabetic Thiazolidinediones Block the Inhibitory Effect of Tumor Necrosis Factor–α on Differentiation, Insulin–Stimulated Glucose Uptake, and Gene Expression in 3T3–L1 Cells", Endrocrinology, vol. 136, p. 1474–1481 (1995).

Trentham et al., "Autoimmunity to Type II Collagen: An Experimental Model of Arthritis", Journal of Experimental Medicine, vol. 146, pp. 857–868 (1977).

Wheeler et al., "A Chiral Synthesis of Dapoxetine Hydrochloride, A Serotonin Re–uptake Inhibitor, and its $^{14}$C Isotopomer", Journal of Labelled Compounds and Radiopharmaceuticals, vol. XXXI, No. 4, pp. 305–315 (1992).

Williams et al., "Both p21$^{ras}$ and pp60$^{v-src}$ are required, but neither alone is sufficient, to activate the Raf–1 kinase", PNAS USA, vol. 89, pp. 2922–2926 (1992).

Winter et al., "Carrageenin–Induced Edema in Hind Paw of the Rat as an Assay for Antiinflammatory Drugs", Proc. Soc. Exp. Biol. Med., vol. 111, pp. 544–547 (1962).

Liu et al., "Cytokine–induced neutrophil chemoattractant mRNA expressed in cerebral ischemia", Neuroscience Letters, vol. 164, pp. 125–128 (1993).

Lee et al., "Low–Molecular–Weight TNF Biosynthesis Inhibitors: Strategies and Prospectives", Circulatory Shock, vol. 44, pp. 97–103 (1995).

Beyaert et al., "The p38/RK mitogen–activated protein kinase pathway regulates interleukin–6 synthesis in response to tumour necrosis factor", EMBO Journal, vol. 15, pp. 1914–1923 (1996).

Joosten et al., "Anticytokine Treatment of Established Type II Collagen–Induced Arthritis in DBA/1 Mice", Arthritis & Rheumatism, vol. 39, pp. 797–809 (1996).

Delarge, J. "A propos de quelques derives de la pyridine disubstituee–2,5", Farmaco–Ed. Sc., vol. 29, pp. 101–108 (1974).

* cited by examiner

SUBSTITUTED PYRIDINE COMPOUNDS AND METHODS OF USE

This application is a division of application Ser. No. 09/642,860, filed Aug. 21, 2000, now U.S. Pat. No. 6,333,341, which is a division of application Ser. No. 09/431,410, filed Nov. 1, 1999, now U.S. Pat. No. 6,184,237 which is a division of application Ser. No. 09/185,119, filed Nov. 3, 1998, now U.S. Pat. No. 6,022,884 which claims the benefit of Provisional Application Serial No. 60/064,953, filed Nov. 7, 1997, which are hereby incorporated by reference.

BACKGROUND OF THE INVENTION

The present invention comprises a new class of compounds useful in treating diseases, such as TNF-α, IL-1β, IL-6 and/or IL-8 mediated diseases and other maladies, such as pain, cancer, and diabetes. In particular, the compounds of the invention are useful for the prophylaxis and treatment of diseases or conditions involving inflammation. This invention also relates to intermediates and processes useful in the preparation of such compounds.

Interleukin-1 (IL-1) and Tumor Necrosis Factor a (TNF-α) are pro-inflammatory cytokines secreted by a variety of cells, including monocytes and macrophages, in response to many inflammatory stimuli (e.g., lipopolysaccharide—LPS) or external cellular stress (e.g., osmotic shock and peroxide).

Elevated levels of TNF-α and/or IL-1 over basal levels have been implicated in mediating or exacerbating a number of disease states including rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

It has been reported that TNF-α plays a role in head trauma, stroke, and ischemia. For instance, in animal models of head trauma (rat), TNF-α levels increased in the contused hemisphere (Shohami et al., *J. Cereb. Blood Flow Metab.* 14, 615 (1994)). In a rat model of ischemia wherein the middle cerebral artery was occluded, the levels of TNF-α mRNA of TNF-α increased (Feurstein et al., *Neurosci. Lett.* 164, 125 (1993)). Administration of TNF-α into the rat cortex has been reported to result in significant neutrophil accumulation in capillaries and adherence in small blood vessels. TNF-α promotes the infiltration of other cytokines (IL-1β, IL-6) and also chemokines, which promote neutrophil infiltration into the infarct area (Feurstein, *Stroke* 25, 1481 ). TNF-α has also been implicated to play a role in type II diabetes (Endocrinol. 130, 43–52, 1992; and Endocrinol. 136, 1474–1481, 1995).

TNF-α appears to play a role in promoting certain viral life cycles and disease states associated with them. For instance, TNF-α secreted by monocytes induced elevated levels of HIV expression in a chronically infected T cell clone (Clouse et al., *J. Immunol.* 142, 431 (1989)). Lahdevirta et al., (*Am. J. Med.* 85, 289 (1988)) discussed the role of TNF-α in the HIV associated states of cachexia and muscle degradation.

TNF-α is upstream in the cytokine cascade of inflammation. As a result, elevated levels of TNF-α may lead to elevated levels of other inflammatory and proinflammatory cytokines, such as IL-1, IL-6, and IL-8.

Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type I and type II diabetes; bone resorption diseases; ischemia reperfusion injury; atherosclerosis; brain trauma; multiple sclerosis; sepsis; septic shock; and toxic shock syndrome. Viruses sensitive to TNF-a inhibition, e.g., HIV-1, HIV-2, HIV-3, are also affected by IL-1.

TNF-α and IL-1 appear to play a role in pancreatic β cell destruction and diabetes. Pancreatic β cells produce insulin which helps mediate blood glucose homeostasis. Deterioration of pancreatic β cells often accompanies type I diabetes. Pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production.

In rheumatoid arthritis models in animals, multiple intra-articular injections of IL-1 have led to an acute and destructive form of arthritis (Chandrasekhar et al., *Clinical Immunol Immunopathol.* 55, 382 (1990)). In studies using cultured rheumatoid synovial cells, IL-1 is a more potent inducer of stromelysin than is TNF-α (Firestein, *Am. J. Pathol.* 140, 1309 (1992)). At sites of local injection, neutrophil, lymphocyte, and monocyte emigration has been observed. The emigration is attributed to the induction of chemokines (e.g., IL-8), and the up-regulation of adhesion molecules (Dinarello, *Eur. Cytokine Netw.* 5, 517–531 (1994)).

IL-1 also appears to play a role in promoting certain viral life cycles. For example, cytokine-induced increase of HIV expression in a chronically infected macrophage line has been associated with a concomitant and selective increase in IL-1 production (Folks et al., *J. Immunol.* 136, 4049 (1986)). Beutler et al. (*J. Immunol.* 135, 3969 (1985)) discussed the role of IL-1 in cachexia. Baracos et al. (*New Eng. J. Med.* 308, 553 (1983)) discussed the role of IL-1 in muscle degeneration.

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis (CIA) in rats and mice), intra-articular administration of TNF-α either prior to or after the induction of CIA led to an accelerated onset of arthritis and a more severe course of the disease (Brahn et al., *Lymphokine Cytokine Res.* 11, 253 (1992); and Cooper, *Clin. Exp. Immunol.* 898, 244 (1992)).

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminished neutrophil infiltration.

Several approaches have been taken to block the effect of TNF-α. One approach involves using soluble receptors for TNF-α (e.g., TNFR-55 or TNFR-75), which have demonstrated efficacy in animal models of TNF-α-mediated disease states. A second approach to neutralizing TNF-α using a monoclonal antibody specific to TNF-α, cA2, has demonstrated improvement in swollen joint count in a Phase II human trial of rheumatoid arthritis (Maini et al., *Immunological Reviews*, pp. 195–223 (1995)). These approaches block the effects of TNF-α and IL-1 by either protein sequestration or receptor antagonism.

The present invention also relates to a method of treating cancer which is mediated by Raf and Raf-inducable proteins. Raf proteins are kinases activated in response to extracellular mitogenic stimuli such as PDGF, EGF, acidic FGF, thrombin, insulin or endothelin, and also in response to oncoproteins such as v-src, v-sis, and v-fms. Raf functions downstream of ras in signal transduction from the cellular membrane to the nucleus. Compounds in the present invention may be oncolytics through the antagonism of Raf kinase. Antisense constructs which reduce cellular levels of c-Raf and hence Raf activity inhibit the growth of rodent fibroblasts in soft agar, while exhibiting little or no general cytotoxicity. This inhibition of growth in soft agar is highly predictive of tumor responsiveness in whole animals. Moreover Raf antisense constructs have shown efficacy in reducing tumor burden in animals. Examples of cancers where Raf kinase is implicated by overexpression include cancers of the brain, larynx, lung, lymphatic system, urinary tract and stomach, including hystocytic lymphoma, lung adenocarcinoma and small cell lung cancers. Other examples include cancers involving overexpression of upstream activators of Raf or Raf-activating oncogenes, including pancreatic and breast carcinoma.

Substituted imidazole and pyrrole compounds have been described for use in the treatment of cytokine mediated diseases by inhibition of proinflammatory cytokines, such as IL-1, IL-6, IL-8 and TNF. Substituted imidazoles for use in the treatment of cytokine mediated diseases have been described in U.S. Pat. No. 5,593,992; WO 93/14081; WO 96/18626; WO 96/21452; WO 96/21654; WO 96/40143; WO 97/05878; WO 97/05878; (each of which is incorporated herein by reference in its entirety). Substituted imidazoles for use in the treatment of inflammation has been described in U.S. Pat. No. 3,929,807 (which is incorporated herein by reference in its entirety). Substituted pyrrole compounds for use in the treatment of cytokine mediated diseases have been described in WO 97/05877; WO 97/05878; WO 97/16426; WO 97/16441; and WO 97/16442 (each of which is incorporated herein by reference in its entirety).

Substituted 2-aminopyridine compounds have been described as nitric oxide synthase inhibitors for use in the treatment of inflammation, neurodegenerative disorders and disorders of gastrointestinal motility in WO 96/18616 and WO 96/18617.

Diaryl substituted pyridine compounds have been described for use in the treatment of inflammation and inflammation related disorders in WO 96/24584 and U.S. Pat. No. 5,596,008.

U.S. Pat. No. 3,980,652, U.S. Pat. No. 3,991,057 and U.S. Pat. No. 4,002,629 describe piperazinyl substituted pyridine compounds for use as anti-inflammatory and cardiovascular agents.

JP 6135934 describes substituted pyridine compounds as phospholipase A2 inhibitors for use as antiphlogistic and anti-pancreatitis agents. GB 1,189,188 describes pyrimidin-2-ylamino substituted pyridine compounds as therapeutically valuable compounds for use as antiphlogistic agents.

BRIEF DESCRIPTION OF THE INVENTION

The present invention comprises a new class of compounds useful in the prophylaxis and treatment of diseases, such as TNF-α, IL-1β, IL-6 and/or IL-8 mediated diseases and other maladies, such as pain, cancer, and diabetes. In particular, the compounds of the invention are useful for the prophylaxis and treatment of diseases or conditions involving inflammation. Accordingly, the invention also comprises pharmaceutical compositions comprising the compounds, methods for the prophylaxis and treatment of TNF-α, IL-1β, IL-6 and/or IL-8 mediated diseases, such as inflammatory, pain and diabetes diseases, using the compounds and compositions of the invention, and intermediates and processes useful for the preparation of the compounds of the invention.

The compounds of the invention are represented by the following general structure:

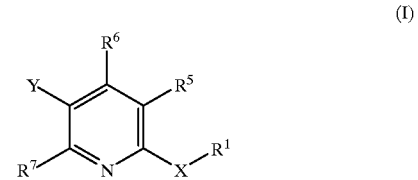

(I)

wherein $R^1$, $R^5$, $R^6$, $R^7$, X and Y are defined below.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In accordance with the present invention, there is provided compounds of the formula:

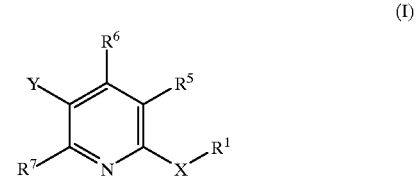

(I)

or a pharmaceutically acceptable salt thereof, wherein
X is O, S, S(O), S(O)$_2$ or NR$^2$; preferably, X is O, S or NR$^2$; more preferably, X is O or NR$^2$; most preferably, X is NR$^2$;
Y is —C(O)—NR$^3$R$^4$ or —NR$^4$—C(O)—R$^3$;
R$^1$ is a cycloalkyl, aryl, heterocyclyl or heteroaryl radical which is optionally substituted by 1–4 radicals of alkyl, halo, haloalkyl, cyano, azido, nitro, amidino, $R^{18}$—$Z^{18}$— or $R^{18}$—$Z^{18}$-alkyl;

preferably, $R^1$ is a cycloalkyl, aryl, heterocyclyl or heteroaryl radical which is optionally substituted by 1–4 radicals of $C_1$–$C_6$ alkyl, halo, $C_1$–$C_6$ haloalkyl of 1–3 halo radicals, cyano, azido, nitro, amidino, $R^{18}$—$Z^{18}$— or $R^{18}$—$Z^{18}$—$C_1$–$C_6$ alkyl;

more preferably, $R^1$ is a cycloalkyl, aryl, heterocyclyl or heteroaryl radical which is optionally substituted by 1–4 radicals of $C_1$–$C_4$ alkyl, halo, $C_1$–$C_4$ haloalkyl of 1–3 halo radicals, cyano, azido, nitro, amidino, $R^{18}$—$Z^{18}$— or $R^{18}$—$Z^{18}$—$C_1$–$C_4$ alkyl;

provided that the total number of aryl, heteroaryl, cycloalkyl and heterocyclyl radicals in $R^1$ is 1–3, preferably, 1–2, and provided when Y is —$NR^4$—C(O)—$R^3$ and X is O or S, $R^1$ is other than a 2-pyrimidinyl radical;

more preferably, $R^1$ is a radical of the formula

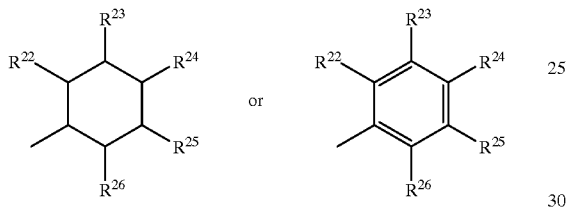

wherein $R^{22}$, $R^{23}$, $R^{24}$, $R^{25}$ and $R^{26}$ are each independently a radical of hydrogen, $C_1$–$C_4$ alkyl, halo, trifluoromethyl, cyano, azido, nitro, amidino, $R^{18}$—$Z^{18}$— or $R^{18}$—$Z^{18}$—$C_1$–$C_4$ alkyl; provided at least one of $R^{21}$, $R^{22}$, $R^{23}$, $R^{24}$ and $R^{25}$ is hydrogen; and provided that the combined total number of aryl and heteroaryl radicals in $R^{22}$, $R^{23}$, $R^{24}$, $R^{25}$ and $R^{26}$ is 0–1;

$R^2$ is a hydrogen or alkyl radical; preferably, $R^2$ is a hydrogen or $C_1$–$C_4$ alkyl radical; more preferably, $R^2$ is a hydrogen or $C_1$–$C_2$ alkyl radical; more preferably, $R^2$ is a hydrogen or methyl radical; and most preferably, $R^2$ is a hydrogen radical;

$R^3$ is an aryl or heteroaryl radical which is optionally substituted by 1–5 radicals of alkyl, halo, haloalkyl, cyano, azido, nitro, amidino, $R^{19}$—$Z^{19}$— or $R^{19}$—$Z^{19}$-alkyl; preferably, $R^3$ is an aryl or heteroaryl radical which is optionally substituted by 1–5 radicals of $C_1$–$C_6$ alkyl, halo, $C_1$–$C_6$ haloalkyl of 1–3 halo radicals, cyano, azido, nitro, amidino, $R^{19}$—$Z^{19}$— or $R^{19}$—$Z^{19}$—$C_1$–$C_6$ alkyl; more preferably, $R^3$ is an aryl or heteroaryl radical which is optionally substituted by 1–5 radicals of $C_1$–$C_6$ alkyl, halo, $C_1$–$C_4$ haloalkyl of 1–3 halo radicals, cyano, azido, nitro, amidino, $R^{19}$—$Z^{19}$— or $R^{19}$—$Z^{19}$—$C_1$–$C_4$ alkyl;

provided that the total number of aryl and heteroaryl radicals in $R^3$ is 1–3, preferably, 1–2; and provided when Y is —C(O)—$NR^3R^4$, $R^3$ is other than a phenyl or naphthyl having an amino, nitro, cyano, carboxy or alkoxycarbonyl substituent bonded to the ring carbon atom adjacent to the ring carbon atom bonded to —$NR^4$—;

more preferably, $R^3$ is a radical of the formula

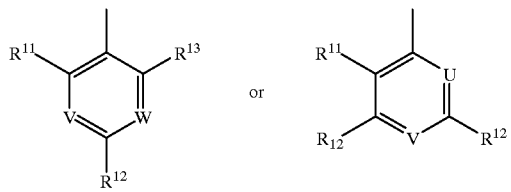

wherein

U is C—$R^{13}$ or N;

V and W are each independently C—$R^{12}$ or N;

$R^{11}$ and $R^{13}$ are each independently a radical of hydrogen, $C_1$–$C_4$ alkyl, halo, trifluoromethyl, cyano, azido, nitro, amidino or $R^{19}$—$Z^{19}$—; preferably, $R^{11}$ and $R^{13}$ are each independently a radical of hydrogen, methyl, ethyl, fluoro, chloro, trifluoromethyl, cyano, azido, nitro, amidino, $R^{19}$—O—, $R^{19}$—$S(O)_2$—, $R^{19}$—O—C(O)—, $R^{19}C(O)$—, $R^{19}$—$NR^{21}$—C(O)— or $R^{19}$—$NR^{21}$—$S(O)_2$—;

each $R^{12}$ is independently a radical of hydrogen, $C_1$–$C_6$ alkyl, halo, $C_1$–$C_4$ haloalkyl of 1–3 halo radicals, $R^{31}$—$Z^{31}$— or $R^{31}$—$Z^{31}$—$C_1$–$C_4$ alkyl; preferably, each $R^{12}$ is independently a radical of hydrogen, methyl, ethyl, fluoro, chloro, trifluoromethyl, trifluoromethoxy, methoxy, ethoxy, amino, methylamino, dimethylamino, acetylamino, aminocarbonyl, methylaminocarbonyl, dimethylaminocarbonyl, aminomethyl, (methylamino)methyl or (dimethylamino)methyl;

provided that the combined total number of aryl and heteroaryl radicals in $R^{11}$, $R^{12}$ and $R^{13}$ is 0–1;

wherein each $R^{31}$ is independently a hydrogen, $C_1$–$C_4$ alkyl, trifluoromethyl, aryl, heteroaryl, aryl-$C_1$–$C_4$ alkyl or heteroaryl-$C_1$–$C_4$ alkyl radical, wherein the aryl and heteroaryl radicals are optionally substituted by 1–2 radicals of hydroxy, methoxy, ethoxy, amino, methylamino, dimethylamino, acetylamino, cyano, halo, methyl, ethyl, trifluoromethyl or trifluoromethoxy;

each $Z^{31}$ is independently —O—, —$NR^{21}$—, —$NR^{21}$—C(O)—, —C(O)—$NR^{21}$—, —NR—$S(O)_2$— or —$S(O)_2$—$NR^{21}$—;

$R^4$ is a hydrogen, alkyl, alkenyl, haloalkyl, haloalkenyl, aryl, heteroaryl, arylalkyl, heteroarylalkyl or $R^{20}$—$Z^{20}$-alkyl radical, wherein the aryl and heteroaryl radicals are optionally substituted by 1–3 radicals of hydroxy, alkoxy, alkylthiol, amino, alkylamino, dialkylamino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy;

preferably, $R^4$ is a radical of hydrogen, $C_1$–$C_6$ alkyl, $C_2$–$C_6$ alkenyl, $C_1$–$C_6$ haloalkyl of 1–3 halo radicals, $C_2$–$C_6$ haloalkenyl of 1–3 halo radicals, aryl, heteroaryl, aryl-$C_1$–C4 alkyl, heteroaryl-$C_1$–$C_4$ alkyl or $R^{20}$—$Z^{20}$—$C_1$–$C_6$ alkyl radical, wherein the aryl and heteroaryl radicals are optionally substituted by 1–3 radicals of hydroxy, $C_1$–$C_4$ alkoxy, $C_1$–$C_4$ alkylthiol, amino, $C_1$–$C_4$ alkylamino, di($C_1$–$C_4$ alkyl)amino, $C_1$–$C_5$ alkanoylamino, $C_1$–$C_4$ alkylsulfonylamino, $C_1$–$C_4$ alkylsulfinyl, $C_1$–$C_4$ alkylsulfonyl, ($C_1$–$C_4$ alkoxy)carbonylamino, ($C_1$–$C_4$ alkoxy)carbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, $R^4$ is a radical of hydrogen, $C_1$–$C_6$ alkyl, aryl, heteroaryl, aryl-$C_1$–$C_4$ alkyl, heteroaryl-$C_1$–$C_4$ alkyl or $R^{20}$—$Z^{20}$—$C_2$–$C_4$ alkyl radical, wherein the aryl and heteroaryl radicals are optionally substituted by 1–2 radicals of hydroxy, $C_1$–$C_4$ alkoxy, $C_1$–$C_4$ alkylthiol, amino, $C_1$–$C_4$ alkylamino, di($C_1$–$C_4$ alkyl)amino, acetylamino, halo, $C_1$–$C_4$ alkyl, trifluoromethyl or trifluoromethoxy;

more preferably, $R^4$ is a radical of hydrogen, $C_1$–$C_6$ alkyl, aryl, heteroaryl, aryl-$C_1$–$C_4$ alkyl, heteroaryl-$C_1$–$C_4$ alkyl or $R^{20}$—$Z^{20}$—$C_2$–$C_4$ alkyl radical, wherein the aryl and heteroaryl radicals are optionally substituted by 1–2 radicals of hydroxy, methoxy, ethoxy, methylthiol, ethylthiol, amino, methylamino, dimethylamino, ethylamino, diethylamino, acetylamino, halo, methyl, ethyl, trifluoromethyl or trifluoromethoxy;

more preferably, $R^4$ is a radical of hydrogen, methyl or ethyl radical;

wherein each $R^{18}$ is independently a hydrogen, alkyl, haloalkyl, aryl, heteroaryl, arylalkyl or heteroarylalkyl radical, wherein the aryl and heteroaryl radicals are optionally substituted by 1–3 radicals of hydroxy, alkoxy, alkylthiol, amino, alkylamino, dialkylamino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy;

preferably, each $R^{18}$ is independently a hydrogen, $C_1$–$C_4$ alkyl, $C_1$–$C_4$ haloalkyl of 1–3 halo radicals, aryl, heteroaryl, aryl-$C_1$–$C_4$ alkyl or heteroaryl-$C_1$–$C_4$ alkyl radical, wherein the aryl and heteroaryl radicals are optionally substituted by 1–3 radicals of hydroxy, $C_1$–$C_4$ alkoxy, $C_1$–$C_4$ alkylthiol, amino, $C_1$–$C_4$ alkylamino, di($C_1$–$C_4$ alkyl)amino, $C_1$–$C_5$ alkanoylamino, $C_1$–$C_4$ alkylsulfonylamino, $C_1$–$C_4$ alkylsulfonyl, $C_1$–$C_4$ alkylsulfonyl, ($C_1$–$C_4$ alkoxy)carbonylamino, ($C_1$–$C_4$ alkoxy)carbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{18}$ is independently a hydrogen, $C_1$–$C_4$ alkyl, trifluoromethyl, aryl, heteroaryl, aryl-$C_1$–$C_2$ alkyl or heteroaryl-$C_1$–$C_2$ alkyl radical, wherein the aryl and heteroaryl radicals are optionally substituted by 1–2 radicals of hydroxy, $C_1$–$C_4$ alkoxy, $C_1$–$C_4$ alkylthiol, amino, $C_1$–$C_4$ alkylamino, di($C_1$–$C_4$ alkyl)amino, acetylamino, cyano, halo, azido, $C_1$–$C_4$ alkyl, trifluoromethyl or trifluoromethoxy;

each $Z^{18}$ is independently —O—, —S—, —S(O)—, —S(O)$_2$—, —CO$_2$—, —C(O)—, —NR$^{21}$—, —NR$^{21}$—C(O)—, —C(O)—NR$^{21}$, —NR$^{21}$—S(O)$_2$— or —S(O)$_2$—NR$^{21}$—; preferably, each $Z^{18}$ is independently —O—, —S—, —S(O)$_2$—, —CO$_2$—, —NR$^{21}$—, —NR$^{21}$—C(O)—, —C(O)—NR$^{21}$—, —NR$^{21}$—S(O)$_2$— or —S(O)$_2$—NR$^{21}$;

wherein each $R^{19}$ is independently a hydrogen, alkyl, haloalkyl, aryl, heteroaryl, arylalkyl or heteroarylalkyl radical, wherein the aryl and heteroaryl radicals are optionally substituted by 1–3 radicals of hydroxy, alkoxy, alkylthiol, amino, alkylamino, dialkylamino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy;

preferably, each $R^{19}$ is independently a hydrogen, $C_1$–$C_4$ alkyl, $C_1$–$C_4$ haloalkyl of 1–3 halo radicals, aryl, heteroaryl, aryl-$C_1$–$C_4$ alkyl or heteroaryl-$C_1$–$C_4$ alkyl radical, wherein the aryl and heteroaryl radicals are optionally substituted by 1–3 radicals of hydroxy, $C_1$–$C_4$ alkoxy, $C_1$–$C_4$ alkylthiol, amino, $C_1$–$C_4$ alkylamino, di($C_1$–$C_4$ alkyl)amino, $C_1$–$C_5$ alkanoylamino, $C_1$–$C_4$ alkylsulfonylamino, $C_1$–$C_4$ alkylsulfinyl, $C_1$–$C_4$ alkylsulfonyl, ($C_1$–$C_4$ alkoxy)carbonylamino, ($C_1$–$C_4$ alkoxy)carbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{19}$ is independently a hydrogen, $C_1$–$C_4$ alkyl, trifluoromethyl, aryl, heteroaryl, aryl-$C_1$–$C_4$ alkyl or heteroaryl-$C_1$–$C_4$ alkyl radical, wherein the aryl and heteroaryl radicals are optionally substituted by 1–2 radicals of hydroxy, $C_1$–$C_4$ alkoxy, $C_1$–$C_4$ alkylthiol, amino, $C_1$–$C_4$ alkylamino, di($C_1$–$C_4$ alkyl)amino, acetylamino, cyano, halo, $C_1$–$C_4$ alkyl, trifluoromethyl or trifluoromethoxy;

more preferably, each $R^{19}$ is independently a hydrogen, $C_1$–$C_4$ alkyl, trifluoromethyl, aryl, heteroaryl, aryl-$C_1$–$C_4$ alkyl or heteroaryl-$C_1$–$C_4$ alkyl radical; wherein the aryl and heteroaryl radicals are optionally substituted by 1–2 radicals of hydroxy, methoxy, ethoxy, amino, methylamino, dimethylamino, acetylamino, cyano, halo, methyl, ethyl, trifluoromethyl or trifluoromethoxy;

more preferably, each $R^{19}$ is independently a hydrogen, methyl, ethyl, trifluoromethyl, phenyl, heteroaryl, phenylmethyl or heteroaryl-methyl radical, wherein the phenyl and heteroaryl radicals are optionally substituted by 1–2 radicals of hydroxy, methoxy, ethoxy, amino, methylamino, dimethylamino, acetylamino, cyano, fluoro, chloro, methyl, ethyl, trifluoromethyl or trifluoromethoxy;

each $Z^{19}$ is independently —O—, —S—, —S(O)—, —S(O)$_2$—, —CO$_2$—, —C(O)—, —NR$^{21}$—, —NR$^{21}$—C(O)—, —C(O)—NR$^{21}$—, —NR$^{21}$—S(O)$_2$— or —S(O)$_2$—NR$^{21}$—; preferably, each $Z^{21}$ is independently —O—, —S(O)$_2$—, —CO$_2$—, —C(O)—, —NR$^{21}$—C(O)—, —C(O)—NR$^{21}$—, —NR$^{21}$—S(O)$_2$— or —S(O)$_2$—NR$^{21}$—; more preferably, each Z is independently —O—, —S(O)$_2$—, —O—C(O)—, —C(O)—, —NR$^{21}$—C(O)— or —NR$^{21}$—S(O)$_2$—;

wherein each $R^{20}$ is independently a hydrogen, alkyl, haloalkyl, aryl, heteroaryl, arylalkyl or heteroarylalkyl radical, wherein the aryl and heteroaryl radicals are optionally substituted by 1–3 radicals of hydroxy, alkoxy, alkylthiol, amino, alkylamino, dialkylamino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy;

preferably, each $R^{20}$ is independently a hydrogen, $C_1$–$C_4$ alkyl, $C_1$–$C_4$ haloalkyl of 1–3 halo radicals, aryl, heteroaryl, aryl-$C_1$–$C_4$ alkyl or heteroaryl-$C_1$–$C_4$ alkyl radical, wherein the aryl and heteroaryl radicals are optionally substituted by 1–3 radicals of hydroxy, $C_1$–$C_4$ alkoxy, $C_1$–$C_4$ alkylthiol, amino, $C_1$–$C_4$ alkylamino, di($C_1$–$C_4$ alkyl)amino, $C_1$–$C_5$ alkanoylamino, $C_1$–$C_4$ alkylsulfonylamino, $C_1$–$C_4$ alkylsulfinyl, $C_1$–$C_4$ alkylsulfonyl, ($C_1$–$C_4$ alkoxy)carbonylamino, ($C_1$–$C_4$ alkoxy)carbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{20}$ is independently a hydrogen, $C_1$–$C_4$ alkyl, aryl, heteroaryl, aryl-$C_1$–$C_2$ alkyl or heteroaryl-$C_1$–$C_2$ alkyl radical, wherein the aryl and heteroaryl radicals are optionally substituted by 1–2 radicals of hydroxy, $C_1$–$C_4$ alkoxy, $C_1$–$C_4$ alkylthiol, amino, $C_1$–$C_4$ alkylamino, di($C_1$–$C_4$ alkyl)amino, acetylamino, halo, $C_1$–$C_4$ alkyl, trifluoromethyl or trifluoromethoxy;

more preferably, each $R^{20}$ is independently a hydrogen, $C_1$–$C_4$ alkyl, aryl, heteroaryl, aryl-$C_1$–$C_2$ alkyl or heteroaryl-$C_1$–$C_2$ alkyl radical, wherein the aryl and heteroaryl radicals are optionally substituted by 1–2 radicals of hydroxy, methoxy, ethoxy, methylthiol, ethylthiol, amino, methylamino, dimethylamino, ethylamino, diethylamino, acetylamino, halo, methyl, ethyl, trifluoromethyl or trifluoromethoxy;

each $Z^{20}$ is independently —O—, —S, —S(O)—, —S(O)$_2$—, —CO$_2$—, —C(O)—, —NR$^{21}$—, —NR$^{21}$—C(O)—, —C(O)—NR$^{21}$—, —NR$^{21}$—S(O)$_2$— or —S(O)$_2$—NR$^{21}$—; preferably, each $Z^{20}$ is independently —O— or —NR$^{21}$—;

wherein each $R^{21}$ is independently a hydrogen or alkyl radical; preferably, each $R^{21}$ is independently a hydrogen or $C_1$–$C_4$ alkyl radical; more preferably, each $R^{21}$ is independently a hydrogen or methyl radical;

$R^5$ and $R^6$ are each independently a hydrogen, alkyl, halo, haloalkyl, haloalkoxy, aminoalkyl, alkylaminoalkyl, dialkylaminoalkyl, amino, alkylamino, dialkylamino, alkanoylamino, alkylsulfonylamino, aminosulfonyl, alkylaminosulfonyl, dialkylaminosulfonyl, hydroxy, hydroxyalkyl, thiol, alkylthiol, alkylsulfinyl, alkylsulfonyl, alkoxy, alkoxyalkyl, cyano, azido, nitro, carboxy, alkoxycarbonyl, aminocarbonyl, alkylaminocarbonyl or dialkylaminocarbonyl radical;

preferably, $R^5$ and $R^6$ are each independently a hydrogen, $C_1$–$C_4$ alkyl, halo, $C_1$–$C_4$ haloalkyl of 1–3 halo radicals, $C_1$–$C_4$ haloalkoxy of 1–3 halo radicals, $C_1$–$C_4$ aminoalkyl, ($C_1$–$C_4$ alkyl)amino-$C_1$–$C_4$ alkyl, di($C_1$–$C_4$ alkyl)amino-$C_1$–$C_4$ alkyl, amino, $C_1$–$C_4$ alkylamino, di($C_1$–$C_4$ alkyl)amino, $C_1$–$C_5$ alkanoylamino, $C_1$–$C_4$ alkylsulfonylamino, aminosulfonyl, $C_1$–$C_4$ alkylaminosulfonyl, di($C_1$–$C_4$ alkyl)aminosulfonyl, hydroxy, $C_1$–$C_4$ hydroxyalkyl, thiol, $C_1$–$C_4$ alkylthiol, $C_1$–$C_4$ alkylsulfonyl, $C_1$–$C_4$ alkylsulfonyl, $C_1$–$C_4$ alkoxy, ($C_1$–$C_4$ alkoxy)$C_1$–$C_4$ alkyl, cyano, azido, nitro, carboxy, ($C_1$–$C_4$ alkoxy)carbonyl, aminocarbonyl, ($C_1$–$C_4$ alkyl)aminocarbonyl or di($C_1$–$C_4$ alkyl)aminocarbonyl radical;

more preferably, $R^5$ and $R^6$ are each independently a hydrogen, $C_1$–$C_4$ alkyl, halo, trifluoromethyl, trifluoromethoxy, amino, $C_1$–$C_4$ alkylamino, di($C_1$–$C_4$ alkyl)amino, $C_1$–$C_5$ alkanoylamino, hydroxy, $C_1$–$C_4$ hydroxyalkyl, $C_1$–$C_4$ alkoxy, cyano, azido, nitro, carboxy, ($C_1$–$C_4$ alkoxy)carbonyl, aminocarbonyl, ($C_1$–$C_4$ alkyl) aminocarbonyl or di ($C_1$–$C_4$ alkyl) aminocarbonyl radical;

more preferably, $R^5$ and $R^6$ are each independently a hydrogen, methyl, ethyl, halo, trifluoromethyl, trifluoromethoxy, amino, $C_1$–$C_2$ alkylamino, di($C_1$–$C_2$ alkyl)amino, hydroxy, methoxy or ethoxy radical; most preferably, $R^5$ and $R^6$ are each a hydrogen radical;

$R^7$ is a hydrogen, alkyl, halo, haloalkyl, haloalkoxy, aminoalkyl, alkylaminoalkyl, dialkylaminoalkyl, aminosulfonyl, alkylaminosulfonyl, dialkylaminosulfonyl, hydroxy, hydroxyalkyl, thiol, alkylthiol, alkylsulfinyl, alkylsulfonyl, alkoxy, alkoxyalkyl, cyano, azido, nitro, carboxy, alkoxycarbonyl, aminocarbonyl, alkylaminocarbonyl or dialkylaminocarbonyl radical;

preferably, $R^7$ is a hydrogen, $C_1$–$C_4$ alkyl, halo, $C_1$–$C_4$ haloalkyl of 1–3 halo radicals, $C_1$–$C_4$ haloalkoxy of 1–3 halo radicals, $C_1$–$C_4$ aminoalkyl, ($C_1$–$C_4$ alkyl)amino-$C_1$–$C_4$ alkyl, di($C_1$–$C_4$ alkyl)amino-$C_1$–$C_4$ alkyl, aminosulfonyl, $C_1$–$C_4$ alkylaminosulfonyl, di($C_1$–$C_4$ alkyl)aminosulfonyl, hydroxy, $C_1$–$C_4$ hydroxyalkyl, thiol, $C_1$–$C_4$ alkylthiol, $C_1$–$C_4$ alkylsulfinyl, $C_1$–$C_4$ alkylsulfonyl, $C_1$–$C_4$ alkoxy, ($C_1$–$C_4$ alkoxy)$C_1$–$C_4$ alkyl, cyano, azido, nitro, carboxy, ($C_1$–$C_4$ alkoxy)carbonyl, aminocarbonyl, ($C_1$–$C_4$ alkyl)aminocarbonyl or di($C_1$–$C_4$ alkyl) aminocarbonyl radical;

more preferably, $R^7$ is a hydrogen, $C_1$–$C_4$ alkyl, halo, trifluoromethyl, trifluoromethoxy, hydroxy, $C_1$–$C_4$ hydroxyalkyl, $C_1$–$C_4$ alkoxy, carboxy, ($C_1$–$C_4$ alkoxy)carbonyl, aminocarbonyl, ($C_1$–$C_4$ alkyl)aminocarbonyl or di($C_1$–$C_4$ alkyl)aminocarbonyl radical;

more preferably, $R^7$ is a hydrogen, methyl, ethyl, halo, trifluoromethyl, trifluoromethoxy, hydroxy, methoxy or ethoxy radical; most preferably, $R^7$ is a hydrogen radical.

The compounds of this invention may have in general several asymmetric centers and are typically depicted in the form of racemic mixtures. This invention is intended to encompass racemic mixtures, partially racemic mixtures and separate enantiomers and diastereomers.

Compounds of interest include the following:

2-cyclohexyloxy-5-(2-chlorophenylcarbonylamino) pyridine;

2-cyclohexyloxy-5-(2-methylphenylcarbonylamino) pyridine;

2-cyclohexyloxy-5-(2,6-dichlorophenylcarbonylamino) pyridine;

2-cyclohexyloxy-5-(2,6-dimethylphenylcarbonylamino) pyridine;

2-(2,4-dimethylphenoxy)-5-(2-chlorophenylcarbonylamino) pyridine;

2-(2,4-dimethylphenoxy)-5-(2,6-dichlorophenylcarbonyl amino)pyridine;

2-(2,4-dimethylphenoxy)-5-(2-methylphenylcarbonylamino) pyridine;

2-(2,6-dimethyl-4-chlorophenoxy)-5-(2,6-dimethylphenyl carbonylamino) pyridine;

2-(2-methyl-4-fluorophenoxy)-5-(2-methylphenylcarbonyl amino)pyridine;

2-(2-methyl-4-chlorophenoxy)-5-(2-chlorophenylcarbonyl amino)pyridine;

2-(2-methyl-4-chlorophenoxy)-5-(2-methylphenylcarbonyl amino)pyridine;

2-(2-methylphenoxy)-5-(2-chlorophenylcarbonylamino) pyridine;

2-(2-methylphenoxy)-5-(2,6-dichlorophenyl carbonylamino)pyridine;

2-(2-methylphenoxy)-5-(2-methylphenylcarbonyl amino) pyridine;

2-(2-methyl-4-chlorophenoxy)-5-(2,6-dichlorophenyl carbonylamino)pyridine;

2-(2-methyl-4-chlorophenoxy)-5-(2,6-dimethylphenyl carbonylamino)pyridine;

2-(4-chlorophenoxy)-5-(2,6-dimethylphenylcarbonylamino) pyridine;

2-(2-methyl-4-fluorophenoxy)-5-(2,6-dichlorophenyl carbonylamino)pyridine;

2-(2-methyl-4-fluorophenoxy)-5-(2,6-dimethylphenyl carbonylamino)pyridine;

2-(2-methylphenoxy)-5-(2,6-dimethylphenyl carbonylamino)pyridine;

2-(2-methyl-4-fluorophenoxy)-5-(2-fluorophenylcarbonyl amino)pyridine;

2-(2,4-dimethylphenoxy)-5-(2,6-dimethylphenylcarbonyl amino)pyridine;
2-(1-naphthyloxy)-5-(2-methylphenylcarbonylamino) pyridine;
2-(1-naphthyloxy)-5-(2,6-dichlorophenylcarbonylamino) pyridine;
2-(1-naphthyloxy)-5-(2,6-dimethylphenylcarbonylamino) pyridine;
2-(2-methyl-3-pyridyloxy)-5-(2,6-dichlorophenylcarbonyl amino)pyridine;
2-(2-methyl-4-chlorophenoxy)-5-((3,5-dimethyl-4-isoxazolyl)carbonylamino)pyridine;
2-(2-methyl-4-chlorophenylthiol)-5-(2-methylphenylcarbonyl amino)pyridine;
2-(2-methyl-4-chlorophenylthiol)-5-(2,6-dimethylphenylcarbonyl amino)pyridine;
2-cyclohexylamino-5-(2,6-dichlorophenylcarbonylamino) pyridine;
2-cyclohexylamino-5-(2,6-dimethylphenylcarbonylamino) pyridine;
2-(2-methylcyclohexylamino)-5-(2,6-dichlorophenylcarbonyl amino)pyridine;
2-(2-methylcyclohexylamino)-5-(2-methylphenylcarbonyl amino)pyridine;
2-(2,4-dimethylphenylamino)-5-(2-fluorophenylcarbonyl amino)pyridine;
2-(2,4-dimethylphenylamino)-5-(2-chlorophenylcarbonyl amino)pyridine;
2-(2,4-dimethylphenylamino)-5-(2,6-dichlorophenylcarbonyl amino)pyridine;
2-(2-methyl-4-chlorophenylamino)-5-(2,6-dichlorophenylcarbonylamino)pyridine;
2-(2,4-dimethylphenylamino)-5-(2-methylphenylcarbonyl amino)pyridine;
2-(2-methylphenylamino)-5-(2-methylphenylcarbonyl amino)pyridine;
2-(2-methylphenylamino)-5-(2,6-dichlorophenylcarbonyl amino)pyridine;
2-(2-methylphenylamino)-5-(2,6-dimethylphenylcarbonyl amino)pyridine;
2-(2,4-dimethylphenylamino)-5-(2,6-dimethylphenylcarbonylamino)pyridine;
2-(2-methyl-4-chlorophenylamino)-5-(2-methylphenyl carbonylamino)pyridine;
2-(2-methyl-4-chlorophenylamino)-5-(2,6-dimethylphenyl carbonylamino)pyridine; and
2-(2-methyl-4-chlorophenylamino)-5-(2-methylphenyl aminocarbonyl)pyridine.

As utilized herein, the following terms shall have the following meanings:

"Alkyl", alone or in combination, means a straight-chain or branched-chain alkyl radical containing preferably 1–15 carbon atoms ($C_1$–$C_{15}$), more preferably 1–8 carbon atoms ($C_1$–$C_8$), even more preferably 1–6 carbon atoms ($C_1$–$C_6$), yet more preferably 1–4 carbon atoms ($C_1$–$C_4$), still more preferably 1–3 carbon atoms ($C_1$–$C_3$), and most preferably 1–2 carbon atoms ($C_1$–$C_2$). Examples of such radicals include methyl, ethyl, n-propyl, isopropyl, n-butyl, isobutyl, sec-butyl, tert-butyl, pentyl, iso-amyl, hexyl, octyl and the like.

"Hydroxyalkyl", alone or in combination, means an alkyl radical as defined above wherein at least one hydrogen radical is replaced with a hydroxyl radical, preferably 1–3 hydrogen radicals are replaced by hydroxyl radicals, more preferably 1–2 hydrogen radicals are replaced by hydroxyl radicals, and most preferably one hydrogen radical is replaced by a hydroxyl radical. Examples of such radicals include hydroxymethyl, 1-, 2-hydroxyethyl, 1-, 2-, 3-hydroxypropyl, 1,3-dihydroxy-2-propyl, 1,3-dihydroxybutyl, 1,2,3,4,5,6-hexahydroxy-2-hexyl and the like.

"Alkenyl", alone or in combination, means a straight-chain or branched-chain hydrocarbon radical having one or more double bonds, preferably 1–2: double bonds and more preferably one double bond, and containing preferably 2–15 carbon atoms ($C_2$–$C_{15}$), more preferably 2–8 carbon atoms ($C_2$–$C_8$), even more preferably 2–6 carbon atoms ($C_2$–$C_6$), yet more preferably 2–4 carbon atoms ($C_2$–$C_4$), and still more preferably 2–3 carbon atoms ($C_2$–$C_3$). Examples of such alkenyl radicals include ethenyl, propenyl, 2-methylpropenyl, 1,4-butadienyl and the like.

"Alkoxy", alone or in combination, means a radical of the type "R—O—" wherein "R" is an alkyl radical as defined above and "O" is an oxygen atom. Examples of such alkoxy radicals include methoxy, ethoxy, n-propoxy, isopropoxy, n-butoxy, iso-butoxy, sec-butoxy, tert-butoxy and the like.

"Alkoxycarbonyl", alone or in combination, means a radical of the type "R—O—C(O)—C(O)—" wherein "R—O—" is an alkoxy radical as defined above and "C(O)" is a carbonyl radical.

"Alkoxycarbonylamino", alone or in combination, means a radical of the type "R—O—C(O)—NH—" wherein "R—O—C(O)" is an alkoxycarbonyl radical as defined above, wherein the amino radical may optionally be substituted, such as with alkyl, aryl, aralkyl, cycloalkyl, cycloalkylalkyl and the like.

"Alkylthio", alone or in combination, means a radical of the type "R—S—" wherein "R" is an alkyl radical as defined above and "S" is a sulfur atom. Examples of such alkylthio radicals include methylthio, ethylthio, n-propylthio, isopropylthio, n-butylthio, iso-butylthio, sec-butylthio, tert-butylthio and the like.

"Alkylsulfinyl", alone or in combination, means a radical of the type "R—S(O)—" wherein "R" is an alkyl radical as defined above and "S(O)$_2$" is a mono-oxygenated sulfur atom. Examples of such alkylsulfinyl radicals include methylsulfinyl, ethylsulfinyl, n-propylsulfinyl, isopropylsulfinyl, n-butylsulfinyl, iso-butylsulfinyl, sec-butylsulfinyl, tert-butylsulfinyl and the like.

"Alkylsulfonyl", alone or in combination, means a radical of the type "R—S(O)$_2$—" wherein "R" is an alkyl radical as defined above and "S(O)$_2$" is a di-oxygenated sulfur atom. Examples of such alkylsulfonyl radicals include methylsulfonyl, ethylsulfonyl, n-propylsulfonyl, isopropylsulfonyl, n-butylsulfonyl, iso-butylsulfonyl, sec-butylsulfonyl, tert-butylsulfonyl and the like.

"Aryl", alone or in combination, means a phenyl or biphenyl radical, which is optionally benzo fused or heterocyclo fused and which is optionally substituted with one or more substituents selected from alkyl, alkoxy, halogen, hydroxy, amino, azido, nitro, cyano, haloalkyl, carboxy, alkoxycarbonyl, cycloalkyl, alkanoylamino, amido, amidino, alkoxycarbonylamino, N-alkylamidino, alkylamino, dialkylamino, aminoalkyl, alkylaminoalkyl, dialkylaminoalkyl, N-alkylamido, N,N-dialkylamido, aralkoxycarbonylamino, alkylthio, alkylsulfinyl, alkylsulfonyl, oxo and the like. Examples of aryl radicals are phenyl, o-tolyl, 4-methoxyphenyl, 2-(tert-butoxy)phenyl, 3-methyl-4-methoxyphenyl, 2-CF$_3$-phenyl, 2-fluorophenyl, 2-chlorophenyl, 3-nitrophenyl, 3-aminophenyl, 3-acetamidophenyl, 2-amino-3-(aminomethyl)phenyl, 6-methyl-3-acetamidophenyl, 6-methyl-2-aminophenyl, 6-methyl-2,3-diaminophenyl, 2-amino-3-methylphenyl, 4,6-dimethyl-2-aminophenyl, 4-hydroxyphenyl, 3-methyl- 4-hydroxyphenyl, 4-(2-methoxyphenyl)phenyl, 2-amino-1-naphthyl, 2-naphthyl, 3-amino-2-naphthyl, 1-methyl-3-amino-2-naphthyl, 2,3-diamino-1-naphthyl, 4,8-dimethoxy-2-naphthyl and the like.

"Aralkyl" and "arylalkyl", alone or in combination, means an alkyl radical as defined above in which at least one hydrogen atom, preferably 1–2, is replaced by an aryl radical as defined above, such as benzyl, 1-, 2-phenylethyl, dibenzylmethyl, hydroxyphenylmethyl, methylphenylmethyl, diphenylmethyl, dichlorophenylmethyl, 4-methoxyphenylmethyl and the like.

"Aralkoxy", alone or in combination, means an alkoxy radical as defined above in which at least one hydrogen atom, preferably 1–2, is replaced by an aryl radical as defined above, such as benzyloxy, 1-, 2-phenylethoxy, dibenzylmethoxy, hydroxyphenylmethoxy, methylphenylmethoxy, dichlorophenylmethoxy, 4-methoxyphenylmethoxy and the like.

"Aralkoxycarbonyl", alone or in combination, means a radical of the type "R—O—C(O)—" wherein "R—O—" is an aralkoxy radical as defined above and "—C(O)—" is a carbonyl radical.

"Alkanoyl", alone or in combination, means a radical of the type "R—C(O)—" wherein "R" is an alkyl radical as defined above and "—C(O)—" is a carbonyl radical. Examples of such alkanoyl radicals include acetyl, trifluoroacetyl, hydroxyacetyl, propionyl, butyryl, valeryl, 4-methylvaleryl, and the like.

"Alkanoylamino", alone or in combination, means a radical of the type "R—C(O)—NH—" wherein "R—C(O)—" is an alkanoyl radical as defined above, wherein the amino radical may optionally be substituted, such as with alkyl, aryl, aralkyl, cycloalkyl, cycloalkylalkyl and the like.

"Aminocarbonyl", alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like.

"Aminosulfonyl", alone or in combination, means an amino substituted sulfonyl radical.

"Benzo", alone or in combination, means the divalent radical $C_6H_4=$ derived from benzene. "Benzo fused" forms a ring system in which benzene and a cycloalkyl or aryl group have two carbons in common, for example tetrahydronaphthylene and the like.

"Bicyclic" as used herein is intended to include both fused ring systems, such as naphthyl and β-carbolinyl, and substituted ring systems, such as biphenyl, phenylpyridyl and diphenylpiperazinyl.

"Cycloalkyl", alone or in combination, means a saturated or partially saturated, preferably one double bond, monocyclic, bicyclic or tricyclic carbocyclic alkyl radical, preferably monocyclic, containing preferably 5–12 carbon atoms ($C_5$–$C_{12}$), more preferably 5–10 carbon atoms ($C_5$–$C_{10}$), even more preferably 5–7 carbon atoms ($C_5$–$C_7$), which is optionally benzo fused or heterocyclo fused and which is optionally substituted as defined herein with respect to the definition of aryl. Examples of such cycloalkyl radicals include cyclopentyl, cyclohexyl, dihydroxycyclohexyl, ethylenedioxycyclohexyl, cycloheptyl, octahydronaphthyl, tetrahydronaphthyl, octahydroquinolinyl, dimethoxytetrahydronaphthyl, 2,3-dihydro-1H-indenyl, azabicyclo[3.2.1]octyl and the like.

"Heteroatoms" means nitrogen, oxygen and sulfur heteroatoms.

"Heterocyclo fused" forms a ring system in which a heterocyclyl or heteroaryl group of 5–6 ring members and a cycloalkyl or aryl group have two carbons in common, for example indole, isoquinoline, tetrahydroquinoline, methylenedioxybenzene and the like.

"Heterocyclyl" means a saturated or partially unsaturated, preferably one double bond, monocyclic or bicyclic, preferably monocyclic, heterocycle radical containing at least one, preferably 1 to 4, more preferably 1 to 3, even more preferably 1–2, nitrogen, oxygen or sulfur atom ring member and having preferably 3–8 ring members in each ring, more preferably 5–8 ring members in each ring and even more preferably 5–6 ring members in each ring. "Heterocyclyl" is intended to include sulfone and sulfoxide derivatives of sulfur ring members and N-oxides of tertiary nitrogen ring members, and carbocyclic fused, preferably 3–6 ring carbon atoms and more preferably 5–6 ring carbon atoms, and benzo fused ring systems. "Heterocyclyl" radicals may optionally be substituted on at least one, preferably 1–4, more preferably 1–3, even more preferably 1–2, carbon atoms by halogen, alkyl, alkoxy, hydroxy, oxo, thioxo, aryl, aralkyl, heteroaryl, heteroaralkyl, amidino, N-alkylamidino, alkoxycarbonylamino, alkylsulfonylamino and the like, and/or on a secondary nitrogen atom by hydroxy, alkyl, aralkoxycarbonyl, alkanoyl, alkoxycarbonyl, heteroaralkyl, aryl or aralkyl radicals. More preferably, "heterocyclyl", alone or in combination, is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals. Examples of such heterocyclyl radicals include pyrrolidinyl, piperidinyl, piperazinyl, morpholinyl, thiamorpholinyl, 4-benzyl-piperazin-1-yl, pyrimidinyl, tetrahydrofuryl, pyrazolidonyl, pyrazolinyl, pyridazinonyl, pyrrolidonyl, tetrahydrothienyl and its sulfoxide and sulfone derivatives, 2,3-dihydroindolyl, tetrahydroquinolinyl, 1,2,3,4-tetrahydroisoquinolinyl, 1,2,3,4-tetrahydro-1-oxo-isoquinolinyl, 2,3-dihydrobenzofuryl, benzopyranyl, methylenedioxyphenyl, ethylenedioxyphenyl and the like.

"Heteroaryl" means a monocyclic or bicyclic, preferably monocyclic, aromatic heterocycle radical, having at least one, preferably 1 to 4, more preferably 1 to 3, even more preferably 1–2, nitrogen, oxygen or sulfur atom ring members and having preferably 5–6 ring members in each ring, which is optionally saturated carbocyclic fused, preferably 3–4 carbon atoms ($C_3$–$C_4$) to form 5–6 ring membered rings and which is optionally substituted as defined above with respect to the definitions of aryl. Examples of such heteroaryl groups include imidazolyl, 1-benzyloxycarbonylimidazol-4-yl, pyrrolyl, pyrazolyl, pyridyl, 3-(2-methyl)pyridyl, 3-(4-trifluoromethyl)pyridyl, pyrimidinyl, 5-(4-trifluoromethyl)pyrimidinyl, pyrazinyl, triazolyl, furyl, thienyl, oxazolyl, thiazolyl, indolyl, quinolinyl, 5,6,7,8-tetrahydroquinolyl, 5,6,7,8-tetrahydroisoquinolinyl, quinoxalinyl, benzothiazolyl, benzofuryl, benzimidiazolyl, benzoxazolyl and the like.

"Heteroaralkyl", and "heteroarylalkyl," alone or in combination, means an alkyl radical as defined above in which at least one hydrogen atom, preferably 1–2, is replaced by a heteroaryl radical as defined above, such as 3-furylpropyl, 2-pyrrolyl propyl, chloroquinolinylmethyl, 2-thienylethyl, pyridylmethyl, 1-imidazolylethyl and the like.

"Halogen" and "halo", alone or in combination, means fluoro, chloro, bromo or iodo radicals.

"Haloalkyl", alone or in combination, means an alkyl radical as defined above in which at least one hydrogen atom, preferably 1–3, is replaced by a halogen radical, more preferably fluoro or chloro radicals. Examples of such haloalkyl radicals include 1,1,1-trifluoroethyl, chloromethyl, 1-bromoethyl, fluoromethyl, difluoromethyl, trifluoromethyl, bis(trifluoromethyl)methyl and the like.

"Pharmacologically acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulphuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al, *J. Pharm . Sci.* 66, 1 (1977).

"Cytokine" means a secreted protein that affects the functions of other cells, particularly as it relates to the modulation of interactions between cells of the immune system or cells involved in the inflammatory response. Examples of cytokines include but are not limited to interleukin 1 (IL-1), preferably IL-1β, interleukin 6 (IL-6), interleukin 8 (IL-8) and TNF, preferably TNF-α (tumor necrosis factor-α).

"TNF, IL-1, IL-6, and/or IL-8 mediated disease or disease state" means all disease states wherein TNF, IL-1, IL-6, and/or IL-8 plays a role, either directly as TNF, IL-1, IL-6, and/or IL-8 itself, or by TNF, IL-1, IL-6, and/or IL-8 inducing another cytokine to be released. For example, a disease state in which IL-1 plays a major role, but in which the production of or action of IL-1 is a result of TNF, would be considered mediated by TNF.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, arylalkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6–10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also sutiable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium flouride reagent, either as a discrete reaction step or in situ during a reaction with the alcohol group. Suitable silylating agents are, for example, trimethylsilyl chloride, tert-buty-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

The symbols used above have the following meanings:

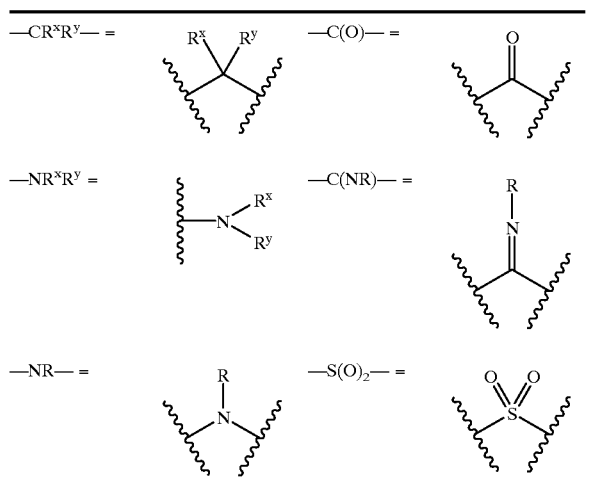

Procedures for preparing the compounds of this invention are set forth below. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

Preparation of Compounds of Formula I

The compounds of the present invention represented by Formula I above can be prepared utilizing the following general procedures. *Hetero-aromatic Nitrogen Compounds; Pyrroles and Pyridines:* Schofield, Kenneth; Plenum Press, New York, N.Y.; (1967) and *Advances in Nitrogen Heterocycles:* JAI Press, Greenwich, Conn.; (1995) describe procedures and references that may be useful in preparing compounds of the present invention.

2-Halo-5-nitro-pyridine analogs, (2) can be treated with the appropriate amine, alcohol, phenol, or thiol (R—X—H) in the presence of base or Cu(I) in an appropriate solvent, such as THF, DMF, DME, DMSO and the like, at a temperature from −20° C. to 120° C. to form 2-substituted-5-nitropyridines (3) (Scheme I). Reduction of the nitro group can be perfomed by treatment of (3) with hydrogen gas in the presence of palladium on carbon or Raney nickel, or alternatively, by treatment with $SnCl_2$ in an alcoholic solvent and in the presence or absence of HCl to obtain 2-substituted-5-aminopyridines (4). The aminopyridines (4) may be alkylated using alkylhalides and an appropriate base or by reductive alkylation employing the appropriate aldehyde or ketone in the presence of a reducing agent, such as sodium triacetoxy borohydride, borane. THF and the like, to form the substituted aminopyridines (5). Either (4) or (5) may be acylated with an appropriate acid halide (e.g., $R^3C(O)Cl$ or $R^3C(O)Br$) in the presence of a base, such as pyridine, DMAP and the like, or alternatively may be acylated with an anhydride, either mixed or symmetrical, or alternatively may be acylated by treatment with the appropriate acid ($R^3CO_2H$) in the presence of a coupling agent such as a carbodiimide reagent: to form the final product (1). Alternatively, substituted 2-bromo-5-nitropyridine analogs may be reduced to, substituted 2-bromo- 5-aminopyridine analogs by the action of $SnBr_2$ in methanolic solvent. Subsequent acylation with an appropriate activated ester (i.e.: $R^3CO_2H$ in the presence of diisopropylcarbodiimide in methylene chloride as solvent) produces 2-bromopyridine-5-carboxamide compounds of structure (5a). Coupling of (5a) with an appropriate phenol in the presence of $Cu(Ac)_2$ and $K_2CO_3$ in DMF at 140° C. provides compounds of formula (1) where X=O.

SCHEME I

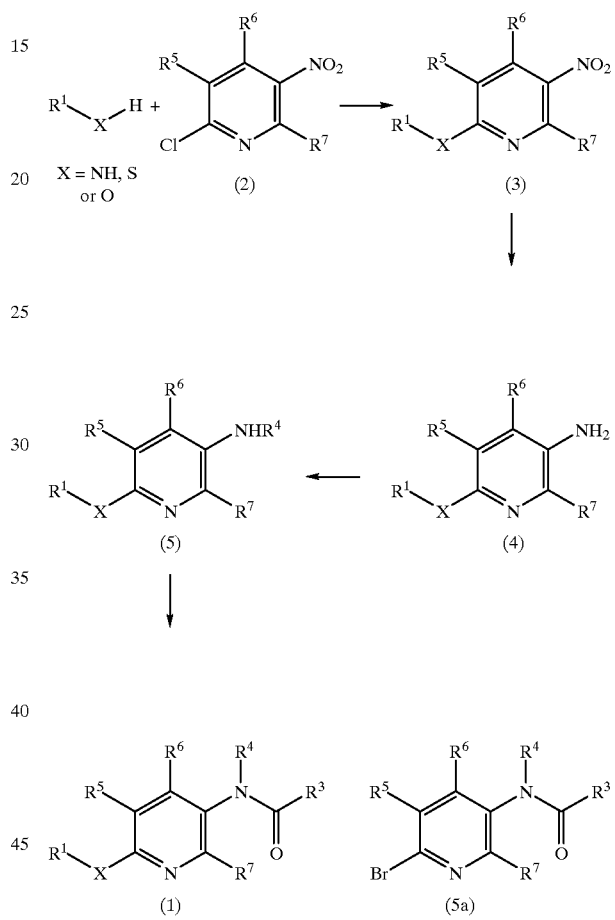

6-Substituted-2-halo-5-nitro-pyridine analogs (6) may be prepared from 2,6-dichloro-5-nitropyridine 15 according to the methods outlined in Scheme II. Treatment with one equivalent of an appropriate nucleophile of $R^7$ or a precursor thereof (such as, $HO^-$, $RO^-$, $AcS^-$, $NC^-$, $RS^-$ and the like) provides (6). Subsequent reaction to form (7) (treatment with $R^1$—X—H in the presence of base or Cu(I) in an appropriate solvent, such as THF, DMF, DME, DMSO and the like, at a temperature from —20° C. to 120° C.) and (8) (reduction of the nitro group and substitution with $R^4$) is as described in Scheme I (cf. Colbry, N. L. et al.; *J. Heterocyclic Chem.*, 21: 1521–1525 (1984); Matsumoto, Jun-ichi, et al.; *J. Heterocyclic Chem.*, 21: 673–679 (1984)). (8) may be reacted with an acid halide or an activated

SCHEME II

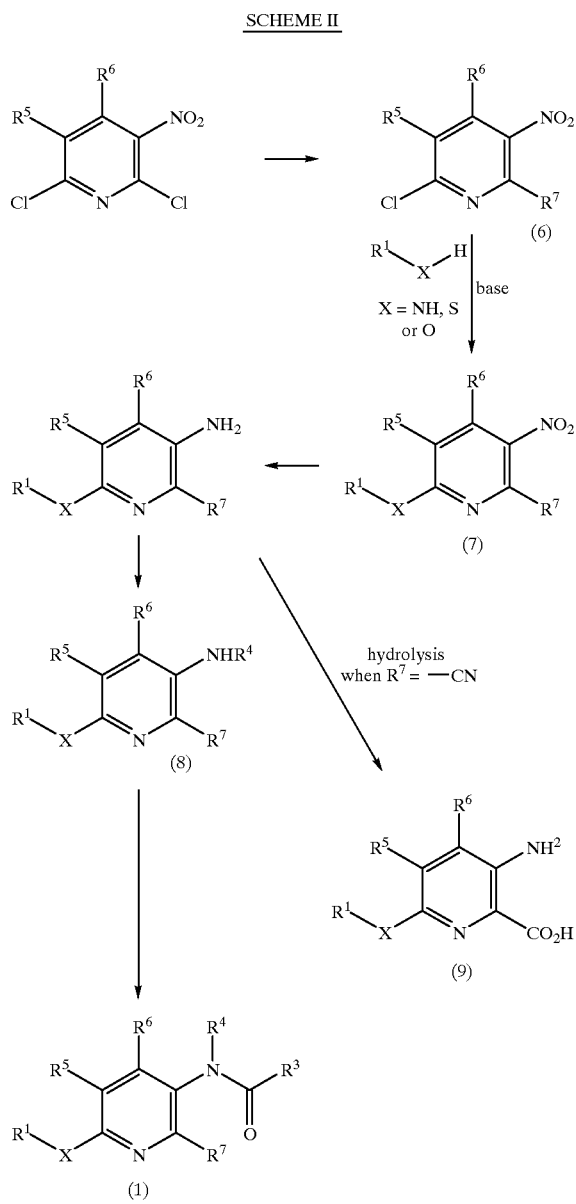

ester as shown in Scheme I to provide compounds of formula (1). Where $R^7$=CN, compounds of formula (8) may be hydrolyzed to acids ($R^7$=CO$_2$H) of formula (9) using acidic media such as HBr and the like. Utilizing the appropriate N-protecting groups, acids of formula (9) may be transformed into esters, amides and alcohols. Compounds of formula (9) and derivatives described above may be be reacted with an acid halide or an activated ester as shown in Scheme I to provide compounds of formula (1). Compounds of formula (8), where $R^7$=—CN, may be reduced to the primary amine ($R^7$=—CH$_2$NH$_2$) using reagents such as BH$_3$ or hydrogen gas in the presence of palladium on carbon or Raney nickel. Subsequent manipulation and reaction of the primary amine may be performed in the presence of the pyridine-5-amine substituent due to it's greater reactivity. Specifically, compounds of formula (8) where R=—CH$_2$NH$_2$ may be alkylated by treatment with an appropriate aldehyde or ketone in the presence of a reducing agent, such as sodium triacetoxy borohydride, or may be acylated by treatment with an appropriate activated ester, chloroformate, isocyanate and the like, or may be sulfonylated by treatment with an appropriate sulfonyl halide. Alternatively, substituted 3-aminopyridine intermediates may be prepared from the corresponding nicotinamide compound using Hofmann's reaction.

When $R^6$ and/or $R^7$ is an alkyl group, such as methyl, in compound (7), containing the appropriate protecting groups of or avoiding the presence of base sensitive groups, can be treated with strong base such as NaNH$_2$, PhLi, NaH or the like at temperatures from −78° C. to 22° C. then treated with electrophiles, such as alkyl halides, aldehydes, ketones and the like (cf. Fuerst, Feustel; *CHEMTECH;* 10: 693–699 (1958); Nishigaki, S. et al.; Chem. Pharm. Bull.; 17: 1827–1831 (1969); Kaiser, Edwin M.; Tetrahedron; 39: 2055–2064 (1983)). Alternatively, the alkyl group may be halogenated and the haloalkyl group may be reacted with a nucleophile, such as an amino group, alkoxy, alkylthiol and the like.

6-Chloronicotinoyl chloride analogs (10) are treated with the appropriate amine ($R^3R^4$NH) in the presence of base in an appropriate solvent, such as dichloromethane, acetonitrile, DMF, THF and the like, at a temperature from −20° C. to 120° C. to form nicotinamides (11) as shown in Scheme III. Alternatively, 6-chloronicotinic acid analogs (12) may be coupled with the appropriate amine via an anhydride, either mixed or symmetrical, or alternatively by treatment with the appropriate amine in the presence of a coupling agent such as a carbodiimide reagent to form the amide (11). 6-Chloronicotinamide analogs (11) are treated with the appropriate $R^1$—X—H in the presence of absence of base, or Cu(I) in an approriate solvent, such as pyridine, ethylene glycol, DMF, DME, DMSO and the like, at a temperature from −20° C. to 180° C. to form the final product (13).

SCHEME III

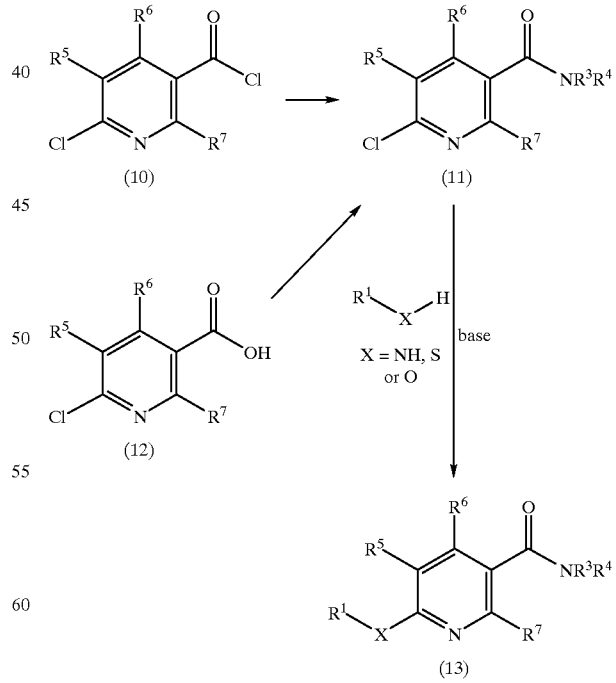

Substituted halopyridines may be readily prepared from the corresponding pyridones using phosphorus oxychloride or pentachloride.

Amines of formula NHR¹R² and NHR³R⁴ are commercially available or can be readily prepared by those skilled in the art from commercially available starting materials. For example, an amide, nitro or cyano group can be reduced under reducing conditions, such as in the prescence of a reducing agent like lithium aluminum hydride and the like, to form the corresponding amine. Alkylation and acylation of amino groups are well known in the art. Chiral and achiral substituted amines can be prepared from chiral amino acids and amino acid amides (for example, alkyl, aryl, heteroaryl, cycloalkyl, arylalkyl, heteroarylalkyl, cycloalkylalkyl and the like) using methods well known in the art, such as H. Brunner, P. Hankofer, U. Holzinger, B. Treittinger and H. Schoenenberger, Eur. J. Med. Chem. 25, 35–44, 1990; M. Freifelder and R. B. Hasbrouck, J. Am. Chem. Soc. 82, 696–698, 1960; Dornow and Fust, Chem. Ber. 87, 985, 1954; M. Kojima and J. Fujita, Bull. Chem. Soc. Jpn. 55, 1454–1459, 1982; W. Wheeler and D. O'Bannon, Journal of Labelled Compounds and Radiopharmaceuticals XXXI, 306, 1992; and S. Davies, N. Garrido, O. Ichihara and I. Walters, J. Chem. Soc., Chem., Commun. 1153, 1993.

Alkyl sulfonic acids, aryl sulfonic acids, heterocyclyl sulfonic acids, heteroaryl sulfonic acids, alkylmercaptans, arylmercaptans, heterocyclylmercaptans, heteroarylmercaptans, alkylhalides, arylhalides, heterocyclylhalides, heteroarylhalides, and the like are commercially available or can be readily prepared from starting materials commercially available using standard methods well known in the art.

Thioether derivatives can be converted into the corresponding sulfone or sulfoxide by oxidizing the thioether derivative with a suitable oxidation agent in a suitable solvent. Suitable oxidation agents include, for example, hydrogen peroxide, sodium meta-perborate, oxone (potassium peroxy monosulfate), meta-chloroperoxybenzoic acid, periodic acid and the like, including mixtures thereof. Suitable solvents include acetic acid (for sodium meta-perborate) and, for other peracids, ethers such as THF and dioxane, and acetonitrile, DMF and the like, including mixtures thereof.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Prodrugs of the compounds of this invention are also contemplated by this invention A prodrug is an active or inactive compound that is modified chemically through in vivo physiological action, such as hydrolysis, metabolism and the like, into a compound of this invention following adminstration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, 4/11/81) discloses Mannich-base hydroxamic acid prodrugs, their preparation and use.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The following Examples illustrate the preparation of compounds of the present invention and intermediates useful in preparing the compounds of the present invention.

EXAMPLE 1

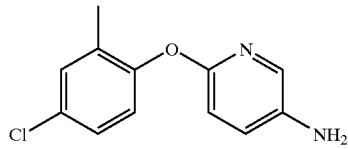

Preparation of 2-(4-Chloro-2-methyl-phenoxy)-5-amino-pyridine

Step A: 2-(4-Chloro-2-methyl-phenoxy)-5-nitropyridine

4-Chloro-2-methylphenol (101 mg, 0.71 mmol) was dissolved in tetrahydrofuran (2.1 mL) and the solution was treated with sodium hydride (60% dispersed in mineral oil, 31 mg, 0.78 mmol). After stirring for 30 minutes at 22° C., 2-chloro-5-nitropyridine (101 mg, 0.64 mmol) was added and the reaction mixture was heated to reflux for 1 hour. The solution was cooled to ambient temperature, quenched with saturated aqueous NH₄Cl and concentrated in vacuo. The residue was redissolved in ethyl acetate then washed 2× with saturated NaHCO₃, saturated NaCl, dried over anhydrous Na₂SO₄ and concentrated in vacuo.

Step B: 2-(4-Chloro-2-methyl-phenoxy)-5-amino-pyridine 2-(4-chloro-2-methyl-phenoxy)-5-nitropyridine (203 mg, 0.77 mmol) was dissolved in 95% ethanol (3 mL) and treated with 20% palladium hydroxide on carbon (50 mg). The reaction mixture was shaken in a hydrogen atmosphere (40 psi) for 1 hour. The solution was filtered through celite and concentrated in vacuo . MS (m/z): 234/236 (M+H)⁺; C₁₂H₁₁N₂OCl requires 234.7.

EXAMPLE 2

The compounds listed in Table 1 were prepared from 2-chloro-5-nitropyridine and the appropriate alcohol, amine or thiol in the same manner as 2-(4-Chloro-2-methyl-phenoxy)-5-amino-pyridine was prepared.

TABLE 1

| | MS (m/z) |
|---|---|
| 2-(4-Chloro-2-methylphenoxy)-5-amino-pyridine | 235 |
| 2-(4-Chloro-2,6-dimethylphenoxy)-5-amino-pyridine | 249 |
| 2-(2-Methyl-pyridin-3-yloxy)-5-amino-pyridine | 201 |
| 2-(4-Fluoro-2-methylphenoxy)-5-amino-pyridine | 218 |
| 2-(2-Isopropylphenoxy)-5-amino-pyridine | 228 |
| 2-(1-Naphthyloxy)-5-amino-pyridine | 236 |
| 2-(Cyclohexyloxy)-5-amino-pyridine | 192 |
| 2-(2-Methylphenoxy)-5-amino-pyridine | 200 |
| 2-(2,4-Dimethylphenoxy)-5-amino-pyridine | 214 |
| 2-(4-Chlorophenoxy)-5-amino-pyridine | 222 |
| 2-(Phenoxy)-5-amino-pyridine | 186 |
| 2-(2-Methylcyclohexylamino)-5-amino-pyridine | 205 |
| 2-(Cyclohexylamino)-5-amino-pyridine | 191 |
| 2-(2-Methylanilino)-5-amino-pyridine | 199 |
| 2-(4-Chloro-2-methylanilino)-5-amino-pyridine | 233 |
| 2-(2,4-Dimethylanilino)-5-amino-pyridine | 212 |
| 2-(4-Chloro-2-methylthiophenoxy)-5-amino-pyridine | 251 |

EXAMPLE 3

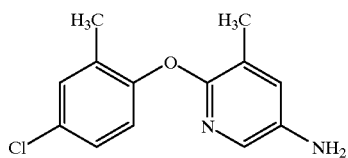

Preparation of 2-(4-Chloro-2-methyl-phenoxy)-3-methyl-5-amino-pyridine

Step A: 2-(4-Chloro-2-methyl-phenoxy)-3-methyl-5-nitropyridine

Sodium hydride (60% in mineral oil, 1.08 g, 27 mmol) was washed 3× with hexanes then a solution of 4-chloro-2-methylphenol (3.50 g, 24.5 mmol) dissolved in tetrahydrofuran (40 mL) was added. The solution was stirred for 20 minutes then 2-chloro-3-methyl-5-nitropyridine (4.02 g, 23.3 mmol) was added and the reaction mixture was heated to reflux for 3 hours. After cooling, the mixture was concentrated in vacuo then dissolved in ethyl acetate and washed with water, 3× with saturated NaHCO$_3$ and saturated NaCl then dried over Na$_2$SO$_4$ and concentrated in vacuo.

Step B: 2-(4-Chloro-2-methyl-phenoxy)-3-methyl-5-amino-pyridine 2-(4-chloro-2-methyl-phenoxy)-3-methyl-5-nitropyridine (5.8 g, 20.8 mmol) was dissolved in 95% ethanol (50 mL) and treated with 20% palladium hydroxide on carbon (350 mg). The reaction mixture was shaken in a hydrogen atmosphere (40 psi) for 1 hour. The solution was filtered through celite and concentrated in vacuo followed by chromatography on SiO$_2$ using 1:1 ethyl acetate/hexanes as eluant. MS (m/z): 248/250 (M+H)$^+$ C$_{13}$H$_{13}$N$_2$OCl requires 248.7.

EXAMPLE 4

The compounds listed in Table 2 were prepared from substituted 2-chloro-5-nitropyridine and 4-chloro-2-methylphenol in the same manner as 2-(4-Chloro-2-methyl-phenoxy)-3-methyl-5-amino-pyridine was prepared.

TABLE 2

| | MS (m/z) |
|---|---|
| 2-(4-Chloro-2-methyl-phenoxy)-4-methyl-5-amino-pyridine | 249 |
| 6-(4-Chloro-2-methyl-phenoxy)-2-methyl-3-amino-pyridine | 249 |
| 6-(4-Chloro-2-methyl-phenoxy)-2,3-diamino-pyridine | 250 |

EXAMPLE 5

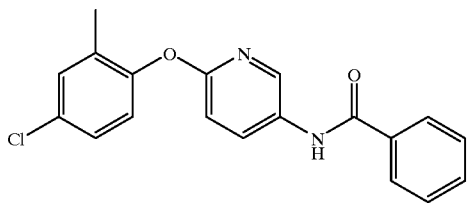

Preparation of N-(2-(4-Chloro-2-methyl-phenoxy)-pyridin-5-yl)-benzamide 2-(4-Chloro-2-methyl-phenoxy)-5-aminopyridine (211 mg, 0.90 mmol) was dissolved in methylene chloride (2.7 mL) then treated with triethylamine (0.19 mL, 1.35 mmol) followed by benzoyl chloride (0.13 mL, 1.12 mmol). The reaction mixture was stirred for 3 hours at 22° C. then saturated aqueous NaHCO$_3$ was added and the mixture was stirred for another hour. The organic layer was separated and washed 2× with 6% aqueous NaHCO$_3$, dried over Na$_2$SO$_4$ and concentrated in vacuo. The residue was chromatographed on silica gel using 1:1 ethyl acetate/hexane as eluent. The product was recovered as a white solid. MS (m/z): 338/340 (M+H)$^+$; C$_{19}$H$_{15}$N$_2$O$_2$Cl requires 338.8.

EXAMPLE 6

The compounds listed in Table 3 were prepared from substituted 5-aminopyridine compounds and the appropriate acid chloride in the same manner as N-(2-(4-Chloro-2-methyl-phenoxy)-pyridin-5-yl)-benzamide was prepared.

TABLE 3

| | MS (m/z) |
|---|---|
| 2-(4-Chloro-2-methyl-phenoxy)-5-(3-pyridylcarbonylamino)pyridine | 340 |
| 2-(4-Chloro-2-methyl-phenoxy)-5-((2,6-dichlorophenyl)carbonylamino)pyridine | 408 |
| 2-(4-Chloro-2-methyl-phenoxy)-5-(4-pyridylcarbonylamino)pyridine | 340 |
| 2-(4-Chloro-2-methyl-phenoxy)-5-((4-methoxyphenyl)carbonylamino)pyridine | 369 |
| 2-(4-Chloro-2-methyl-phenoxy)-5-((4-pentylphenyl)carbonylamino)pyridine | 409 |
| 2-(4-Chloro-2-methyl-phenoxy)-5-(2-naphthylcarbonylamino)pyridine | 389 |
| 2-(4-Chloro-2-methyl-phenoxy)-5-(2-thienylcarbonylamino)pyridine | 345 |
| 2-(4-Chloro-2-methyl-phenoxy)-5-((3,5-dimethyl-4-isoxazolyl)carbonylamino)pyridine | 358 |
| 2-(4-Chloro-2-methyl-phenoxy)-5-((5-benzo[1,3]dioxol-yl)carbonylamino)pyridine | 383 |
| 2-(4-Chloro-2-methyl-phenoxy)-5-((5-tert-butyl- | 399 |

TABLE 3-continued

| | MS (m/z) |
|---|---|
| 2-methyl-2H-pyrazol-3-yl)carbonylamino)pyridine | |
| 2-(4-Chloro-2-methyl-phenoxy)-5-((2-benzo[b]thiophenyl)carbonylamino)pyridine | 395 |
| 2-(4-Chloro-2-methyl-phenoxy)-5-((2-methoxyphenyl)carbonylamino)pyridine | 369 |
| 2-(4-Chloro-2-methyl-phenoxy)-5-((3,5-dichlorophenyl)carbonylamino)pyridine | 408 |
| 2-(4-Chloro-2-methyl-phenoxy)-5-((2,6-dimethylphenyl)carbonylamino)pyridine | 367 |
| 2-(4-Chloro-2-methyl-phenoxy)-5-((2-methylphenyl)carbonylamino)pyridine | 353 |
| 2-(4-Chloro-2-methyl-phenoxy)-5-((2-nitrophenyl)carbonylamino)pyridine | 384 |
| 2-(4-Chloro-2-methyl-phenoxy)-5-((2-acetoxyphenyl)carbonylamino)pyridine | 397 |
| 2-(4-chloro-2,6-dimethylphenoxy)-5-((2,6-dichlorophenyl)carbonylamino)pyridine | 422 |
| 2-(4-chloro-2,6-dimethylphenoxy)-5-((2,6-dimethylphenyl)carbonylamino)pyridine | 381 |
| 2-(2-methyl-pyridin-3-yloxy)-5-((2,6-dichlorophenyl)carbonylamino)pyridine | 374 |
| 2-(2-methyl-pyridin-3-yloxy)-5-((2,6-dimethylphenyl)carbonylamino)pyridine | 333 |
| 2-(2-methyl-pyridin-3-yloxy)-5-((2-methylphenyl)carbonylamino)pyridine | 319 |
| 2-(4-fluoro-2-methylphenoxy)-5-((2,6-dichlorophenyl)carbonylamino)pyridine | 391 |
| 2-(4-fluoro-2-methylphenoxy)-5-((2,6-dimethylphenyl)carbonylamino)pyridine | 350 |
| 2-(4-fluoro-2-methylphenoxy)-5-((2-methylphenyl)carbonylamino)pyridine | 336 |
| 2-(4-fluoro-2-methylphenoxy)-5-( (2-trifluoromethylphenyl)carbonylamino)pyridine | 390 |
| 2-(4-fluoro-2-methylphenoxy)-5-((2-fluorophenyl)carbonyl amino)pyridine | 340 |
| 2-(2-isopropylphenoxy)-5-((2,6-dichlorophenyl)carbonylamino)pyridine | 401 |
| 2-(2-isopropylphenoxy)-5-((2,6-dimethylphenyl)carbonylamino)pyridine | 360 |
| 2-(2-isopropylphenoxy)-5-((2-methylphenyl)carbonylamino)pyridine | 346 |
| 2-(1-naphthyloxy)-5-((2,6-dichlorophenyl)carbonylamino)pyridine | 409 |
| 2-(1-naphthyloxy)-5-((2,6-dimethylphenyl)carbonylamino)pyridine | 368 |
| 2-(1-naphthyloxy)-5-((2-methylphenyl)carbonylamino)pyridine | 354 |
| 2-(cyclohexyloxy)-5-((2,6-dichlorophenyl)carbonylamino)pyridine | 365 |
| 2-(cyclohexyloxy)-5-((2,6-dimethylphenyl)carbonylamino)pyridine | 324 |
| 2-(cyclohexyloxy)-5-((2-chlorophenyl)carbonylamino)pyridine | 331 |
| 2-(cyclohexyloxy)-5-((2-methylphenyl)carbonylamino)pyridine | 310 |
| 2-(2-methylphenoxy)-5-((2,6-dichlorophenyl)carbonylamino)pyridine | 373 |
| 2-(2-methylphenoxy)-5-((2,6-dimethylphenyl)carbonylamino)pyridine | 332 |
| 2-(2-methylphenoxy)-5-((2-chlorophenyl)carbonylamino)pyridine | 339 |
| 2-(2-methylphenoxy)-5-((2-methylphenyl)carbonylamino)pyridine | 318 |
| 2-(2,4-dimethylphenoxy)-5-((2,6-dichlorophenyl)carbonylamino)pyridine | 387 |
| 2-(2,4-dimethylphenoxy)-5-((2,6-dimethylphenyl)carbonylamino)pyridine | 346 |
| 2-(2,4-dimethylphenoxy)-5-((2-chlorophenyl)carbonylamino)pyridine | 353 |
| 2-(2,4-dimethylphenoxy)-5-((2-methylphenyl)carbonylamino)pyridine | 332 |
| 2-(4-chlorophenoxy)-5-((2,6-dichlorophenyl)carbonylamino)pyridine | 394 |
| 2-(4-chlorophenoxy)-5-((2,6-dimethylphenyl)carbonylamino)pyridine | 353 |
| 2-(2-methylcyclohexylamino)-5-((2,6-dichlorophenyl)carbonylamino)pyridine | 378 |
| 2-(2-methylcyclohexylamino)-5-((2-methylphenyl)carbonylamino)pyridine | 323 |
| 2-(cyclohexylamino)-5-((2,6-dichlorophenyl)carbonylamino)pyridine | 364 |
| 2-(cyclohexylamino)-5-((2,6-dimethylphenyl)carbonylamino)pyridine | 323 |
| 2-(cyclohexylamino)-5-((2-methylphenyl)carbonylamino)pyridine | 309 |
| 2-(2-methylanilino)-5-((2,6-dichlorophenyl)carbonylamino)pyridine | 372 |
| 2-(2-methylanilino)-5-(2,6-dimethylphenyl)carbonylamino)pyridine | 331 |
| 2-(2-methylanilino)-5-((2-methylphenyl)carbonylamino)pyridine | 317 |
| 2-(4-chloro-2-methylanilino)-5-((2,6-dichlorophenyl)carbonylamino)pyridine | 407 |
| 2-(4-chloro-2-methylanilino)-5-((2,6-dimethylphenyl)carbonylamino)pyridine | 366 |
| 2-(4-chloro-2-methylanilino)-5-((2-methylphenyl)carbonylamino)pyridine | 352 |
| 2-(2,4-dimethylanilino)5-((2,6-dichlorophenyl)carbonylamino)pyridine | 386 |
| 2-(2,4-dimethylanilino)-5-((2,6-dimethylphenyl)carbonylamino)pyridine | 345 |
| 2-(2,4-dimethylanilino)-5-((2-methylphenyl)carbonylamino)pyridine | 331 |
| 2-(2,4-dimethylanilino)-5-((2-chlorophenyl)carbonylamino)pyridine | 352 |
| 2-(2,4-dimethylanilino)-5-((2-fluorophenyl)carbonylamino)pyridine | 335 |
| 2-(4-chloro-2-methyl-thiophenyl)-5-((2,6-dichlorophenyl)carbonylamino)pyridine | 424 |
| 2-(4-chloro-2-methyl-thiophenyl)-5-((2,6-dimethylphenyl)carbonylamino)pyridine | 383 |
| 2-(4-chloro-2-methyl-thiophenyl)-5-((2-methylphenyl)carbonylamino)pyridine | 369 |

EXAMPLE 7

The compounds listed in Table 4 were prepared from substituted 5-aminopyridine compounds and the appropriate acid chloride in the same manner as N-(2-(4-Chloro-2-methyl-phenoxy)-pyridin-5-yl)-benzamide was prepared.

TABLE 4

| | MS (m/z) |
|---|---|
| 2-(4-Chloro-2-methyl-phenoxy)-5-((2,6-dichlorophenyl)carbonylamino)-3-methyl-pyridine | 422 |
| 2-(4-Chloro-2-methyl-phenoxy)-5-((2-chlorophenyl)carbonylamino)-3-methyl-pyridine | 387 |
| 2-(4-Chloro-2-methyl-phenoxy)-5-((2-methylphenyl)carbonylamino)-3-methyl-pyridine | 367 |
| 2-(4-Chloro-2-methyl-phenoxy)-5-((2,6-dimethylphenyl)carbonylamino)-3-methyl-pyridine | 332 |
| 2-(4-Chloro-2-methyl-phenoxy)-5-((2,6-dichlorophenyl)carbonylamino)-4-methyl-pyridine | 422 |
| 2-(4-Chloro-2-methyl-phenoxy)-5-((2-fluoro-6-trifluoromethylphenyl)carbonylamino-4-methyl-pyridine | 439 |
| 2-(4-Chloro-2-methyl-phenoxy)-5-((2,4,6-triisopropylphenyl)carbonylamino)-4-methyl-pyridine | 479 |
| 2-(4-Chloro-2-methyl-phenoxy)-5-((2-methylphenyl)carbonylamino)-6-methyl-pyridine | 367 |
| 2-(4-Chloro-2-methyl-phenoxy)-5-((2-chlorophenyl)carbonylamino)-6-methyl-pyridine | 387 |
| 2-(4-Chloro-2-methyl-phenoxy)-5-((2,6-dichlorophenyl)carbonylamino)-6-methyl-pyridine | 422 |

TABLE 4-continued

| | MS (m/z) |
|---|---|
| 2-(4-Chloro-2-methyl-phenoxy)-5-((2,6-dichlorophenyl)carbonylamino)-6-amino-pyridine | 423 |
| 2-(4-Chloro-2-methyl-phenoxy)-5-((2-chlorophenyl)carbonylamino)-6-amino-pyridine | 388 |
| 2-(4-Chloro-2-methyl-phenoxy)-5-((2,6-dimethylphenyl)carbonylamino)-6-amino-pyridine | 382 |
| 2-(4-Chloro-2-methyl-phenoxy)-5-((2-methylphenyl)carbonylamino)-6-amino-pyridine | 368 |

EXAMPLE 8

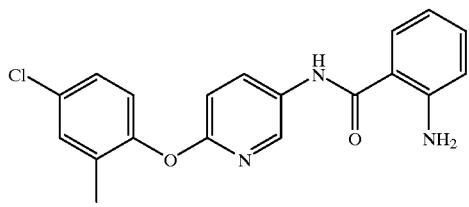

Preparation of 2-Amino-N-(6-(4-chloro-2-methyl-phenoxy)-pyridin-3-yl)-benzamide

N-(6-(4-chloro-2-methyl-phenoxy)-pyridin-3-yl)-2-nitro-benzamide (301 mg, 0.7 mmol) was dissolved in 95% ethanol (4 mL) and treated with 20% palladium hydroxide on carbon (Pearlman's catalyst, 50 mg) and subjected to a hydrogen atmosphere (40 psi) for 2 hours. The catalyst was removed by filtration and the solvents were removed in vacuo. The product was purified by chromatography on SiO2 using 1:1 ethyl acetate/hexanes as eluent. MS (m/z): 353/355 (M+H)$^+$; $C_{19}H_{16}N_3O_2Cl$ requires 353.8.

EXAMPLE 9

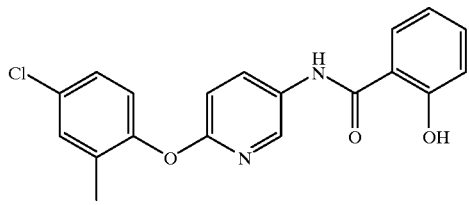

Preparation of N-(6-(4-chloro-2-methyl-phenoxy)-pyridin-3-yl)-2-hydroxy-benzamide Acetic acid 2-(6-(4-chloro-2-methyl.-phenoxy)-pyridin-3-ylcarbamoyl)-phenyl ester (304 mg, 0.77 mmol) dissolved in tetrahydrofuran (3.8 mL) was treated with an aqueous lithium hydroxide solution (1.0 M, 3.8 mL, 3.8 mmol). The solution was stirred for 30 minutes at 22° C. then quenched with aqueous saturated NH$_4$Cl. The mixture was diluted with ethyl acetate then the organics were washed with water, 2× saturated NaHCO$_3$, saturated NaCl, dried over Na$_2$SO$_4$ and concentrated in vacuo. MS (m/z): 354/356 (M+H)$^+$; $C_{19}H_{15}N_2O_3Cl$ requires 354.8.

EXAMPLE 10

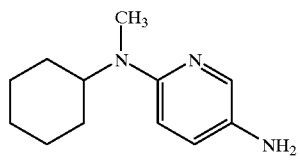

Preparation of 2-(N-Cyclohexyl-N-methylamino)-5-amino-pyridine

Step A: 2-(Cyclohexylamino)-5-nitro-pyridine

Sodium hydride (60% dispersion in mineral oil, 1.99 g, 49.8 mmol) was washed 3× with hexanes then a solution of cyclohexylamine (3.8 mL, 33.2 mmol) dissolved in tetrahydrofuran (50 mL) was added. After stirring for 30 minutes at 22° C., 2-chloro-5-nitropyridine (5.00 g, 31.5 mmol) was added and the reaction mixture was heated to reflux for 3 hours. The solution was cooled to ambient temperature, quenched with saturated aqueous NH$_4$Cl and concentrated in vacuo. The residue was redissolved in ethyl acetate then washed 2× with saturated NaHCO$_3$, saturated NaCl, dried over anhydrous Na$_2$SO$_4$ and concentrated in vacuo. The product was recovered as a brown oil.

Step B: 2-(N-Cyclohexyl-N-methylamino)-5-nitro-pyridine

Sodium hydride (60% dispersion in mineral oil, 0.38 g, 9.48 mmol) was washed 3× with hexanes then a solution of 2-cyclohexylamino-5-nitropyridine (1.88 g, 8.5 mmol) dissolved in dimethylformamide (20 mL) was added. After stirring for 30 minutes at 22° C., the reaction mixture was cooled to 0° C. and methyl iodide (0.55 mL, 8.9 mmol) was added. The solution was stirred for 1.5 hours at 0° C. followed by quenching with saturated aqueous NH$_4$Cl. The reaction mixture was diluted with ethyl acetate and extracted 5× with water (200 mL), saturated NaCl, dried over Na$_2$SO$_4$ and concentrated in vacuo oil was chromatographed on SiO$_2$ using 2:1 hexanes/ethyl acetate as eluent.

Step C: 2-(N-Cyclohexyl-N-methylamino)-5-amino-pyridine

Cyclohexyl-methyl-(5-nitro-pyridin-2-yl)-amine (1.72 g, 7.3 mmol) was dissolved in ethanol (80 mL) and treated with 20% palladium hydroxide on carbon (Pearlman's catalyst, 0.5 g) and the mixture was shaken under a hydrogen atmosphere (50 psi) for 6 hours. The catalyst was removed by filtration through celite then the filtrate was concentrated in vacuo and the resultant oil was chromotographed on SiO$_2$ using 1:1 ethyl acetate/hexanes as eluent. MS (m/z): 206 (M+H)$^+$; $C_{12}H_{19}N_3$ requires 205.3.

EXAMPLE 11

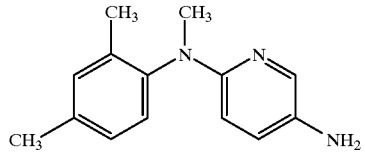

Preparation of 2-(N-(2,4-dimethyl-phenyl)-N-methylamino)-5-amino-pyridine 2-(N-(2,4-dimethylphenyl)-N-methylamino)-5-amino-pyridine was prepared from 1-amino-2,4-dimethylbenzene and 2-chloro-5-nitropyridine in the same manner as 2-(N-Cyclohexyl-N-methylamino)-5-amino-pyridine was prepared.

EXAMPLE 12

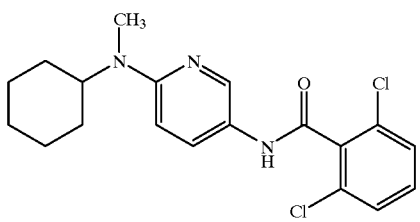

Preparation of 2,6-Dichloro-N-(2-(N'-cyclohexyl-N'-methylamino)-pyridin-5-yl)-benzamide 2-(N-Cyclohexyl-N-methylamino)-5-amino-pyridine (26 mg, 0.13 mmol) dissolved in methylene chloride (0.25 mL) was treated with triethylamine (0.026 mL, 0.18 mmol) followed by a solution of 2,6-dichlorobenzoyl chloride (31 mg, 0.15 mmol) dissolved in methylene chloride (0.15 mL). The reaction mixture was shaken at 22° C. for 18 hours followed by quenching with saturated aqueous $NH_4Cl$ and stirring for an additional 5 hours. The organic layer was separated and dried over $Na_2SO_4$ then concentrated in vacuo. The crude product was purified by chromatography on $SiO_2$ using 1:1 ethyl acetate/hexane as eluent. MS (m/z): 378/380 (M+H)$^+$; $C_{19}H_{21}N_3OC$; requires 377.

EXAMPLE 13

The compounds listed in Table 5 were prepared from substituted 5-aminopyridine compounds and the appropriate acid chloride in the same manner as 2,6-Dichloro-N-(2-(N'-cyclohexyl-N'-methylamino)-pyridin-5-yl)-benzamide was prepared.

TABLE 5

| | MS (m/z) |
|---|---|
| 2-(N-cyclohexyl-N-methylamino)-5-((2,6-dichlorophenyl)carbonylamino)pyridine | 378 |
| 2-(N-cyclohexyl-N-methylamino)-5-((2-chlorophenyl)carbonylamino)pyridine | 344 |
| 2-(N-cyclohexyl-N-methylamino)-5-((2-methylphenyl)carbonylamino)pyridine | 323 |
| 2-(N-cyclohexyl-N-methylamino)-5-((2,6-dimethylphenyl)carbonylamino)pyridine | 337 |
| 2-(2,4-dimethylphenyl)-5-((2,6-dimethylphenyl)carbonylamino)pyridine | 359 |
| 2-(2,4-dimethylphenyl)-5-((2-methylphenyl)carbonylamino)pyridine | 345 |
| 2-(2,4-dimethylphenyl)-5-((2-chlorophenyl)carbonylamino)pyridine | 366 |
| 2-(2,4-dimethylphenyl)-5-((2-fluorophenyl)carbonylamino)pyridine | 349 |
| 2-(2,4-dimethylphenyl)-5-((2,6-dichlorophenyl)carbonylamino)pyridine | 400 |

EXAMPLE 14

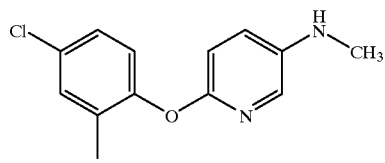

Preparation of 2-(4-Chloro-2-methyl-phenoxy)-5-(N-methylamino)pyridine 2-(4-Chloro-2-methyl-phenoxy)-5-aminopyridine (2.15 g, 9.16 mmol) was combined with powdered sodium hydroxide (1.46 g, 36.6 mmol), potassium carbonate (1.27 g, 9.16 mmol), tetrabutyl ammonium bromide (60 mg, 0.18 mmol) and toluene (10 mL) was stirred for 1 hour at 35° C. A solution of dimethyl sulfate (0.91 mL, 9.6 mmol) dissolved in toluene (5 mL) was added slowly. The mixture was heated at 35° C. for 20 hours. After cooling, the solids were removed by filtration and the solvent was concentrated in vacuo. The desired material was purified by chromatography on $SiO_2$ using 30% ethyl acetate / hexanes as eluent. MS (m/z): 248/250 (M+H)$^+$; $C_{13}H_{13}N_2OCl$ requires 249.

EXAMPLE 15

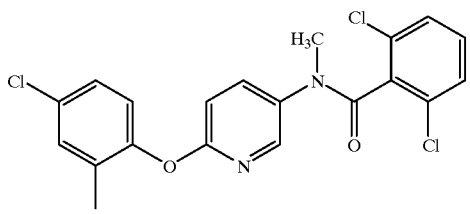

Preparation of 2 6-Dichloro-N-(6-(4-chloro-2-methyl-phenoxy)-pyridin-3-yl)-N-methyl-benzamide 2-(4-Chloro-2-methyl-phenoxy)-5-(N-methylamino) pyridine (32 mg, 0.13 mmol) dissolved in methylene chloride (0.25 mL) was treated with triethylamine (0.026 mL, 0.18 mmol) followed by a solution of 2,6-dichlorobenzoyl chloride (31 mg, 0.15 mmol) dissolved in methylene chloride (0.15 mL). The reaction mixture was shaken at 22° C. for 18 hours followed by quenching with saturated aqueous $NH_4Cl$ and stirring for an additional 5 hours. The organic layer was separated and dried over $Na_2SO_4$ then concentrated in vacuo. The crude product was purified by chromatography on $SiO_2$ using 1:1 ethyl acetate/hexane as eluent. MS (m/z): 422/424 (M+H)$^+$; $C_{20}H_{15}N_2O_2Cl_3$ requires 422.

EXAMPLE 16

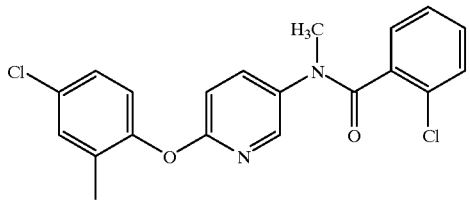

Preparation of 2-Chloro-N-(6-(4-chloro-2-methyl-phenoxy)-pyridin-3-yl)-N-methyl-benzamide 2-Chloro-N-(6-(4-chloro-2-methyl-phenoxy)-pyridin-3-yl)-N-methyl-benzamide was prepared from 2-(4-Chloro-2-methyl-phenoxy)-5-(N-methylamino)pyridine and 2-chlorobenzoyl chloride in the same manner as 2,6-Dichloro-N-(6-(4-chloro-2-methyl-phenoxy)-pyridin-3-yl)-N-methyl-benzamide was prepared.

EXAMPLE 17

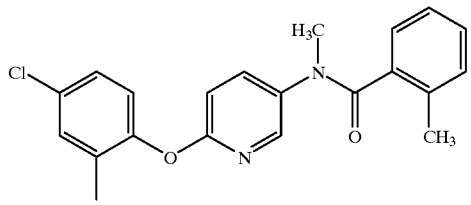

Preparation of 2-Methyl-N-(6-(4-chloro-2-methyl-phenoxy)-pyridin-3-yl)-N-methyl-benzamide 2-Methyl-N-(6-(4-chloro-2-methyl-phenoxy)-pyridin-3-yl)-N-methyl-benzamide was prepared from 2-(4-Chloro-2-methyl-phenoxy)-5-(N-methylamino)pyridine and 2-methylbenzoyl chloride in the same manner as 2,6-Dichloro-N-(6-(4-chloro-2-methyl-phenoxy)-pyridin-3-yl)-N-methyl-benzamide was prepared.

EXAMPLE 18

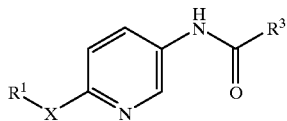

General procedure for the synthesis of 2-substituted-5-acylamino-pyridines

A solution of the 2-substituted-5-aminopyridine (10 mmol), triethylamine (20 mmol) and an acid chloride (20 mmol) in ethanol free chloroform (250 mL) was shaken for 16 hours. The mixture was then diluted with saturated aqueous sodium hydrogencarbonate (50 mL) and dichloromethane (500 mL), and shaken for 30 min. The mixture was then filtered through anhydrous magnesium sulfate, washing with dichloromethane (250 mL). Concentration of the filtrate under reduced pressure afforded the desired 2-substituted-5-acylamino-pyridines.

The compounds listed in Table 6 were prepared from substituted 5-aminopyridine compounds and the appropriate acid chloride according to the general procedure above.

TABLE 6

| $R^1X$ | $R^3$ | MS (m/z) |
|---|---|---|
| 4-chloro-2-methylphenoxy | 4-biphenyl | 415 |
| 4-chloro-2-methylphenoxy | 3,4-dimethoxyphenyl | 319 |
| 4-chloro-2-methylphenoxy | 2-(trifluoromethyl)phenyl | 407 |
| 4-chloro-2-methylphenoxy | 2,4-difluorophenyl | 375 |
| 4-chloro-2-methylphenoxy | 4-cyanophenyl | 364 |
| 4-chloro-2-methylphenoxy | 3-(trifluoromethyl)phenyl | 407 |
| 4-chloro-2-methylphenoxy | 3-cyanophenyl | 364 |
| 4-chloro-2-methylphenoxy | 2-naphthyl | 389 |
| 4-chloro-2-methylphenoxy | 2-methoxyphenyl | 369 |
| 4-chloro-2-methylphenoxy | 3,4,5-trimethylphenyl | 429 |
| 4-chloro-2-methylphenoxy | 4-nitrophenyl | 384 |
| 4-chloro-2-methylphenoxy | 3,4-dichlorophenyl | 408 |
| 4-chloro-2-methylphenoxy | 5-nitrofuran-2-yl | 374 |
| 4-chloro-2-methylphenoxy | 3-bromophenyl | 418 |
| 4-chloro-2-methylphenoxy | 3-pyridyl | 340 |
| 4-chloro-2-methylphenaxy | 2-ethoxynaphth-1-yl | 433 |
| 4-chloro-2-methylphenoxy | 2,3-dichlorophenyl | 408 |
| 4-chloro-2-methylphenoxy | 3-nitrophenyl | 384 |
| 4-chloro-2-methylphenoxy | 6-chloropyrid-3-yl | 374 |
| 4-chloro-2-methylphenoxy | 4-(trifluoromethoxy)phenyl | 423 |
| 4-chloro-2-methylphenoxy | 2-fluoro-4-(trifluoromethyl)phenyl | 425 |
| 4-chloro-2-methylphenoxy | 2-acetoxyphenyl | 397 |
| 4-chloro-2-methylphenoxy | 5-methylisoxazol-3-yl | 344 |
| 4-chloro-2-methylphenoxy | 2-(phenylthio)pyrid-3-yl | 448 |
| 4-chloro-2-methylphenoxy | 2-(trifluoromethoxy)phenyl | 423 |
| 4-chloro-2-methylphenoxy | 1-phenyl-5-propyl-pyrazin-4-yl | 447 |
| 4-chloro-2-methylphenoxy | 2-ethoxyphenyl | 383 |
| 4-chloro-2-methylphenoxy | 3-chlorothien-2-yl | 379 |
| 4-chloro-2-methylphenoxy | 3-bromothien-2-yl | 424 |
| 4-chloro-2-methylphenoxy | 1-(2-(2-methyl)propyl)-3-methylpyrazol-5-yl | 399 |
| 4-chloro-2-methylphenoxy | 3,5-dichlorophenyl | 408 |
| 4-chloro-2-methylphenoxy | 2-(propylthio)pyridin-3-yl- | 414 |
| 4-chloro-2-methylphenoxy | 2-(ethylthio)pyridin-3-yl | 400 |
| 4-chloro-2-methylphenoxy | 3-bromopyridin-5-yl | 419 |
| 4-chloro-2-methylphenoxy | 4-methyl-1,2,3-thiadiazol-5-yl | 361 |
| 4-chloro-2-methylphenoxy | 1-methyl-3-(2-(2-methyl)propyl)pyrazol-5-yl | 399 |
| 4-chloro-2-methylphenoxy | 3-chlorobenzo[b]thiophen-2-yl | 429 |
| 4-chloro-2-methylphenoxy | 4-chlorophenyl | 373 |
| 4-chloro-2-methylphenoxy | 4-methyl-2-phenyl-1,2,3-triazol-5-yl | 420 |
| 4-chloro-2-methylphenoxy | benzo[b]thiophen-2-yl | 395 |
| 4-chloro-2-methylphenoxy | 3,4-dimethylphenyl | 367 |
| 4-chloro-2-methylphenoxy | 2-(phenoxy)pyridin-3-yl | 432 |
| 4-chloro-2-methylphenoxy | 2-(methylthio)pyridin-3-yl | 386 |
| 4-chloro-2-methylphenoxy | 5-methyl-3-phenylisoxazol-4-yl | 420 |
| 4-chloro-2-methylphenoxy | 4-chloro-1,3-dimethyl pyrazolo[3,4-b]pyridin-3-yl | 442 |
| 4-chloro-2-methylphenoxy | 2-chloro-6-methylpyridin-4-yl | 388 |
| 4-chloro-2-methylphenoxy | 3,5-dimethylisoxazol-4-yl | 358 |

TABLE 6-continued

| R¹X | R³ | MS (m/z) |
|---|---|---|
| 4-chloro-2-methylphenoxy | 1-naphthyl | 389 |
| 4-chloro-2-methylphenoxy | 2-fluorophenyl | 357 |
| 4-chloro-2-methylphenoxy | 4-propylphenyl | 381 |
| 4-chloro-2-methylphenoxy | 4-(trifluoromethyl)phenyl | 407 |
| 4-chloro-2-methylphenoxy | 3-fluorophenyl | 357 |
| 4-chloro-2-methylphenoxy | 2,6-difluorophenyl | 375 |
| 4-chloro-2-methylphenoxy | 2-chlorophenyl | 373 |
| 4-chloro-2-methylphenoxy | 3-(chloromethyl)phenyl | 387 |
| 4-chloro-2-methylphenoxy | 4-(2-(2-methyl)propyl)phenyl | 395 |
| 4-chloro-2-methylphenoxy | 3-chlorophenyl | 373 |
| 4-chloro-2-methylphenoxy | 2-nitrophenyl | 384 |
| 4-chloro-2-methylphenoxy | 3,5-dimethoxyphenyl | 399 |
| 4-chloro-2-methylphenoxy | 2,6-dichlorophenyl | 408 |
| 4-chloro-2-methylphenoxy | 2,4-dichlorophenyl | 408 |
| 4-chloro-2-methylphenoxy | 4-fluorophenyl | 357 |
| 4-chloro-2-methylphenoxy | 4-butylphenyl | 395 |
| 4-chloro-2-methylphenoxy | 2-methylphenyl | 353 |
| 4-chloro-2-methylphenoxy | phenyl | 339 |
| 4-chloro-2-methylphenoxy | 4-ethylphenyl | 367 |
| 4-chloro-2-methylphenoxy | 2,3-difluorophenyl | 375 |
| 4-chloro-2-methylphenoxy | 2,6-dimethoxyphenyl | 399 |
| 4-chloro-2-methylphenoxy | 2,5-difluorophenyl | 375 |
| 4-chloro-2-methylphenoxy | 4-ethoxyphenyl | 383 |
| 4-chloro-2-methylphenoxy | 2,4,6-trichlorophenyl | 442 |
| 4-chloro-2-methylphenoxy | 3-methylphenyl | 353 |
| 4-chloro-2-methylphenoxy | 2-fluoro-5-(trifluoromethyl)phenyl | 425 |
| 4-chloro-2-methylphenoxy | 3-methoxyphenyl | 369 |
| 4-chloro-2-methylphenoxy | thien-2-yl | 345 |
| 4-chloro-2-methylphenoxy | 2-bromophenyl | 418 |
| 4-chloro-2-methylphenoxy | 4-bromophenyl | 418 |
| 4-chloro-2-methylphenoxy | 4-fluoro-3-(trifluoromethyl)phenyl | 425 |
| 4-chloro-2-methylphenoxy | 3-(trifluoromethoxy)phenyl | 423 |
| 4-chloro-2-methylphenoxy | 9-fluorenon-4-yl | 441 |
| 4-chloro-2-methylphenoxy | isoxazol-5-yl | 330 |
| 4-chloro-2-methylphenoxy | benzofuroxan-5-yl | 397 |
| 4-chloro-2-methylphenoxy | 2-chloropyrid-3-yl | 374 |
| 4-chloro-2-methylphenoxy | 3,5-difluorophenyl | 375 |
| 4-chloro-2-methylphenoxy | 2-(4-methylphenoxy)pyridin-3-yl | 446 |
| 4-chloro-2-methylphenoxy | pyridin-4-yl | 340 |
| 4-chloro-2-methylphenoxy | anthraquinon-2-yl | 469 |
| 4-chloro-2-methylphenoxy | 2-iodophenyl | 465 |
| 1-naphthoxy | 4-biphenyl | 416 |
| 1-naphthoxy | 3,4-dimethoxyphenyl | 400 |
| 1-naphthoxy | 2-(trifluoromethyl)phenyl | 408 |
| 1-naphthoxy | 2,4-difluorophenyl | 376 |
| 1-naphthoxy | 4-cyanophenyl | 365 |
| 1-naphthoxy | 3-(trifluoromethyl)phenyl | 408 |
| 1-naphthoxy | 3-cyanophenyl | 365 |
| 1-naphthoxy | 2-naphthyl | 390 |
| 1-naphthoxy | 2-methoxyphenyl | 370 |
| 1-naphthoxy | 3,4,5-trimethylphenyl | 430 |
| 1-naphthoxy | 4-nitrophenyl | 385 |
| 1-naphthoxy | 3,4-dichlorophenyl | 409 |
| 1-naphthoxy | 5-nitrofuran-2-yl | 375 |
| 1-naphthoxy | 3-bromophenyl | 419 |
| 1-naphthoxy | 3-pyridyl | 341 |
| 1-naphthoxy | 2-ethoxynaphth-1-yl | 334 |
| 1-naphthoxy | 2,3-dichlorophenyl | 409 |
| 1-naphthoxy | 3-nitrophenyl | 385 |
| 1-naphthoxy | 6-chloropyrid-3-yl | 376 |
| 1-naphthoxy | 4-(trifluoromethoxy)phenyl | 424 |
| 1-naphthoxy | 2-fluoro-4-(trifluoromethyl)phenyl | 426 |
| 1-naphthoxy | 3-bromothiophenyl | 425 |
| 1-naphthoxy | 2-acetoxyphenyl | 398 |
| 1-naphthoxy | 5-methylisoxazol-3-yl | 345 |
| 1-naphthoxy | 2-(phenylthio)pyrid-3-yl | 449 |
| 1-naphthoxy | 2-(trifluoromethoxy)phenyl | 424 |
| 1-naphthoxy | 1-phenyl-5-propylpyrazin-4-yl | 448 |
| 1-naphthoxy | 2-ethoxyphenyl | 384 |
| 1-naphthoxy | 3-chlorothien-2-yl | 381 |
| 1-naphthoxy | 1-(2-(2-methyl)propyl)-3-methylpyrazol-5-yl | 400 |
| 1-naphthoxy | 3,5-dichlorophenyl | 409 |
| 1-naphthoxy | 2-(propylthio)pyridin-3-yl | 415 |
| 1-naphthoxy | 2-(ethylthio)pyridin-3-yl | 401 |
| 1-naphthoxy | 3-bromopyridin-5-yl | 420 |
| 1-naphthoxy | 4-methyl-1,2,3-thiadiazol-5-yl | 362 |
| 1-naphthoxy | 1-methyl-3-(2-(2-methyl)propyl)pyrazol-5-yl | 400 |
| 1-naphthoxy | 3-chlorobenzo[b]thiophen-2-yl | 431 |
| 1-naphthoxy | 4-chlorophenyl | 375 |
| 1-naphthoxy | 4-methyl-2-phenyl-1,2,3-triazol-5-yl | 421 |
| 1-naphthoxy | benzo[b]thiophen-2-yl | 396 |
| 1-naphthoxy | 3,4-dimethylphenyl | 368 |
| 1-naphthoxy | 2-(phenoxy)pyridin-3-yl | 433 |
| 1-naphthoxy | 2-(methylthio)pyridin-3-yl | 387 |
| 1-naphthoxy | 5-methyl-3-phenylisoxazol-4-yl | 421 |
| 1-naphthoxy | 4-chloro-1,3-dimethylpyrazolo[3,4-b]pyridin-3-yl | 444 |
| 1-naphthoxy | 2-chloro-6-methylpyridin-4-yl | 390 |
| 1-naphthoxy | 3,5-dimethylisoxazol-4-yl | 359 |
| 1-naphthoxy | 1-naphthyl | 390 |
| 1-naphthoxy | 2-fluorophenyl | 358 |
| 1-naphthoxy | 4-propylphenyl | 382 |
| 1-naphthoxy | 4-(trifluoromethyl)phenyl | 408 |
| 1-naphthoxy | 3-fluorophenyl | 358 |
| 1-naphthoxy | 2,6-difluorophenyl | 376 |
| 1-naphthoxy | 2-chlorophenyl | 375 |
| 1-naphthoxy | 3-(chloromethyl)phenyl | 389 |
| 1-naphthoxy | 4-(2-(2-methyl)propyl)phenyl | 396 |
| 1-naphthoxy | 3-chlorophenyl | 375 |
| 1-naphthoxy | 2-nitrophenyl | 385 |

TABLE 6-continued

| R¹X | R³ | MS (m/z) |
|---|---|---|
| 1-naphthoxy | 3,5-dimethoxyphenyl | 400 |
| 1-naphthoxy | 2,6-dichlorophenyl | 409 |
| 1-naphthoxy | 2,4-dichlorophenyl | 409 |
| 1-naphthoxy | 4-fluorophenyl | 358 |
| 1-naphthoxy | 4-butylphenyl | 396 |
| 1-naphthoxy | 2-methylphenyl | 354 |
| 1-naphthoxy | phenyl | 340 |
| 1-naphthoxy | 4-ethylphenyl | 368 |
| 1-naphthoxy | 2,3-difluorophenyl | 376 |
| 1-naphthoxy | 2,6-dimethoxyphenyl | 400 |
| 1-naphthoxy | 3,4-difluorophenyl | 376 |
| 1-naphthoxy | 2,5-difluorophenyl | 376 |
| 1-naphthoxy | 4-ethoxyphenyl | 384 |
| 1-naphthoxy | 2,4,6-trichlorophenyl | 444 |
| 1-naphthoxy | 3-methylphenyl | 354 |
| 1-naphthoxy | 2-fluoro-5-(trifluoromethyl)phenyl | 426 |
| 1-naphthoxy | 3-methoxyphenyl | 370 |
| 1-naphthoxy | thien-2-yl | 346 |
| 1-naphthoxy | 2-bromophenyl | 419 |
| 1-naphthoxy | 4-bromophenyl | 419 |
| 1-naphthoxy | 4-fluoro-3-(trifluoromethyl)phenyl | 426 |
| 1-naphthoxy | 3-(trifluoromethoxy)phenyl | 424 |
| 1-naphthoxy | 9-fluorenon-4-yl | 442 |
| 1-naphthoxy | isoxazol-5-yl | 331 |
| 1-naphthoxy | benzofuroxan-5-yl | 398 |
| 1-naphthoxy | 2-chloropyrid-3-yl | 376 |
| 1-naphthoxy | 3,5-difluorophenyl | 376 |
| 1-naphthoxy | 2-(4-methylphenoxy)pyridin-3-yl | 447 |
| 1-naphthoxy | pyridin-4-yl | 341 |
| 1-naphthoxy | anthraquinon-2-yl | 470 |
| 1-naphthoxy | 2-iodophenyl | 466 |
| 2-(2-propyl)phenoxy | 4-biphenyl | 408 |
| 2-(2-propyl)phenoxy | 3,4-dimethoxyphenyl | 392 |
| 2-(2-propyl)phenoxy | 2-(trifluoromethyl)phenyl | 400 |
| 2-(2-propyl)phenoxy | 2,4-difluorophenyl | 368 |
| 2-(2-propyl)phenoxy | 4-cyanophenyl | 357 |
| 2-(2-propyl)phenoxy | 3-(trifluoromethyl)phenyl | 400 |
| 2-(2-propyl)phenoxy | 3-cyanophenyl | 357 |
| 2-(2-propyl)phenoxy | 2-naphthyl | 382 |
| 2-(2-propyl)phenoxy | 2-methoxyphenyl | 362 |
| 2-(2-propyl)phenoxy | 3,4,5,-trimethylphenyl | 422 |
| 2-(2-propyl)phenoxy | 4-nitrophenyl | 377 |
| 2-(2-propyl)phenoxy | 3,4-dichlorophenyl | 401 |
| 2-(2-propyl)phenoxy | 5-nitrofuran-2-yl | 367 |
| 2-(2-propyl)phenoxy | 3-bromophenyl | 411 |
| 2-(2-propyl)phenoxy | 3-pyridyl | 333 |
| 2-(2-propyl)phenoxy | 2-ethoxynaphth-1-yl | 426 |
| 2-(2-propyl)phenoxy | 2,3-dichlorophenyl | 401 |
| 2-(2-propyl)phenoxy | 3-nitrophenyl | 377 |
| 2-(2-propyl)phenoxy | 6-chloropyrid-3-yl | 368 |
| 2-(2-propyl)phenoxy | 4-(trifluoromethoxy)phenyl | 416 |
| 2-(2-propyl)phenoxy | 2-fluoro-4-(trifluoromethyl)phenyl | 418 |
| 2-(2-propyl)phenoxy | 3-bromothiophenyl | 417 |
| 2-(2-propyl)phenoxy | 2-acetoxyphenyl | 390 |
| 2-(2-propyl)phenoxy | 5-methylisoxazol-3-yl | 337 |
| 2-(2-propyl)phenoxy | 2-(phenylthio)pyrid-3-yl | 442 |
| 2-(2-propyl)phenoxy | 2-(trifluoromethoxy)phenyl | 416 |
| 2-(2-propyl)phenoxy | 1-phenyl-5-propylpyrazin-4-yl | 441 |
| 2-(2-propyl)phenoxy | 2-ethoxyphenyl | 376 |
| 2-(2-propyl)phenoxy | 3-chlorothien-2-yl | 373 |
| 2-(2-propyl)phenoxy | 1-(2-(2-methyl)propyl)-3-methylpyrazol-5-yl | 392 |
| 2-(2-propyl)phenoxy | 3,5-dichlorophenyl | 401 |
| 2-(2-propyl)phenoxy | 2-(propylthio)pyridin-3-yl | 407 |
| 2-(2-propyl)phenoxy | 2-(ethylthio)pyridin-3-yl | 393 |
| 2-(2-propyl)phenoxy | 3-bromopyridin-5-yl | 412 |
| 2-(2-propyl)phenoxy | 4-methyl-1,2,3-thiadiazol-5-yl | 354 |
| 2-(2-propyl)phenoxy | 1-methyl-3-(2-(2-methyl)propyl)pyrazol-5-yl | 392 |
| 2-(2-propyl)phenoxy | 3-chlorobenzo[b]thiophen-2-yl | 423 |
| 2-(2-propyl)phenoxy | 4-chlorophenyl | 367 |
| 2-(2-propyl)phenoxy | 4-methyl-2-phenyl-1,2,3-triazol-5-yl | 413 |
| 2-(2-propyl)phenoxy | benzo[b]thiophen-2-yl | 388 |
| 2-(2-propyl)phenoxy | 3,4-dimethylphenyl | 360 |
| 2-(2-propyl)phenoxy | 2-(phenoxy)pyridin-3-yl | 425 |
| 2-(2-propyl)phenoxy | 2-(methylthio)pyridin-3-yl | 379 |
| 2-(2-propyl)phenoxy | 5-methyl-3-phenylisoxazol-4-yl | 413 |
| 2-(2-propyl)phenoxy | 4-chloro-1,3-dimethylpyrazolo[3,4-b]pyridin-3-yl | 436 |
| 2-(2-propyl)phenoxy | 2-chloro-6-methylpyridin-4-yl | 382 |
| 2-(2-propyl)phenoxy | 3,5-dimethylisoxazol-4-yl | 351 |
| 2-(2-propyl)phenoxy | 1-naphthyl | 382 |
| 2-(2-propyl)phenoxy | 2-fluorophenyl | 350 |
| 2-(2-propyl)phenoxy | 4-propylphenyl | 374 |
| 2-(2-propyl)phenoxy | 4-(trifluoromethyl)phenyl | 400 |
| 2-(2-propyl)phenoxy | 3-fluorophenyl | 350 |
| 2-(2-propyl)phenoxy | 2,6-difluorophenyl | 368 |
| 2-(2-propyl)phenoxy | 2-chlorophenyl | 367 |
| 2-(2-propyl)phenoxy | 3-(chloromethyl)phenyl- | 381 |
| 2-(2-propyl)phenoxy | 4-(2-(2-methyl)propyl)phenyl | 388 |
| 2-(2-propyl)phenoxy | 3-chlorophenyl | 367 |
| 2-(2-propyl)phenoxy | 2-nitrophenyl | 377 |
| 2-(2-propyl)phenoxy | 3,5-dimethoxyphenyl | 392 |
| 2-(2-propyl)phenoxy | 2,6-dichlorophenyl | 401 |
| 2-(2-propyl)phenoxy | 2,4-dichlorophenyl | 401 |
| 2-(2-propyl)phenoxy | 4-fluorophenyl | 350 |
| 2-(2-propyl)phenoxy | 4-butylphenyl | 388 |
| 2-(2-propyl)phenoxy | 2-methylphenyl | 346 |
| 2-(2-propyl)phenoxy | phenyl | 332 |
| 2-(2-propyl)phenoxy | 4-ethylphenyl | 360 |
| 2-(2-propyl)phenoxy | 2,3-difluorophenyl | 368 |
| 2-(2-propyl)phenoxy | 2,6-dimethoxyphenyl | 392 |
| 2-(2-propyl)phenoxy | 3,4-difluorophenyl | 368 |
| 2-(2-propyl)phenoxy | 2,5-difluorophenyl | 368 |
| 2-(2-propyl)phenoxy | 4-ethoxyphenyl | 376 |
| 2-(2-propyl)phenoxy | 2,4,6-trichlorophenyl | 436 |
| 2-(2-propyl)phenoxy | 3-methylphenyl | 346 |
| 2-(2-propyl)phenoxy | 2-fluoro-5-(trifluoromethyl)phenyl | 418 |
| 2-(2-propyl)phenoxy | 3-methoxyphenyl | 362 |
| 2-(2-propyl)phenoxy | thien-2-yl | 338 |
| 2-(2-propyl)phenoxy | 2-bromophenyl | 411 |
| 2-(2-propyl)phenoxy | 4-bromophenyl | 411 |
| 2-(2-propyl)phenoxy | 4-fluoro-3-(trifluoromethyl)phenyl | 418 |
| 2-(2-propyl)phenoxy | 3-(trifluoromethoxy)phenyl | 416 |
| 2-(2-propyl)phenoxy | 9-fluorenon-4-yl | 434 |
| 2-(2-propyl)phenoxy | isoxazol-5-yl | 323 |
| 2-(2-propyl)phenoxy | benzofuroxan-5-yl | 390 |
| 2-(2-propyl)phenoxy | 2-chloropyrid-3-yl | 368 |
| 2-(2-propyl)phenoxy | 3,5-difluorophenyl | 368 |
| 2-(2-propyl)phenoxy | 2-(4-methylphenoxy)pyridin-3-yl | 439 |
| 2-(2-propyl)phenoxy | pyridin-4-yl | 333 |
| 2-(2-propyl)phenoxy | anthraquinon-2-yl | 462 |
| 2-(2-propyl)phenoxy | 2-iodophenyl | 458 |
| 3-fluoro-5-methylphenoxy | 4-biphenyl | 398 |
| 3-fluoro-5-methylphenoxy | 3,4-dimethoxyphenyl | 382 |
| 3-fluoro-5-methylphenoxy | 2-(trifluoromethyl)phenyl | 390 |
| 3-fluoro-5-methylphenoxy | 2,4-difluorophenyl | 358 |
| 3-fluoro-5-methylphenoxy | 4-cyanophenyl- | 347 |
| 3-fluoro-5-methylphenoxy | 3-(trifluoromethyl)phenyl | 390 |
| 3-fluoro-5-methylphenoxy | 3-cyanophenyl | 347 |

TABLE 6-continued

| R¹X | R³ | MS (m/z) |
|---|---|---|
| 3-fluoro-5-methylphenoxy | 2-naphthyl | 372 |
| 3-fluoro-5-methylphenoxy | 2-methoxyphenyl- | 352 |
| 3-fluoro-5-methylphenoxy | 3,4,5,-trimethylphenyl | 412 |
| 3-fluoro-5-methylphenoxy | 4-nitrophenyl | 367 |
| 3-fluoro-5-methylphenoxy | 3,4-dichlorophenyl | 391 |
| 3-fluoro-5-methylphenoxy | 5-nitrofuran-2-yl | 357 |
| 3-fluoro-5-methylphenoxy | 3-bromophenyl | 401 |
| 3-fluoro-5-methylphenoxy | 3-pyridyl | 323 |
| 3-fluoro-5-methylphenoxy | 2-ethoxynaphth-1-yl | 416 |
| 3-fluoro-5-methylphenoxy | 2,3-dichlorophenyl | 391 |
| 3-fluoro-5-methylphenoxy | 3-nitrophenyl | 367 |
| 3-fluoro-5-methylphenoxy | 6-chloropyrid-3-yl | 358 |
| 3-fluoro-5-methylphenoxy | 4-(trifluoromethoxy)phenyl | 406 |
| 3-fluoro-5-methylphenoxy | 2-fluoro-4-(trifluoromethyl)phenyl | 408 |
| 3-fluoro-5-methylphenoxy | 3-bromothienyl | 407 |
| 3-fluoro-5-methylphenoxy | 2-acetoxyphenyl | 380 |
| 3-fluoro-5-methylphenoxy | 5-methylisoxazol-3-yl | 327 |
| 3-fluoro-5-methylphenoxy | 2-(phenylthio)pyrid-3-yl | 431 |
| 3-fluoro-5-methylphenoxy | 2-(trifluoromethoxy)phenyl | 406 |
| 3-fluoro-5-methylphenoxy | 1-phenyl-5-propylpyrazin-4-yl | 430 |
| 3-fluoro-5-methylphenoxy | 2-ethoxyphenyl | 366 |
| 3-fluoro-5-methylphenoxy | 3-chlorothien-2-yl | 363 |
| 3-fluoro-5-methylphenoxy | 1-(2-(2-methyl)propyl)-3-methylpyrazol-5-yl | 382 |
| 3-fluoro-5-methylphenoxy | 3,5-dichlorophenyl- | 391 |
| 3-fluoro-5-methylphenoxy | 2-(propylthio)pyridin-3-yl | 397 |
| 3-fluoro-5-methylphenoxy | 2-(ethylthio)pyridin-3-yl | 383 |
| 3-fluoro-5-methylphenoxy | 3-bromopyridin-5-yl | 402 |
| 3-fluoro-5-methylphenoxy | 4-methyl-1,2,3-thiadiazol-5-yl | 344 |
| 3-fluoro-5-methylphenoxy | 1-methyl-3-(2-(2-methyl)propyl)pyrazol-5-yl | 382 |
| 3-fluoro-5-methylphenoxy | 3-chlorobenzo[b]thiophen-2-yl | 413 |
| 3-fluoro-5-methylphenoxy | 4-chlorophenyl | 357 |
| 3-fluoro-5-methylphenoxy | 4-methyl-2-phenyl-1,2,3-triazol-5-yl | 403 |
| 3-fluoro-5-methylphenoxy | benzo[b]thiophen-2-yl | 378 |
| 3-fluoro-5-methylphenoxy | 3,4-dimethylphenyl | 350 |
| 3-fluoro-5-methylphenoxy | 2-(phenoxy)pyridin-3-yl | 415 |
| 3-fluoro-5-methylphenoxy | 2-(methylthio)pyridin-3-yl | 369 |
| 3-fluoro-5-methylphenoxy | 5-methyl-3-phenylisoxazol-4-yl | 403 |
| 3-fluoro-5-methylphenoxy | 4-chloro-1,3-dimethyl pyrazolo[3,4-b]pyridin-3-yl | 426 |
| 3-fluoro-5-methylphenoxy | 2-chloro-6-methylpyridin-4-yl | 372 |
| 3-fluoro-5-methylphenoxy | 3,5-dimethylisoxazol-4-yl | 341 |
| 3-fluoro-5-methylphenoxy | 1-naphthyl | 372 |
| 3-fluoro-5-methylphenoxy | 2-fluorophenyl | 340 |
| 3-fluoro-5-methylphenoxy | 4-propylphenyl | 364 |
| 3-fluoro-5-methylphenoxy | 4-(trifluoromethyl)phenyl | 390 |
| 3-fluoro-5-methylphenoxy | 3-fluorophenyl | 340 |
| 3-fluoro-5-methylphenoxy | 2,6-difluorophenyl | 358 |
| 3-fluoro-5-methylphenoxy | 2-chlorophenyl | 357 |
| 3-fluoro-5-methylphenoxy | 3-(chloromethyl)phenyl | 371 |
| 3-fluoro-5-methylphenoxy | 4-(2-(2-methyl)propyl)phenyl | 378 |
| 3-fluoro-5-methylphenoxy | 3-chlorophenyl | 357 |
| 3-fluoro-5-methylphenoxy | 2-nitrophenyl | 367 |
| 3-fluoro-5-methylphenoxy | 3,5-dimethoxyphenyl | 382 |
| 3-fluoro-5-methylphenoxy | 2,6-dichlorophenyl | 391 |
| 3-fluoro-5-methylphenoxy | 2,4-dichlorophenyl | 391 |
| 3-fluoro-5-methylphenoxy | 4-fluorophenyl | 340 |
| 3-fluoro-5-methylphenoxy | 4-butylphenyl | 378 |
| 3-fluoro-5-methylphenoxy | 2-methylphenyl | 336 |
| 3-fluoro-5-methylphenoxy | phenyl | 322 |
| 3-fluoro-5-methylphenoxy | 4-ethylphenyl | 350 |
| 3-fluoro-5-methylphenoxy | 2,3-difluorophenyl | 358 |
| 3-fluoro-5-methylphenoxy | 2,6-dimethoxyphenyl | 382 |
| 3-fluoro-5-methylphenoxy | 3,4-difluorophenyl | 358 |
| 3-fluoro-5-methylphenoxy | 2,5-difluorophenyl | 358 |
| 3-fluoro-5-methylphenoxy | 4-ethoxyphenyl | 366 |
| 3-fluoro-5-methylphenoxy | 2,4,6-trichlorophenyl | 426 |
| 3-fluoro-5-methylphenoxy | 3-methylphenyl | 336 |
| 3-fluoro-5-methylphenoxy | 2-fluoro-5-(trifluoromethyl)phenyl | 408 |
| 3-fluoro-5-methylphenoxy | 3-methoxyphenyl | 352 |
| 3-fluoro-5-methylphenoxy | thien-2-yl | 328 |
| 3-fluoro-5-methylphenoxy | 2-bromophenyl | 401 |
| 3-fluoro-5-methylphenoxy | 4-bromophenyl | 401 |
| 3-fluoro-5-methylphenoxy | 4-fluoro-3-(trifluoromethyl)phenyl | 408 |
| 3-fluoro-5-methylphenoxy | 3-(trifluoromethoxy)phenyl | 406 |
| 3-fluoro-5-methylphenoxy | 9-fluorenon-4-yl | 424 |
| 3-fluoro-5-methylphenoxy | isoxazol-5-yl | 313 |
| 3-fluoro-5-methylphenoxy | benzofuroxan-5-yl | 380 |

TABLE 6-continued

| R¹X | R³ | MS (m/z) |
|---|---|---|
| methylphenoxy | | |
| 3-fluoro-5-methylphenoxy | 2-chloropyrid-3-yl | 358 |
| 3-fluoro-5-methylphenoxy | 3,5-difluorophenyl | 358 |
| 3-fluoro-5-methylphenoxy | 2-(4-methylphenoxy)pyridin-3-yl | 429 |
| 3-fluoro-5-methylphenoxy | pyridin-4-yl | 323 |
| 3-fluoro-5-methylphenoxy | anthraquinon-2-yl | 452 |
| 3-fluoro-5-methylphenoxy | 2-iodophenyl | 448 |
| 2-methylpyrid-3-yloxy | 4-biphenyl | 381 |
| 2-methylpyrid-3-yloxy | 3,4-dimethoxyphenyl | 365 |
| 2-methylpyrid-3-yloxy | 2-(trifluoromethyl)phenyl | 373 |
| 2-methylpyrid-3-yloxy | 2,4-difluorophenyl | 341 |
| 2-methylpyrid-3-yloxy | 4-cyanophenyl | 330 |
| 2-methylpyrid-3-yloxy | 3-(trifluoromethyl)phenyl | 373 |
| 2-methylpyrid-3-yloxy | 3-cyanophenyl | 330 |
| 2-methylpyrid-3-yloxy | 2-naphthyl | 355 |
| 2-methylpyrid-3-yloxy | 2-methoxyphenyl | 335 |
| 2-methylpyrid-3-yloxy | 3,4,5-trimethylphenyl | 395 |
| 2-methylpyrid-3-yloxy | 4-nitrophenyl | 350 |
| 2-methylpyrid-3-yloxy | 3,4-dichlorophenyl | 374 |
| 2-methylpyrid-3-yloxy | 5-nitrofuran-2-yl | 340 |
| 2-methylpyrid-3-yloxy | 3-bromophenyl | 384 |
| 2-methylpyrid-3-yloxy | 3-pyridyl | 306 |
| 2-methylpyrid-3-yloxy | 2-ethoxynaphth-1-yl | 399 |
| 2-methylpyrid-3-yloxy | 2,3-dichlorophenyl | 374 |
| 2-methylpyrid-3-yloxy | 3-nitrophenyl | 350 |
| 2-methylpyrid-3-yloxy | 6-chloropyrid-3-yl | 341 |
| 2-methylpyrid-3-yloxy | 4-(trifluoromethoxy)phenyl | 389 |
| 2-methylpyrid-3-yloxy | 2-fluoro-4-(trifluoromethyl)phenyl | 391 |
| 2-methylpyrid-3-yloxy | 3-bromothienyl | 390 |
| 2-methylpyrid-3-yloxy | 2-acetoxyphenyl | 363 |
| 2-methylpyrid-3-yloxy | 5-methylisoxazol-3-yl | 310 |
| 2-methylpyrid-3-yloxy | 2-(phenylthio)pyrid-3-yl | 414 |
| 2-methylpyrid-3-yloxy | 2-(trifluoromethoxy)phenyl | 389 |
| 2-methylpyrid-3-yloxy | 1-phenyl-5-propylpyrazin-4-yl | 413 |
| 2-methylpyrid-3-yloxy | 2-ethoxyphenyl | 349 |
| 2-methylpyrid-3-yloxy | 3-chlorothien-2-yl | 346 |
| 2-methylpyrid-3-yloxy | 1-(2-(2-methyl)propyl)-3-methylpyrazol-5-yl | 365 |
| 2-methylpyrid-3-yloxy | 3,5-dichlorophenyl | 374 |
| 2-methylpyrid-3-yloxy | 2-(propylthio)pyridin-3-yl | 380 |
| 2-methylpyrid-3-yloxy | 2-(ethylthio)pyridin-3-yl | 366 |
| 2-methylpyrid-3-yloxy | 3-bromopyridin-5-yl | 385 |
| 2-methylpyrid-3-yloxy | 4-methyl-1,2,3-thiadiazol-5-yl | 327 |
| 2-methylpyrid-3-yloxy | 1-methyl-3-(2-(2-methyl)propyl)pyrazol-5-yl | 365 |
| 2-methylpyrid-3-yloxy | 3-chlorobenzo[b]thiophen-2-yl | 396 |
| 2-methylpyrid-3-yloxy | 4-chlorophenyl | 340 |
| 2-methylpyrid-3-yloxy | 4-methyl-2-phenyl-1,2,3-triazol-5-yl | 386 |
| 2-methylpyrid-3-yloxy | benzo[b]thiophen-2-yl | 361 |
| 2-methylpyrid-3-yloxy | 3,4-dimethylphenyl | 333 |
| 2-methylpyrid-3-yloxy | 2-(phenoxy)pyridin-3-yl | 398 |
| 2-methylpyrid-3-yloxy | 2-(methylthio)pyridin-3-yl | 352 |
| 2-methylpyrid-3-yloxy | 5-methyl-3-phenylisoxazol-4-yl | 386 |
| 2-methylpyrid-3-yloxy | 4-chloro-1,3-dimethyl pyrazolo [3,4-b]pyridin-3-yl | 409 |
| 2-methylpyrid-3-yloxy | 2-chloro-6-methylpyridin-4-yl | 355 |
| 2-methylpyrid-3-yloxy | 3,5-dimethylisoxazol-4-yl | 324 |
| 2-methylpyrid-3-yloxy | 1-naphthyl | 355 |
| 2-methylpyrid-3-yloxy | 2-fluorophenyl | 323 |
| 2-methylpyrid-3-yloxy | 4-propylphenyl | 347 |
| 2-methylpyrid-3-yloxy | 4-(trifluoromethyl)phenyl | 373 |
| 2-methylpyrid-3-yloxy | 3-fluorophenyl | 323 |
| 2-methylpyrid-3-yloxy | 2,6-difluorophenyl | 341 |
| 2-methylpyrid-3-yloxy | 2-chlorophenyl | 340 |
| 2-methylpyrid-3-yloxy | 3-(chloromethyl)phenyl | 354 |
| 2-methylpyrid-3-yloxy | 4-(2-(2-methyl)propyl)phenyl | 361 |
| 2-methylpyrid-3-yloxy | 3-chlorophenyl | 340 |
| 2-methylpyrid-3-yloxy | 2-nitrophenyl | 350 |
| 2-methylpyrid-3-yloxy | 3,5-dimethoxyphenyl | 365 |
| 2-methylpyrid-3-yloxy | 2,6-dichlorophenyl | 374 |
| 2-methylpyrid-3-yloxy | 2,4-dichlorophenyl | 374 |
| 2-methylpyrid-3-yloxy | 4-fluorophenyl | 323 |
| 2-methylpyrid-3-yloxy | 4-butylphenyl | 361 |
| 2-methylpyrid-3-yloxy | 2-methylphenyl | 319 |
| 2-methylpyrid-3-yloxy | phenyl | 305 |
| 2-methylpyrid-3-yloxy | 4-ethylphenyl | 333 |
| 2-methylpyrid-3-yloxy | 2,3-difluorophenyl | 341 |
| 2-methylpyrid-3-yloxy | 2,6-dimethoxyphenyl | 365 |
| 2-methylpyrid-3-yloxy | 3,4-difluorophenyl | 341 |
| 2-methylpyrid-3-yloxy | 2,5-difluorophenyl | 341 |
| 2-methylpyrid-3-yloxy | 4-ethoxyphenyl | 349 |
| 2-methylpyrid-3-yloxy | 2,4,6-trichlorophenyl | 409 |
| 2-methylpyrid-3-yloxy | 3-methylphenyl | 319 |
| 2-methylpyrid-3-yloxy | 2-fluoro-5-(trifluoromethyl)phenyl | 391 |
| 2-methylpyrid-3-yloxy | 3-methoxyphenyl | 335 |
| 2-methylpyrid-3-yloxy | thien-2-yl | 311 |
| 2-methylpyrid-3-yloxy | 2-bromophenyl | 384 |
| 2-methylpyrid-3-yloxy | 4-bromophenyl | 384 |
| 2-methylpyrid-3-yloxy | 4-fluoro-3-(trifluoromethyl)phenyl | 391 |
| 2-methylpyrid-3-yloxy | 3-(trifluoromethoxy)phenyl | 389 |
| 2-methylpyrid-3-yloxy | 9-fluorenon-4-yl | 407 |
| 2-methylpyrid-3-yloxy | isoxazol-5-yl | 296 |
| 2-methylpyrid-3-yloxy | benzofuroxan-5-yl | 363 |
| 2-methylpyrid-3-yloxy | 2-chloropyrid-3-yl | 341 |
| 2-methylpyrid-3-yloxy | 3,5-difluorophenyl | 341 |
| 2-methylpyrid-3-yloxy | 2-(4-methylphenoxy)pyridin-3-yl | 412 |
| 2-methylpyrid-3-yloxy | pyridin-4-yl | 306 |
| 2-methylpyrid-3-yloxy | anthraquinon-2-yl | 435 |
| 2-methylpyrid-3-yloxy | 2-iodophenyl | 431 |
| 4-chloro-2,5-dimethylphenoxy | 3,4-dimethoxyphenyl | 413 |
| 4-chloro-2,5-dimethylphenoxy | 2-(trifluoromethyl)phenyl | 421 |
| 4-chloro-2,5-dimethylphenoxy | 2,4-difluorophenyl | 389 |
| 4-chloro-2,5-dimethylphenoxy | 3-(trifluoromethyl)phenyl | 421 |
| 4-chloro-2,5-dimethylphenoxy | 2-naphthyl | 403 |
| 4-chloro-2,5-dimethylphenoxy | 2-methoxyphenyl | 484 |
| 4-chloro-2,5-dimethylphenoxy | 3,4,5-trimethylphenyl | 443 |
| 4-chloro-2,5-dimethylphenoxy | 3,4-dichlorophenyl | 422 |
| 4-chloro-2,5-dimethylphenoxy | 3-bromophenyl | 432 |
| 4-chloro-2,5-dimethylphenoxy | 3-pyridyl | 354 |
| 4-chloro-2,5-dimethylphenoxy | 2-ethoxynaphth-1-yl | 447 |
| 4-chloro-2,5-dimethylphenoxy | 2,3-dichlorophenyl | 422 |
| 4-chloro-2,5-dimethylphenoxy | 6-chloropyrid-3-yl | 388 |
| 4-chloro-2,5-dimethylphenoxy | 4-(trifluoromethoxy)phenyl | 437 |
| 4-chloro-2,5-dimethylphenoxy | 2-fluoro-4-(trifluoromethyl)phenyl | 439 |
| 4-chloro-2,5-dimethylphenoxy | 3-bromothienyl | 438 |
| 4-chloro-2,5-dimethylphenoxy | 2-acetoxyphenyl | 411 |
| 4-chloro-2,5-dimethylphenoxy | 5-methylisoxazol-3-yl | 358 |

TABLE 6-continued

| R¹X | R³ | MS (m/z) |
|---|---|---|
| 4-chloro-2,5-dimethylphenoxy | 2-(phenylthio)pyrid-3-yl | 462 |
| 4-chloro-2,5-dimethylphenoxy | 2-(trifluoromethoxy)phenyl | 437 |
| 4-chloro-2,5-dimethylphenoxy | 1-phenyl-5-propylpyrazin-4-yl | 461 |
| 4-chloro-2,5-dimethylphenoxy | 2-ethoxyphenyl | 397 |
| 4-chloro-2,5-dimethylphenoxy | 3-chlorothien-2-yl | 393 |
| 4-chloro-2,5-dimethylphenoxy | 1-(2-(2-methyl)propyl)-3-methylpyrazol-5-yl | 413 |
| 4-chloro-2,5-dimethylphenoxy | 3,5-dichlorophenyl | 422 |
| 4-chloro-2,5-dimethylphenoxy | 2-(propylthio)pyridin-3-yl | 428 |
| 4-chloro-2,5-dimethylphenoxy | 2-(ethylthio)pyridin-3-yl | 414 |
| 4-chloro-2,5-dimethylphenoxy | 3-bromopyridin-5-yl | 433 |
| 4-chloro-2,5-dimethylphenoxy | 4-methyl-1,2,3-thiadiazol-5-yl | 375 |
| 4-chloro-2,5-dimethylphenoxy | 1-methyl-3-(2-(2-methyl)propyl)pyrazol-5-yl | 413 |
| 4-chloro-2,5-dimethylphenoxy | 3-chlorobenzo[b]thiophen-2-yl | 443 |
| 4-chloro-2,5-dimethylphenoxy | 4-chlorophenyl | 387 |
| 4-chloro-2,5-dimethylphenoxy | 4-methyl-2-phenyl-1,2,3-triazol-5-yl | 434 |
| 4-chloro-2,5-dimethylphenoxy | benzo[b]thiophen-2-yl | 409 |
| 4-chloro-2,5-dimethylphenoxy | 3,4-dimethylphenyl | 381 |
| 4-chloro-2,5-dimethylphenoxy | 2-(phenoxy)pyridin-3-yl | 446 |
| 4-chloro-2,5-dimethylphenoxy | 2-(methylthio)pyridin-3-yl | 400 |
| 4-chloro-2,5-dimethylphenoxy | 5-methyl-3-phenylisoxazol-4-yl | 434 |
| 4-chloro-2,5-dimethylphenoxy | 4-chloro-1,3-dimethyl pyrazolo[3,4-b]pyridin-3-yl | 456 |
| 4-chloro-2,5-dimethylphenoxy | 2-chloro-6-methylpyridin-4-yl | 402 |
| 4-chloro-2,5-dimethylphenoxy | 3,5-dimethylisoxazol-4-yl | 372 |
| 4-chloro-2,5-dimethylphenoxy | 1-naphthyl | 403 |
| 4-chloro-2,5-dimethylphenoxy | 2-fluorophenyl | 371 |
| 4-chloro-2,5-dimethylphenoxy | 4-propylphenyl | 395 |
| 4-chloro-2,5-dimethylphenoxy | 3-fluorophenyl | 371 |
| 4-chloro-2,5-dimethylphenoxy | 2,6-difluorophenyl | 389 |
| 4-chloro-2,5-dimethylphenoxy | 2-chlorophenyl | 387 |
| 4-chloro-2,5-dimethylphenoxy | 3-(chloromethyl)phenyl | 401 |
| 4-chloro-2,5-dimethylphenoxy | 4-(2-(2-methyl)propyl)phenyl | 409 |
| 4-chloro-2,5-dimethylphenoxy | 3-chlorophenyl | 387 |
| 4-chloro-2,5-dimethylphenoxy | 3,5-dimethoxyphenyl | 413 |
| 4-chloro-2,5-dimethylphenoxy | 2,6-dichlorophenyl | 422 |
| 4-chloro-2,5-dimethylphenoxy | 2,4-dichlorophenyl | 422 |
| 4-chloro-2,5-dimethylphenoxy | 4-fluorophenyl | 371 |
| 4-chloro-2,5-dimethylphenoxy | 4-butylphenyl | 409 |
| 4-chloro-2,5-dimethylphenoxy | 2-methylphenyl | 367 |
| 4-chloro-2,5-dimethylphenoxy | phenyl | 353 |
| 4-chloro-2,5-dimethylphenoxy | 4-ethylphenyl | 381 |
| 4-chloro-2,5-dimethylphenoxy | 2,3-difluorophenyl | 389 |
| 4-chloro-2,5-dimethylphenoxy | 2,6-dimethoxyphenyl | 413 |
| 4-chloro-2,5-dimethylphenoxy | 3,4-difluorophenyl | 389 |
| 4-chloro-2,5-dimethylphenoxy | 2,5-difluorophenyl | 389 |
| 4-chloro-2,5-dimethylphenoxy | 4-ethoxyphenyl | 397 |
| 4-chloro-2,5-dimethylphenoxy | 2,4,6-trichlorophenyl | 456 |
| 4-chloro-2,5-dimethylphenoxy | 3-methylphenyl | 367 |
| 4-chloro-2,5-dimethylphenoxy | 2-fluoro-5-(trifluoromethyl)phenyl | 439 |
| 4-chloro-2,5-dimethylphenoxy | 3-methoxyphenyl | 383 |
| 4-chloro-2,5-dimethylphenoxy | 2-bromophenyl | 432 |
| 4-chloro-2,5-dimethylphenoxy | 4-bromophenyl | 432 |
| 4-chloro-2,5-dimethylphenoxy | 4-fluoro-3-(trifluoromethyl)phenyl | 439 |
| 4-chloro-2,5-dimethylphenoxy | 3-(trifluoromethoxy)phenyl | 437 |
| 4-chloro-2,5-dimethylphenoxy | 9-fluorenon-4-yl | 455 |
| 4-chloro-2,5-dimethylphenoxy | isoxazol-5-yl | 344 |
| 4-chloro-2,5-dimethylphenoxy | benzofuroxan-5-yl | 411 |
| 4-chloro-2,5-dimethylphenoxy | 2-chloropyrid-3-yl | 388 |
| 4-chloro-2,5-dimethylphenoxy | 2-(4-methylphenoxy)pyridin-3-yl | 460 |
| 4-chloro-2,5-dimethylphenoxy | pyridin-4-yl | 354 |
| 4-chloro-2,5-dimethylphenoxy | anthraquinon-2-yl | 483 |
| 4-chloro-2,5-dimethylphenoxy | 2-iodophenyl | 479 |
| 4-chloro-2,5-dimethylphenoxy | 4-pentylphenyl | 423 |
| 4-chloro-2,5-dimethylphenoxy | 2-(4-chlorophenylthio)pyridin-3-yl | 496 |
| 4-chloro-2,5-dimethylphenoxy | 2,6-dimethylphenyl | 381 |
| 4-chloro-2,5-dimethylphenoxy | 2,5-dimethoxyphenyl | 413 |
| 4-chloro-2,5-dimethylphenoxy | 2,5-dichloropyridin-3-yl | 423 |
| 4-chloro-2,5-dimethylphenoxy | 2-chloro-6-methoxypyridin-4-yl | 418 |
| 4-chloro-2,5-dimethylphenoxy | 2,3-dichloropyridin-5-yl | 423 |
| 4-chloro-2,5-dimethylphenoxy | 1-naphthyl | 417 |
| 4-chloro-2,5-dimethylphenoxy | 2,4-dimethoxyphenyl | 413 |
| 4-chloro-2,5-dimethylphenoxy | 3,5-bis(trifluoromethyl)phenyl | 489 |
| 4-chloro-2,5-dimethylphenoxy | 2-(4-chlorophenoxy)pyridin-3-yl | 480 |
| 4-chloro-2,5-dimethylphenoxy | pentafluorophenyl | 443 |
| 4-methoxyphenoxy | 3,4-dimethoxyphenyl | 380 |
| 4-methoxyphenoxy | 2-(trifluoromethyl)phenyl | 388 |
| 4-methoxyphenoxy | 2,4-difluorophenyl | 356 |
| 4-methoxyphenoxy | 3-(trifluoromethyl)phenyl | 388 |

TABLE 6-continued

| R¹X | R³ | MS (m/z) |
|---|---|---|
| 4-methoxyphenoxy | 2-naphthyl | 370 |
| 4-methoxyphenoxy | 2-methoxyphenyl | 350 |
| 4-methoxyphenoxy | 3,4,5-trimethylphenyl | 410 |
| 4-methoxyphenoxy | 3,4-dichlorophenyl | 389 |
| 4-methoxyphenoxy | 3-bromophenyl | 399 |
| 4-methoxyphenoxy | 3-pyridyl | 321 |
| 4-methoxyphenoxy | 2-ethoxynaphth-1-yl | 414 |
| 4-methoxyphenoxy | 2,3-dichlorophenyl | 389 |
| 4-methoxyphenoxy | 6-chloropyrid-3-yl | 356 |
| 4-methoxyphenoxy | 4-(trifluoromethoxy)phenyl | 404 |
| 4-methoxyphenoxy | 2-fluoro-4-(trifluoromethyl)phenyl | 406 |
| 4-methoxyphenoxy | 3-bromothienyl | 405 |
| 4-methoxyphenoxy | 2-acetoxyphenyl | 378 |
| 4-methoxyphenoxy | 5-methylisoxazol-3-yl | 325 |
| 4-methoxyphenoxy | 2-(phenylthio)pyrid-3-yl | 429 |
| 4-methoxyphenoxy | 2-(trifluoromethoxy)phenyl | 404 |
| 4-methoxyphenoxy | 1-phenyl-5-propylpyrazin-4-yl | 428 |
| 4-methoxyphenoxy | 2-ethoxyphenyl | 364 |
| 4-methoxyphenoxy | 3-chlorothien-2-yl | 361 |
| 4-methoxyphenoxy | 1-(2-(2-methyl)propyl)-3-methylpyrazol-5-yl | 380 |
| 4-methoxyphenoxy | 3,5-dichlorophenyl | 389 |
| 4-methoxyphenoxy | 2-(propylthio)pyridin-3-yl | 395 |
| 4-methoxyphenoxy | 2-(ethylthio)pyridin-3-yl | 381 |
| 4-methoxyphenoxy | 3-bromopyridin-5-yl | 400 |
| 4-methoxyphenoxy | 4-methyl-1,2,3-thiadiazol-5-yl | 342 |
| 4-methoxyphenoxy | 1-methyl-3-(2-(2-methyl)propyl)pyrazol-5-yl | 380 |
| 4-methoxyphenoxy | 3-chlorobenzo[b]thiophen-2-yl | 411 |
| 4-methoxyphenoxy | 4-chlorophenyl | 355 |
| 4-methoxyphenoxy | 4-methyl-2-phenyl-1,2,3-triazol-5-yl | 401 |
| 4-methoxyphenoxy | benzo[b]thiophen-2-yl | 376 |
| 4-methoxyphenoxy | 3,4-dimethylphenyl | 348 |
| 4-methoxyphenoxy | 2-(phenoxy)pyridin-3-yl | 413 |
| 4-methoxyphenoxy | 2-(methylthio)pyridin-3-yl | 367 |
| 4-methoxyphenoxy | 5-methyl-3-phenylisoxazol-4-yl | 401 |
| 4-methoxyphenoxy | 4-chloro-1,3-dimethyl pyrazolo[3,4-b]pyridin-3-yl | 424 |
| 4-methoxyphenoxy | 2-chloro-6-methylpyridin-4-yl | 370 |
| 4-methoxyphenoxy | 3,5-dimethylisoxazol-4-yl | 339 |
| 4-methoxyphenoxy | 1-naphthyl | 370 |
| 4-methoxyphenoxy | 2-fluorophenyl | 338 |
| 4-methoxyphenoxy | 4-propylphenyl | 362 |
| 4-methoxyphenoxy | 3-fluorophenyl | 338 |
| 4-methoxyphenoxy | 2,6-difluorophenyl | 356 |
| 4-methoxyphenoxy | 2-chlorophenyl | 355 |
| 4-methoxyphenoxy | 3-(chloromethyl)phenyl | 369 |
| 4-methoxyphenoxy | 4-(2-(2-methyl)propyl)phenyl | 376 |
| 4-methoxyphenoxy | 3-chlorophenyl | 355 |
| 4-methoxyphenoxy | 3,5-dimethoxyphenyl | 380 |
| 4-methoxyphenoxy | 2,6-dichlorophenyl | 389 |
| 4-methoxyphenoxy | 2,4-dichlorophenyl | 389 |
| 4-methoxyphenoxy | 4-fluorophenyl | 338 |
| 4-methoxyphenoxy | 4-butylphenyl | 376 |
| 4-methoxyphenoxy | 2-methylphenyl | 334 |
| 4-methoxyphenoxy | phenyl | 320 |
| 4-methoxyphenoxy | 4-ethylphenyl | 348 |
| 4-methoxyphenoxy | 2,3-difluorophenyl | 356 |
| 4-methoxyphenoxy | 2,6-dimethoxyphenyl | 380 |
| 4-methoxyphenoxy | 3,4-difluorophenyl | 356 |
| 4-methoxyphenoxy | 2,5-difluorophenyl | 356 |
| 4-methoxyphenoxy | 4-ethoxyphenyl | 364 |
| 4-methoxyphenoxy | 2,4,6-trichlorophenyl | 424 |
| 4-methoxyphenoxy | 3-methylphenyl | 334 |
| 4-methoxyphenoxy | 2-fluoro-5-(trifluoromethyl)phenyl | 406 |
| 4-methoxyphenoxy | 3-methoxyphenyl | 350 |
| 4-methoxyphenoxy | 2-bromophenyl | 399 |
| 4-methoxyphenoxy | 4-bromophenyl | 399 |
| 4-methoxyphenoxy | 4-fluoro-3-(trifluoromethyl)phenyl | 406 |
| 4-methoxyphenoxy | 3-(trifluoromethoxy)phenyl | 404 |
| 4-methoxyphenoxy | 9-fluorenon-4-yl | 422 |
| 4-methoxyphenoxy | isoxazol-5-yl | 311 |
| 4-methoxyphenoxy | benzofuroxan-5-yl | 378 |
| 4-methoxyphenoxy | 2-chloropyrid-3-yl | 356 |
| 4-methoxyphenoxy | 2-(4-methylphenoxy)pyridin-3-yl | 427 |
| 4-methoxyphenoxy | pyridin-4-yl | 321 |
| 4-methoxyphenoxy | anthraquinon-2-yl | 450 |
| 4-methoxyphenoxy | 2-iodophenyl | 446 |
| 4-methoxyphenoxy | 4-pentylphenyl | 390 |
| 4-methoxyphenoxy | 2-(4-chlorophenylthio)pyridin-3-yl | 464 |
| 4-methoxyphenoxy | 2,6-dimethylphenyl | 348 |
| 4-methoxyphenoxy | 2,5-dimethoxyphenyl | 380 |
| 4-methoxyphenoxy | 2,5-dichloropyridin-3-yl | 390 |
| 4-methoxyphenoxy | 2-chloro-6-methoxypyridin-4-yl | 386 |
| 4-methoxyphenoxy | 2,3-dichloropyridin-5-yl | 390 |
| 4-methoxyphenoxy | 1-naphthyl | 384 |
| 4-methoxyphenoxy | 2,4-dimethoxyphenyl | 380 |
| 4-methoxyphenoxy | 3,5-bis(trifluoromethyl)phenyl | 456 |
| 4-methoxyphenoxy | 2-(4-chlorophenoxy)pyridin-3-yl | 448 |
| 4-methoxyphenoxy | pentafluorophenyl | 410 |
| 2-(2-propoxy)phenoxy | 3,4-dimethoxyphenyl | 408 |
| 2-(2-propoxy)phenoxy | 2-(trifluoromethyl)phenyl | 416 |
| 2-(2-propoxy)phenoxy | 2,4-difluorophenyl | 384 |
| 2-(2-propoxy)phenoxy | 3-(trifluoromethyl)phenyl | 416 |
| 2-(2-propoxy)phenoxy | 2-naphthyl | 398 |
| 2-(2-propoxy)phenoxy | 2-methoxyphenyl | 378 |
| 2-(2-propoxy)phenoxy | 3,4,5-trimethylphenyl | 438 |
| 2-(2-propoxy)phenoxy | 3,4-dichlorophenyl | 417 |
| 2-(2-propoxy)phenoxy | 3-bromophenyl | 427 |
| 2-(2-propoxy)phenoxy | 3-pyridyl | 349 |
| 2-(2-propoxy)phenoxy | 2-ethoxynaphth-1-yl | 442 |
| 2-(2-propoxy)phenoxy | 2,3-dichlorophenyl | 417 |
| 2-(2-propoxy)phenoxy | 6-chloropyrid-3-yl | 384 |
| 2-(2-propoxy)phenoxy | 4-(trifluoromethoxy)phenyl | 432 |
| 2-(2-propoxy)phenoxy | 2-fluoro-4-(trifluoromethyl)phenyl | 434 |
| 2-(2-propoxy)phenoxy | 3-bromothienyl | 433 |
| 2-(2-propoxy)phenoxy | 2-acetoxyphenyl | 406 |
| 2-(2-propoxy)phenoxy | 5-methylisoxazol-3-yl | 353 |
| 2-(2-propoxy)phenoxy | 2-(phenylthio)pyrid-3-yl | 458 |
| 2-(2-propoxy)phenoxy | 2-(trifluoromethoxy)phenyl | 432 |
| 2-(2-propoxy)phenoxy | 1-phenyl-5-propylpyrazin-4-yl | 457 |
| 2-(2-propoxy)phenoxy | 2-ethoxyphenyl | 392 |
| 2-(2-propoxy)phenoxy | 3-chlorothien-2-yl | 389 |
| 2-(2-propoxy)phenoxy | 1-(2-(2-methyl)propyl)-3-methylpyrazol-5-yl | 408 |
| 2-(2-propoxy)phenoxy | 3,5-dichlorophenyl | 417 |
| 2-(2-propoxy)phenoxy | 2-(propylthio)pyridin-3-yl | 423 |
| 2-(2-propoxy)phenoxy | 2-(ethylthio)pyridin-3-yl | 409 |
| 2-(2-propoxy)phenoxy | 3-bromopyridin-5-yl | 428 |
| 2-(2-propoxy)phenoxy | 4-methyl-1,2,3-thiadiazol-5-yl | 370 |
| 2-(2-propoxy)phenoxy | 1-methyl-3-(2-(2-methyl)propyl)pyrazol-5-yl | 408 |
| 2-(2-propoxy)phenoxy | 3-chlorobenzo[b]thiophen-2-yl | 439 |
| 2-(2-propoxy)phenoxy | 4-chlorophenyl | 383 |
| 2-(2-propoxy)phenoxy | 4-methyl-2-phenyl-1,2,3-triazol-5-yl | 429 |
| 2-(2-propoxy)phenoxy | benzo[b]thiophen-2-yl | 404 |
| 2-(2-propoxy)phenoxy | 3,4-dimethylphenyl | 376 |
| 2-(2-propoxy)phenoxy | 2-(phenoxy)pyridin-3-yl | 441 |
| 2-(2-propoxy)phenoxy | 2-(methylthio)pyridin-3-yl | 395 |
| 2-(2-propoxy)phenoxy | 5-methyl-3-phenylisoxazol-4-yl | 429 |

TABLE 6-continued

| R¹X | R³ | MS (m/z) |
|---|---|---|
| 2-(2-propoxy)phenoxy | 4-chloro-1,3-dimethyl pyrazolo[3,4-b]pyridin-3-yl | 452 |
| 2-(2-propoxy)phenoxy | 2-chloro-6-methylpyridin-4-yl | 398 |
| 2-(2-propoxy)phenoxy | 3,5-dimethylisoxazol-4-yl | 367 |
| 2-(2-propoxy)phenoxy | 1-naphthyl | 398 |
| 2-(2-propoxy)phenoxy | 2-fluorophenyl | 366 |
| 2-(2-propoxy)phenoxy | 4-propylphenyl | 390 |
| 2-(2-propoxy)phenoxy | 3-fluorophenyl | 366 |
| 2-(2-propoxy)phenoxy | 2,6-difluorophenyl | 384 |
| 2-(2-propoxy)phenoxy | 2-chlorophenyl | 383 |
| 2-(2-propoxy)phenoxy | 3-(chloromethyl)phenyl | 397 |
| 2-(2-propoxy)phenoxy | 4-(2-(2-methyl)propyl)phenyl | 404 |
| 2-(2-propoxy)phenoxy | 3-chlorophenyl | 383 |
| 2-(2-propoxy)phenoxy | 3,5-dimethoxyphenyl | 408 |
| 2-(2-propoxy)phenoxy | 2,6-dichlorophenyl | 417 |
| 2-(2-propoxy)phenoxy | 2,4-dichlorophenyl | 417 |
| 2-(2-propoxy)phenoxy | 4-fluorophenyl | 366 |
| 2-(2-propoxy)phenoxy | 4-butylphenyl | 404 |
| 2-(2-propoxy)phenoxy | 2-methylphenyl | 362 |
| 2-(2-propoxy)phenoxy | phenyl | 348 |
| 2-(2-propoxy)phenoxy | 4-ethylphenyl | 376 |
| 2-(2-propoxy)phenoxy | 2,3-difluorophenyl | 384 |
| 2-(2-propoxy)phenoxy | 2,6-dimethoxyphenyl | 408 |
| 2-(2-propoxy)phenoxy | 3,4-difluorophenyl | 384 |
| 2-(2-propoxy)phenoxy | 2,5-difluorophenyl | 384 |
| 2-(2-propoxy)phenoxy | 4-ethoxyphenyl | 392 |
| 2-(2-propoxy)phenoxy | 2,4,6-trichlorophenyl | 452 |
| 2-(2-propoxy)phenoxy | 3-methylphenyl | 362 |
| 2-(2-propoxy)phenoxy | 2-fluoro-5-(trifluoromethyl)phenyl | 434 |
| 2-(2-propoxy)phenoxy | 3-methoxyphenyl | 378 |
| 2-(2-propoxy)phenoxy | 2-bromophenyl | 427 |
| 2-(2-propoxy)phenoxy | 4-bromophenyl | 427 |
| 2-(2-propoxy)phenoxy | 4-fluoro-3-(trifluoromethyl)phenyl | 434 |
| 2-(2-propoxy)phenoxy | 3-(trifluoromethoxy)phenyl | 432 |
| 2-(2-propoxy)phenoxy | 9-fluorenon-4-yl | 450 |
| 2-(2-propoxy)phenoxy | isoxazol-5-yl | 339 |
| 2-(2-propoxy)phenoxy | benzofuroxan-5-yl | 406 |
| 2-(2-propoxy)phenoxy | 2-chloropyrid-3-yl | 384 |
| 2-(2-propoxy)phenoxy | 2-(4-methylphenoxy)pyridin-3-yl | 455 |
| 2-(2-propoxy)phenoxy | pyridin-4-yl | 349 |
| 2-(2-propoxy)phenoxy | anthraquinon-2-yl | 478 |
| 2-(2-propoxy)phenoxy | 2-iodophenyl | 474 |
| 2-(2-propoxy)phenoxy | 4-pentylphenyl | 419 |
| 2-(2-propoxy)phenoxy | 2-(4-chlorophenylthio)pyridin-3-yl | 492 |
| 2-(2-propoxy)phenoxy | 2,6-dimethylphenyl | 376 |
| 2-(2-propoxy)phenoxy | 2,5-dimethoxyphenyl | 408 |
| 2-(2-propoxy)phenoxy | 2,5-dichloropyridin-3-yl | 418 |
| 2-(2-propoxy)phenoxy | 2-chloro-6-methoxypyridin-4-yl | 414 |
| 2-(2-propoxy)phenoxy | 2,3-dichloropyridin-5-yl | 418 |
| 2-(2-propoxy)phenoxy | 1-naphthyl | 412 |
| 2-(2-propoxy)phenoxy | 2,4-dimethoxyphenyl | 408 |
| 2-(2-propoxy)phenoxy | 3,5-bis (trifluoromethyl) phenyl | 484 |
| 2-(2-propoxy)phenoxy | 2-(4-chlorophenoxy)pyridin-3-yl | 476 |
| 2-(2-propoxy)phenoxy | pentafluorophenyl | 438 |
| 4-fluorophenoxy | 3,4-dimethoxyphenyl | 368 |
| 4-fluorophenoxy | 2-(trifluoromethyl)phenyl | 376 |
| 4-fluorophenoxy | 2,4-difluorophenyl | 344 |
| 4-fluorophenoxy | 3-(trifluoromethyl)phenyl | 376 |
| 4-fluorophenoxy | 2-naphthyl | 358 |
| 4-fluorophenoxy | 2-methoxyphenyl | 338 |
| 4-fluorophenoxy | 3,4,5-trimethylphenyl | 398 |
| 4-fluorophenoxy | 3,4-dichlorophenyl | 377 |
| 4-fluorophenoxy | 3-bromophenyl | 387 |
| 4-fluorophenoxy | 3-pyridyl | 309 |
| 4-fluorophenoxy | 2-ethoxynaphth-1-yl | 402 |
| 4-fluorophenoxy | 2,3-dichlorophenyl | 377 |
| 4-fluorophenoxy | 6-chloropyrid-3-yl | 344 |
| 4-fluorophenoxy | 4-(trifluoromethoxy)phenyl | 392 |
| 4-fluorophenoxy | 2-fluoro-4-(trifluoromethyl)phenyl | 394 |
| 4-fluorophenoxy | 3-bromothienyl | 393 |
| 4-fluorophenoxy | 2-acetoxyphenyl | 366 |
| 4-fluorophenoxy | 5-methylisoxazol-3-yl | 313 |
| 4-fluorophenoxy | 2-(phenylthio)pyrid-3-yl | 417 |
| 4-fluorophenoxy | 2-(trifluoromethoxy)phenyl | 392 |
| 4-fluorophenoxy | 1-phenyl-5-propylpyrazin-4-yl | 416 |
| 4-fluorophenoxy | 2-ethoxyphenyl | 352 |
| 4-fluorophenoxy | 3-chlorothien-2-yl | 349 |
| 4-fluorophenoxy | 1-(2-(2-methyl)propyl)-3-methylpyrazol-5-yl | 368 |
| 4-fluorophenoxy | 3,5-dichlorophenyl | 377 |
| 4-fluorophenoxy | 2-(propylthio)pyridin-3-yl | 383 |
| 4-fluorophenoxy | 2-(ethylthio)pyridin-3-yl | 369 |
| 4-fluorophenoxy | 3-bromopyridin-5-yl | 388 |
| 4-fluorophenoxy | 4-methyl-1,2,3-thiadiazol-5-yl | 330 |
| 4-fluorophenoxy | 1-methyl-3-(2-(2-methyl)propyl)pyrazol-5-yl | 368 |
| 4-fluorophenoxy | 3-chlorobenzo[b]thiophen-2-yl | 399 |
| 4-fluorophenoxy | 4-chlorophenyl | 343 |
| 4-fluorophenoxy | 4-methyl-2-phenyl-1,2,3-triazol-5-yl | 389 |
| 4-fluorophenoxy | benzo[b]thiophen-2-yl | 364 |
| 4-fluorophenoxy | 3,4-dimethylphenyl | 336 |
| 4-fluorophenoxy | 2-(phenoxy)pyridin-3-yl | 401 |
| 4-fluorophenoxy | 2-(methylthio)pyridin-3-yl | 355 |
| 4-fluorophenoxy | 5-methyl-3-phenylisoxazol-4-yl | 389 |
| 4-fluorophenoxy | 4-chloro-1,3-dimethyl pyrazolo[3,4-b]pyridin-3-yl | 412 |
| 4-fluorophenoxy | 2-chloro-6-methylpyridin-4-yl | 358 |
| 4-fluorophenoxy | 3,5-dimethylisoxazol-4-yl | 327 |
| 4-fluorophenoxy | 1-naphthyl | 358 |
| 4-fluorophenoxy | 2-fluorophenyl | 326 |
| 4-fluorophenoxy | 4-propylphenyl | 350 |
| 4-fluorophenoxy | 3-fluorophenyl | 326 |
| 4-fluorophenoxy | 2,6-difluorophenyl | 344 |
| 4-fluorophenoxy | 2-chlorophenyl | 343 |
| 4-fluorophenoxy | 3-(chloromethyl)phenyl | 357 |
| 4-fluorophenoxy | 4-(2-(2-methyl)propyl)phenyl | 364 |
| 4-fluorophenoxy | 3-chlorophenyl | 343 |
| 4-fluorophenoxy | 3,5-dimethoxyphenyl | 368 |
| 4-fluorophenoxy | 2,6-dichlorophenyl | 377 |
| 4-fluorophenoxy | 2,4-dichlorophenyl | 377 |
| 4-fluorophenoxy | 4-fluorophenyl | 326 |
| 4-fluorophenoxy | 4-butylphenyl | 364 |
| 4-fluorophenoxy | 2-methylphenyl | 322 |
| 4-fluorophenoxy | phenyl | 308 |
| 4-fluorophenoxy | 4-ethylphenyl | 336 |
| 4-fluorophenoxy | 2,3-difluorophenyl | 344 |
| 4-fluorophenoxy | 2,6-dimethoxyphenyl | 368 |
| 4-fluorophenoxy | 3,4-difluorophenyl | 344 |
| 4-fluorophenoxy | 2,5-difluorophenyl | 344 |
| 4-fluorophenoxy | 4-ethoxyphenyl | 352 |
| 4-fluorophenoxy | 2,4,6-trichlorophenyl | 412 |
| 4-fluorophenoxy | 3-methylphenyl | 322 |
| 4-fluorophenoxy | 2-fluoro-5-(trifluoromethyl)phenyl | 394 |
| 4-fluorophenoxy | 3-methoxyphenyl | 338 |
| 4-fluorophenoxy | 2-bromophenyl | 387 |
| 4-fluorophenoxy | 4-bromophenyl | 387 |
| 4-fluorophenoxy | 4-fluoro-3-(trifluoromethyl)phenyl | 394 |
| 4-fluorophenoxy | 3-(trifluoromethoxy)phenyl | 392 |
| 4-fluorophenoxy | 9-fluorenon-4-yl | 410 |
| 4-fluorophenoxy | isoxazol-5-yl | 299 |
| 4-fluorophenoxy | benzofuroxan-5-yl | 366 |

TABLE 6-continued

| R¹X | R³ | MS (m/z) |
|---|---|---|
| 4-fluorophenoxy | 2-chloropyrid-3-yl | 344 |
| 4-fluorophenoxy | 2-(4-methylphenoxy)pyridin-3-yl | 415 |
| 4-fluorophenoxy | pyridin-4-yl | 309 |
| 4-fluorophenoxy | anthraquinon-:2-yl | 438 |
| 4-fluorophenoxy | 2-iodophenyl | 434 |
| 4-fluorophenoxy | 4-pentylphenyl | 378 |
| 4-fluorophenoxy | 2-(4-chlorophenylthio)pyridin-3-yl | 452 |
| 4-fluorophenoxy | 2,6-dimethylphenyl | 336 |
| 4-fluorophenoxy | 2,5-dimethoxyphenyl | 368 |
| 4-fluorophenoxy | 2,5-dichloropyridin-3-yl | 378 |
| 4-fluorophenoxy | 2-chloro-6-methoxypyridin-4-yl | 374 |
| 4-fluorophenoxy | 2,3-dichloropyridin-5-yl | 378 |
| 4-fluorophenoxy | 1-naphthyl | 372 |
| 4-fluorophenoxy | 2,4-dimethoxyphenyl | 368 |
| 4-fluorophenoxy | 3,5-bis(trifluoromethyl)phenyl | 444 |
| 4-fluorophenoxy | 2-(4-chlorophenoxy)pyridin-3-yl | 436 |
| 4-fluorophenoxy | pentafluorophenyl | 398 |
| 4-chlorophenoxy | 3,4-dimethoxyphenyl | 385 |
| 4-chlorophenoxy | 2-(trifluoromethyl)phenyl | 393 |
| 4-chlorophenoxy | 2,4-difluorophenyl | 361 |
| 4-chlorophenoxy | 3-(trifluoromethyl)phenyl | 393 |
| 4-chlorophenoxy | 2-naphthyl | 375 |
| 4-chlorophenoxy | 2-methoxyphenyl | 355 |
| 4-chlorophenoxy | 3,4,5-trimethylphenyl | 415 |
| 4-chlorophenoxy | 3,4-dichlorophenyl | 394 |
| 4-chlorophenoxy | 3-bromophenyl | 404 |
| 4-chlorophenoxy | 3-pyridyl | 326 |
| 4-chlorophenoxy | 2-ethoxynaphth-1-yl | 419 |
| 4-chlorophenoxy | 2,3-dichlorophenyl | 394 |
| 4-chlorophenoxy | 6-chloropyrid-3-yl | 360 |
| 4-chlorophenoxy | 4-(trifluoromethoxy)phenyl | 409 |
| 4-chlorophenoxy | 2-fluoro-4-(trifluoromethyl)phenyl | 411 |
| 4-chlorophenoxy | 3-bromothienyl | 410 |
| 4-chlorophenoxy | 2-acetoxyphenyl | 383 |
| 4-chlorophenoxy | 5-methylisoxazol-3-yl | 330 |
| 4-chlorophenoxy | 2-(phenylthio)pyrid-3-yl | 434 |
| 4-chlorophenoxy | 2-(trifluoromethoxy)phenyl | 409 |
| 4-chlorophenoxy | 1-phenyl-5-propylpyrazin-4-yl | 433 |
| 4-chlorophenoxy | 2-ethoxyphenyl | 369 |
| 4-chlorophenoxy | 3-chlorothien-2-yl | 365 |
| 4-chlorophenoxy | 1-(2-(2-methyl)propyl)-3-methylpyrazol-5-yl | 385 |
| 4-chlorophenoxy | 3,5-dichlorophenyl | 394 |
| 4-chlorophenoxy | 2-(propylthio)pyridin-3-yl | 400 |
| 4-chlorophenoxy | 2-(ethylthio)pyridin-3-yl | 386 |
| 4-chlorophenoxy | 3-bromopyridin-5-yl | 405 |
| 4-chlorophenoxy | 4-methyl-1,2,3-thiadiazol-5-yl | 347 |
| 4-chlorophenoxy | 1-methyl-3-(2-(2-methyl)propyl)pyrazol-5-yl | 385 |
| 4-chlorophenoxy | 3-chlorobenzo[b]thiophen-2-yl | 415 |
| 4-chlorophenoxy | 4-chlorophenyl | 359 |
| 4-chlorophenoxy | 4-methyl-2-phenyl-1,2,3-triazol-5-yl | 406 |
| 4-chlorophenoxy | benzo[b]thiophen-2-yl | 381 |
| 4-chlorophenoxy | 3,4-dimethylphenyl | 353 |
| 4-chlorophenoxy | 2-(phenoxy)pyridin-3-yl | 418 |
| 4-chlorophenoxy | 2-(methylthio)pyridin-3-yl | 372 |
| 4-chlorophenoxy | 5-methyl-3-phenylisoxazol-4-yl | 406 |
| 4-chlorophenoxy | 4-chloro-1,3-dimethyl pyrazolo[3,4-b]pyridin-3-yl | 428 |
| 4-chlorophenoxy | 2-chloro-6-methylpyridin-4-yl | 374 |
| 4-chlorophenoxy | 3,5-dimethylisoxazol-4-yl | 344 |
| 4-chlorophenoxy | 1-naphthyl | 375 |
| 4-chlorophenoxy | 2-fluorophenyl | 343 |
| 4-chlorophenoxy | 4-propylphenyl | 367 |
| 4-chlorophenoxy | 3-fluorophenyl | 343 |
| 4-chlorophenoxy | 2,6-difluorophenyl | 361 |
| 4-chlorophenoxy | 2-chlorophenyl | 359 |
| 4-chlorophenoxy | 3-(chloromethyl)phenyl | 373 |
| 4-chlorophenoxy | 4-(2-(2-methyl)propyl)phenyl | 381 |
| 4-chlorophenoxy | 3-chlorophenyl | 359 |
| 4-chlorophenoxy | 3,5-dimethoxyphenyl | 385 |
| 4-chlorophenoxy | 2,6-dichlorophenyl | 394 |
| 4-chlorophenoxy | 2,4-dichlorophenyl | 394 |
| 4-chlorophenoxy | 4-fluorophenyl | 343 |
| 4-chlorophenoxy | 4-butylphenyl | 381 |
| 4-chlorophenoxy | 2-methylphenyl | 339 |
| 4-chlorophenoxy | phenyl | 325 |
| 4-chlorophenoxy | 4-ethylphenyl | 353 |
| 4-chlorophenoxy | 2,3-difluorophenyl | 361 |
| 4-chlorophenoxy | 2,6-dimethoxyphenyl | 385 |
| 4-chlorophenoxy | 3,4-difluorophenyl | 361 |
| 4-chlorophenoxy | 2,5-difluorophenyl | 361 |
| 4-chlorophenoxy | 4-ethoxyphenyl | 369 |
| 4-chlorophenoxy | 2,4,6-trichlorophenyl | 428 |
| 4-chlorophenoxy | 3-methylphenyl | 339 |
| 4-chlorophenoxy | 2-fluoro-5-(trifluoromethyl)phenyl | 411 |
| 4-chlorophenoxy | 3-methoxyphenyl | 355 |
| 4-chlorophenoxy | 2-bromophenyl | 404 |
| 4-chlorophenoxy | 4-bromophenyl | 404 |
| 4-chlorophenoxy | 4-fluoro-3-(trifluoromethyl)phenyl | 411 |
| 4-chlorophenoxy | 3-(trifluoromethoxy)phenyl | 409 |
| 4-chlorophenoxy | 9-fluorenon-4-yl | 427 |
| 4-chlorophenoxy | isoxazol-5-yl | 316 |
| 4-chlorophenoxy | benzofuroxan-5-yl | 383 |
| 4-chlorophenoxy | 2-chloropyrid-3-yl | 360 |
| 4-chlorophenoxy | 2-(4-methylphenoxy)pyridin-4-yl | 432 |
| 4-chlorophenoxy | pyridin-4-yl | 326 |
| 4-chlorophenoxy | anthraquinon-2-yl | 455 |
| 4-chlorophenoxy | 2-iodophenyl | 451 |
| 4-chlorophenoxy | 4-pentylphenyl | 395 |
| 4-chlorophenoxy | 2-(4-chlorophenylthio)pyridin-3-yl | 468 |
| 4-chlorophenoxy | 2,6-dimethylphenyl | 353 |
| 4-chlorophenoxy | 2,5-dimethoxyphenyl | 385 |
| 4-chlorophenoxy | 2,5-dichloropyridin-3-yl | 395 |
| 4-chlorophenoxy | 2-chloro-6-methoxypyridin-4-yl | 390 |
| 4-chlorophenoxy | 2,3-dichloropyridin-5-yl | 395 |
| 4-chlorophenoxy | 1-naphthyl | 389 |
| 4-chlorophenoxy | 2,4-dimethoxyphenyl | 385 |
| 4-chlorophenoxy | 3,5-bis(trifluoromethyl)phenyl | 461 |
| 4-chlorophenoxy | 2-(4-chlorophenoxy)pyridin-3-yl | 452 |
| 4-chlorophenoxy | pentafluorophenyl | 415 |
| 2,4-difluorophenoxy | 3,4-dimethoxyphenyl | 386 |
| 2,4-difluorophenoxy | 2-(trifluoromethyl)phenyl | 394 |
| 2,4-difluorophenoxy | 2,4-difluorophenyl | 362 |
| 2,4-difluorophenoxy | 3-(trifluoromethyl)phenyl | 394 |
| 2,4-difluorophenoxy | 2-naphthyl | 376 |
| 2,4-difluorophenoxy | 2-methoxyphenyl | 356 |
| 2,4-difluorophenoxy | 3,4,5-trimethylphenyl | 416 |
| 2,4-difluorophenoxy | 3,4-dichlorophenyl | 395 |
| 2,4-difluorophenoxy | 3-bromophenyl | 405 |
| 2,4-difluorophenoxy | 3-pyridyl | 327 |
| 2,4-difluorophenoxy | 2-ethoxynaphth-1-yl | 420 |
| 2,4-difluorophenoxy | 2,3-dichlorophenyl | 395 |
| 2,4-difluorophenoxy | 6-chloropyrid-3-yl | 362 |
| 2,4-difluorophenoxy | 4-(trifluoromethoxy)phenyl | 410 |
| 2,4-difluorophenoxy | 2-fluoro-4-(trifluoromethyl)phenyl | 412 |
| 2,4-difluorophenoxy | 3-bromothienyl | 411 |
| 2,4-difluorophenoxy | 2-acetoxyphenyl | 384 |
| 2,4-difluorophenoxy | 5-methylisoxazol-3-yl | 331 |
| 2,4-difluorophenoxy | 2-(phenylthio)pyrid-3-yl | 435 |

TABLE 6-continued

| R¹X | R³ | MS (m/z) |
|---|---|---|
| 2,4-difluorophenoxy | 2-(trifluoromethoxy)phenyl | 410 |
| 2,4-difluorophenoxy | 1-phenyl-5-propylpyrazin-4-yl | 434 |
| 2,4-difluorophenoxy | 2-ethoxyphenyl | 370 |
| 2,4-difluorophenoxy | 3-chlorothien-2-yl | 367 |
| 2,4-difluorophenoxy | 1-(2-(2-methyl)propyl)-3-methylpyrazol-5-yl | 386 |
| 2,4-difluorophenoxy | 3,5-dichlorophenyl | 395 |
| 2,4-difluorophenoxy | 2-(propylthio)pyridin-3-yl | 401 |
| 2,4-difluorophenoxy | 2-(ethylthio)pyridin-3-yl | 387 |
| 2,4-difluorophenoxy | 3-bromopyridin-3-yl | 406 |
| 2,4-difluorophenoxy | 4-methyl-1,2,3-thiadiazol-5-yl | 348 |
| 2,4-difluorophenoxy | 1-methyl-3-(2-(2-methyl)propyl)pyrazol-5-yl | 386 |
| 2,4-difluorophenoxy | 3-chlorobenzo[b]thiophen-2-yl | 417 |
| 2,4-difluorophenoxy | 4-chlorophenyl | 361 |
| 2,4-difluorophenoxy | 4-methyl-2-phenyl-1,2,3-triazol-5-yl | 407 |
| 2,4-difluorophenoxy | benzo[b]thiophen-2-yl | 382 |
| 2,4-difluorophenoxy | 3,4-dimethylphenyl | 354 |
| 2,4-difluorophenoxy | 2-(phenoxy)pyridin-3-yl | 409 |
| 2,4-difluorophenoxy | 2-(methylthio)pyridin-3-yl | 373 |
| 2,4-difluorophenoxy | 5-methyl-3-phenylisoxazol-4-yl | 407 |
| 2,4-difluorophenoxy | 4-chloro-1,3-dimethyl pyrazolo[3,4-b]pyridin-3-yl | 430 |
| 2,4-difluorophenoxy | 2-chloro-6-methylpyridin-4-yl | 376 |
| 2,4-difluorophenoxy | 3,5-dimethylisoxazol-4-yl | 345 |
| 2,4-difluorophenoxy | 1-naphthyl | 376 |
| 2,4-difluorophenoxy | 2-fluorophenyl | 344 |
| 2,4-difluorophenoxy | 4-propylphenyl | 363 |
| 2,4-difluorophenoxy | 3-fluorophenyl | 344 |
| 2,4-difluorophenoxy | 2,6-difluorophenyl | 362 |
| 2,4-difluorophenoxy | 2-chlorophenyl | 361 |
| 2,4-difluorophenoxy | 3-(chloromethyl)phenyl | 375 |
| 2,4-difluorophenoxy | 4-(2-(2-methyl)propyl)phenyl | 382 |
| 2,4-difluorophenoxy | 3-chlorophenyl | 361 |
| 2,4-difluorophenoxy | 3,5-dimethoxyphenyl | 386 |
| 2,4-difluorophenoxy | 2,6-dichlorophenyl | 395 |
| 2,4-difluorophenoxy | 2,4-dichlorophenyl | 392 |
| 2,4-difluorophenoxy | 4-fluorophenyl | 344 |
| 2,4-difluorophenoxy | 4-butylphenyl | 382 |
| 2,4-difluorophenoxy | 2-methylphenyl | 340 |
| 2,4-difluorophenoxy | phenyl | 326 |
| 2,4-difluorophenoxy | 4-ethylphenyl | 354 |
| 2,4-difluorophenoxy | 2,3-difluorophenyl | 362 |
| 2,4-difluorophenoxy | 2,6-dimethoxyphenyl | 386 |
| 2,4-difluorophenoxy | 3,4-difluorophenyl | 362 |
| 2,4-difluorophenoxy | 2,5-difluorophenyl | 362 |
| 2,4-difluorophenoxy | 4-ethoxyphenyl | 370 |
| 2,4-difluorophenoxy | 2,4,6-trichlorophenyl | 430 |
| 2,4-difluorophenoxy | 3-methylphenyl | 340 |
| 2,4-difluorophenoxy | 2-fluoro-5-(trifluoromethyl)phenyl | 412 |
| 2,4-difluorophenoxy | 3-methoxyphenyl | 356 |
| 2,4-difluorophenoxy | 2-bromophenyl | 405 |
| 2,4-difluorophenoxy | 4-bromophenyl | 405 |
| 2,4-difluorophenoxy | 4-fluoro-3-(trifluoromethyl)phenyl | 412 |
| 2,4-difluorophenoxy | 3-(trifluoromethoxy)phenyl | 410 |
| 2,4-difluorophenoxy | 9-fluorenon-4-yl | 428 |
| 2,4-difluorophenoxy | isoxazol-5-yl | 317 |
| 2,4-difluorophenoxy | benzofuroxan-5-yl | 384 |
| 2,4-difluorophenoxy | 2-chloropyrid-3-yl | 362 |
| 2,4-difluorophenoxy | 2-(4-methylphenoxy)pyridin-3-yl | 433 |
| 2,4-difluorophenoxy | pyridin-4-yl | 327 |
| 2,4-difluorophenoxy | anthraquinon-2-yl | 456 |
| 2,4-difluorophenoxy | 2-iodophenyl | 452 |
| 2,4-difluorophenoxy | 4-pentylphenyl | 396 |
| 2,4-difluorophenoxy | 2-(4-chlorophenylthio) | 470 |
| 2,4-difluorophenoxy | pyridin-3-yl | |
| 2,4-difluorophenoxy | 2,6-dimethylphenyl | 354 |
| 2,4-difluorophenoxy | 2,5-dimethoxyphenyl | 386 |
| 2,4-difluorophenoxy | 2,5-dichloropyridin-3-yl | 396 |
| 2,4-difluorophenoxy | 2-chloro-6-methoxypyridin-4-yl | 392 |
| 2,4-difluorophenoxy | 2,3-dichloropyridin-5-yl | 396 |
| 2,4-difluorophenoxy | 1-naphthyl | 390 |
| 2,4-difluorophenoxy | 2,4-dimethoxyphenyl | 386 |
| 2,4-difluorophenoxy | 3,5-bis(trifluoromethyl)phenyl | 462 |
| 2,4-difluorophenoxy | 2-(4-chlorophenoxy)pyridin-3-yl | 454 |
| 2,4-difluorophenoxy | pentafluorophenyl | 416 |
| 4-thiomethylphenoxy | 3,4-dimethoxyphenyl | 396 |
| 4-thiomethylphenoxy | 2-(trifluoromethyl)phenyl | 404 |
| 4-thiomethylphenoxy | 2,4-difluorophenyl | 372 |
| 4-thiomethylphenoxy | 3-(trifluoromethyl)phenyl | 404 |
| 4-thiomethylphenoxy | 2-naphthyl | 386 |
| 4-thiomethylphenoxy | 2-methoxyphenyl | 366 |
| 4-thiomethylphenoxy | 3,4,5,-trimethylphenyl | 426 |
| 4-thiomethylphenoxy | 3,4-dichlorophenyl | 405 |
| 4-thiomethylphenoxy | 3-bromophenyl | 415 |
| 4-thiomethylphenoxy | 3-pyridyl | 337 |
| 4-thiomethylphenoxy | 2-ethoxynaphth-1-yl | 430 |
| 4-thiomethylphenoxy | 2,3-dichlorophenyl | 405 |
| 4-thiomethylphenoxy | 6-chloropyrid-3-yl | 372 |
| 4-thiomethylphenoxy | 4-(trifluoromethoxy)phenyl | 420 |
| 4-thiomethylphenoxy | 2-fluoro-4-(trifluoromethyl)phenyl | 422 |
| 4-thiomethylphenoxy | 3-bromothienyl | 421 |
| 4-thiomethylphenoxy | 2-acetoxyphenyl | 394 |
| 4-thiomethylphenoxy | 5-methylisoxazol-3-yl | 341 |
| 4-thiomethylphenoxy | 2-(phenylthio)pyrid-3-yl | 446 |
| 4-thiomethylphenoxy | 2-(trifluoromethoxy)phenyl | 420 |
| 4-thiomethylphenoxy | 1-phenyl-5-propylpyrazin-4-yl | 445 |
| 4-thiomethylphenoxy | 2-ethoxyphenyl | 380 |
| 4-thiomethylphenoxy | 3-chlorothien-2-yl | 377 |
| 4-thiomethylphenoxy | 1-(2-(2-methyl)propyl)-3-methylpyrazol-5-yl | 396 |
| 4-thiomethylphenoxy | 3,5-dichlorophenyl | 405 |
| 4-thiomethylphenoxy | 2-(propylthio)pyridin-3-yl | 412 |
| 4-thiomethylphenoxy | 2-(ethylthio)pyridin-3-yl | 397 |
| 4-thiomethylphenoxy | 3-bromopyridin-5-yl | 416 |
| 4-thiomethylphenoxy | 4-methyl-1,2,3-thiadiazol-5-yl | 358 |
| 4-thiomethylphenoxy | 1-methyl-3-(2-(2-methyl)propyl)pyrazol-5-yl | 396 |
| 4-thiomethylphenoxy | 3-chlorobenzo[b]thiophen-2-yl | 427 |
| 4-thiomethylphenoxy | 4-chlorophenyl | 371 |
| 4-thiomethylphenoxy | 4-methyl-2-phenyl-1,2,3-triazol-5-yl | 417 |
| 4-thiomethylphenoxy | benzo[b]thiophen-2-yl | 392 |
| 4-thiomethylphenoxy | 3,4-dimethylphenyl | 364 |
| 4-thiomethylphenoxy | 2-(phenoxy)pyridin-3-yl | 429 |
| 4-thiomethylphenoxy | 2-(methylthio)pyridin-3-yl | 383 |
| 4-thiomethylphenoxy | 5-methyl-3-phenylisoxazol-4-yl | 417 |
| 4-thiomethylphenoxy | 4-chloro-1,3-dimethyl pyrazolo[3,4-b]pyridin-3-yl | 440 |
| 4-thiomethylphenoxy | 2-chloro-6-methylpyridin-4-yl | 386 |
| 4-thiomethylphenoxy | 3,5-dimethylisoxazol-4-yl | 355 |
| 4-thiomethylphenoxy | 1-naphthyl | 386 |
| 4-thiomethylphenoxy | 2-fluorophenyl | 354 |
| 4-thiomethylphenoxy | 4-propylphenyl | 378 |
| 4-thiomethylphenoxy | 3-fluorophenyl | 354 |
| 4-thiomethylphenoxy | 2,6-difluorophenyl | 372 |
| 4-thiomethylphenoxy | 2-chlorophenyl | 371 |
| 4-thiomethylphenoxy | 3-(chloromethyl)phenyl | 385 |
| 4-thiomethylphenoxy | 4-(2-(2-methyl)propyl)phenyl | 392 |
| 4-thiomethylphenoxy | 3-chlorophenyl | 371 |

TABLE 6-continued

| R¹X | R³ | MS (m/z) |
|---|---|---|
| 4-thiomethylphenoxy | 3,5-dimethoxyphenyl | 396 |
| 4-thiomethylphenoxy | 2,6-dichlorophenyl | 405 |
| 4-thiomethylphenoxy | 2,4-dichlorophenyl | 405 |
| 4-thiomethylphenoxy | 4-fluorophenyl | 354 |
| 4-thiomethylphenoxy | 4-butylphenyl | 392 |
| 4-thiomethylphenoxy | 2-methylphenyl | 350 |
| 4-thiomethylphenoxy | phenyl | 336 |
| 4-thiomethylphenoxy | 4-ethylphenyl | 364 |
| 4-thiomethylphenoxy | 2,3-difluorophenyl | 372 |
| 4-thiomethylphenoxy | 2,6-dimethoxyphenyl | 396 |
| 4-thiomethylphenoxy | 3,4-difluorophenyl | 372 |
| 4-thiomethylphenoxy | 2,5-difluorophenyl | 372 |
| 4-thiomethylphenoxy | 4-ethoxyphenyl | 380 |
| 4-thiomethylphenoxy | 2,4,6-trichlorophenyl | 440 |
| 4-thiomethylphenoxy | 3-methylphenyl | 350 |
| 4-thiomethylphenoxy | 2-fluoro-5-(trifluoromethyl)phenyl | 422 |
| 4-thiomethylphenoxy | 3-methoxyphenyl | 366 |
| 4-thiomethylphenoxy | 2-bromophenyl | 415 |
| 4-thiomethylphenoxy | 4-bromophenyl | 415 |
| 4-thiomethylphenoxy | 4-fluoro-3-(trifluoromethyl)phenyl | 422 |
| 4-thiomethylphenoxy | 3-(trifluoromethoxy)phenyl | 420 |
| 4-thiomethylphenoxy | 9-fluorenon-4-yl | 438 |
| 4-thiomethylphenoxy | isoxazol-5-yl | 327 |
| 4-thiomethylphenoxy | benzofuroxan-5-yl | 394 |
| 4-thiomethylphenoxy | 2-chloropyrid-3-yl | 372 |
| 4-thiomethylphenoxy | 2-(4-methylphenoxy)pyridin-3-yl | 443 |
| 4-thiomethylphenoxy | pyridin-4-yl | 337 |
| 4-thiomethylphenoxy | anthraquinon-2-yl | 466 |
| 4-thiomethylphenoxy | 2-iodophenyl | 462 |
| 4-thiomethylphenoxy | 4-pentylphenyl | 407 |
| 4-thiomethylphenoxy | 2-(4-chlorophenylthio)pyridin-3-yl | 480 |
| 4-thiomethylphenoxy | 2,6-dimethylphenyl | 364 |
| 4-thiomethylphenoxy | 2,5-dimethoxyphenyl | 396 |
| 4-thiomethylphenoxy | 2,5-dichloropyridin-3-yl | 406 |
| 4-thiomethylphenoxy | 2-chloro-6-methoxypyridin-4-yl | 402 |
| 4-thiomethylphenoxy | 2,3-dichloropyridin-5-yl | 406 |
| 4-thiomethylphenoxy | 1-naphthyl | 400 |
| 4-thiomethylphenoxy | 2,4-dimethoxyphenyl | 396 |
| 4-thiomethylphenoxy | 3,5-bis(trifluoromethyl)phenyl | 372 |
| 4-thiomethylphenoxy | 2-(4-chlorophenoxy)pyridin-3-yl | 464 |
| 4-thiomethylphenoxy | pentafluorophenyl | 426 |
| 4-(2-(2-methyl)propyl)phenoxy | 3,4-dimethoxyphenyl | 406 |
| 4-(2-(2-methyl)propyl)phenoxy | 2-(trifluoromethyl)phenyl | 414 |
| 4-(2-(2-methyl)propyl)phenoxy | 2,4-difluorophenyl | 382 |
| 4-(2-(2-methyl)propyl)phenoxy | 3-(trifluoromethyl)phenyl | 414 |
| 4-(2-(2-methyl)propyl)phenoxy | 2-naphthyl | 396 |
| 4-(2-(2-methyl)propyl)phenoxy | 2-methoxyphenyl | 376 |
| 4-(2-(2-methyl)propyl)phenoxy | 3,4,5-trimethylphenyl | 436 |
| 4-(2-(2-methyl)propyl)phenoxy | 3,4-dichlorophenyl | 415 |
| 4-(2-(2-methyl)propyl)phenoxy | 3-bromophenyl | 425 |
| 4-(2-(2-methyl)propyl)phenoxy | 3-pyridyl | 347 |
| 4-(2-(2-methyl)propyl)phenoxy | 2-ethoxynaphth-1-yl | 441 |
| 4-(2-(2-methyl)propyl)phenoxy | 2,3-dichlorophenyl | 415 |
| 4-(2-(2-methyl)propyl)phenoxy | 6-chloropyrid-3-yl | 382 |
| 4-(2-(2-methyl)propyl)phenoxy | 4-(trifluoromethoxy)phenyl | 430 |
| 4-(2-(2-methyl)propyl)phenoxy | 2-fluoro-4-(trifluoromethyl)phenyl | 432 |
| 4-(2-(2-methyl)propyl)phenoxy | 3-bromothienyl | 431 |
| 4-(2-(2-methyl)propyl)phenoxy | 2-acetoxyphenyl | 404 |
| 4-(2-(2-methyl)propyl)phenoxy | 5-methylisoxazol-3-yl | 351 |
| 4-(2-(2-methyl)propyl)phenoxy | 2-(phenylthio)pyrid-3-yl | 456 |
| 4-(2-(2-methyl)propyl)phenoxy | 2-(trifluoromethoxy)phenyl | 430 |
| 4-(2-(2-methyl)propyl)phenoxy 4-yl | 1-phenyl-5-propylpyrazin- | 455 |
| 4-(2-(2-methyl)propyl)phenoxy | 2-ethoxyphenyl | 390 |
| 4-(2-(2-methyl)propyl)phenoxy | 3-chlorothien-2-yl | 387 |
| 4-(2-(2-methyl)propyl)phenoxy | 1-(2-(2-methyl)propyl)-3-methylpyrazol-5-yl | 406 |
| 4-(2-(2-methyl)propyl)phenoxy | 3,5-dichlorophenyl | 415 |
| 4-(2-(2-methyl)propyl)phenoxy | 2-(propylthio)pyridin-3-yl | 422 |
| 4-(2-(2-methyl)propyl)phenoxy | 2-(ethylthio)pyridin-3-yl | 407 |
| 4-(2-(2-methyl)propyl)phenoxy | 3-bromopyridin-5-yl | 426 |
| 4-(2-(2-methyl)propyl)phenoxy | 4-methyl-1,2,3-thiadiazol-5-yl | 368 |
| 4-(2-(2-methyl)propyl)phenoxy | 1-methyl-3-(2-(2-methyl)propyl)pyrazol-5-yl | 406 |
| 4-(2-(2-methyl)propyl)phenoxy | 3-chlorobenzo[b]thiophen-2-yl | 437 |
| 4-(2-(2-methyl)propyl)phenoxy | 4-chlorophenyl | 381 |
| 4-(2-(2-methyl)propyl)phenoxy | 4-methyl-2-phenyl-1,2,3-triazol-5-yl | 427 |
| 4-(2-(2-methyl)propyl)phenoxy | benzo[b]thiophen-2-yl | 402 |
| 4-(2-(2-methyl)propyl)phenoxy | 3,4-dimethylphenyl | 374 |
| 4-(2-(2-methyl)propyl)phenoxy | 2-(phenoxy)pyridin-3-yl | 439 |
| 4-(2-(2-methyl)propyl)phenoxy | 2-(methylthio)pyridin-3-yl | 393 |
| 4-(2-(2-methyl)propyl)phenoxy | 5-methyl-3-phenylisoxazol-4-yl | 427 |
| 4-(2-(2-methyl)propyl)phenoxy | 4-chloro-1,3-dimethyl pyrazolo[3,4-b]pyridin-3-yl | 450 |
| 4-(2-(2-methyl)propyl)phenoxy | 2-chloro-6-methylpyridin-4-yl | 396 |
| 4-(2-(2-methyl)propyl)phenoxy | 3,5-dimethylisoxazol-4-yl | 365 |
| 4-(2-(2-methyl)propyl)phenoxy | 1-naphthyl | 396 |
| 4-(2-(2-methyl)propyl)phenoxy | 2-fluorophenyl | 364 |
| 4-(2-(2-methyl)propyl)phenoxy | 4-propylphenyl | 388 |
| 4-(2-(2-methyl)propyl)phenoxy | 3-fluorophenyl | 364 |
| 4-(2-(2-methyl)propyl)phenoxy | 2,6-difluorophenyl | 382 |
| 4-(2-(2-methyl)propyl)phenoxy | 2-chlorophenyl | 381 |
| 4-(2-(2-methyl)propyl)phenoxy | 3-(chloromethyl)phenyl | 395 |
| 4-(2-(2-methyl)propyl)phenoxy | 4-(2-(2-methyl)propyl)phenyl | 402 |
| 4-(2-(2-methyl)propyl)phenoxy | 3-chlorophenyl | 381 |
| 4-(2-(2-methyl)propyl)phenoxy | 3,5-dimethoxyphenyl | 406 |
| 4-(2-(2-methyl)propyl)phenoxy | 2,6-dichlorophenyl | 415 |

TABLE 6-continued

| R¹X | R³ | MS (m/z) |
|---|---|---|
| 4-(2-(2-methyl)propyl)phenoxy | 2,4-dichlorophenyl | 415 |
| 4-(2-(2-methyl)propyl)phenoxy | 4-fluorophenyl | 364 |
| 4-(2-(2-methyl)propyl)phenoxy | 4-butylphenyl | 402 |
| 4-(2-(2-methyl)propyl)phenoxy | 2-methylphenyl | 360 |
| 4-(2-(2-methyl)propyl)phenoxy | phenyl | 346 |
| 4-(2-(2-methyl)propyl)phenoxy | 4-ethylphenyl | 374 |
| 4-(2-(2-methyl)propyl)phenoxy | 2,3-difluorophenyl | 382 |
| 4-(2-(2-methyl)propyl)phenoxy | 2,6-dimethoxyphenyl | 406 |
| 4-(2-(2-methyl)propyl)phenoxy | 3,4-difluorophenyl | 382 |
| 4-(2-(2-methyl)propyl)phenoxy | 2,5-difluorophenyl | 382 |
| 4-(2-(2-methyl)propyl)phenoxy | 4-ethoxyphenyl | 390 |
| 4-(2-(2-methyl)propyl)phenoxy | 2,4,6-trichlorophenyl | 450 |
| 4-(2-(2-methyl)propyl)phenoxy | 3-methylphenyl | 360 |
| 4-(2-(2-methyl)propyl)phenoxy | 2-fluoro-5-(trifluoromethyl)phenyl | 432 |
| 4-(2-(2-methyl)propyl)phenoxy | 3-methoxyphenyl | 376 |
| 4-(2-(2-methyl)propyl)phenoxy | 2-bromophenyl | 425 |
| 4-(2-(2-methyl)propyl)phenoxy | 4-bromophenyl | 425 |
| 4-(2-(2-methyl)propyl)phenoxy | 4-fluoro-3-(trifluoromethyl)phenyl | 432 |
| 4-(2-(2-methyl)propyl)phenoxy | 3-(trifluoromethoxy)phenyl | 430 |
| 4-(2-(2-methyl)propyl)phenoxy | 9-fluorenon-4-yl | 448 |
| 4-(2-(2-methyl)propyl)phenoxy | isoxazol-5-yl | 338 |
| 4-(2-(2-methyl)propyl)phenoxy | benzofuroxan-5-yl | 404 |
| 4-(2-(2-methyl)propyl)phenoxy | 2-chloropyrid-3-yl | 382 |
| 4-(2-(2-methyl)propyl)phenoxy | 2-(4-methylphenoxy)pyridin-3-yl | 454 |
| 4-(2-(2-methyl)propyl)phenoxy | pyridin-4-yl | 347 |
| 4-(2-(2-methyl)propyl)phenoxy | anthraquinon-2-yl | 476 |
| 4-(2-(2-methyl)propyl)phenoxy | 2-iodophenyl | 472 |
| 4-(2-(2-methyl)propyl)phenoxy | 4-pentylphenyl | 417 |
| 4-(2-(2-methyl)propyl)phenoxy | 2-(4-chlorophenylthio)pyridin-3-yl | 490 |
| 4-(2-(2-methyl)propyl)phenoxy | 2,6-dimethylphenyl | 374 |
| 4-(2-(2-methyl)propyl)phenoxy | 2,5-dimethoxyphenyl | 406 |
| 4-(2-(2-methyl)propyl)phenoxy | 2,5-dichloropyridin-3-yl | 416 |
| 4-(2-(2-methyl)propyl)phenoxy | 2-chloro-6-methoxypyridin-4-yl | 412 |
| 4-(2-(2-methyl)propyl)phenoxy | 2,3-dichloropyridin-5-yl | 416 |
| 4-(2-(2-methyl)propyl)phenoxy | 1-naphthyl | 410 |
| 4-(2-(2-methyl)propyl)phenoxy | 2,4-dimethoxyphenyl | 406 |
| 4-(2-(2-methyl)propyl)phenoxy | 3,5-bis(trifluoromethyl)phenyl | 482 |
| 4-(2-(2-methyl)propyl)phenoxy | 2-(4-chlorophenoxy)pyridin-3-yl | 474 |
| 4-(2-(2-methyl)propyl)phenoxy | pentafluorophenyl | 436 |
| 2,3-dimethylphenoxy | 3,4-dimethoxyphenyl | 378 |
| 2,3-dimethylphenoxy | 2-(trifluoromethyl)phenyl | 386 |
| 2,3-dimethylphenoxy | 2,4-difluorophenyl | 354 |
| 2,3-dimethylphenoxy | 3-(trifluoromethyl)phenyl | 386 |
| 2,3-dimethylphenoxy | 2-naphthyl | 368 |
| 2,3-dimethylphenoxy | 2-methoxyphenyl | 348 |
| 2,3-dimethylphenoxy | 3,4,5-trimethylphenyl | 408 |
| 2,3-dimethylphenoxy | 3,4-dichlorophenyl | 387 |
| 2,3-dimethylphenoxy | 3-bromophenyl | 397 |
| 2,3-dimethylphenoxy | 3-pyridyl | 319 |
| 2,3-dimethylphenoxy | 2-ethoxynaphth-1-yl | 412 |
| 2,3-dimethylphenoxy | 2,3-dichlorophenyl | 387 |
| 2,3-dimethylphenoxy | 6-chloropyrid-3-yl | 354 |
| 2,3-dimethylphenoxy | 4-(trifluoromethoxy)phenyl | 402 |
| 2,3-dimethylphenoxy | 2-fluoro-4-(trifluoromethyl)phenyl | 404 |
| 2,3-dimethylphenoxy | 3-bromothienyl | 403 |
| 2,3-dimethylphenoxy | 2-acetoxyphenyl | 376 |
| 2,3-dimethylphenoxy | 5-methylisoxazol-3-yl | 323 |
| 2,3-dimethylphenoxy | 2-(phenylthio)pyrid-3-yl | 427 |
| 2,3-dimethylphenoxy | 2-(trifluoromethoxy)phenyl | 402 |
| 2,3-dimethylphenoxy | 1-phenyl-5-propylpyrazin-4-yl | 426 |
| 2,3-dimethylphenoxy | 2-ethoxyphenyl | 362 |
| 2,3-dimethylphenoxy | 3-chlorothien-2-yl | 359 |
| 2,3-dimethylphenoxy | 1-(2-(2-methyl)propyl)-3-methylpyrazol-5-yl | 378 |
| 2,3-dimethylphenoxy | 3,5-dichlorophenyl | 387 |
| 2,3-dimethylphenoxy | 2-(propylthio)pyridin-3-yl | 393 |
| 2,3-dimethylphenoxy | 2-(ethylthio)pyridin-3-yl | 379 |
| 2,3-dimethylphenoxy | 3-bromopyridin-5-yl | 398 |
| 2,3-dimethylphenoxy | 4-methyl-1,2,3-thiadiazol-5-yl | 340 |
| 2,3-dimethylphenoxy | 1-methyl-3-(2-(2-methyl)propyl)pyrazol-5-yl | 378 |
| 2,3-dimethylphenoxy | 3-chlorobenzo[b]thiophen-2-yl | 409 |
| 2,3-dimethylphenoxy | 4-chlorophenyl | 353 |
| 2,3-dimethylphenoxy | 4-methyl-2-phenyl-1,2,3-triazol-5-yl | 399 |
| 2,3-dimethylphenoxy | benzo[b]thiophen-2-yl | 374 |
| 2,3-dimethylphenoxy | 3,4-dimethylphenyl | 346 |
| 2,3-dimethylphenoxy | 2-(phenoxy)pyridin-3-yl | 411 |
| 2,3-dimethylphenoxy | 2-(methylthio)pyridin-3-yl | 365 |
| 2,3-dimethylphenoxy | 5-methyl-3-phenylisoxazol-4-yl | 399 |
| 2,3-dimethylphenoxy | 4-chloro-1,3-dimethyl pyrazolo[3,4-b]pyridin-3-yl | 422 |
| 2,3-dimethylphenoxy | 2-chloro-6-methylpyridin-4-yl | 368 |
| 2,3-dimethylphenoxy | 3,5-dimethylisoxazol-4-yl | 337 |
| 2,3-dimethylphenoxy | 1-naphthyl | 368 |
| 2,3-dimethylphenoxy | 2-fluorophenyl | 336 |
| 2,3-dimethylphenoxy | 4-propylphenyl | 360 |
| 2,3-dimethylphenoxy | 3-fluorophenyl | 336 |
| 2,3-dimethylphenoxy | 2,6-difluorophenyl | 354 |
| 2,3-dimethylphenoxy | 2-chlorophenyl | 353 |
| 2,3-dimethylphenoxy | 3-(chloromethyl)phenyl | 368 |
| 2,3-dimethylphenoxy | 4-(2-(2-methyl)propyl)phenyl | 374 |
| 2,3-dimethylphenoxy | 3-chlorophenyl | 353 |
| 2,3-dimethylphenoxy | 3,5-dimethoxyphenyl | 378 |
| 2,3-dimethylphenoxy | 2,6-dichlorophenyl | 387 |
| 2,3-dimethylphenoxy | 2,4-dichlorophenyl | 387 |
| 2,3-dimethylphenoxy | 4-fluorophenyl | 336 |
| 2,3-dimethylphenoxy | 4-butylphenyl | 374 |
| 2,3-dimethylphenoxy | 2-methylphenyl | 332 |
| 2,3-dimethylphenoxy | phenyl | 318 |
| 2,3-dimethylphenoxy | 4-ethylphenyl | 346 |
| 2,3-dimethylphenoxy | 2,3-difluorophenyl | 354 |
| 2,3-dimethylphenoxy | 2,6-dimethoxyphenyl | 378 |
| 2,3-dimethylphenoxy | 3,4-difluorophenyl | 354 |

TABLE 6-continued

| R¹X | R³ | MS (m/z) |
|---|---|---|
| 2,3-dimethylphenoxy | 2,5-difluorophenyl | 354 |
| 2,3-dimethylphenoxy | 4-ethoxyphenyl | 362 |
| 2,3-dimethylphenoxy | 2,4,6-trichlorophenyl | 422 |
| 2,3-dimethylphenoxy | 3-methylphenyl | 332 |
| 2,3-dimethylphenoxy | 2-fluoro-5-(trifluoromethyl)phenyl | 404 |
| 2,3-dimethylphenoxy | 3-methoxyphenyl | 348 |
| 2,3-dimethylphenoxy | 2-bromophenyl | 397 |
| 2,3-dimethylphenoxy | 4-bromophenyl | 397 |
| 2,3-dimethylphenoxy | 4-fluoro-3-(trifluoromethyl)phenyl | 404 |
| 2,3-dimethylphenoxy | 3-(trifluoromethoxy)phenyl | 402 |
| 2,3-dimethylphenoxy | 9-fluorenon-4-yl | 420 |
| 2,3-dimethylphenoxy | isoxazol-5-yl | 609 |
| 2,3-dimethylphenoxy | benzofuroxan-5-yl | 376 |
| 2,3-dimethylphenoxy | 2-chloropyrid-3-yl | 354 |
| 2,3-dimethylphenoxy | 2-(4-methylphenoxy)pyridin-3-yl | 425 |
| 2,3-dimethylphenoxy | pyridin-4-yl | 319 |
| 2,3-dimethylphenoxy | anthraquinon-2-yl | 448 |
| 2,3-dimethylphenoxy | 2-iodophenyl | 444 |
| 2,3-dimethylphenoxy | 4-pentylphenyl | 388 |
| 2,3-dimethylphenoxy | 2-(4-chlorophenylthio)pyridin-3-yl | 462 |
| 2,3-dimethylphenoxy | 2,6-dimethylphenyl | 346 |
| 2,3-dimethylphenoxy | 2,5-dimethoxyphenyl | 378 |
| 2,3-dimethylphenoxy | 2,5-dichloropyridin-3-yl | 388 |
| 2,3-dimethylphenoxy | 2-chloro-6-methoxypyridin-4-yl | 384 |
| 2,3-dimethylphenoxy | 2,3-dichloropyridin-5-yl | 388 |
| 2,3-dimethylphenoxy | 1-naphthyl | 382 |
| 2,3-dimethylphenoxy | 2,4-dimethoxyphenyl | 378 |
| 2,3-dimethylphenoxy | 3,5-bis(trifluoromethyl)phenyl | 454 |
| 2,3-dimethylphenoxy | 2-(4-chlorophenoxyl pyridin-3-yl | 446 |
| 2,3-dimethylphenoxy | pentafluorophenyl | 408 |
| 3,5-(bis-2-propyl)phenoxy | 3,4-dimethoxyphenyl | 434 |
| 3,5-(bis-2-propyl)phenoxy | 2-(trifluoromethyl)phenyl | 442 |
| 3,5-(bis-2-propyl)phenoxy | 2,4-difluorophenyl | 410 |
| 3,5-(bis-2-propyl)phenoxy | 3-(trifluoromethyl)phenyl | 442 |
| 3,5-(bis-2-propyl)phenoxy | 2-naphthyl | 425 |
| 3,5-(bis-2-propyl)phenoxy | 2-methoxyphenyl | 404 |
| 3,5-(bis-2-propyl)phenoxy | 3,4,5-trimethylphenyl | 465 |
| 3,5-(bis-2-propyl)phenoxy | 3,4-dichlorophenyl | 443 |
| 3,5-(bis-2-propyl)phenoxy | 3-bromophenyl | 453 |
| 3,5-(bis-2-propyl)phenoxy | 3-pyridyl | 375 |
| 3,5-(bis-2-propyl)phenoxy | 2-ethoxynaphth-1-yl | 469 |
| 3,5-(bis-2-propyl)phenoxy | 2,3-dichlorophenyl | 443 |
| 3,5-(bis-2-propyl)phenoxy | 6-chloropyrid-3-yl | 410 |
| 3,5-(bis-2-propyl)phenoxy | 4-(trifluoromethoxy)phenyl | 458 |
| 3,5-(bis-2-propyl)phenoxy | 2-fluoro-4-(trifluoromethyl)phenyl | 460 |
| 3,5-(bis-2-propyl)phenoxy | 3-bromothienyl | 459 |
| 3,5-(bis-2-propyl)phenoxy | 2-acetoxyphenyl | 432 |
| 3,5-(bis-2-propyl)phenoxy | 5-methylisoxazol-3-yl | 379 |
| 3,5-(bis-2-propyl)phenoxy | 2-(phenylthiopyrid-3-yl | 484 |
| 3,5-(bis-2-propyl)phenoxy | 2-(trifluoromethoxy)phenyl | 458 |
| 3,5-(bis-2-propyl)phenoxy | 1-phenyl-5-propylpyrazin-4-yl | 483 |
| 3,5-(bis-2-propyl)phenoxy | 2-ethoxyphenyl | 418 |
| 3,5-(bis-2-propyl)phenoxy | 3-chlorothiophen-2-yl | 415 |
| 3,5-(bis-2-propyl)phenoxy | 1-(2-(2-methyl)propyl)-3-methylpyrazol-5-yl | 435 |
| 3,5-(bis-2-propyl)phenoxy | 3,5-dichlorophenyl | 443 |
| 3,5-(bis-2-propyl)phenoxy | 2-(propylthio)pyridin-3-yl | 450 |
| 3,5-(bis-2-propyl)phenoxy | 2-(ethylthio)pyridin-3-yl | 436 |
| 3,5-(bis-2-propyl)phenoxy | 3-bromopyridin-5-yl | 454 |
| 3,5-(bis-2-propyl)phenoxy | 4-methyl-1,2,3-thiadiazol-5-yl | 396 |
| 3,5-(bis-2-propyl)phenoxy | 1-methyl-3-(2-(2-methyl)propyl)pyrazol-5-yl | 435 |
| 3,5-(bis-2-propyl)phenoxy | 3-chlorobenzo[b]thiophen-2-yl | 465 |
| 3,5-(bis-2-propyl)phenoxy | 4-chlorophenyl | 409 |
| 3,5-(bis-2-propyl)phenoxy | 4-methyl-2-phenyl-1,2,3-triazol-5-yl | 456 |
| 3,5-(bis-2-propyl)phenoxy | benzo[b]thiophen-2-yl | 431 |
| 3,5-(bis-2-propyl)phenoxy | 3,4-dimethylphenyl | 402 |
| 3,5-(bis-2-propyl)phenoxy | 2-(phenoxy)pyridin-3-yl | 468 |
| 3,5-(bis-2-propyl)phenoxy | 2-(methylthio)pyridin-3-yl | 422 |
| 315-(bis-2-propyl)phenoxy | 5-methyl-3-phenylisoxazol-4-yl | 456 |
| 3,5-(bis-2-propyl)phenoxy | 4-chloro-1,3-dimethyl pyrazolo[3,4-b]pyridin-3-yl | 478 |
| 3,5-(bis-2-propyl)phenoxy | 2-chloro-6-methylpyridin-4-yl | 424 |
| 3,5-(bis-2-propyl)phenoxy | 3,5-dimethylisoxazol-4-yl | 393 |
| 3,5-(bis-2-propyl)phenoxy | 1-naphthyl | 425 |
| 3,5-(bis-2-propyl)phenoxy | 2-fluorophenyl | 392 |
| 3,5-(bis-2-propyl)phenoxy | 4-propylphenyl | 417 |
| 3,5-(bis-2-propyl)phenoxy | 3-fluorophenyl | 392 |
| 3,5-(bis-2-propyl)phenoxy | 2,6-difluorophenyl | 410 |
| 3,5-(bis-2-propyl)phenoxy | 2-chlorophenyl | 409 |
| 315-(bis-2-propyl)phenoxy | 3-(chloromethyl)phenyl | 423 |
| 3,5-(bis-2-propyl)phenoxy | 4-(2-(2-methyl)propyl)phenyl | 431 |
| 3,5-(bis-2-propyl)phenoxy | 3-chlorophenyl | 409 |
| 3,5-(bis-2-propyl)phenoxy | 3,5-dimethoxyphenyl | 434 |
| 3,5-(bis-2-propyl)phenoxy | 2,6-dichlorophenyl | 443 |
| 3,5-(bis-2-propyl)phenoxy | 2,4-dichlorophenyl | 443 |
| 3,5-(bis-2-propyl)phenoxy | 4-fluorophenyl | 392 |
| 3,5-(bis-2-propyl)phenoxy | 4-butylphenyl | 431 |
| 3,5-(bis-2-propyl)phenoxy | 2-methylphenyl | 388 |
| 3,5-(bis-2-propyl)phenoxy | phenyl | 374 |

TABLE 6-continued

| R¹X | R³ | MS (m/z) |
|---|---|---|
| 3,5-(bis-2-propyl)phenoxy | 4-ethylphenyl | 402 |
| 3,5-(bis-2-propyl)phenoxy | 2,3-difluorophenyl | 410 |
| 3,5-(bis-2-propyl)phenoxy | 2,6-dimethoxyphenyl | 434 |
| 3,5-(bis-2-propyl)phenoxy | 3,4-difluorophenyl | 410 |
| 3,5-(bis-2-propyl)phenoxy | 2,5-difluorophenyl | 410 |
| 3,5-(bis-2-propyl)phenoxy | 4-ethoxyphenyl | 418 |
| 3,5-(bis-2-propyl)phenoxy | 2,4,6-trichlorophenyl | 478 |
| 3,5-(bis-2-propyl)phenoxy | 3-methylphenyl | 388 |
| 3,5-(bis-2-propyl)phenoxy | 2-fluoro-5-(trifluoromethyl)phenyl | 460 |
| 3,5-(bis-2-propyl)phenoxy | 3-methoxyphenyl | 404 |
| 3,5-(bis-2-propyl)phenoxy | 2-bromophenyl | 453 |
| 3,5-(bis-2-propyl)phenoxy | 4-bromophenyl | 453 |
| 3,5-(bis-2-propyl)phenoxy | 4-fluoro-3-(trifluoromethyl)phenyl | 460 |
| 3,5-(bis-2-propyl)phenoxy | 3-(trifluoromethoxy)phenyl | 458 |
| 3,5-(bis-2-propyl)phenoxy | 9-fluorenon-4-yl | 477 |
| 3,5-(bis-2-propyl)phenoxy | isoxazol-5-yl | 365 |
| 3,5-(bis-2-propyl)phenoxy | benzofuroxan-5-yl | 432 |
| 3,5-(bis-2-propyl)phenoxy | 2-chloropyrid-3-yl | 410 |
| 3,5-(bis-2-propyl)phenoxy | 2-(4-methylphenoxy)pyridin-3-yl | 482 |
| 3,5-(bis-2-propyl)phenoxy | pyridin-4-yl | 375 |
| 3,5-(bis-2-propyl)phenoxy | anthraquinon-2-yl | 505 |
| 3,5-(bis-2-propyl)phenoxy | 2-iodophenyl | 500 |
| 3,5-(bis-2-propyl)phenoxy | 4-pentylphenyl | 445 |
| 3,5-(bis-2-propyl)phenoxy | 2-(4-chlorophenylthio)pyridin-3-yl | 518 |
| 3,5-(bis-2-propyl)phenoxy | 2,6-dimethylphenyl | 402 |
| 3,5-(bis-2-propyl)phenoxy | 2,5-dimethoxyphenyl | 434 |
| 3,5-(bis-2-propyl)phenoxy | 2,5-dichloropyridin-3-yl | 444 |
| 3,5-(bis-2-propyl)phenoxy | 2-chloro-6-methoxypyridin-4-yl | 440 |
| 3,5-(bis-2-propyl)phenoxy | 2,3-dichloropyridin-5-yl | 444 |
| 3,5-(bis-2-propyl)phenoxy | 1-naphthyl | 439 |
| 3,5-(bis-2-propyl)phenoxy | 2,4-dimethoxyphenyl | 434 |
| 3,5-(bis-2-propyl)phenoxy | 3,5-bis(trifluoromethyl)phenyl | 510 |
| 3,5-(bis-2-propyl)phenoxy | 2-(4-chlorophenoxy)pyridin-3-yl | 502 |
| 3,5-(bis-2-propyl)phenoxy | pentafluorophenyl | 464 |
| 3-trifluoromethyl phenoxy | 3,4-dimethoxyphenyl | 418 |
| 3-trifluoromethyl phenoxy | 2-(trifluoromethyl)phenyl | 426 |
| 3-trifluoromethyl phenoxy | 2,4-difluorophenyl | 394 |
| 3-trifluoromethyl phenoxy | 3-(trifluoromethyl)phenyl | 426 |
| 3-trifluoromethyl phenoxy | 2-naphthyl | 408 |
| 3-trifluoromethyl phenoxy | 2-methoxyphenyl | 388 |
| 3-trifluoromethyl phenoxy | 3,4,5-trimethylphenyl | 448 |
| 3-trifluoromethyl phenoxy | 3,4-dichlorophenyl | 427 |
| 3-trifluoromethyl phenoxy | 3-bromophenyl | 437 |
| 3-trifluoromethyl phenoxy | 3-pyridyl | 359 |
| 3-trifluoromethyl phenoxy | 2-ethoxynaphth-1-yl | 452 |
| 3-trifluoromethyl phenoxy | 2,3-dichlorophenyl | 427 |
| 3-trifluoromethyl phenoxy | 6-chloropyrid-3-yl | 394 |
| 3-trifluoromethyl phenoxy | 4-(trifluoromethoxy)phenyl | 442 |
| 3-trifluoromethyl phenoxy | 2-fluoro-4-(trifluoromethyl)phenyl | 444 |
| 3-trifluoromethyl phenoxy | 3-bromothienyl | 443 |
| 3-trifluoromethyl phenoxy | 2-acetoxyphenyl | 416 |
| 3-trifluoromethyl phenoxy | 5-methylisoxazol-3-yl | 363 |
| 3-trifluoromethyl phenoxy | 2-(phenylthio)pyrid-3-yl | 467 |
| 3-trifluoromethyl phenoxy | 2-(trifluoromethoxy)phenyl | 442 |
| 3-trifluoromethyl phenoxy | 1-phenyl-5-propylpyrazin-4-yl | 466 |
| 3-trifluoromethyl phenoxy | 2-ethoxyphenyl | 402 |
| 3-trifluoromethyl phenoxy | 3-chlorothien-2-yl | 399 |
| 3-trifluoromethyl phenoxy | 1-(2-(2-methyl)propyl)-3-methylpyrazol-5-yl | 418 |
| 3-trifluoromethyl phenoxy | 3,5-dichlorophenyl | 427 |
| 3-trifluoromethyl phenoxy | 2-(propylthio)pyridin-3-yl | 433 |
| 3-trifluoromethyl phenoxy | 2-(ethylthio)pyridin-3-yl | 419 |
| 3-trifluoromethyl phenoxy | 3-bromopyridin-5-yl | 438 |
| 3-trifluoromethyl phenoxy | 4-methyl-1,2,3-thiadiazol-5-yl | 380 |
| 3-trifluoromethyl phenoxy | 1-methyl-3-(2-(2-methyl)propyl)pyrazol-5-yl | 418 |
| 3-trifluoromethyl phenoxy | 3-chlorobenzo[b]thiophen-2-yl | 449 |
| 3-trifluoromethyl phenoxy | 4-chlorophenyl | 393 |
| 3-trifluoromethyl phenoxy | 4-methyl-2-phenyl-1,2,3-triazol-5-yl | 439 |
| 3-trifluoromethyl phenoxy | benzo[b]thiophen-2-yl | 414 |
| 3-trifluoromethyl phenoxy | 3,4-dimethylphenyl | 386 |
| 3-trifluoromethyl phenoxy | 2-(phenoxy)pyridin-3-yl | 451 |
| 3-trifluoromethyl phenoxy | 2-(methylthio)pyridin-3-yl | 405 |
| 3-trifluoromethyl phenoxy | 5-methyl-3-phenylisoxazol-4-yl | 439 |
| 3-trifluoromethyl phenoxy | 4-chloro-1,3-dimethyl pyrazolo[3,4-b]pyridin-3-yl | 462 |
| 3-trifluoromethyl phenoxy | 2-chloro-6-methylpyridin-4-yl | 408 |
| 3-trifluoromethyl phenoxy | 3,5-dimethylisoxazol-4-yl | 377 |
| 3-trifluoromethyl phenoxy | 1-naphthyl | 408 |

TABLE 6-continued

| R¹X | R³ | MS (m/z) |
|---|---|---|
| phenoxy 3-trifluoromethyl | 2-fluorophenyl | 476 |
| phenoxy 3-trifluoromethyl | 4-propylphenyl | 400 |
| phenoxy 3-trifluoromethyl | 3-fluorophenyl | 376 |
| phenoxy 3-trifluoromethyl | 2,6-difluorophenyl | 394 |
| phenoxy 3-trifluoromethyl | 2-chlorophenyl | 393 |
| phenoxy 3-trifluoromethyl | 3-(chloromethyl)phenyl | 407 |
| phenoxy 3-trifluoromethyl | 4-(2-(2-methyl)propyl) phenyl | 414 |
| phenoxy 3-trifluoromethyl | 3-chlorophenyl | 393 |
| phenoxy 3-trifluoromethyl | 3,5-dimethoxyphenyl | 418 |
| phenoxy 3-trifluoromethyl | 2,6-dichlorophenyl | 427 |
| phenoxy 3-trifluoromethyl | 2,4-dichlorophenyl | 427 |
| phenoxy 3-trifluoromethyl | 4-fluorophenyl | 376 |
| phenoxy 3-trifluoromethyl | 4-butylphenyl | 414 |
| phenoxy 3-trifluoromethyl | 2-methylphenyl | 372 |
| phenoxy 3-trifluoromethyl | phenyl | 358 |
| phenoxy 3-trifluoromethyl | 4-ethylphenyl | 386 |
| phenoxy 3-trifluoromethyl | 2,3-difluorophenyl | 394 |
| phenoxy 3-trifluoromethyl | 2,6-dimethoxyphenyl | 418 |
| phenoxy 3-trifluoromethyl | 3,4-difluorophenyl | 394 |
| phenoxy 3-trifluoromethyl | 2,5-difluorophenyl | 394 |
| phenoxy 3-trifluoromethyl | 4-ethoxyphenyl | 402 |
| phenoxy 3-trifluoromethyl | 2,4,6-trichlorophenyl | 462 |
| phenoxy 3-trifluoromethyl | 3-methylphenyl | 372 |
| phenoxy 3-trifluoromethyl | 2-fluoro-5-(trifluoromethyl)phenyl | 444 |
| phenoxy 3-trifluoromethyl | 3-methoxyphenyl | 388 |
| phenoxy 3-trifluoromethyl | 2-bromophenyl | 437 |
| phenoxy 3-trifluoromethyl | 4-bromophenyl | 437 |
| phenoxy 3-trifluoromethyl | 4-fluoro-3-(trifluoromethyl)phenyl | 444 |
| phenoxy 3-trifluoromethyl | 3-(trifluoromethoxy)phenyl | 442 |
| phenoxy 3-trifluoromethyl | 9-fluorenon-4-yl | 460 |
| phenoxy 3-trifluoromethyl | isoxazol-5-yl | 349 |
| phenoxy 3-trifluoromethyl | benzofuroxan-5-yl | 416 |
| phenoxy 3-trifluoromethyl | 2-chloropyrid-3-yl | 394 |
| phenoxy 3-trifluoromethyl | 2-(4-methylphenoxy)pyridin-3-yl | 465 |
| phenoxy 3-trifluoromethyl | pyridin-4-yl | 359 |
| phenoxy 3-trifluoromethyl | anthraquinon-2-yl | 488 |
| phenoxy 3-trifluoromethyl | 2-iodophenyl | 484 |
| phenoxy 3-trifluoromethyl | 4-pentylphenyl | 428 |
| phenoxy 3-trifluoromethyl | 2-(4-chlorophenylthio) pyridin-3-yl | 502 |
| phenoxy 3-trifluoromethyl | 2,6-dimethylphenyl | 386 |
| phenoxy 3-trifluoromethyl | 2,5-dimethoxyphenyl | 418 |
| phenoxy 3-trifluoromethyl | 2,5-dichloropyridin-3-yl | 428 |
| phenoxy 3-trifluoromethyl | 2-chloro-6-methoxypyridin-4-yl | 424 |
| phenoxy 3-trifluoromethyl | 2,3-dichloropyridin-5-yl | 428 |
| phenoxy 3-trifluoromethyl | 1-naphthyl | 422 |
| phenoxy 3-trifluoromethyl | 2,4-dimethoxyphenyl | 418 |
| phenoxy 3-trifluoromethyl | 3,5-bis(trifluoromethyl)phenyl | 494 |
| phenoxy 3-trifluoromethyl | 2-(4-chlorophenoxy)pyridin-3-yl | 486 |
| phenoxy 3-trifluoromethyl | pentafluorophenyl | 448 |
| 2,6-dichlorophenoxy | 3,4-dimethoxyphenyl | 419 |
| 2,6-dichlorophenoxy | 2-(trifluoromethyl)phenyl | 427 |
| 2,6-dichlorophenoxy | 2,4-difluorophenyl | 395 |
| 2,6-dichlorophenoxy | 3-(trifluoromethyl)phenyl | 427 |
| 2,6-dichlorophenoxy | 2-naphthyl | 409 |
| 2,6-dichlorophenoxy | 2-methoxyphenyl | 389 |
| 2,6-dichlorophenoxy | 3,4,5-trimethylphenyl | 449 |
| 2,6-dichlorophenoxy | 3,4-dichlorophenyl | 428 |
| 2,6-dichlorophenoxy | 3-bromophenyl | 438 |
| 2,6-dichlorophenoxy | 3-pyridyl | 361 |
| 2,6-dichlorophenoxy | 2-ethoxynaphth-1-yl | 453 |
| 2,6-dichlorophenoxy | 2,3-dichlorophenyl | 428 |
| 2,6-dichlorophenoxy | 6-chloropyrid-3-yl | 395 |
| 2,6-dichlorophenoxy | 4-(trifluoromethoxy)phenyl | 443 |
| 2,6-dichlorophenoxy | 2-fluoro-4-(trifluoromethyl)phenyl | 445 |
| 2,6-dichlorophenoxy | 3-bromothienyl | 444 |
| 2,6-dichlorophenoxy | 2-acetoxyphenyl | 417 |
| 2,6-dichlorophenoxy | 5-methylisoxazol-3-yl | 364 |
| 2,6-dichlorophenoxy | 2-(phenylthio)pyrid-3-yl | 468 |
| 2,6-dichlorophenoxy | 2-(trifluoromethoxy)phenyl | 443 |
| 2,6-dichlorophenoxy | 1-phenyl-5-propylpyrazin-4-yl | 467 |
| 2,6-dichlorophenoxy | 2-ethoxypheny) | 403 |
| 2,6-dichlorophenoxy | 3-chlorothien-2-yl | 400 |
| 2,6-dichlorophenoxy | 1-(2-(2-methyl)propyl)-3-methylpyrazol-5-yl | 419 |
| 2,6-dichlorophenoxy | 3,5-dichlorophenyl | 428 |
| 2,6-dichlorophenoxy | 2-(propylthio)pyridin-3-yl | 434 |
| 2,6-dichlorophenoxy | 2-(ethylthio)pyridin-3-yl | 420 |
| 2,6-dichlorophenoxy | 3-bromopyridin-5-yl | 439 |
| 2,6-dichlorophenoxy | 4-methyl-1,2,3-thiadiazol-5-yl | 381 |
| 2,6-dichlorophenoxy | 1-methyl-3-(2-(2-methyl)propyl)pyrazol-5-yl | 419 |
| 2,6-dichlorophenoxy | 3-chlorobenzo[b]thiophen-2-yl | 450 |
| 2,6-dichlorophenoxy | 4-chlorophenyl | 394 |
| 2,6-dichlorophenoxy | 4-methyl-2-phenyl-1,2,3-triazol-5-yl | 440 |
| 2,6-dichlorophenoxy | benzo[b]thiophen-2-yl | 415 |
| 2,6-dichlorophenoxy | 3,4-dimethylphenyl | 387 |
| 2,6-dichlorophenoxy | 2-(phenoxy)pyridin-3-yl | 452 |
| 2,6-dichlorophenoxy | 2-(methylthio)pyridin-3-yl | 406 |
| 2,6-dichlorophenoxy | 5-methyl-3-phenylisoxazol-4-yl | 440 |
| 2,6-dichlorophenoxy | 4-chloro-1,3-dimethyl pyrazolo[3,4-b]pyridin-3-yl | 463 |
| 2,6-dichlorophenoxy | 2-chloro-6-methylpyridin-4-yl | 409 |
| 2,6-dichlorophenoxy | 3,5-dimethylisoxazol-4-yl | 378 |
| 2,6-dichlorophenoxy | 1-naphthyl | 409 |

TABLE 6-continued

| R¹X | R³ | MS (m/z) |
|---|---|---|
| 2,6-dichlorophenoxy | 2-fluorophenyl | 377 |
| 2,6-dichlorophenoxy | 4-propylphenyl | 401 |
| 2,6-dichlorophenoxy | 3-fluorophenyl | 377 |
| 2,6-dichlorophenoxy | 2,6-difluorophenyl | 395 |
| 2,6-dichlorophenoxy | 2-chlorophenyl | 394 |
| 2,6-dichlorophenoxy | 3-(chloromethyl)phenyl | 408 |
| 2,6-dichlorophenoxy | 4-(2-(2-methyl)propyl)phenyl | 415 |
| 2,6-dichlorophenoxy | 3-chlorophenyl | 694 |
| 2,6-dichlorophenoxy | 3,5-dimethoxyphenyl | 419 |
| 2,6-dichlorophenoxy | 2,6-dichlorophenyl | 428 |
| 2,6-dichlorophenoxy | 2,4-dichlorophenyl | 428 |
| 2,6-dichlorophenoxy | 4-fluorophenyl | 377 |
| 2,6-dichlorophenoxy | 4-butylphenyl | 415 |
| 2,6-dichlorophenoxy | 2-methylphenyl | 373 |
| 2,6-dichlorophenoxy | phenyl | 359 |
| 2,6-dichlorophenoxy | 4-ethylphenyl | 387 |
| 2,6-dichlorophenoxy | 2,3-difluorophenyl | 395 |
| 2,6-dichlorophenoxy | 2,6-dimethoxyphenyl | 419 |
| 2,6-dichlorophenoxy | 3,4-difluorophenyl | 395 |
| 2,6-dichlorophenoxy | 2,5-difluorophenyl | 395 |
| 2,6-dichlorophenoxy | 4-ethoxyphenyl | 403 |
| 2,6-dichlorophenoxy | 2,4,6-trichlorophenyl | 463 |
| 2,6-dichlorophenoxy | 3-methylphenyl | 373 |
| 2,6-dichlorophenoxy | 2-fluoro-5-(trifluoromethyl)phenyl | 445 |
| 2,6-dichlorophenoxy | 3-methoxyphenyl | 389 |
| 2,6-dichlorophenoxy | 2-bromophenyl | 438 |
| 2,6-dichlorophenoxy | 4-bromophenyl | 438 |
| 2,6-dichlorophenoxy | 4-fluoro-3-(trifluoromethyl)phenyl | 445 |
| 2,6-dichlorophenoxy | 3-(trifluoromethoxy)phenyl | 443 |
| 2,6-dichlorophenoxy | 9-fluorenon-4-yl | 461 |
| 2,6-dichlorophenoxy | isoxazol-5-yl | 350 |
| 2,6-dichlorophenoxy | benzofuroxan-5-yl | 417 |
| 2,6-dichlorophenoxy | 2-chloropyrid-3-yl | 395 |
| 2,6-dichlorophenoxy | 2-(4-methylphenoxy)pyridin-3-yl | 466 |
| 2,6-dichlorophenoxy | pyridin-4-yl | 360 |
| 2,6-dichlorophenoxy | anthraquinon-2-yl | 489 |
| 2,6-dichlorophenoxy | 2-iodophenyl | 485 |
| 2,6-dichlorophenoxy | 4-pentylphenyl | 429 |
| 2,6-dichlorophenoxy | 2-(4-chlorophenylthio)pyridin-3-yl | 503 |
| 2,6-dichlorophenoxy | 2,6-dimethylphenyl | 387 |
| 2,6-dichlorophenoxy | 2,5-dimethoxyphenyl | 419 |
| 2,6-dichlorophenoxy | 2,5-dichloropyridin-3-yl | 429 |
| 2,6-dichlorophenoxy | 2-chloro-6-methoxypyridin-4-yl | 425 |
| 2,6-dichlorophenoxy | 2,3-dichloropyridin-5-yl | 429 |
| 2,6-dichlorophenoxy | 1-naphthyl | 413 |
| 2,6-dichlorophenoxy | 2,4-dimethoxyphenyl | 419 |
| 2,6-dichlorophenoxy | 3,5-bis(trifluoromethyl)phenyl | 495 |
| 2,6-dichlorophenoxy | 2-(4-chlorophenoxy)pyridin-3-yl | 487 |
| 2,6-dichlorophenoxy | pentafluorophenyl | 449 |
| 2,4-dichlorophenoxy | 3,4-dimethoxyphenyl | 419 |
| 2,4-dichlorophenoxy | 2-(trifluoromethyl)phenyl | 427 |
| 2,4-dichlorophenoxy | 2,4-difluorophenyl | 395 |
| 2,4-dichlorophenoxy | 3-(trifluoromethyl)phenyl | 427 |
| 2,4-dichlorophenoxy | 2-naphthyl | 409 |
| 2,4-dichlorophenoxy | 2-methoxyphenyl | 389 |
| 2,4-dichlorophenoxy | 3,4,5-trimethylphenyl | 449 |
| 2,4-dichlorophenoxy | 3,4-dichlorophenyl | 428 |
| 2,4-dichlorophenoxy | 3-bromophenyl | 438 |
| 2,4-dichlorophenoxy | 3-pyridyl | 361 |
| 2,4-dichlorophenoxy | 2-ethoxynaphth-1-yl | 453 |
| 2,4-dichlorophenoxy | 2,3-dichlorophenyl | 428 |
| 2,4-dichlorophenoxy | 6-chloropyrid-3-yl | 395 |
| 2,4-dichlorophenoxy | 4-(trifluoromethoxy)phenyl | 443 |
| 2,4-dichlorophenoxy | 2-fluoro-4-(trifluoromethyl)phenyl | 445 |
| 2,4-dichlorophenoxy | 3-bromothienyl | 444 |
| 2,4-dichlorophenoxy | 2-acetoxyphenyl | 417 |
| 2,4-dichlorophenoxy | 5-methylisoxazol-3-yl | 364 |
| 2,4-dichlorophenoxy | 2-(phenylthio)pyrid-3-yl | 468 |
| 2,4-dichlorophenoxy | 2-(trifluoromethoxy)phenyl | 443 |
| 2,4-dichlorophenoxy | 1-phenyl-5-propylpyrazin-4-yl | 467 |
| 2,4-dichlorophenoxy | 2-ethoxyphenyl | 403 |
| 2,4-dichlorophenoxy | 3-chlorothien-2-yl | 400 |
| 2,4-dichlorophenoxy | 1-(2-(2-methyl)propyl)-3-methylpyrazol-5-yl | 419 |
| 2,4-dichlorophenoxy | 3,5-dichlorophenyl | 428 |
| 2,4-dichlorophenoxy | 2-(propylthio)pyridin-3-yl | 434 |
| 2,4-dichlorophenoxy | 2-(ethylthio)pyridin-3-yl | 420 |
| 2,4-dichlorophenoxy | 3-bromopyridin-5-yl | 439 |
| 2,4-dichlorophenoxy | 4-methyl-1,2,3-thiadiazol-5-yl | 381 |
| 2,4-dichlorophenoxy | 1-methyl-3-(2-(2-methyl)propyl)pyrazol-5-yl | 419 |
| 2,4-dichlorophenoxy | 3-chlorobenzo[b]thiophen-2-yl | 450 |
| 2,4-dichlorophenoxy | 4-chlorophenyl | 394 |
| 2,4-dichlorophenoxy | 4-methyl-2-phenyl-1,2,3-triazol-5-yl | 440 |
| 2,4-dichlorophenoxy | benzo[b]thiophen-2-yl | 415 |
| 2,4-dichlorophenoxy | 3,4-dimethylphenyl | 387 |
| 2,4-dichlorophenoxy | 2-(phenoxy)pyridin-3-yl | 452 |
| 2,4-dichlorophenoxy | 2-(methylthio)pyridin-3-yl | 406 |
| 2,4-dichlorophenoxy | 5-methyl-3-phenylisoxazol-4-yl | 440 |
| 2,4-dichlorophenoxy | 4-chloro-1,3-dimethyl pyrazolo[3,4-b]pyridin-3-yl | 463 |
| 2,4-dichlorophenoxy | 2-chloro-6-methylpyridin-4-yl | 409 |
| 2,4-dichlorophenoxy | 3,5-dimethylisoxazol-4-yl | 378 |
| 2,4-dichlorophenoxy | 1-naphthyl | 409 |
| 2,4-dichlorophenoxy | 2-fluorophenyl | 377 |
| 2,4-dichlorophenoxy | 4-propylphenyl | 401 |
| 2,4-dichlorophenoxy | 3-fluorophenyl | 377 |
| 2,4-dichlorophenoxy | 2,6-difluorophenyl | 395 |
| 2,4-dichlorophenoxy | 2-chlorophenyl | 394 |
| 2,4-dichlorophenoxy | 3-(chloromethyl)phenyl | 408 |
| 2,4-dichlorophenoxy | 4-(2-(2-methyl)propyl)phenyl | 415 |
| 2,4-dichlorophenoxy | 3-chlorophenyl | 694 |
| 2,4-dichlorophenoxy | 3,5-dimethoxyphenyl | 419 |
| 2,4-dichlorophenoxy | 2,6-dichlorophenyl | 428 |
| 2,4-dichlorophenoxy | 2,4-dichlorophenyl | 428 |
| 2,4-dichlorophenoxy | 4-fluorophenyl | 377 |
| 2,4-dichlorophenoxy | 4-butylphenyl | 415 |
| 2,4-dichlorophenoxy | 2-methylphenyl | 373 |
| 2,4-dichlorophenoxy | phenyl | 359 |
| 2,4-dichlorophenoxy | 4-ethylphenyl | 387 |
| 2,4-dichlorophenoxy | 2,3-difluorophenyl | 395 |
| 2,4-dichlorophenoxy | 2,6-dimethoxyphenyl | 419 |
| 2,4-dichlorophenoxy | 3,4-difluorophenyl | 395 |
| 2,4-dichlorophenoxy | 2,5-difluorophenyl | 395 |
| 2,4-dichlorophenoxy | 4-ethoxyphenyl | 403 |
| 2,4-dichlorophenoxy | 2,4,6-trichlorophenyl | 463 |
| 2,4-dichlorophenoxy | 3-methylphenyl | 373 |
| 2,4-dichlorophenoxy | 2-fluoro-5-(trifluoromethyl)phenyl | 445 |
| 2,4-dichlorophenoxy | 3-methoxyphenyl | 389 |
| 2,4-dichlorophenoxy | 2-bromophenyl | 438 |
| 2,4-dichlorophenoxy | 4-bromophenyl | 438 |
| 2,4-dichlorophenoxy | 4-fluoro-3-(trifluoromethyl)phenyl | 445 |
| 2,4-dichlorophenoxy | 3-(trifluoromethoxy)phenyl | 443 |
| 2,4-dichlorophenoxy | 9-fluorenon-4-yl | 461 |
| 2,4-dichlorophenoxy | isoxazol-5-yl | 350 |
| 2,4-dichlorophenoxy | benzofuroxan-5-yl | 417 |
| 2,4-dichlorophenoxy | 2-chloropyrid-3-yl | 395 |
| 2,4-dichlorophenoxy | 2-(4-methylphenoxy)pyridin-3-yl | 466 |
| 2,4-dichlorophenoxy | pyridin-4-yl | 360 |
| 2,4-dichlorophenoxy | anthraquinon-2-yl | 489 |
| 2,4-dichlorophenoxy | 2-iodophenyl | 485 |
| 2,4-dichlorophenoxy | 4-pentylphenyl | 429 |

TABLE 6-continued

| R¹X | R³ | MS (m/z) |
|---|---|---|
| 2,4-dichlorophenoxy | 2-(4-chlorophenylthio)pyridin-3-yl | 503 |
| 2,4-dichlorophenoxy | 2,6-dimethylphenyl | 387 |
| 2,4-dichlorophenoxy | 2,5-dimethoxyphenyl | 419 |
| 2,4-dichlorophenoxy | 2,5-dichloropyridin-3-yl | 429 |
| 2,4-dichlorophenoxy | 2-chloro-6-methoxypyridin-4-yl | 425 |
| 2,4-dichlorophenoxy | 2,3-dichloropyridin-5-yl | 429 |
| 2,4-dichlorophenoxy | 1-naphthyl | 413 |
| 2,4-dichlorophenoxy | 2,4-dimethoxyphenyl | 419 |
| 2,4-dichlorophenoxy | 3,5-bis(trifluoromethyl)phenyl | 495 |
| 2,4-dichlorophenoxy | 2-(4-chlorophenoxy)pyridin-3-yl | 487 |
| 2,4-dichlorophenoxy | pentafluorophenyl | 449 |
| 4-chloro-3-methylphenoxy | 3,4-dimethoxyphenyl | 319 |
| 4-chloro-3-methylphenoxy | 2-(trifluoromethyl)phenyl | 407 |
| 4-chloro-3-methylphenoxy | 2,4-difluorophenyl | 375 |
| 4-chloro-3-methylphenoxy | 3-(trifluoromethyl)phenyl | 407 |
| 4-chloro-3-methylphenoxy | 2-naphthyl | 389 |
| 4-chloro-3-methylphenoxy | 2-methoxyphenyl | 369 |
| 4-chloro-3-methylphenoxy | 3,4,5-trimethylphenyl | 429 |
| 4-chloro-3-methylphenoxy | 3,4-dichlorophenyl | 408 |
| 4-chloro-3-methylphenoxy | 3-bromophenyl | 418 |
| 4-chloro-3-methylphenoxy | 3-pyridyl | 340 |
| 4-chloro-3-methylphenoxy | 2-ethoxynaphth-1-yl | 433 |
| 4-chloro-3-methylphenoxy | 2,3-dichlorophenyl | 408 |
| 4-chloro-3-methylphenoxy | 6-chloropyrid-3-yl | 374 |
| 4-chloro-3-methylphenoxy | 4-(trifluoromethoxy)phenyl | 423 |
| 4-chloro-3-methylphenoxy | 2-fluoro-4-(trifluoromethyl)phenyl | 425 |
| 4-chloro-3-methylphenoxy | 3-bromothienyl | 424 |
| 4-chloro-3-methylphenoxy | 2-acetoxyphenyl | 397 |
| 4-chloro-3-methylphenoxy | 5-methylisoxazol-3-yl | 344 |
| 4-chloro-3-methylphenoxy | 2-(phenylthio)pyrid-3-yl | 448 |
| 4-chloro-3-methylphenoxy | 2-(trifluoromethoxy)phenyl | 423 |
| 4-chloro-3-methylphenoxy | 1-phenyl-5-propylpyrazin-4-yl | 447 |
| 4-chloro-3-methylphenoxy | 2-ethoxyphenyl | 383 |
| 4-chloro-3-methylphenoxy | 3-chlorothien-2-yl | 379 |
| 4-chloro-3-methylphenoxy | 1-(2-(2-methyl)propyl)-3-methylpyrazol-5-yl | 399 |
| 4-chloro-3-methylphenoxy | 3,5-dichlorophenyl | 408 |
| 4-chloro-3-methylphenoxy | 2-(propylthio)pyridin-3-yl | 414 |
| 4-chloro-3-methylphenoxy | 2-(ethylthio)pyridin-3-yl | 400 |
| 4-chloro-3-methylphenoxy | 3-bromopyridin-5-yl | 419 |
| 4-chloro-3-methylphenoxy | 4-methyl-1,2,3-thiadiazol-5-yl | 361 |
| 4-chloro-3-methylphenoxy | 1-methyl-3-(2-(2-methyl)propyl)pyrazol-5-yl | 399 |
| 4-chloro-3-methylphenoxy | 3-chlorobenzo[b]thiophen-2-yl | 429 |
| 4-chloro-3-methylphenoxy | 4-chlorophenyl | 373 |
| 4-chloro-3-methylphenoxy | 4-methyl-2-phenyl-1,2,3-triazol-5-yl | 420 |
| 4-chloro-3-methylphenoxy | benzo[b]thiophen-2-yl | 395 |
| 4-chloro-3-methylphenoxy | 3,4-dimethylphenyl | 367 |
| 4-chloro-3-methylphenoxy | 2-(phenoxy)pyridin-3-yl | 432 |
| 4-chloro-3-methylphenoxy | 2-(methylthio)pyridin-3-yl | 386 |
| 4-chloro-3-methylphenoxy | 5-methyl-3-phenylisoxazol-4-yl | 420 |
| 4-chloro-3-methylphenoxy | 4-chloro-1,3-dimethyl pyrazolo[3,4-b]pyridin-3-yl | 442 |
| 4-chloro-3-methylphenoxy | 2-chloro-6-methylpyridin-4-yl | 388 |
| 4-chloro-3-methylphenoxy | 3,5-dimethylisoxazol-4-yl | 358 |
| 4-chloro-3-methylphenoxy | 1-naphthyl | 389 |
| 4-chloro-3-methylphenoxy | 2-fluorophenyl | 357 |
| 4-chloro-3-methylphenoxy | 4-propylphenyl | 381 |
| 4-chloro-3-methylphenoxy | 4-(trifluoromethyl)phenyl | 407 |
| 4-chloro-3-methylphenoxy | 3-fluorophenyl | 357 |
| 4-chloro-3-methylphenoxy | 2,6-difluorophenyl | 375 |
| 4-chloro-3-methylphenoxy | 2-chlorophenyl | 373 |
| 4-chloro-3-methylphenoxy | 3-(chloromethyl)phenyl | 387 |
| 4-chloro-3-methylphenoxy | 4-(2-(2-methyl)propyl)phenyl | 395 |
| 4-chloro-3-methylphenoxy | 3-chlorophenyl | 373 |
| 4-chloro-3-methylphenoxy | 3,5-dimethoxyphenyl | 399 |
| 4-chloro-3-methylphenoxy | 2,6-dichlorophenyl | 408 |
| 4-chloro-3-methylphenoxy | 2,4-dichlorophenyl | 408 |
| 4-chloro-3-methylphenoxy | 4-fluorophenyl | 357 |
| 4-chloro-3-methylphenoxy | 4-butylphenyl | 395 |
| 4-chloro-3-methylphenoxy | 2-methylphenyl | 353 |
| 4-chloro-3-methylphenoxy | phenyl | 339 |
| 4-chloro-3-methylphenoxy | 4-ethylphenyl | 367 |
| 4-chloro-3-methylphenoxy | 2,3-difluorophenyl | 375 |
| 4-chloro-3-methylphenoxy | 2,6-dimethoxyphenyl | 399 |
| 4-chloro-3-methylphenoxy | 3,4-difluorophenyl | 375 |
| 4-chloro-3-methylphenoxy | 2,5-difluorophenyl | 375 |
| 4-chloro-3-methylphenoxy | 4-ethoxyphenyl | 383 |
| 4-chloro-3-methylphenoxy | 2,4,6-trichlorophenyl | 442 |
| 4-chloro-3-methylphenoxy | 3-methylphenyl | 353 |
| 4-chloro-3-methylphenoxy | 2-fluoro-5-(trifluoromethyl)phenyl | 425 |
| 4-chloro-3-methylphenoxy | 3-methoxyphenyl | 369 |

TABLE 6-continued

| R¹X | R³ | MS (m/z) |
|---|---|---|
| 4-chloro-3-methylphenoxy | 2-bromophenyl | 418 |
| 4-chloro-3-methylphenoxy | 4-bromophenyl | 418 |
| 4-chloro-3-methylphenoxy | 4-fluoro-3-(trifluoromethyl-)phenyl | 425 |
| 4-chloro-3-methylphenoxy | 3-(trifluoromethoxy)phenyl | 423 |
| 4-chloro-3-methylphenoxy | 9-fluorenon-4-yl | 441 |
| 4-chloro-3-methylphenoxy | isoxazol-5-yl | 330 |
| 4-chloro-3-methylphenoxy | benzofuroxan-5-yl | 397 |
| 4-chloro-3-methylphenoxy | 2-chloropyrid-3-yl- | 374 |
| 4-chloro-3-methylphenoxy | 2-(4-methylphenoxy)pyridin-3-yl | 446 |
| 4-chloro-3-methylphenoxy | pyridin-4-yl | 340 |
| 4-chloro-3-methylphenoxy | anthraquinon-2-yl | 469 |
| 4-chloro-3-methylphenoxy | 2-iodophenyl | 465 |
| 4-chloro-3-methylphenoxy | 4-pentylphenyl | 409 |
| 4-chloro-3-methylphenoxy | 2-(4-chlorophenylthio)pyridin-3-yl | 482 |
| 4-chloro-3-methylphenoxy | 2,6-dimethylphenyl | 367 |
| 4-chloro-3-methylphenoxy | 2,5-dimethoxyphenyl | 399 |
| 4-chloro-3-methylphenoxy | 2,5-dichloropyridin-3-yl | 409 |
| 4-chloro-3-methylphenoxy | 2-chloro-6-methoxypyridin-4-yl | 404 |
| 4-chloro-3-methylphenoxy | 2,3-dichloropyridin-5-yl | 409 |
| 4-chloro-3-methylphenoxy | 1-naphthyl | 403 |
| 4-chloro-3-methylphenoxy | 2,4-dimethoxyphenyl | 399 |
| 4-chloro-3-methylphenoxy | 3,5-bis (trifluoromethyl)phenyl | 475 |
| 4-chloro-3-methylphenoxy | 2-(4-chlorophenoxy)pyridin-3-yl | 466 |
| 4-chloro-3-methylphenoxy | pentafluorophenyl | 429 |
| 4-chloro-2-cyclohexylphenoxy | 3,4-dimethoxyphenyl | 467 |
| 4-chloro-2-cyclohexylphenoxy | 2-(trifluoromethyl)phenyl | 475 |
| 4-chloro-2-cyclohexylphenoxy | 2,4-difluorophenyl | 443 |
| 4-chloro-2-cyclohexylphenoxy | 3-(trifluoromethyl)phenyl | 475 |
| 4-chloro-2-cyclohexylphenoxy | 2-naphthyl | 457 |
| 4-chloro-2-cyclohexylphenoxy | 2-methoxyphenyl | 437 |
| 4-chloro-2-cyclohexylphenoxy | 3,4,5-trimethylphenyl | 497 |
| 4-chloro-2-cyclohexylphenoxy | 3,4-dichlorophenyl | 176 |
| 4-chloro-2-cyclohexylphenoxy | 3-bromophenyl | 486 |
| 4-chloro-2-cyclohexylphenoxy | 3-pyridyl | 408 |
| 4-chloro-2-cyclohexylphenoxy | 2-ethoxynaphth-1-yl | 501 |
| 4-chloro-2-cyclohexylphenoxy | 2,3-dichlorophenyl | 476 |
| 4-chloro-2-cyclohexylphenoxy | 6-chloropyrid-3-yl | 442 |
| 4-chloro-2-cyclohexylphenoxy | 4-(trifluoromethoxy)phenyl | 491 |
| 4-chloro-2-cyclohexylphenoxy | 2-fluoro-4-(trifluoromethyl)phenyl | 493 |
| 4-chloro-2-cyclohexylphenoxy | 3-bromothienyl | 492 |
| 4-chloro-2-cyclohexylphenoxy | 2-acetoxyphenyl | 465 |
| 4-chloro-2-cyclohexylphenoxy | 5-methylisoxazol-3-yl | 412 |
| 4-chloro-2-cyclohexylphenoxy | 2-(phenylthio)pyrid-3-yl | 516 |
| 4-chloro-2-cyclohexylphenoxy | 2-(trifluoromethoxy)phenyl | 491 |
| 4-chloro-2-cyclohexylphenoxy | 1-phenyl-5-propylpyrazin-4-yl | 515 |
| 4-chloro-2-cyclohexylphenoxy | 2-ethoxyphenyl | 451 |
| 4-chloro-2-cyclohexylphenoxy | 3-chlorothien-2-yl | 447 |
| 4-chloro-2-cyclohexylphenoxy | 1-(2-(2-methyl)propyl)-3-methylpyrazol-5-yl | 467 |
| 4-chloro-2-cyclohexylphenoxy | 3,5-dichlorophenyl | 476 |
| 4-chloro-2-cyclohexylphenoxy | 2-(propylthio)pyridin-3-yl | 482 |
| 4-chloro-2-cyclohexylphenoxy | 2-(ethylthio)pyridin-3-yl | 468 |
| 4-chloro-2-cyclohexylphenoxy | 3-bromopyridin-5-yl | 487 |
| 4-chloro-2-cyclohexylphenoxy | 4-methyl-1,2,3-thiadiazol-5-yl | 429 |
| 4-chloro-2-cyclohexylphenoxy | 1-methyl-3-(2-(2-methyl)propyl)pyrazol-5-yl | 467 |
| 4-chloro-2-cyclohexylphenoxy | 3-chlorobenzo[b]thiophen-2-yl | 497 |
| 4-chloro-2-cyclohexylphenoxy | 4-chlorophenyl | 441 |
| 4-chloro-2-cyclohexylphenoxy | 4-methyl-2-phenyl-1,2,3-triazol-5-yl | 488 |
| 4-chloro-2-cyclohexylphenoxy | benzo[b]thiophen-2-yl | 463 |
| 4-chloro-2-cyclohexylphenoxy | 3,4-dimethylphenyl | 435 |
| 4-chloro-2-cyclohexylphenoxy | 2-(phenoxy)pyridin-3-yl | 500 |
| 4-chloro-2-cyclohexylphenoxy | 2-(methylthio)pyridin-3-yl | 454 |
| 4-chloro-2-cyclohexylphenoxy | 5-methyl-3-phenylisoxazol-4-yl | 488 |
| 4-chloro-2-cyclohexylphenoxy | 4-chloro-1,3-dimethyl pyrazolo[3,4-b]pyridin-3-yl | 510 |
| 4-chloro-2-cyclohexylphenoxy | 2-chloro-6-methylpyridin-4-yl | 456 |
| 4-chloro-2-cyclohexylphenoxy | 3,5-dimethylisoxazol-4-yl | 426 |
| 4-chloro-2-cyclohexylphenoxy | 1-naphthyl | 457 |
| 4-chloro-2-cyclohexylphenoxy | 2-fluorophenyl | 425 |
| 4-chloro-2-cyclohexylphenoxy | 4-propylphenyl | 449 |
| 4-chloro-2-cyclohexylphenoxy | 3-fluorophenyl | 425 |
| 4-chloro-2-cyclohexylphenoxy | 2,6-difluorophenyl | 443 |
| 4-chloro-2-cyclohexylphenoxy | 2-chlorophenyl | 441 |
| 4-chloro-2-cyclohexylphenoxy | 3-(chloromethyl)phenyl | 455 |
| 4-chloro-2-cyclohexylphenoxy | 4-(2-(2-methyl)propyl)phenyl | 463 |
| 4-chloro-2-cyclohexylphenoxy | 3-chlorophenyl | 441 |
| 4-chloro-2-cyclohexylphenoxy | 3,5-dimethoxyphenyl | 467 |
| 4-chloro-2-cyclohexylphenoxy | 2,6-dichlorophenyl | 476 |

TABLE 6-continued

| R¹X | R³ | MS (m/z) |
|---|---|---|
| 4-chloro-2-cyclohexylphenoxy | 2,4-dichlorophenyl | 476 |
| 4-chloro-2-cyclohexylphenoxy | 4-fluorophenyl | 425 |
| 4-chloro-2-cyclohexylphenoxy | 4-butylphenyl | 463 |
| 4-chloro-2-cyclohexylphenoxy | 2-methylphenyl | 421 |
| 4-chloro-2-cyclohexylphenoxy | phenyl | 407 |
| 4-chloro-2-cyclohexylphenoxy | 4-ethylphenyl | 435 |
| 4-chloro-2-cyclohexylphenoxy | 2,3-difluorophenyl | 443 |
| 4-chloro-2-cyclohexylphenoxy | 2,6-dimethoxyphenyl | 467 |
| 4-chloro-2-cyclohexylphenoxy | 3,4-difluorophenyl | 443 |
| 4-chloro-2-cyclohexylphenoxy | 2,5-difluorophenyl | 443 |
| 4-chloro-2-cyclohexylphenoxy | 4-ethoxyphenyl | 451 |
| 4-chloro-2-cyclohexylphenoxy | 2,4,6-trichlorophenyl | 510 |
| 4-chloro-2-cyclohexylphenoxy | 3-methylphenyl | 421 |
| 4-chloro-2-cyclohexylphenoxy | 2-fluoro-5-(trifluoromethyl)phenyl | 493 |
| 4-chloro-2-cyclohexylphenoxy | 3-methoxyphenyl | 437 |
| 4-chloro-2-cyclohexylphenoxy | 2-bromophenyl | 486 |
| 4-chloro-2-cyclohexylphenoxy | 4-bromophenyl | 486 |
| 4-chloro-2-cyclohexylphenoxy | 4-fluoro-3-(trifluoromethyl)phenyl | 493 |
| 4-chloro-2-cyclohexylphenoxy | 3-(trifluoromethoxy)phenyl | 491 |
| 4-chloro-2-cyclohexylphenoxy | 9-fluorenon-4-yl | 503 |
| 4-chloro-2-cyclohexylphenoxy | isoxazol-5-yl | 398 |
| 4-chloro-2-cyclohexylphenoxy | benzofuroxan-5-yl | 465 |
| 4-chloro-2-cyclohexylphenoxy | 2-chloropyrid-3-yl | 442 |
| 4-chloro-2-cyclohexylphenoxy | 2-(4-methylphenoxy)pyridin-3-yl | 514 |
| 4-chloro-2-cyclohexylphenoxy | pyridin-4-yl | 408 |
| 4-chloro-2-cyclohexylphenoxy | anthraquinon-2-yl | 537 |
| 4-chloro-2-cyclohexylphenoxy | 2-iodophenyl | 533 |
| 4-chloro-2-cyclohexylphenoxy | 4-pentylphenyl | 477 |
| 4-chloro-2-cyclohexylphenoxy | 2-(4-chlorophenylthio)pyridin-3-yl | 550 |
| 4-chloro-2-cyclohexylphenoxy | 2,6-dimethylphenyl | 435 |
| 4-chloro-2-cyclohexylphenoxy | 2,5-dimethoxyphenyl | 467 |
| 4-chloro-2-cyclohexylphenoxy | 2,5-dichloropyridin-3-yl | 477 |
| 4-chloro-2-cyclohexylphenoxy | 2-chloro-6-methoxypyridin-4-yl | 472 |
| 4-chloro-2-cyclohexylphenoxy | 2,3-dichloropyridin-5-yl | 477 |
| 4-chloro-2-cyclohexylphenoxy | 1-naphthyl | 471 |
| 4-chloro-2-cyclohexylphenoxy | 2,4-dimethoxyphenyl | 467 |
| 4-chloro-2-cyclohexylphenoxy | 3,5-bis(trifluoromethyl)phenyl | 546 |
| 4-chloro-2-cyclohexylphenoxy | 2-(4-chlorophenoxy)pyridin-3-yl | 534 |
| 4-chloro-2-cyclohexylphenoxy | pentafluorophenyl | 497 |
| 4-chloro-3,5-dimethylphenoxy | 3,4-dimethoxyphenyl | 413 |
| 4-chloro-3,5-dimethylphenoxy | 2-(trifluoromethyl-)phenyl | 421 |
| 4-chloro-3,5-dimethylphenoxy | 2,4-difluorophenyl | 389 |
| 4-chloro-3,5-dimethylphenoxy | 3-(trifluoromethyl)phenyl | 421 |
| 4-chloro-3,5-dimethylphenoxy | 2-naphthyl | 403 |
| 4-chloro-3,5-dimethylphenoxy | 2-methoxyphenyl | 484 |
| 4-chloro-3,5-dimethylphenoxy | 3,4,5-trimethylphenyl | 443 |
| 4-chloro-3,5-dimethylphenoxy | 3,4-dichlorophenyl | 422 |
| 4-chloro-3,5-dimethylphenoxy | 3-bromophenyl | 432 |
| 4-chloro-3,5-dimethylphenoxy | 3-pyridyl | 354 |
| 4-chloro-3,5-dimethylphenoxy | 2-ethoxynaphth-1-yl | 447 |
| 4-chloro-3,5-dimethylphenoxy | 2,3-dichlorophenyl | 422 |
| 4-chloro-3,5-dimethylphenoxy | 6-chloropyrid-3-yl | 388 |
| 4-chloro-3,5-dimethylphenoxy | 4-(trifluoromethoxy)phenyl | 437 |
| 4-chloro-3,5-dimethylphenoxy | 2-fluoro-4-(trifluoromethyl)phenyl | 439 |
| 4-chloro-3,5-dimethylphenoxy | 3-bromothienyl | 438 |
| 4-chloro-3,5-dimethylphenoxy | 2-acetoxyphenyl | 411 |
| 4-chloro-3,5-dimethylphenoxy | 5-methylisoxazol-3-yl | 358 |
| 4-chloro-3,5-dimethylphenoxy | 2-(phenylthio)pyrid-3-yl | 462 |
| 4-chloro-3,5-dimethylphenoxy | 2-(trifluoromethoxy)phenyl | 437 |
| 4-chloro-3,5-dimethylphenoxy | 1-phenyl-5-propylpyrazin-4-yl | 461 |
| 4-chloro-3,5-dimethylphenoxy | 2-ethoxyphenyl | 397 |
| 4-chloro-3,5-dimethylphenoxy | 3-chlorothien-2-yl | 393 |
| 4-chloro-3,5-dimethylphenoxy | 1-(2-(2-methyl)propyl)-3-methylpyrazol-5-yl | 413 |
| 4-chloro-3,5-dimethylphenoxy | 3,5-dichlorophenyl | 422 |
| 4-chloro-3,5-dimethylphenoxy | 2-(propylthio)pyridin-3-yl | 428 |
| 4-chloro-3,5-dimethylphenoxy | 2-(ethylthio)pyridin-3-yl | 414 |
| 4-chloro-3,5-dimethylphenoxy | 3-bromopyridin-5-yl | 433 |
| 4-chloro-3,5-dimethylphenoxy | 4-methyl-1,2,3-thiadiazol-5-yl | 375 |
| 4-chloro-3,5-dimethylphenoxy | 1-methyl-3-(2-(2-methyl)propyl)pyrazol-5-yl- | 413 |
| 4-chloro-3,5-dimethylphenoxy | 3-chlorobenzo[b]thiophen-2-yl | 443 |
| 4-chloro-3,5-dimethylphenoxy | 4-chlorophenyl | 387 |
| 4-chloro-3,5-dimethylphenoxy | 4-methyl-2-phenyl-1,2,3-triazol-5-yl | 434 |
| 4-chloro-3,5-dimethylphenoxy | benzo[b]thiophen-2-yl | 409 |
| 4-chloro-3,5-dimethylphenoxy | 3,4-dimethylphenyl | 381 |
| 4-chloro-3,5-dimethylphenoxy | 2-(phenoxy)pyridin-3-yl | 446 |
| 4-chloro-3,5-dimethylphenoxy | 2-(methylthio)pyridin-3-yl | 400 |

TABLE 6-continued

| R¹X | R³ | MS (m/z) |
|---|---|---|
| 4-chloro-3,5-dimethylphenoxy | 5-methyl-3-phenylisoxazol-4-yl | 434 |
| 4-chloro-35-dimethylphenoxy | 4-chloro-1,3-dimethyl pyrazolo[3,4-b]pyridin-3-yl | 456 |
| 4-chloro-3,5-dimethylphenoxy | 2-chloro-6-methylpyridin 4-yl | 402 |
| 4-chloro-3,5-dimethylphenoxy | 3,5-dimethylisoxazol-4-yl | 372 |
| 4-chloro-3,5-dimethylphenoxy | 1-naphthyl | 403 |
| 4-chloro-3,5-dimethylphenoxy | 2-fluorophenyl | 371 |
| 4-chloro-3,5-dimethylphenoxy | 4-propylphenyl | 395 |
| 4-chloro-3,5-dimethylphenoxy | 3-fluorophenyl | 371 |
| 4-chloro-3,5-dimethylphenoxy | 2,6-difluorophenyl | 389 |
| 4-chloro-3,5-dimethylphenoxy | 2-chlorophenyl | 387 |
| 4-chloro-3,5-dimethylphenoxy | 3-(chloromethyl)phenyl | 401 |
| 4-chloro-3,5-dimethylphenoxy | 4-(2-(2-methyl)propyl)phenyl | 409 |
| 4-chloro-3,5-dimethylphenoxy | 3-chlorophenyl | 387 |
| 4-chloro-3,5-dimethylphenoxy | 3,5-dimethoxyphenyl | 413 |
| 4-chloro-3,5-dimethylphenoxy | 2,6-dichlorophenyl | 422 |
| 4-chloro-3,5-dimethylphenoxy | 2,4-dichlorophenyl | 422 |
| 4-chloro-3,5-dimethylphenoxy | 4-fluorophenyl | 371 |
| 4-chloro-3,5-dimethylphenoxy | 4-butylphenyl | 409 |
| 4-chloro-3,5-dimethylphenoxy | 2-methyl-phenyl | 367 |
| 4-chloro-3,5-dimethylphenoxy | phenyl | 353 |
| 4-chloro-3,5-dimethylphenoxy | 4-ethylphenyl | 381 |
| 4-chloro-3,5-dimethylphenoxy | 2,3-difluorophenyl | 389 |
| 4-chloro-3,5-dimethylphenoxy | 2,6-dimethoxyphenyl | 413 |
| 4-chloro-3,5-dimethylphenoxy | 3,4-difluorophenyl | 389 |
| 4-chloro-3,5-dimethylphenoxy | 2,5-difluorophenyl | 389 |
| 4-chloro-3,5-dimethylphenoxy | 4-ethoxyphenyl | 397 |
| 4-chloro-3,5-dimethylphenoxy | 2,4,6-trichlorophenyl | 456 |
| 4-chloro-3,5-dimethylphenoxy | 3-methylphenyl | 367 |
| 4-chloro-3,5-dimethylphenoxy | 2-fluoro-5-(trifluorphenyl)phenyl | 439 |
| 4-chloro-3,5-dimethylphenoxy | 3-methoxyphenyl | 383 |
| 4-chloro-3,5-dimethylphenoxy | 2-bromophenyl | 432 |
| 4-chloro-3,5-dimethylphenoxy | 4-bromophenyl | 432 |
| 4-chloro-3,5-dimethylphenoxy | 4-fluoro-3-(trifluoromethyl-)phenyl | 439 |
| 4-chloro-3,5-dimethyl-phenoxy | 3-(trifluoromethoxy)phenyl | 437 |
| 4-chloro-3,5-dimethylphenoxy | 9-fluorenon-4-yl | 455 |
| 4-chloro-3,5-dimethylphenoxy | isoxazol-5-yl | 344 |
| 4-chloro-3,5-dimethylphenoxy | benzofuroxan-5-yl | 411 |
| 4-chloro-3,5-dimethyl-phenoxy | 2-chloropyrid-3-yl | 388 |
| 4-chloro-3,5-dimethylphenoxy | 2-(4-methylphenoxy)pyridin-3-yl | 460 |
| 4-chloro-3,5-dimethylphenoxy | pyridin-4-yl | 354 |
| 4-chloro-3,5-dimethylphenoxy | anthraquinon-2-yl | 483 |
| 4-chloro-3,5-dimethylphenoxy | 2-iodophenyl | 479 |
| 4-chloro-3,5-dimethylphenoxy | 4-pentylphenyl | 423 |
| 4-chloro-3,5-dimethylphenoxy | 2-(4-chlorophenylthio)pyridin-3-yl | 496 |
| 4-chloro-3,5-dimethylphenoxy | 2,6-dimethylphenyl | 381 |
| 4-chloro-3,5-dimethylphenoxy | 2,5-dimethoxyphenyl | 413 |
| 4-chloro-3,5-dimethylphenoxy | 2,5-dichloropyridin-3-yl | 423 |
| 4-chloro-3,5-dimethylphenoxy | 2-chloro-6-methoxypyridin-4-yl | 418 |
| 4-chloro-3,5-dimethylphenoxy | 2,3-dichloropyridin-5-yl | 423 |
| 4-chloro-3,5-dimethylphenoxy | 1-naphthyl | 417 |
| 4-chloro-3,5-dimethylphenoxy | 2,4-dimethoxyphenyl | 413 |
| 4-chloro-3,5-dimethylphenoxy | 3,5-bis(trifluoromethyl)phenyl | 489 |
| 4-chloro-3,5-dimethylphenoxy | 2-(4-chlorophenoxy)pyridin-3-yl | 480 |
| 4-chloro-3,5-dimethylphenoxy | pentafluorophenyl | 443 |
| pyrid-3-yloxy | 3,4-dimethoxyphenyl | 351 |
| pyrid-3-yloxy | 2-(trifluoromethyl)phenyl | 359 |
| pyrid-3-yloxy | 2,4-difluorophenyl | 327 |
| pyrid-3-yloxy | 3-(trifluoromethyl)phenyl | 359 |
| pyrid-3-yloxy | 2-naphthyl | 341 |
| pyrid-3-yloxy | 2-methoxyphenyl | 321 |
| pyrid-3-yloxy | 3,4,5-trimethylphenyl | 381 |
| pyrid-3-yloxy | 3,4-dichlorophenyl | 360 |
| pyrid-3-yloxy | 3-bromophenyl | 370 |
| pyrid-3-yloxy | 3-pyridyl | 292 |
| pyrid-3-yloxy | 2-ethoxynaphth-1-yl | 385 |
| pyrid-3-yloxy | 2,3-dichlorophenyl | 360 |
| pyrid-3-yloxy | 6-chloropyrid-3-yl | 327 |
| pyrid-3-yloxy | 4-(trifluoromethoxy)phenyl | 375 |
| pyrid-3-yloxy | 2-fluoro-4-(trifluoromethyl)phenyl | 377 |
| pyrid-3-yloxy | 3-bromothienyl | 376 |
| pyrid-3-yloxy | 2-acetoxyphenyl | 349 |
| pyrid-3-yloxy | 5-methylisoxazol-3-yl | 296 |
| pyrid-3-yloxy | 2-(phenylthio)pyrid-3-yl | 400 |
| pyrid-3-yloxy | 2-(trifluoromethoxy)phenyl | 375 |
| pyrid-3-yloxy | 1-phenyl-5-propylpyrazin-4-yl | 399 |
| pyrid-3-yloxy | 2-ethoxyphenyl | 335 |
| pyrid-3-yloxy | 3-chlorothien-2-yl | 332 |
| pyrid-3-yloxy | 1-(2-(2-methyl)propyl)-3-methylpyrazol-5-yl | 351 |
| pyrid-3-yloxy | 3,5-dichlorophenyl | 360 |
| pyrid-3-yloxy | 2-(propylthio)pyridin-3-yl | 366 |
| pyrid-3-yloxy | 2-(ethylthio)pyridin-3-yl | 352 |
| pyrid-3-yloxy | 3-bromopyridin-5-yl | 371 |
| pyrid-3-yloxy | 4-methyl-1,2,3-thiadiazol-5-yl | 313 |
| pyrid-3-yloxy | 1-methyl-3-(2-(2-methyl)propyl)pyrazol-5-yl | 351 |
| pyrid-3-yloxy | 3-chlorobenzo[b]thiophen-2-yl | 382 |
| pyrid-3-yloxy | 4-chlorophenyl | 326 |
| pyrid-3-yloxy | 4-methyl-2-phenyl-1,2,3-triazol-5-yl | 372 |
| pyrid-3-yloxy | benzo[b]thiophen-2-yl | 347 |
| pyrid-3-yloxy | 3,4-dimethylphenyl | 319 |

TABLE 6-continued

| R¹X | R³ | MS (m/z) |
|---|---|---|
| pyrid-3-yloxy | 2-(phenoxy)pyridin-3-yl | 384 |
| pyrid-3-yloxy | 2-(methylthio)pyridin-3-yl | 338 |
| pyrid-3-yloxy | 5-methyl-3-phenylisoxazol-4-yl | 372 |
| pyrid-3-yloxy | 4-chloro-1,3-dimethyl pyrazolo[3,4-b]pyridin-3-yl | 395 |
| pyrid-3-yloxy | 2-chloro-6-methylpyridin-4-yl | 341 |
| pyrid-3-yloxy | 3,5-dimethylisoxazol-4-yl | 310 |
| pyrid-3-yloxy | 1-naphthyl | 341 |
| pyrid-3-yloxy | 2-fluorophenyl | 309 |
| pyrid-3-yloxy | 4-propylphenyl | 333 |
| pyrid-3-yloxy | 3-fluorophenyl | 309 |
| pyrid-3-yloxy | 2,6-difluorophenyl | 327 |
| pyrid-3-yloxy | 2-chlorophenyl | 326 |
| pyrid-3-yloxy | 3-(chloromethyl)phenyl | 340 |
| pyrid-3-yloxy | 4-(2-(2-methyl)propyl)phenyl | 347 |
| pyrid-3-yloxy | 3-chlorophenyl | 326 |
| pyrid-3-yloxy | 3,5-dimethoxyphenyl | 351 |
| pyrid-3-yloxy | 2,6-dichlorophenyl | 360 |
| pyrid-3-yloxy | 2,4-dichlorophenyl | 360 |
| pyrid-3-yloxy | 4-fluorophenyl | 309 |
| pyrid-3-yloxy | 4-butylphenyl | 347 |
| pyrid-3-yloxy | 2-methylphenyl | 305 |
| pyrid-3-yloxy | phenyl | 291 |
| pyrid-3-yloxy | 4-ethylphenyl | 319 |
| pyrid-3-yloxy | 2,3-difluorophenyl | 327 |
| pyrid-3-yloxy | 2,6-dimethoxyphenyl | 351 |
| pyrid-3-yloxy | 3,4-difluorophenyl | 327 |
| pyrid-3-yloxy | 2,5-difluorophenyl | 327 |
| pyrid-3-yloxy | 4-ethoxyphenyl | 335 |
| pyrid-3-yloxy | 2,4,6-trichlorophenyl | 395 |
| pyrid-3-yloxy | 3-methylphenyl | 305 |
| pyrid-3-yloxy | 2-fluoro-5-(trifluoromethyl)phenyl | 377 |
| pyrid-3-yloxy | 3-methoxyphenyl | 321 |
| pyrid-3-yloxy | 2-bromophenyl | 370 |
| pyrid-3-yloxy | 4-bromophenyl | 370 |
| pyrid-3-yloxy | 4-fluoro-3-(trifluoromethyl)phenyl | 377 |
| pyrid-3-yloxy | 3-(trifluoromethoxy)phenyl | 375 |
| pyrid-3-yloxy | 9-fluorenon-4-yl | 393 |
| pyrid-3-yloxy | isoxazol-5-yl | 282 |
| pyrid-3-yloxy | benzofuroxan-5-yl | 349 |
| pyrid-3-yloxy | 2-chloropyrid-3-yl | 327 |
| pyrid-3-yloxy | 2-(4-methylphenoxy)pyridin-3-yl | 398 |
| pyrid-3-yloxy | pyridin-4-yl | 292 |
| pyrid-3-yloxy | anthraquinon-2-yl | 421 |
| pyrid-3-yloxy | 2-iodophenyl | 417 |
| pyrid-3-yloxy | 4-pentylphenyl | 361 |
| pyrid-3-yloxy | 2-(4-chlorophenylthio)pyridin-3-yl | 435 |
| pyrid-3-yloxy | 2,6-dimethylphenyl | 319 |
| pyrid-3-yloxy | 2,5-dimethoxyphenyl | 354 |
| pyrid-3-yloxy | 2,5-dichloropyridin-3-yl- | 361 |
| pyrid-3-yloxy | 2-chloro-6-methoxypyridin-4-yl | 357 |
| pyrid-3-yloxy | 2,3-dichloropyridin-5-yl | 361 |
| pyrid-3-yloxy | 1-naphthyl | 355 |
| pyrid-3-yloxy | 2,4-dimethoxyphenyl | 351 |
| pyrid-3-yloxy | 3,5-bis(trifluoromethyl)phenyl | 427 |
| pyrid-3-yloxy | 2-(4-chlorophenoxy)pyridin-3-yl | 419 |
| pyrid-3-yloxy | pentafluorophenyl | 381 |
| 4-bromophenoxy | 3,4-dimethoxyphenyl | 429 |
| 4-bromophenoxy | 2-(trifluoromethyl)phenyl | 437 |
| 4-bromophenoxy | 2,4-difluorophenyl | 405 |
| 4-bromophenoxy | 3-(trifluoromethyl)phenyl | 437 |
| 4-bromophenoxy | 2-naphthyl | 419 |
| 4-bromophenoxy | 2-methoxyphenyl | 399 |
| 4-bromophenoxy | 3,4,5-trimethylphenyl | 459 |
| 4-bromophenoxy | 3,4-dichlorophenyl | 438 |
| 4-bromophenoxy | 3-bromophenyl | 448 |
| 4-bromophenoxy | 3-pyridyl | 370 |
| 4-bromophenoxy | 2-ethoxynaphth-1-yl | 463 |
| 4-bromophenoxy | 2,3-dichlorophenyl | 438 |
| 4-bromophenoxy | 6-chloropyrid-3-yl | 405 |
| 4-bromophenoxy | 4-(trifluoromethoxy)phenyl | 453 |
| 4-bromophenoxy | 2-fluoro-4-(trifluoromethyl)phenyl | 455 |
| 4-bromophenoxy | 3-bromothienyl | 454 |
| 4-bromophenoxy | 2-acetoxyphenyl | 427 |
| 4-bromophenoxy | 5-methylisoxazol-3-yl | 374 |
| 4-bromophenoxy | 2-(phenylthio)pyrid-3-yl | 478 |
| 4-bromophenoxy | 2-(trifluoromethoxy)phenyl | 453 |
| 4-bromophenoxy | 1-phenyl-5-propylpyrazin-4-yl | 477 |
| 4-bromophenoxy | 2-ethoxyphenyl | 413 |
| 4-bromophenoxy | 3-chlorothien-2-yl | 410 |
| 4-bromophenoxy | 1-(2-(2-methyl)propyl)-3-methylpyrazol-5-yl | 429 |
| 4-bromophenoxy | 3,5-dichlorophenyl | 438 |
| 4-bromophenoxy | 2-(propylthio)pyridin-3-yl | 444 |
| 4-bromophenoxy | 2-(ethylthio)pyridin-3-yl | 430 |
| 4-bromophenoxy | 3-bromopyridin-5-yl | 449 |
| 4-bromophenoxy | 4-methyl-1,2,3-thiadiazol-5-yl | 391 |
| 4-bromophenoxy | 1-methyl-3-(2-(2-methyl)propyl)pyrazol-5-yl | 429 |
| 4-bromophenoxy | 3-chlorobenzo[b]thiophen-2-yl | 460 |
| 4-bromophenoxy | 4-chlorophenyl | 404 |
| 4-bromophenoxy | 4-methyl-2-phenyl-1,2,3-triazol-5-yl | 450 |
| 4-bromophenoxy | benzo[b]thiophen-2-yl | 425 |
| 4-bromophenoxy | 3,4-dimethylphenyl | 397 |
| 4-bromophenoxy | 2-(phenoxy)pyridin-3-yl | 462 |
| 4-bromophenoxy | 2-(methylthio)pyridin-3-yl | 416 |
| 4-bromophenoxy | 5-methyl-3-phenylisoxazol-4-yl | 450 |
| 4-bromophenoxy | 4-chloro-1,3-dimethyl pyrazolo[3,4-b]pyridin-3-yl | 473 |
| 4-bromophenoxy | 2-chloro-6-methylpyridin-4-yl | 419 |
| 4-bromophenoxy | 3,5-dimethylisoxazol-4-yl | 388 |
| 4-bromophenoxy | 1-naphthyl | 419 |
| 4-bromophenoxy | 2-fluorophenyl | 387 |
| 4-bromophenoxy | 4-propylphenyl | 411 |
| 4-bromophenoxy | 3-fluorophenyl | 387 |
| 4-bromophenoxy | 2,6-difluorophenyl | 405 |
| 4-bromophenoxy | 2-chlorophenyl | 414 |
| 4-bromophenoxy | 3-(chloromethyl)phenyl | 418 |
| 4-bromophenoxy | 4-(2-(2-methyl)propyl)phenyl | 425 |
| 4-bromophenoxy | 3-chlorophenyl | 404 |
| 4-bromophenoxy | 3,5-dimethoxyphenyl | 429 |
| 4-bromophenoxy | 2,6-dichlorophenyl | 438 |
| 4-bromophenoxy | 2,4-dichlorophenyl | 438 |
| 4-bromophenoxy | 4-fluorophenyl | 387 |
| 4-bromophenoxy | 4-butylphenyl | 425 |
| 4-bromophenoxy | 2-methylphenyl | 383 |
| 4-bromophenoxy | phenyl | 369 |
| 4-bromophenoxy | 4-ethylphenyl | 397 |
| 4-bromophenoxy | 2,3-difluorophenyl | 405 |
| 4-bromophenoxy | 2,6-dimethoxyphenyl | 429 |
| 4-bromophenoxy | 3,4-difluorophenyl | 405 |
| 4-bromophenoxy | 2,5-difluorophenyl | 405 |
| 4-bromophenoxy | 4-ethoxyphenyl | 413 |
| 4-bromophenoxy | 2,4,6-trichlorophenyl | 473 |
| 4-bromophenoxy | 3-methylphenyl | 383 |
| 4-bromophenoxy | 2-fluoro-5-(trifluoromethyl)phenyl | 455 |
| 4-bromophenoxy | 3-methoxyphenyl | 399 |
| 4-bromophenoxy | 2-bromophenyl | 448 |
| 4-bromophenoxy | 4-bromophenyl | 448 |
| 4-bromophenoxy | 4-fluoro-3-(trifluoromethyl)phenyl | 455 |

TABLE 6-continued

| R¹X | R³ | MS (m/z) |
|---|---|---|
| 4-bromophenoxy | 3-(trifluoromethoxy)phenyl | 453 |
| 4-bromophenoxy | 9-fluorenon-4-yl | 471 |
| 4-bromophenoxy | isoxazol-5-yl | 360 |
| 4-bromophenoxy | benzo furoxan-5-yl | 427 |
| 4-bromophenoxy | 2-chloropyrid-3-yl | 360 |
| 4-bromophenoxy | 2-(4-methylphenoxy)pyridin-3-yl | 476 |
| 4-bromophenoxy | pyridin-4-yl | 370 |
| 4-bromophenoxy | anthraquinon-2-yl | 499 |
| 4-bromophenoxy | 2-iodophenyl | 495 |
| 4-bromophenoxy | 4-pentylphenyl | 439 |
| 4-bromophenoxy | 2-(4-chlorophenylthio)pyridin-3-yl | 513 |
| 4-bromophenoxy | 2,6-dimethylphenyl | 397 |
| 4-bromophenoxy | 2,5-dimethoxyphenyl | 429 |
| 4-bromophenoxy | 2,5-dichloropyridin-3-yl | 439 |
| 4-bromophenoxy | 2-chloro-6-methoxypyridin-4-yl | 435 |
| 4-bromophenoxy | 2,3-dichloropyridin-5-yl | 439 |
| 4-bromophenoxy | 1-naphthyl | 433 |
| 4-bromophenoxy | 2,4-dimethoxyphenyl | 429 |
| 4-bromophenoxy | 3,5-bis(trifluoromethyl)phenyl | 505 |
| 4-bromophenoxy | 2-(4-chlorophenoxy)pyridin-3-yl | 497 |
| 4-bromophenoxy | pentafluorophenyl | 459 |
| 4-chloro-2-methylphenylthio | 4-biphenyl | 431 |
| 4-chloro-2-methylphenylthio | 3,4-dimethoxyphenyl | 415 |
| 4-chloro-2-methylphenylthio | 2-(trifluoromethyl)phenyl | 423 |
| 4-chloro-2-methylphenylthio | 2,4-difluorophenyl | 391 |
| 4-chloro-2-methylphenylthio | 4-cyanophenyl | 380 |
| 4-chloro-2-methylphenylthio | 3-(trifluoromethyl)phenyl | 423 |
| 4-chloro-2-methylphenylthio | 3-cyanophenyl | 380 |
| 4-chloro-2-methylphenylthio | 2-naphthyl | 405 |
| 4-chloro-2-methylphenylthio | 2-methoxyphenyl | 385 |
| 4-chloro-2-methylphenylthio | 3,4,5-trimethylphenyl | 445 |
| 4-chloro-2-methylphenylthio | 4-nitrophenyl | 400 |
| 4-chloro-2-methylphenylthio | 3,4-dichlorophenyl | 424 |
| 4-chloro-2-methylphenylthio | 5-nitrofuran-2-yl | 390 |
| 4-chloro-2-methylphenylthio | 3-bromophenyl | 434 |
| 4-chloro-2-methylphenylthio | 3-pyridyl | 356 |
| 4-chloro-2-methylphenylthio | 2-ethoxynaphth-1-yl | 449 |
| 4-chloro-2-methylphenylthio | 2,3-dichlorophenyl | 424 |
| 4-chloro-2-methylphenylthio | 3-nitrophenyl | 400 |
| 4-chloro-2-methylphenylthio | 6-chloropyrid-3-yl | 390 |
| 4-chloro-2-methylphenylthio | 4-(trifluoromethoxy)phenyl | 439 |
| 4-chloro-2-methylphenylthio | 2-fluoro-4-(trifluoromethyl)phenyl | 441 |
| 4-chloro-2-methylphenylthio | 3-bromothienyl | 440 |
| 4-chloro-2-methylphenylthio | 2-acetoxyphenyl | 413 |
| 4-chloro-2-methylphenylthio | 5-methylisoxazol-3-yl | 360 |
| 4-chloro-2-methylphenyl thio | 2-(phenylthio)pyrid-3-yl | 464 |
| 4-chloro-2-methylphenylthio | 2-(trifluoromethoxy)phenyl | 439 |
| 4-chloro-2-methylphenylthio | 1-phenyl-5-propylpyrazin-4-yl | 463 |
| 4-chloro-2-methylphenylthio | 2-ethoxyphenyl | 399 |
| 4-chloro-2-methylphenylthio | 3-chlorothien-2-yl | 395 |
| 4-chloro-2-methylphenylthio | 1-(2-(2-methyl)propyl)-3-methylpyrazol-5-yl | 415 |
| 4-chloro-2-methylphenylthio | 3,5-dichlorophenyl | 424 |
| 4-chloro-2-methylphenylthio | 2-(propylthio)pyridin-3-yl | 430 |
| 4-chloro-2-methylphenylthio | 2-(ethylthio)pyridin-3-yl | 416 |
| 4-chloro-2-methylphenylthio | 3-bromopyridin-5-yl | 435 |
| 4-chloro-2-methylphenylthio | 4-methyl-1,2,3-thiadiazol-5-yl | 377 |
| 4-chloro-2-methylphenylthio | 1-methyl-3-(2-(2-methyl)propyl)pyrazol-5-yl | 415 |
| 4-chloro-2-methylphenylthio | 3-chlorobenzo[b]thiophen-2-yl | 445 |
| 4-chloro-2-methylphenylthio | 4-chlorophenyl | 389 |
| 4-chloro-2-methylphenylthio | 4-methyl-2-phenyl-1,2,3-triazol-5-yl | 436 |
| 4-chloro-2-methylphenylthio | benzo[b]thiophen-2-yl | 411 |
| 4-chloro-2-methylphenylthio | 3,4-dimethylphenyl | 383 |
| 4-chloro-2-methylphenylthio | 2-(phenoxy)pyridin-3-yl | 448 |
| 4-chloro-2-methylphenylthio | 2-(methylthio)pyridin-3-yl | 402 |
| 4-chloro-2-methylphenylthio | 5-methyl-3-phenylisoxazol-4-yl | 436 |
| 4-chloro-2-methylphenylthio | 4-chloro-1,3-dimethyl pyrazolo[3,4-b]pyridin-3-4-yl | 458 |
| 4-chloro-2-methylphenylthio | 2-chloro-6-methylpyridin-4-yl | 404 |
| 4-chloro-2-methylphenylthio | 3,5-dimethylisoxazol-4-yl | 374 |
| 4-chloro-2-methylphenylthio | 1-naphthyl | 405 |
| 4-chloro-2-methylphenylthio | 2-fluorophenyl | 373 |
| 4-chloro-2-methylphenylthio | 4-propylphenyl | 397 |
| 4-chloro-2-methylphenylthio | 4-(trifluoromethyl)phenyl | 423 |
| 4-chloro-2-methylphenylthio | 3-fluorophenyl | 373 |
| 4-chloro-2-methylphenylthio | 2,6-difluorophenyl | 391 |
| 4-chloro-2-methylphenylthio | 2-chlorophenyl | 389 |
| 4-chloro-2-methylphenylthio | 3-(chloromethyl)phenyl | 403 |
| 4-chloro-2-methylphenylthio | 4-(2-(2-methyl)propyl)phenyl | 411 |
| 4-chloro-2-methylphenylthio | 3-chlorophenyl | 389 |
| 4-chloro-2-methylphenylthio | 2-nitrophenyl | 400 |
| 4-chloro-2-methylphenylthio | 3,5-dimethoxyphenyl | 415 |
| 4-chloro-2-methylphenylthio | 2,6-dichlorophenyl | 424 |
| 4-chloro-2-methylphenylthio | 2,4-dichlorophenyl | 424 |
| 4-chloro-2-methylphenylthio | 4-fluorophenyl | 373 |

TABLE 6-continued

| R¹X | R³ | MS (m/z) |
|---|---|---|
| 4-chloro-2-methylphenylthio | 4-butylphenyl | 411 |
| 4-chloro-2-methylphenylthio | 2-methylphenyl | 369 |
| 4-chloro-2-methylphenylthio | phenyl | 355 |
| 4-chloro-2-methylphenylthio | 4-ethylphenyl | 383 |
| 4-chloro-2-methylphenylthio | 2,3-difluorophenyl | 391 |
| 4-chloro-2-methylphenylthio | 2,6-dimethoxyphenyl | 415 |
| 4-chloro-2-methylphenylthio | 3,4-difluorophenyl | 391 |
| 4-chloro-2-methylphenylthio | 2,5-difluorophenyl | 391 |
| 4-chloro-2-methylphenylthio | 4-ethoxyphenyl | 399 |
| 4-chloro-2-methylphenylthio | 2,4,6-trichlorophenyl | 458 |
| 4-chloro-2-methylphenylthio | 3-methylphenyl | 369 |
| 4-chloro-2-methylphenylthio | 2-fluoro-5-(trifluoromethyl)phenyl | 441 |
| 4-chloro-2-methylphenylthio | 3-methoxyphenyl | 385 |
| 4-chloro-2-methylphenylthio | thien-2-yl | 361 |
| 4-chloro-2-methylphenylthio | 2-bromophenyl | 434 |
| 4-chloro-2-methylphenylthio | 4-bromophenyl | 434 |
| 4-chloro-2-methylphenylthio | 4-fluoro-3-(trifluoromethyl)phenyl | 441 |
| 4-chloro-2-methylphenylthio | 3-(trifluoromethoxy)phenyl | 439 |
| 4-chloro-2-methylphenylthio | 9-fluorenon-4-yl | 457 |
| 4-chloro-2-methylphenylthio | isoxazol-5-yl | 346 |
| 4-chloro-2-methylphenylthio | benzofuroxan-5-yl | 413 |
| 4-chloro-2-methylphenylthio | 2-chloropyrid-3-yl | 390 |
| 4-chloro-2-methylphenylthio | 3,5-difluorophenyl | 391 |
| 4-chloro-2-methylphenylthio | 2-(4-methylphenoxy)pyridin-3-yl | 462 |
| 4-chloro-2-methylphenylthio | pyridin-4-yl | 356 |
| 4-chloro-2-methylphenylthio | anthraquinon-2-yl | 485 |
| 4-chloro-2-methylphenylthio | 2-iodophenyl | 481 |
| 4-chloro-2-methylanilino | 4-biphenyl | 414 |
| 4-chloro-2-methylanilino | 3,4-dimethoxyphenyl | 398 |
| 4-chloro-2-methylanilino | 2-(trifluoromethyl)phenyl | 406 |
| 4-chloro-2-methylanilino | 2,4-difluorophenyl | 374 |
| 4-chloro-2-methylanilino | 4-cyanophenyl | 363 |
| 4-chloro-2-methylanilino | 3-(trifluoromethyl)phenyl | 406 |
| 4-chloro-2-methylanilino | 3-cyanophenyl | 363 |
| 4-chloro-2-methylanilino | 2-naphthyl | 388 |
| 4-chloro-2-methylanilino | 2-methoxyphenyl | 368 |
| 4-chloro-2-methylanilino | 3,4,5-trimethylphenyl | 428 |
| 4-chloro-2-methylanilino | 4-nitrophenyl | 383 |
| 4-chloro-2-methylanilino | 3,4-dichlorophenyl | 407 |
| 4-chloro-2-methylanilino | 5-nitrofuran-2-yl | 373 |
| 4-chloro-2-methylanilino | 3-bromophenyl | 417 |
| 4-chloro-2-methylanilino | 3-pyridyl | 339 |
| 4-chloro-2-methylanilino | 2-ethoxynaphth-1-yl | 432 |
| 4-chloro-2-methylanilino | 2,3-dichlorophenyl | 407 |
| 4-chloro-2-methylanilino | 3-nitrophenyl | 383 |
| 4-chloro-2-methylanilino | 6-chloropyrid-3-yl | 373 |
| 4-chloro-2-methylanilino | 4-(trifluoromethoxy)phenyl | 422 |
| 4-chloro-2-methylanilino | 2-fluoro-4-(trifluoromethyl)phenyl | 424 |
| 4-chloro-2-methylanilino | 3-bromothienyl | 423 |
| 4-chloro-2-methylanilino | 2-acetoxyphenyl | 396 |
| 4-chloro-2-methylanilino | 5-methylisoxazol-3-yl | 343 |
| 4-chloro-2-methylanilino | 2-(phenylthio)pyrid-3-yl | 447 |
| 4-chloro-2-methylanilino | 2-(trifluoromethoxy)phenyl | 422 |
| 4-chloro-2-methylanilino | 1-phenyl-5-propylpyrazin-4-yl | 446 |
| 4-chloro-2-methylanilino | 2-ethoxyphenyl | 382 |
| 4-chloro-2-methylanilino | 3-chlorothien-2-yl | 378 |
| 4-chloro-2-methylanilino | 1-(2-(2-methyl)propyl)-3-methylpyrazol-5-yl | 398 |
| 4-chloro-2-methylanilino | 3,5-dichlorophenyl | 407 |
| 4-chloro-2-methylanilino | 2-(propylthio)pyridin-3-yl | 413 |
| 4-chloro-2-methylanilino | 2-(ethylthio)pyridin-3-yl | 399 |
| 4-chloro-2-methylanilino | 3-bromopyridin-5-yl | 418 |
| 4-chloro-2-methylanilino | 4-methyl-1,2,3-thiadiazol-5-yl | 360 |
| 4-chloro-2-methylanilino | 1-methyl-3-(2-(2-methyl)propyl)pyrazol-5-yl | 398 |
| 4-chloro-2-methylanilino | 3-chlorobenzo[b]thiophen-2-yl | 428 |
| 4-chloro-2-methylanilino | 4-chlorophenyl | 372 |
| 4-chloro-2-methylanilino | 4-methyl-2-phenyl-1,2,3-triazol-5-yl | 419 |
| 4-chloro-2-methylanilino | benzo[b]thiophen-2-yl | 394 |
| 4-chloro-2-methylanilino | 3,4-dimethylphenyl | 366 |
| 4-chloro-2-methylanilino | 2-(phenoxy)pyridin-3-yl | 431 |
| 4-chloro-2-methylanilino | 2-(methylthio)pyridin-3-yl | 385 |
| 4-chloro-2-methylanilino | 5-methyl-3-phenylisoxazol-4-yl | 419 |
| 4-chloro-2-methylanilino | 4-chloro-1,3-dimethylpyrazolo [3,4-b]pyridin-3-yl | 441 |
| 4-chloro-2-methylanilino | 2-chloro-6-methylpyridin-4-yl | 387 |
| 4-chloro-2-methylanilino | 3,5-dimethylisoxazol-4-yl | 357 |
| 4-chloro-2-methylanilino | 1-naphthyl | 388 |
| 4-chloro-2-methylanilino | 2-fluorophenyl | 356 |

TABLE 6-continued

| R¹X | R³ | MS (m/z) |
|---|---|---|
| 4-chloro-2-methylanilino | 4-propylphenyl | 380 |
| 4-chloro-2-methylanilino | 4-(trifluoromethyl)phenyl | 406 |
| 4-chloro-2-methylanilino | 3-fluorophenyl | 356 |
| 4-chloro-2-methylanilino | 2,6-difluorophenyl | 374 |
| 4-chloro-2-methylanilino | 2-chlorophenyl | 372 |
| 4-chloro-2-methylanilino | 3-(chloromethyl)phenyl | 386 |
| 4-chloro-2-methylanilino | 4-(2-(2-methyl)propyl)phenyl | 394 |
| 4-chloro-2-methylanilino | 3-chlorophenyl | 372 |
| 4-chloro-2-methylanilino | 2-nitrophenyl | 383 |
| 4-chloro-2-methylanilino | 3,5-dimethoxyphenyl | 398 |
| 4-chloro-2-methylanilino | 2,6-dichlorophenyl | 407 |
| 4-chloro-2-methylanilino | 2,4-dichlorophenyl | 407 |
| 4-chloro-2-methylanilino | 4-fluorophenyl | 356 |
| 4-chloro-2-methylanilino | 4-butylphenyl | 394 |
| 4-chloro-2-methylanilino | 2-methylphenyl | 352 |
| 4-chloro-2-methylanilino | phenyl | 338 |
| 4-chloro-2-methylanilino | 4-ethylphenyl | 366 |
| 4-chloro-2-methylanilino | 2,3-difluorophenyl | 374 |
| 4-chloro-2-methylanilino | 2,6-dimethoxyphenyl | 398 |
| 4-chloro-2-methylanilino | 3,4-difluorophenyl | 374 |
| 4-chloro-2-methylanilino | 2,5-difluorophenyl | 374 |
| 4-chloro-2-methylanilino | 4-ethoxyphenyl | 382 |
| 4-chloro-2-methylanilino | 2,4,6-trichlorophenyl | 441 |
| 4-chloro-2-methylanilino | 3-methylphenyl | 352 |
| 4-chloro-2-methylanilino | 2-fluoro-5-(trifluoromethyl)phenyl | 424 |
| 4-chloro-2-methylanilino | 3-methoxyphenyl | 368 |
| 4-chloro-2-methylanilino | thien-2-yl | 344 |
| 4-chloro-2-methylanilino | 2-bromophenyl | 417 |
| 4-chloro-2-methylanilino | 4-bromophenyl | 417 |
| 4-chloro-2-methylanilino | 4-fluoro-3-(trifluoromethyl)phenyl | 424 |
| 4-chloro-2-methylanilino | 3-(trifluoromethoxy)phenyl | 422 |
| 4-chloro-2-methylanilino | 9-fluorenon-4-yl | 440 |
| 4-chloro-2-methylanilino | isoxazol-5-yl | 329 |
| 4-chloro-2-methylanilino | benzofuroxan-5-yl | 396 |
| 4-chloro-2-methylanilino | 2-chloropyrid-3-yl | 373 |
| 4-chloro-2-methylanilino | 3,5-difluorophenyl | 374 |
| 4-chloro-2-methylanilino | 2-(4-methylphenoxy)pyridin-3-yl | 445 |
| 4-chloro-2-methylanilino | pyridin-4-yl | 339 |
| 4-chloro-2-methylanilino | anthraquinon-2-yl | 468 |
| 4-chloro-2-methylanilino | 2-iodophenyl | 464 |

The compounds listed in Table 7 can be prepared from substituted 5-aminopyridine compounds and the appropriate acid chloride according to the general procedure above.

TABLE 7

| R¹X | R³ |
|---|---|
| 4-chloro-2-methylphenoxy | 3,4-difluorphenyl |
| 4-chloro-2-methylphenoxy | 4-pentylphenyl |
| 4-chloro-2-methylphenoxy | 2-(4-chlorophenylthio)pyridin-3-yl |
| 4-chloro-2-methylphenoxy | 2,6-dimethylphenyl |
| 4-chloro-2-methylphenoxy | 2,5-dimethoxyphenyl |
| 4-chloro-2-methylphenoxy | 2,5-dichloropyridin-3-yl |
| 4-chloro-2-methylphenoxy | 2-chloro-6-methoxypyridin-4-yl |
| 4-chloro-2-methylphenoxy | 2,3-dichloropyridin-5-yl |
| 4-chloro-2-methylphenoxy | 1-naphthyl |
| 4-chloro-2-methylphenoxy | 2,4-dimethoxyphenyl |
| 4-chloro-2-methylphenoxy | 3,5-bis(trifluoromethyl)phenyl |
| 4-chloro-2-methylphenoxy | 2-(4-chlorophenoxy)pyridin-3-yl |
| 4-chloro-2-methylphenoxy | pentafluorophenyl |
| 1-naphthoxy | 4-pentylphenyl |
| 1-naphthoxy | 2-(4-chlorophenylthio)pyridin-3-yl |
| 1-naphthoxy | 2,6-dimethylphenyl |
| 1-naphthoxy | 2,5-dimethoxyphenyl |
| 1-naphthoxy | 2,5-dichloropyridin-3-yl |
| 1-naphthoxy | 2-chloro-6-methoxypyridin-4-yl |
| 1-naphthoxy | 2,3-dichloropyridin-5-yl |
| 1-naphthoxy | 1-naphthyl |
| 1-naphthoxy | 2,4-dimethoxyphenyl |
| 1-naphthoxy | 3,5-bis(trifluoromethyl)phenyl |
| 1-naphthoxy | 2-(4-chlorophenoxy)pyridin-3-yl |
| 1-naphthoxy | pentafluorophenyl |
| 2-(2-propyl)phenoxy | 4-pentylphenyl |
| 2-(2-propyl)phenoxy | 2-(4-chlorophenylthio)pyridin-3-yl |
| 2-(2-propyl)phenoxy | 2,6-dimethylphenyl |
| 2-(2-propyl)phenoxy | 2,5-dimethoxyphenyl |
| 2-(2-propyl)phenoxy | 2,5-dichloropyridin-3-yl |
| 2-(2-propyl)phenoxy | 2-chloro-6-methoxypyridin-4-yl |
| 2-(2-propyl)phenoxy | 2,3-dichloropyridin-5-yl |
| 2-(2-propyl)phenoxy | 1-naphthyl |
| 2-(2-propyl)phenoxy | 2,4-dimethoxyphenyl |
| 2-(2-propyl)phenoxy | 3,5-bis(trifluoromethyl)phenyl |
| 2-(2-propyl)phenoxy | 2-(4-chlorophenoxy)pyridin-3-yl |
| 2-(2-propyl)phenoxy | pentafluorophenyl |
| 3-fluoro-5-methylphenoxy | 4-pentylphenyl |
| 3-fluoro-5-methylphenoxy | 2-(4-chlorophenylthio)pyridin-3-yl |
| 3-fluoro-5-methylphenoxy | 2,6-dimethylphenyl |
| 3-fluoro-5-methylphenoxy | 2,5-dimethoxyphenyl |
| 3-fluoro-5-methylphenoxy | 2,5-dichloropyridin-3-yl |
| 3-fluoro-5-methylphenoxy | 2-chloro-6-methoxypyridin-4-yl |
| 3-fluoro-5-methylphenoxy | 2,3-dichloropyridin-5-yl |
| 3-fluoro-5-methylphenoxy | 1-naphthyl |

TABLE 7-continued

| R¹X | R³ |
|---|---|
| 3-fluoro-5-methylphenoxy | 2,4-dimethoxyphenyl |
| 3-fluoro-5-methylphenoxy | 3,5-bis(trifluoromethyl)phenyl |
| 3-fluoro-5-methylphenoxy | 2-(4-chlorophenoxy)pyridin-3-yl |
| 3-fluoro-5-methylphenoxy | pentafluorophenyl |
| 2-methylpyrid-3-yloxy | 4-pentylphenyl |
| 2-methylpyrid-3-yloxy | 2-(4-chlorophenylthio)pyridin-3-yl |
| 2-methylpyrid-3-yloxy | 2,6-dimethylphenyl |
| 2-methylpyrid-3-yloxy | 2,5-dimethoxyphenyl |
| 2-methylpyrid-3-yloxy | 2,5-dichloropyridin-3-yl |
| 2-methylpyrid-3-yloxy | 2-chloro-6-methoxypyridin-4-yl |
| 2-methylpyrid-3-yloxy | 2,3-dichloropyridin-5-yl |
| 2-methylpyrid-3-yloxy | 1-naphthyl |
| 2-methylpyrid-3-yloxy | 2,4-dimethoxyphenyl |
| 2-methylpyrid-3-yloxy | 3,5-bis(trifluoromethyl)phenyl |
| 2-methylpyrid-3-yloxy | 2-(4-chlorophenoxy)pyridin-3-yl |
| 2-methylpyrid-3-yloxy | pentafluorophenyl |
| 4-methoxyphenoxy | 4-biphenyl |
| 4-methoxyphenoxy | 4-cyanophenyl |
| 4-methoxyphenoxy | 3-cyanophenyl |
| 4-methoxyphenoxy | 4-nitrophenyl |
| 4-methoxyphenoxy | 5-nitrofuran-2-yl |
| 4-methoxyphenoxy | 3-nitrophenyl |
| 4-methoxyphenoxy | 4-(trifluoromethyl)phenyl |
| 4-methoxyphenoxy | 2-nitrophenyl |
| 4-methoxyphenoxy | thien-2-yl |
| 2-(2-propoxy)phenoxy | 4-biphenyl |
| 2-(2-propoxy)phenoxy | 4-cyanophenyl |
| 2-(2-propoxy)phenoxy | 3-cyanophenyl |
| 2-(2-propoxy)phenoxy | 4-nitrophenyl |
| 2-(2-propoxy)phenoxy | 5-nitrofuran-2-yl |
| 2-(2-propoxy)phenoxy | 3-nitrophenyl |
| 2-(2-propoxy)phenoxy | 2-nitrophenyl |
| 2-(2-propoxy)phenoxy | thien-2-yl |
| 2-(2-propoxy)phenoxy | 3,5-difluorophenyl |
| 4-fluorophenoxy | 4-biphenyl |
| 4-fluorophenoxy | 4-cyanophenyl |
| 4-fluorophenoxy | 3-cyanophenyl |
| 4-fluorophenoxy | 4-nitrophenyl |
| 4-fluorophenoxy | 5-nitrofuran-2-yl |
| 4-fluorophenoxy | 3-nitrophenyl |
| 4-fluorophenoxy | 2-nitrophenyl |
| 4-fluorophenoxy | 4-(trifluoromethyl)phenyl |
| 4-fluorophenoxy | thien-2-yl |
| 4-fluorophenoxy | 3,5-difluorophenyl |
| 4-chlorophenoxy | 4-biphenyl |
| 4-chlorophenoxy | 4-cyanophenyl |
| 4-chlorophenoxy | 3-cyanophenyl |
| 4-chlorophenoxy | 4-nitrophenyl |
| 4-chlorophenoxy | 5-nitrofuran-2-yl |
| 4-chlorophenoxy | 3-nitrophenyl |
| 4-chlorophenoxy | 2-nitrophenyl |
| 4-chlorophenoxy | 4-(trifluoromethyl)phenyl |
| 4-chlorophenoxy | thien-2-yl |
| 4-chlorophenoxy | 3,5-difluorophenyl |
| 2,4-difluorophenoxy | 4-biphenyl |
| 2,4-difluorophenoxy | 4-cyanophenyl |
| 2,4-difluorophenoxy | 3-cyanophenyl |
| 2,4-difluorophenoxy | 4-nitrophenyl |
| 2,4-difluorophenoxy | 5-nitrofuran-2-yl |
| 2,4-difluorophenoxy | 3-nitrophenyl |
| 2,4-difluorophenoxy | 4-(trifluoromethyl)phenyl |
| 2,4-difluorophenoxy | 2-nitrophenyl |
| 4-chloro-2,5-dimethylphenoxy | 4-biphenyl |
| 4-chloro-2,5-dimethylphenoxy | 4-cyanophenyl |
| 4-chloro-2,5-dimethylphenoxy | 3-cyanophenyl |
| 4-chloro-2,5-dimethylphenoxy | 4-nitrophenyl |
| 4-chloro-2,5-dimethylphenoxy | 5-nitrofuran-2-yl |
| 4-chloro-2,5-dimethylphenoxy | 3-nitrophenyl |
| 4-chloro-2,5-dimethylphenoxy | 4-(trifluoromethyl)phenyl |
| 4-chloro-2,5-dimethylphenoxy | 2-nitrophenyl |
| 4-chloro-2,5-dimethylphenoxy | thien-2-yl |
| 4-chloro-2,5-dimethylphenoxy | 3,5-difluorophenyl |
| 4-methoxyphenoxy | 3,5-difluorophenyl |
| 2-(2-propoxy)phenoxy | 4-(trifluoromethyl)phenyl |
| 2,4-difluorophenoxy | thien-2-yl |
| 2,4-difluorophenoxy | 3,5-difluorophenyl |
| 4-thiomethylphenoxy | 4-biphenyl |
| 4-thiomethylphenoxy | 4-cyanophenyl |
| 4-thiomethylphenoxy | 3-cyanophenyl |
| 4-thiomethylphenoxy | 4-nitrophenyl |
| 4-thiomethylphenoxy | 5-nitrofuran-2-yl |
| 4-thiomethylphenoxy | 3-nitrophenyl |
| 4-thiomethylphenoxy | 4-(trifluoromethyl)phenyl |
| 4-thiomethylphenoxy | 2-nitrophenyl |
| 4-thiomethylphenoxy | thien-2-yl |
| 4-thiomethylphenoxy | 3,5-difluorophenyl |
| 4-(2-(2-methyl)propyl)phenoxy | 4-biphenyl |
| 4-(2-(2-methyl)propyl)phenoxy | 4-cyanophenyl |
| 4-(2-(2-methyl)propyl)phenoxy | 3-cyanophenyl |
| 4-(2-(2-methyl)propyl)phenoxy | 4-nitrophenyl |
| 4-(2-(2-methyl)propyl)phenoxy | 5-nitrofuran-2-yl |
| 4-(2-(2-methyl)propyl)phenoxy | 3-nitrophenyl |
| 4-(2-(2-methyl)propyl)phenoxy | 4-(trifluoromethyl)phenyl |
| 4-(2-(2-methyl)propyl)phenoxy | 2-nitrophenyl |
| 4-(2-(2-methyl)propyl)phenoxy | thien-2-yl |
| 4-(2-(2-methyl)propyl)phenoxy | 3,5-difluorophenyl |
| 2,3-dimethylphenoxy | 4-biphenyl |
| 2,3-dimethylphenoxy | 4-cyanophenyl |
| 2,3-dimethylphenoxy | 3-cyanophenyl |
| 2,3-dimethylphenoxy | 4-nitrophenyl |
| 2,3-dimethylphenoxy | 5-nitrofuran-2-yl |
| 2,3-dimethylphenoxy | 3-nitrophenyl |
| 2,3-dimethylphenoxy | 4-(trifluoromethyl)phenyl |
| 2,3-dimethylphenoxy | 2-nitrophenyl |
| 2,3-dimethylphenoxy | thien-2-yl |
| 2,3-dimethylphenoxy | 3,5-difluorophenyl |
| 3,5-(bis-2-propyl)phenoxy | 4-biphenyl |
| 3,5-(bis-2-propyl)phenoxy | 4-cyanophenyl |
| 3,5-(bis-2-propyl)phenoxy | 3-cyanophenyl |
| 3,5-(bis-2-propyl)phenoxy | 4-nitrophenyl |
| 3,5-(bis-2-propyl)phenoxy | 5-nitrofuran-2-yl |
| 3,5-(bis-2-propyl)phenoxy | 3-nitrophenyl |
| 3,5-(bis-2-propyl)phenoxy | 4-(trifluoromethyl)phenyl |
| 3,5-(bis-2-propyl)phenoxy | 2-nitrophenyl |
| 3,5-(bis-2-propyl)phenoxy | thien-2-yl |
| 3,5-(bis-2-propyl)phenoxy | 3,5-difluorophenyl |
| 3-trifluoromethyl phenoxy | 4-biphenyl |
| 3-trifluoromethyl phenoxy | 4-cyanophenyl |
| 3-trifluoromethyl phenoxy | 3-cyanophenyl |
| 3-trifluoromethyl phenoxy | 4-nitrophenyl |
| 3-trifluoromethyl phenoxy | 5-nitrofuran-2-yl |
| 3-trifluoromethyl phenoxy | 3-nitrophenyl |
| 3-trifluoromethyl phenoxy | 4-(trifluoromethyl)phenyl |
| 3-trifluoromethyl phenoxy | 2-nitrophenyl |
| 3-trifluoromethyl phenoxy | thien-2-yl |
| 3-trifluoromethyl phenoxy | 3,5-difluorophenyl |
| 2,6-dichlorophenoxy | 4-biphenyl |
| 2,6-dichlorophenoxy | 4-cyanophenyl |

TABLE 7-continued

| R¹X | R³ |
|---|---|
| 2,6-dichlorophenoxy | 3-cyanophenyl |
| 2,6-dichlorophenoxy | 4-nitrophenyl |
| 2,6-dichlorophenoxy | 5-nitrofuran-2-yl |
| 2,6-dichlorophenoxy | 3-nitrophenyl |
| 2,6-dichlorophenoxy | 4-(trifluoromethyl)phenyl |
| 2,6-dichlorophenoxy | 2-nitrophenyl |
| 2,6-dichlorophenoxy | thien-2-yl |
| 2,6-dichlorophenoxy | 3,5-difluorophenyl |
| 2,4-dichlorophenoxy | 4-biphenyl |
| 2,4-dichlorophenoxy | 4-cyanophenyl |
| 2,4-dichlorophenoxy | 3-cyanophenyl |
| 2,4-dichlorophenoxy | 4-nitrophenyl |
| 2,4-dichlorophenoxy | 5-nitrofuran-2-yl |
| 2,4-dichlorophenoxy | 3-nitrophenyl |
| 2,4-dichlorophenoxy | 4-(trifluoromethyl)phenyl |
| 2,4-dichlorophenoxy | 2-nitrophenyl |
| 2,4-dichlorophenoxy | thien-2-yl |
| 2,4-dichlorophenoxy | 3,5-difluorophenyl |
| 4-chloro-3-methylphenoxy | 4-biphenyl |
| 4-chloro-3-methylphenoxy | 4-cyanophenyl |
| 4-chloro-3-methylphenoxy | 3-cyanophenyl |
| 4-chloro-3-methylphenoxy | 4-nitrophenyl |
| 4-chloro-3-methylphenoxy | 5-nitrofuran-2-yl |
| 4-chloro-3-methylphenoxy | 3-nitrophenyl |
| 4-chloro-3-methylphenoxy | 2-nitrophenyl |
| 4-chloro-3-methylphenoxy | thien-2-yl |
| 4-chloro-3-methylphenoxy | 3,5-difluorophenyl |
| 4-chloro-2-cyclohexylphenoxy | 4-biphenyl |
| 4-chloro-2-cyclohexylphenoxy | 4-cyanophenyl |
| 4-chloro-2-cyclohexylphenoxy | 3-cyanophenyl |
| 4-chloro-2-cyclohexylphenoxy | 4-nitrophenyl |
| 4-chloro-2-cyclohexylphenoxy | 5-nitrofuran-2-yl |
| 4-chloro-2-cyclohexylphenoxy | 3-nitrophenyl |
| 4-chloro-2-cyclohexylphenoxy | 4-(trifluoromethyl)phenyl |
| 4-chloro-2-cyclohexylphenoxy | 2-nitrophenyl |
| 4-chloro-2-cyclohexylphenoxy | thien-2-yl |
| 4-chloro-2-cyclohexylphenoxy | 3,5-difluorophenyl |
| 4-chloro-3,5-dimethylphenoxy | 4-biphenyl |
| 4-chloro-3,5-dimethylphenoxy | 4-cyanophenyl |
| 4-chloro-3,5-dimethylphenoxy | 3-cyanophenyl |
| 4-chloro-3,5-dimethylphenoxy | 4-nitrophenyl |
| 4-chloro-3,5-dimethylphenoxy | 5-nitrofuran-2-yl |
| 4-chloro-3,5-dimethylphenoxy | 3-nitrophenyl |
| 4-chloro-3,5-dimethylphenoxy | 4-(trifluoromethyl)phenyl |
| 4-chloro-3,5-dimethylphenoxy | 2-nitrophenyl |
| 4-chloro-3,5-dimethylphenoxy | thien-2-yl |
| 4-chloro-3,5-dimethylphenoxy | 3,5-difluorophenyl |
| pyrid-3-yloxy | 4-biphenyl |
| pyrid-3-yloxy | 4-cyanophenyl |
| pyrid-3-yloxy | 3-cyanophenyl |
| pyrid-3-yloxy | 4-nitrophenyl |
| pyrid-3-yloxy | 5-nitrofuran-2-yl |
| pyrid-3-yloxy | 3-nitrophenyl |
| pyrid-3-yloxy | 4-(trifluoromethyl)phenyl |
| pyrid-3-yloxy | 2-nitrophenyl |
| pyrid-3-yloxy | thien-2-yl |
| pyrid-3-yloxy | 3,5-difluorophenyl |
| 4-bromophenoxy | 4-biphenyl |
| 4-bromophenoxy | 4-cyanophenyl |
| 4-bromophenoxy | 3-cyanophenyl |
| 4-bromophenoxy | 4-nitrophenyl |
| 4-bromophenoxy | 5-nitrofuran-2-yl |
| 4-bromophenoxy | 3-nitrophenyl |
| 4-bromophenoxy | 4-(trifluoromethyl)phenyl |
| 4-bromophenoxy | 2-nitrophenyl |
| 4-bromophenoxy | thien-2-yl |
| 4-bromophenoxy | 3,5-difluorophenyl |
| 4-chloro-2-methylphenylthio | 4-pentylphenyl |
| 4-chloro-2-methylphenylthio | 2-(4-chlorophenylthio)pyridin-3-yl |
| 4-chloro-2-methylphenylthio | 2,6-dimethylphenyl |
| 4-chloro-2-methylphenylthio | 2,5-dimethoxyphenyl |
| 4-chloro-2-methylphenylthio | 2,5-dichloropyridin-3-yl |
| 4-chloro-2-methylphenylthio | 2-chloro-6-methoxypyridin-4-yl |
| 4-chloro-2-methylphenylthio | 2,3-dichloropyridin-5-yl |
| 4-chloro-2-methylphenylthio | 1-naphthyl |
| 4-chloro-2-methylphenylthio | 2,4-dimethoxyphenyl |
| 4-chloro-2-methylphenylthio | 3,5-bis(trifluoromethyl)phenyl |
| 4-chloro-2-methylphenylthio | 2-(4-chlorophenoxy)pyridin-3-yl |
| 4-chloro-2-methylphenylthio | pentafluorophenyl |
| 4-chloro-2-methylanilino | 4-pentylphenyl |
| 4-chloro-2-methylanilino | 2-(4-chlorophenylthio)pyridin-3-yl |
| 4-chloro-2-methylanilino | 2,6-dimethylphenyl |
| 4-chloro-2-methylanilino | 2,5-dimethoxyphenyl |
| 4-chloro-2-methylanilino | 2,5-dichloropyridin-3-yl |
| 4-chloro-2-methylanilino | 2-chloro-6-methoxypyridin-4-yl |
| 4-chloro-2-methylanilino | 2,3-dichloropyridin-5-yl |
| 4-chloro-2-methylanilino | 1-naphthyl |
| 4-chloro-2-methylanilino | 2,4-dimethoxyphenyl |
| 4-chloro-2-methylanilino | 3,5-bis(trifluoromethyl)phenyl |
| 4-chloro-2-methylanilino | 2-(4-chlorophenoxy)pyridin-3-yl |
| 4-chloro-2-methylanilino | pentafluorophenyl |

EXAMPLE 19

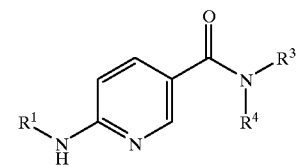

General procedure for the synthesis of 6-(substituted-amino)-N-substituted nicotinamides Step A. General procedure for the preparation of 6-chloro-N-substituted nicotinamide:

To a suspension of 6-chloronicotinoyl chloride (1.76 g, 10.0 mmol) in dry dichloromethane (10 mL) was added the amine ($R^3R^4NH$) (10.0 mmol) followed by the dropwise addition of triethylamine (1.7 mL, 12.2 mmol). After stirring for 40 min. at room temperature, the mixture was diluted with dichloromethane, washed with aqueous 1 M hydrochloric acid, saturated aqueous sodium hydrogencarbonate and water, dried over sodium sulfate and concentrated to dryness under reduce pressure to afford the desired nicotinamide.

The following compounds were prepared according to this procedure using the appropriate substituted amine:

6-Chloro-N-o-tolylnicotinamide: MS (m/z): 247/249 (M+H)⁺; $C_{13}H_{11}Cl_1N_2O_1$ requires 246.5.
6-Chloro-N-(2-fluorophenyl)nicotinamide: MS (m/z): 251/253 (M+H)⁺; $C_{12}H_8Cl_1F_1N_2O_1$ requires 250.7.
6-Chloro-N-(2,6-dimethylphenyl)nicotinamide: MS (m/z): 261/263 (M+H)⁺; $C_{14}H_{13}Cl_1N_2O_1$ requires 260.7.
6-Chloro-N-(2-phenoxyphenyl)nicotinamide: MS (m/z): 325/327 (M+H)⁺; $C_{18}H_{13}ClN_2O_1$ requires 324.8.
6-Chloro-N-phenylnicotinamide: MS (m/z): 233/235 (M+H)⁺; $C_{12}H_8ClN_2O_1$ requires 232.7.
6-Chloro-N-(2,4-difluorophenyl)nicotinamide: MS (m/z): 269/271 (M+H)⁺; $C_{12}H_7Cl_1F_2N_2O_1$ requires 2:68.6.
6-Chloro-N-(2,6-diisopropylphenyl)nicotinamide: MS (m/z): 317/319 (M+H)⁺; $C_{18}H_{21}Cl_1N_2O_1$ requires 316.8.
6-Chloro-N-(4-chlorophenyl)-N-methylnicotinamide: MS (m/z): 281/283 (M+H)⁺; $C_{13}H_{10}Cl_2N_2O_1$ requires 281.1.
6-Chloro-N-(2,4-dimethoxyphenyl)nicotinamide: MS (m/z): 293/295 (M+H)⁺; $C_{14}H_{13}Cl_1N_2O_3$ requires 292.7.
6-Chloro-N-(3-methoxyphenyl)nicotinamide: MS (m/z): 263/265 (M+H)⁺; $C_{13}H_{11}Cl_1N_2O_2$ requires 262.7.
6-Chloro-N-(4-methoxyphenyl)nicotinamide: MS (m/z): 263/265 (M+H)⁺; $C_{13}H_{11}Cl_1N_2O_2$ requires 262.7.
6-Chloro-N-(2-methoxyphenyl)nicotinamide: MS (m/z): 263/265 (M+H)⁺; $C_{13}H_{11}Cl_1N_2O_2$ requires 262.7.
6-Chloro-N-methyl-N-phenylnicotinamide: MS (m/z): 247/249 (M+H)⁺; $C_{13}H_{11}Cl_1N_2O_1$ requires 246.7.
N-Benzyl-6-chloronicotinamide: MS (m/z): 247/249 (M+H)⁺; $C_{13}H_{11}Cl_1N_2O_1$ requires 246.7.

Step B. General procedure for the preparation of 6-(substituted-amino)-N-substituted nicotinamides A mixture of the 6-chloro-N-substituted nicotinamide (12.5 mmol) and amine ($R^1NH_2$ or $R^1NHCH_3$) (20 mmol) in ethylene glycol (50 mL) or pyridine (alkylamines) (50 mL) was heated to 140° C. for 20 hours. After cooling to room temperature, the mixture was diluted with dichloromethane/methanol (9:1, 250 mL) and filtered through a plug of silica gel, washing with additional dichloromethane/methanol (9:1, 250 mL). Concentration under reduced pressure afforded the desired 6-(substituted-amino)-N-substituted nicotinamide.

The compounds listed in Tables 8–11 were prepared from 6-chloro-N-substituted nicotinamides compounds and the appropriate amine according to the general procedure above.

TABLE 8

| R³ | R¹ | MS (m/z) |
|---|---|---|
| o-tolyl | phenyl | 303 |
| o-tolyl | o-tolyl | 317 |
| o-tolyl | 4-chloro-2-methylphenyl | 352 |
| o-tolyl | 2-fluorophenyl | 321 |
| o-tolyl | 3-fluorophenyl | 321 |

TABLE 8-continued

| R³ | R¹ | MS (m/z) |
|---|---|---|
| o-tolyl | 4-fluorophenyl | 321 |
| o-tolyl | 2,4-difluorophenyl | 339 |
| o-tolyl | 2-methoxyphenyl | 333 |
| o-tolyl | 3-methoxyphenyl | 333 |
| o-tolyl | 4-methoxyphenyl | 333 |
| o-tolyl | 2,4-dimethoxyphenyl | 363 |
| o-tolyl | 2-phenoxyphenyl | 395 |
| o-tolyl | 3-phenoxyphenyl | 395 |
| o-tolyl | 4-phenoxyphenyl | 395 |
| o-tolyl | 4-biphenyl | 379 |
| o-tolyl | 4-benzylphenyl | 393 |
| o-tolyl | 4-(trifluoromethoxy)phenyl | 387 |
| o-tolyl | cyclohexyl | 309 |
| o-tolyl | 2-methylcyclohexyl | 323 |
| o-tolyl | cycloheptyl | 323 |
| o-tolyl | indan-1-yl | 343 |
| o-tolyl | 2-dicyclohexyl | 492 |
| 2-fluorophenyl | phenyl | 307 |
| 2-fluorophenyl | o-tolyl | 321 |
| 2-fluorophenyl | 4-chloro-2-methylphenyl | 356 |
| 2-fluorophenyl | 2-fluorophenyl | 325 |
| 2-fluorophenyl | 3-fluorophenyl | 325 |
| 2-fluorophenyl | 4-fluorophenyl | 325 |
| 2-fluorophenyl | 2,4-difluorophenyl | 343 |
| 2-fluorophenyl | 2-methoxyphenyl | 337 |
| 2-fluorophenyl | 3-methoxyphenyl | 337 |
| 2-fluorophenyl | 4-methoxyphenyl | 337 |
| 2-fluorophenyl | 2,4-dimethoxyphenyl | 367 |
| 2-fluorophenyl | 2-phenoxyphenyl | 399 |
| 2-fluorophenyl | 3-phenoxyphenyl | 399 |
| 2-fluorophenyl | 4-phenoxyphenyl | 399 |
| 2-fluorophenyl | 4-biphenyl | 383 |
| 2-fluorophenyl | 4-benzylphenyl | 397 |
| 2-fluorophenyl | 4-(trifluoromethoxy)phenyl | 391 |
| 2-fluorophenyl | cyclohexyl | 313 |
| 2-fluorophenyl | 2-methylcyclohexyl | 327 |
| 2-fluorophenyl | cycloheptyl | 327 |
| 2-fluorophenyl | indan-1-yl | 347 |
| 2-fluorophenyl | 2-dicyclohexyl | 395 |
| 2,6-dimethylphenyl | phenyl | 317 |
| 2,6-dimethylphenyl | o-tolyl | 331 |
| 2,6-dimethylphenyl | 4-chloro-2-methylphenyl | 366 |
| 2,6-dimethylphenyl | 2-fluorophenyl | 335 |
| 2,6-dimethylphenyl | 3-fluorophenyl | 335 |
| 2,6-dimethylphenyl | 4-fluorophenyl | 335 |
| 2,6-dimethylphenyl | 2,4-difluorophenyl | 353 |
| 2,6-dimethylphenyl | 2-methoxyphenyl | 347 |
| 2,6-dimethylphenyl | 3-methoxyphenyl | 347 |
| 2,6-dimethylphenyl | 4-methoxyphenyl | 347 |
| 2,6-dimethylphenyl | 2,4-dimethoxyphenyl | 377 |
| 2,6-dimethylphenyl | 2-phenoxyphenyl | 409 |
| 2,6-dimethylphenyl | 3-phenoxyphenyl | 409 |
| 2,6-dimethylphenyl | 4-phenoxyphenyl | 409 |
| 2,6-dimethylphenyl | 4-biphenyl | 393 |
| 2,6-dimethylphenyl | 4-benzylphenyl | 407 |
| 2,6-dimethylphenyl | 4-(trifluoromethoxy)phenyl | 401 |
| 2,6-dimethylphenyl | cyclohexyl | 323 |
| 2,6-dimethylphenyl | 2-methylcyclohexyl | 337 |
| 2,6-dimethylphenyl | cycloheptyl | 667 |
| 2,6-dimethylphenyl | indan-1-yl | 357 |
| 2,6-dimethylphenyl | 2-dicyclohexyl | 406 |
| 2-phenoxyphenyl | phenyl | 381 |
| 2-phenoxyphenyl | o-tolyl | 395 |
| 2-phenoxyphenyl | 4-chloro-2-methylphenyl | 430 |
| 2-phenoxyphenyl | 2-fluorophenyl | 399 |
| 2-phenoxyphenyl | 3-fluorophenyl | 399 |

TABLE 8-continued

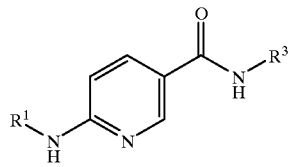

| R³ | R¹ | MS (m/z) |
|---|---|---|
| 2-phenoxyphenyl | 4-fluorophenyl | 399 |
| 2-phenoxyphenyl | 2,4-difluorophenyl | 417 |
| 2-phenoxyphenyl | 2-methoxyphenyl | 411 |
| 2-phenoxyphenyl | 3-methoxyphenyl | 411 |
| 2-phenoxyphenyl | 4-methoxyphenyl | 411 |
| 2-phenoxyphenyl | 2,4-dimethoxyphenyl | 441 |
| 2-phenoxyphenyl | 2-phenoxyphenyl | 473 |
| 2-phenoxyphenyl | 3-phenoxyphenyl | 473 |
| 2-phenoxyphenyl | 4-phenoxyphenyl | 473 |
| 2-phenoxyphenyl | 4-biphenyl | 457 |
| 2-phenoxyphenyl | 4-benzylphenyl | 472 |
| 2-phenoxyphenyl | 4-(trifluoromethoxy)phenyl | 465 |
| 2-phenoxyphenyl | cyclohexyl | 387 |
| 2-phenoxyphenyl | 2-methylcyclohexyl | 401 |
| 2-phenoxyphenyl | cycloheptyl | 401 |
| 2-phenoxyphenyl | indan-1-yl | 421 |
| 2-phenoxyphenyl | 2-cyclohexyl | 470 |
| phenyl | phenyl | 289 |
| phenyl | o-tolyl | 303 |
| phenyl | 4-chloro-2-methylphenyl | 338 |
| phenyl | 2-fluorophenyl | 307 |
| phenyl | 3-fluorophenyl | 307 |
| phenyl | 4-fluorophenyl | 307 |
| phenyl | 2,4-difluorophenyl | 325 |
| phenyl | 2-methoxyphenyl | 319 |
| phenyl | 3-methoxyphenyl | 319 |
| phenyl | 4-methoxyphenyl | 319 |
| phenyl | 2,4-dimethoxyphenyl | 349 |
| phenyl | 2-phenoxyphenyl | 381 |
| phenyl | 3-phenoxyphenyl | 381 |
| phenyl | 4-phenoxyphenyl | 381 |
| phenyl | 4-biphenyl | 365 |
| phenyl | 4-benzylphenyl | 379 |
| phenyl | 4-(trifluoromethoxy)phenyl | 373 |
| phenyl | cyclohexyl | 295 |
| phenyl | 2-methylcyclohexyl | 309 |
| phenyl | cycloheptyl | 309 |
| phenyl | indan-1-yl | 329 |
| phenyl | 2-dicyclohexyl | 377 |
| 2,4-difluorophenyl | phenyl | 325 |
| 2,4-difluorophenyl | o-tolyl | 339 |
| 2,4-difluorophenyl | 4-chloro-2-methylphenyl | 374 |
| 2,4-difluorophenyl | 2-fluorophenyl | 343 |
| 2,4-difluorophenyl | 3-fluorophenyl | 343 |
| 2,4-difluorophenyl | 4-fluorophenyl | 343 |
| 2,4-difluorophenyl | 2,4-difluorophenyl | 361 |
| 2,4-difluorophenyl | 2-methoxyphenyl | 355 |
| 2,4-difluorophenyl | 3-methoxyphenyl | 355 |
| 2,4-difluorophenyl | 4-methoxyphenyl | 355 |
| 2,4-difluorophenyl | 2,4-dimethoxyphenyl | 385 |
| 2,4-difluorophenyl | 2-phenoxyphenyl | 417 |
| 2,4-difluorophenyl | 3-phenoxyphenyl | 417 |
| 2,4-difluorophenyl | 4-phenoxyphenyl | 417 |
| 2,4-difluorophenyl | 4-biphenyl | 401 |
| 2,4-difluorophenyl | 4-benzylphenyl | 415 |
| 2,4-difluorophenyl | 4-(trifluoromethoxy)phenyl | 409 |
| 2,4-difluorophenyl | cyclohexyl | 331 |
| 2,4-difluorophenyl | 2-methylcyclohexyl | 345 |
| 2,4-difluorophenyl | cycloheptyl | 345 |
| 2,4-difluorophenyl | indan-1-yl | 365 |
| 2,4-difluorophenyl | 2-dicyclohexyl | 413 |
| 2,6-diisopropylphenyl | phenyl | 373 |
| 2,6-diisopropylphenyl | o-tolyl | 387 |
| 2,6-diisopropylphenyl | 4-chloro-2-methylphenyl | 422 |
| 2,6-diisopropylphenyl | 2-fluorophenyl | 391 |
| 2,6-diisopropylphenyl | 3-fluorophenyl | 391 |

TABLE 8-continued

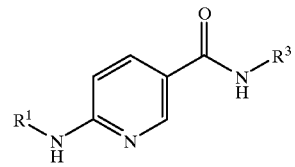

| R³ | R¹ | MS (m/z) |
|---|---|---|
| 2,6-diisopropylphenyl | 4-fluorophenyl | 391 |
| 2,6-diisopropylphenyl | 2,4-difluorophenyl | 409 |
| 2,6-diisopropylphenyl | 2-methoxyphenyl | 403 |
| 2,6-diisopropylphenyl | 3-methoxyphenyl | 403 |
| 2,6-diisopropylphenyl | 4-methoxyphenyl | 403 |
| 2,6-diisopropylphenyl | 2,4-dimethoxyphenyl | 434 |
| 2,6-diisopropylphenyl | 2-phenoxyphenyl | 466 |
| 2,6-diisopropylphenyl | 3-phenoxyphenyl | 466 |
| 2,6-diisopropylphenyl | 4-phenoxyphenyl | 466 |
| 2,6-diisopropylphenyl | 4-biphenyl | 450 |
| 2,6-diisopropylphenyl | 4-benzylphenyl | 464 |
| 2,6-diisopropylphenyl | 4-(trifluoromethoxy)phenyl | 457 |
| 2,6-diisopropylphenyl | cyclohexyl | 380 |
| 2,6-diisopropylphenyl | 2-methylcyclohexyl | 394 |
| 2,6-diisopropylphenyl | cycloheptyl | 394 |
| 2,6-diisopropylphenyl | indan-1-yl | 414 |
| 2,6-diisopropylphenyl | 2-dicyclohexyl | 462 |
| 2,4-dimethoxyphenyl | phenyl | 349 |
| 2,4-dimethoxyphenyl | o-tolyl | 363 |
| 2,4-dimethoxyphenyl | 4-chloro-2-methylphenyl | 398 |
| 2,4-dimethoxyphenyl | 2-fluorophenyl | 367 |
| 2,4-dimethoxyphenyl | 3-fluorophenyl | 367 |
| 2,4-dimethoxyphenyl | 4-fluorophenyl | 367 |
| 2,4-dimethoxyphenyl | 2,4-difluorophenyl | 385 |
| 2,4-dimethoxyphenyl | 2-methoxyphenyl | 379 |
| 2,4-dimethoxyphenyl | 3-methoxyphenyl | 379 |
| 2,4-dimethoxyphenyl | 4-methoxyphenyl | 379 |
| 2,4-dimethoxyphenyl | 2,4-dimethoxyphenyl | 409 |
| 2,4-dimethoxyphenyl | 2-phenoxyphenyl | 441 |
| 2,4-dimethoxyphenyl | 3-phenoxyphenyl | 441 |
| 2,4-dimethoxyphenyl | 4-phenoxyphenyl | 441 |
| 2,4-dimethoxyphenyl | 4-biphenyl | 425 |
| 2,4-dimethoxyphenyl | 4-benzylphenyl | 439 |
| 2,4-dimethoxyphenyl | 4-(trifluoromethoxy)phenyl | 433 |
| 2,4-dimethoxyphenyl | 3-trifluoromethylphenyl | 417 |
| 2,4-dimethoxyphenyl | cyclohexyl | 355 |
| 2,4-dimethoxyphenyl | 2-methylcyclohexyl | 369 |
| 3-methoxyphenyl | phenyl | 319 |
| 3-methoxyphenyl | o-tolyl | 333 |
| 3-methoxyphenyl | 4-chloro-2-methylphenyl | 368 |
| 3-methoxyphenyl | 2-fluorophenyl | 337 |
| 3-methoxyphenyl | 3-fluorophenyl | 337 |
| 3-methoxyphenyl | 4-fluorophenyl | 337 |
| 3-methoxyphenyl | 2,4-difluorophenyl | 355 |
| 3-methoxyphenyl | 2-methoxyphenyl | 349 |
| 3-methoxyphenyl | 3-methoxyphenyl | 349 |
| 3-methoxyphenyl | 4-methoxyphenyl | 349 |
| 3-methoxyphenyl | 2,4-dimethoxyphenyl | 379 |
| 3-methoxyphenyl | 2-phenoxyphenyl | 411 |
| 3-methoxyphenyl | 3-phenoxyphenyl | 411 |
| 3-methoxyphenyl | 4-phenoxyphenyl | 411 |
| 3-methoxyphenyl | 4-biphenyl | 395 |
| 3-methoxyphenyl | 4-benzylphenyl | 409 |
| 3-methoxyphenyl | 4-(trifluoromethoxy)phenyl | 403 |
| 3-methoxyphenyl | 3-trifluoromethylphenyl | 387 |
| 3-methoxyphenyl | cyclohexyl | 625 |
| 3-methoxyphenyl | 2-methylcyclohexyl | 339 |
| 4-methoxyphenyl | phenyl | 319 |
| 4-methoxyphenyl | o-tolyl | 333 |
| 4-methoxyphenyl | 4-chloro-2-methylphenyl | 368 |
| 4-methoxyphenyl | 2-fluorophenyl | 337 |
| 4-methoxyphenyl | 3-fluorophenyl | 337 |
| 4-methoxyphenyl | 4-fluorophenyl | 337 |
| 4-methoxyphenyl | 2,4-difluorophenyl | 355 |
| 4-methoxyphenyl | 2-methoxyphenyl | 349 |
| 4-methoxyphenyl | 3-methoxyphenyl | 349 |

TABLE 8-continued

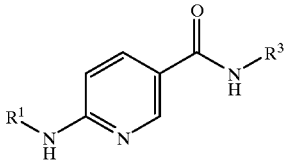

| R³ | R¹ | MS (m/z) |
|---|---|---|
| 4-methoxyphenyl | 4-methoxyphenyl | 349 |
| 4-methoxyphenyl | 2,4-dimethoxyphenyl | 379 |
| 4-methoxyphenyl | 2-phenoxyphenyl | 411 |
| 4-methoxyphenyl | 3-phenoxyphenyl | 411 |
| 4-methoxyphenyl | 4-phenoxyphenyl | 411 |
| 4-methoxyphenyl | 4-biphenyl | 395 |
| 4-methoxyphenyl | 4-benzylphenyl | 409 |
| 4-methoxyphenyl | 4-(trifluoromethoxy)phenyl | 403 |
| 4-methoxyphenyl | 3-trifluoromethylphenyl | 387 |
| 4-methoxyphenyl | cyclohexyl | 625 |
| 4-methoxyphenyl | 2-methylcyclohexyl | 339 |
| 2-methoxyphenyl | phenyl | 319 |
| 2-methoxyphenyl | o-tolyl | 333 |
| 2-methoxyphenyl | 4-chloro-2-methylphenyl | 368 |
| 2-methoxyphenyl | 2-fluorophenyl | 337 |
| 2-methoxyphenyl | 3-fluorophenyl | 337 |
| 2-methoxyphenyl | 4-fluorophenyl | 337 |
| 2-methoxyphenyl | 2,4-difluorophenyl | 355 |
| 2-methoxyphenyl | 2-methoxyphenyl | 349 |
| 2-methoxyphenyl | 3-methoxyphenyl | 349 |
| 2-methoxyphenyl | 4-methoxyphenyl | 349 |
| 2-methoxyphenyl | 2,4-dimethoxyphenyl | 379 |
| 2-methoxyphenyl | 2-phenoxyphenyl | 411 |
| 2-methoxyphenyl | 3-phenoxyphenyl | 411 |
| 2-methoxyphenyl | 4-phenoxyphenyl | 411 |
| 2-methoxyphenyl | 4-biphenyl | 395 |
| 2-methoxyphenyl | 4-benzylphenyl | 409 |
| 2-methoxyphenyl | 4-(trifluoromethoxy)phenyl | 403 |
| 2-methoxyphenyl | 3-trifluoromethylphenyl | 387 |
| 2-methoxyphenyl | cyclohexyl | 625 |
| 2-methoxyphenyl | 2-methylcyclohexyl | 339 |

TABLE 9

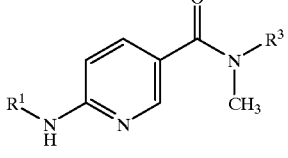

| R³ | R¹ | MS (m/z) |
|---|---|---|
| 4-chlorophenyl | phenyl | 338 |
| 4-chlorophenyl | o-tolyl | 352 |
| 4-chlorophenyl | 4-chloro-2-methylphenyl | 386 |
| 4-chlorophenyl | 2-fluorophenyl | 356 |
| 4-chlorophenyl | 3-fluorophenyl | 356 |
| 4-chlorophenyl | 4-fluorophenyl | 356 |
| 4-chlorophenyl | 2,4-difluorophenyl | 374 |
| 4-chlorophenyl | 2-methoxyphenyl | 368 |
| 4-chlorophenyl | 3-methoxyphenyl | 368 |
| 4-chlorophenyl | 4-methoxyphenyl | 368 |
| 4-chlorophenyl | 2,4-dimethoxyphenyl | 398 |
| 4-chlorophenyl | 2-phenoxyphenyl | 430 |
| 4-chlorophenyl | 3-phenoxyphenyl | 430 |
| 4-chlorophenyl | 4-phenoxyphenyl | 430 |
| 4-chlorophenyl | 4-biphenyl | 414 |
| 4-chlorophenyl | 4-benzylphenyl | 428 |
| 4-chlorophenyl | 4-(trifluoromethoxy)phenyl | 422 |
| 4-chlorophenyl | cyclohexyl | 344 |

TABLE 9-continued

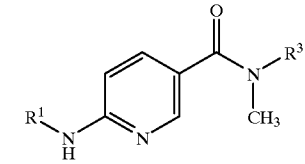

| R³ | R¹ | MS (m/z) |
|---|---|---|
| 4-chlorophenyl | 2-methylcyclohexyl | 358 |
| phenyl | phenyl | 303 |
| phenyl | o-tolyl | 317 |
| phenyl | 4-chloro-2-methylphenyl | 352 |
| phenyl | 2-fluorophenyl | 321 |
| phenyl | 3-fluorophenyl | 321 |
| phenyl | 4-fluorophenyl | 321 |
| phenyl | 2,4-difluorophenyl | 339 |
| phenyl | 2-methoxyphenyl | 333 |
| phenyl | 3-methoxyphenyl | 333 |
| phenyl | 4-methoxyphenyl | 333 |
| phenyl | 2,4-dimethoxyphenyl | 363 |
| phenyl | 2-phenoxyphenyl | 395 |
| phenyl | 3-phenoxyphenyl | 395 |
| phenyl | 4-phenoxyphenyl | 395 |
| phenyl | 4-biphenyl | 379 |
| phenyl | 4-benzylphenyl | 393 |
| phenyl | 4-(trifluoromethoxy)phenyl | 387 |
| phenyl | 3-trifluoromethylphenyl | 371 |
| phenyl | cyclohexyl | 309 |
| phenyl | 2-methylcyclohexyl | 323 |

TABLE 10

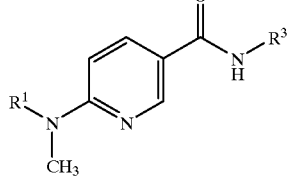

| R³ | R¹ | MS (m/z) |
|---|---|---|
| o-tolyl | N-methylphenyl | 317 |
| o-tolyl | 4-chloro-N-methylphenyl | 352 |
| o-tolyl | N-methylcyclohexyl | 323 |
| 2-fluorophenyl | N-methylphenyl | 321 |
| 2-fluorophenyl | 4-chloro-N-methylphenyl | 356 |
| 2-fluorophenyl | N-methylcyclohexyl | 327 |
| 2,6-dimethylphenyl | N-methylphenyl | 331 |
| 2,6-dimethylphenyl | 4-chloro-N-methylphenyl | 366 |
| 2,6-dimethylphenyl | N-methylcyclohexyl | 337 |
| 2-phenoxyphenyl | N-methylphenyl | 395 |
| 2-phenoxyphenyl | 4-chloro-N-methylphenyl | 430 |
| 2-phenoxyphenyl | N-methylcyclohexyl | 401 |
| phenyl | N-methylphenyl | 303 |
| phenyl | 4-chloro-N-methylphenyl | 338 |
| phenyl | N-methylcyclohexyl | 309 |
| 2,4-difluorophenyl | N-methylphenyl | 339 |
| 2,4-difluorophenyl | 4-chloro-N-methylphenyl | 374 |
| 2,4-difluorophenyl | N-methylcyclohexyl | 345 |
| 2,6-diisopropylphenyl | N-methylphenyl | 387 |
| 2,6-diisopropylphenyl | 4-chloro-N-methylphenyl | 422 |
| 2,6-diisopropylphenyl | N-methylcyclohexyl | 394 |
| 2,4-dimethoxyphenyl | N-methylphenyl | 363 |
| 2,4-dimethoxyphenyl | 4-chloro-N-methylphenyl | 398 |
| 2,4-dimethoxyphenyl | N-methylcyclohexyl | 369 |
| 3-methoxyphenyl | N-methylphenyl | 333 |
| 3-methoxyphenyl | 4-chloro-N-methylphenyl | 368 |
| 3-methoxyphenyl | N-methylcyclohexyl | 339 |

TABLE 10-continued

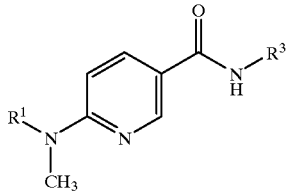

| R³ | R¹ | MS (m/z) |
|---|---|---|
| 4-methoxyphenyl | N-methylphenyl | 333 |
| 4-methoxyphenyl | 4-chloro-N-methylphenyl | 368 |
| 4-methoxyphenyl | N-methylcyclohexyl | 339 |
| 2-methoxyphenyl | N-methylphenyl | 333 |
| 2-methoxyphenyl | 4-chloro-N-methylphenyl | 368 |
| 2-methoxyphenyl | N-methylcyclohexyl | 339 |

TABLE 11

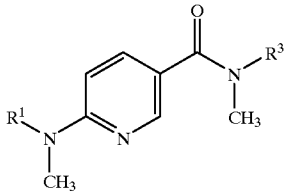

| R³ | R¹ | MS (m/z) |
|---|---|---|
| 4-chlorophenyl | phenyl | 352 |
| 4-chlorophenyl | 4-chlorophenyl | 386 |
| 4-chlorophenyl | cyclohexyl | 358 |
| phenyl | phenyl | 317 |
| phenyl | 4-chlorophenyl | 352 |
| phenyl | cyclohexyl | 323 |

The compounds listed in Tables 12–13 can be prepared from 6-chloro-N-substituted nicotinamides compounds and the appropriate amine according to the general procedure above.

TABLE 12

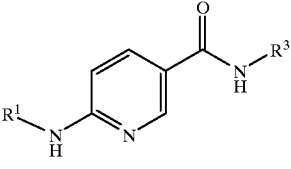

| R¹X | R³ |
|---|---|
| o-tolyl | 3-trifluoromethylphenyl |
| 2-fluorophenyl | 3-trifluoromethylphenyl |
| 2,6-dimethylphenyl | 3-trifluoromethylphenyl |
| 2-phenoxyphenyl | 3-trifluoromethylphenyl |
| phenyl | 3-trifluoromethylphenyl |
| 2,4-difluorophenyl | 3-trifluoromethylphenyl |
| 2,6-diisopropylphenyl | 3-trifluoromethylphenyl |
| 2,4-dimethoxyphenyl | cycloheptyl |
| 2,4-dimethoxyphenyl | indan-1-yl |
| 2,4-dimethoxyphenyl | 2-dicyclohexyl |
| 3-methoxyphenyl | cycloheptyl |
| 3-methoxyphenyl | indan-1-yl |
| 3-methoxyphenyl | 2-dicyclohexyl |

TABLE 12-continued

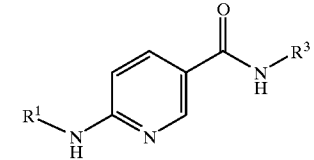

| R¹X | R³ |
|---|---|
| 4-methoxyphenyl | cyclohexyl |
| 4-methoxyphenyl | indan-1-yl |
| 4-methoxyphenyl | 2-dicyclohexyl |
| 2-methoxyphenyl | cycloheptyl |
| 2-methoxyphenyl | indan-1-yl |
| 2-methoxyphenyl | 2-dicyclohexyl |

TABLE 13

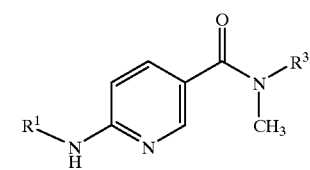

| R¹X | R³ |
|---|---|
| 4-chlorophenyl | 3-trifluoromethylphenyl |
| 4-chlorophenyl | cycloheptyl |
| 4-chlorophenyl | indan-1-yl |
| 4-chlorophenyl | 2-dicyclohexyl |
| phenyl | cycloheptyl |
| phenyl | indan-1-yl |
| phenyl | 2-dicyclohexyl |

EXAMPLE 20

The following assays were used to characterize the ability of compounds of the invention to inhibit the production of TNF-α and IL-1-β. The second assay measured the inhibition of TNF-α and/or IL-1-β in mice after oral administration of the test compounds. The third assay, a glucagon binding inhibition in vitro assay, can be used to characterize the ability of compounds of the invention to inhibit glucagon binding. The fourth assay, a Cyclooxygenase enzyme (COX-1 and COX-2) inhibition activity in vitro assay, can be used to characterize the ability of compounds of the invention to inhibit COX-1 and/or COX-2. The fifth assay, a Raf-kinase inhibition assay, can be used to characterize the compounds of the invention to inhibit phosphorylation of MEK by activated Raf-kinase.

Lipopolysaccharide-activated monocyte TNF production assay

Isolation of monocytes

Test compounds were evaluated in vitro for the ability to inhibit the production of tumor necrosis factor (TNF) by monocytes activated with bacterial lipopolysaccharide (LPS). Fresh residual source leukocytes (a byproduct of plateletpheresis) were obtained from a local blood bank, and peripheral blood mononuclear cells (PBMCs) were isolated by density gradient centrifugation on Ficol-Paque Plus (Pharmacia). PBMCs were suspended at $2 \times 10^6$/ml in DMEM supplemented to contain 2% FCS, 10 mM, 0.3 mg/ml glutamate, 100 U/ml penicillin G and 100 mg/ml streptomycin sulfate (complete media). Cells were plated into Falcon flat bottom, 96 well culture plates (200 µl/well) and cultured overnight at 37° C. and 6% $CO_2$. Non-adherent cells were removed by washing with 200 µl/well of fresh medium. Wells containing adherent cells (~70% monocytes) were replenished with 100 µl of fresh medium.

Preparation of test compound stock solutions

Test compounds were dissolved in DMSO. Compound stock solutions were prepared to an initial concentration of 10–50 µM. Stocks were diluted initially to 20–200 µM in complete media. Nine two-fold serial dilutions of each compound were then prepared in complete medium.

Treatment of cells with test compounds and activation of TNF production with lipopolysaccharide One hundred microliters of each test compound dilution were added to microtiter wells containing adherent monocytes and 100 µl complete medium. Monocytes were cultured with test compounds for 60 min at which time 25 µl of complete medium containing 30 ng/ml lipopolysaccharide from *E. coli* K532 were added to each well. Cells were cultured an additional 4 hrs. Culture supernatants were then removed and TNF presence in the supernatants was quantified using an ELISA.

TNF ELISA

Flat bottom, 96 well Corning High Binding ELISA plates were coated overnight (4° C.) with 150 µL/well of 3 µg/ml murine anti-human TNF-α MAb (R&D Systems #MAB210). Wells were then blocked for 1 hr at room temperature with 200 µL/well of $CaCl_2$-free ELISA buffer supplemented to contain 20 mg/ml BSA (standard ELISA buffer: 20 mM, 150 mM NaCl, 2 mM $CaCl_2$, 0.15 mM thimerosal, pH 7.4). Plates were washed and replenished with 100 µl of test supernatants (diluted 1:3) or standards. Standards consisted of eleven 1.5-fold serial dilutions from a stock of 1 ng/ml recombinant human TNF (R&D Systems). Plates were incubated at room temperature for 1 hr on orbital shaker (300 rpm), washed and replenished with 100 µl/well of 0.5 µg/ml goat anti-human TNF-α (R&D systems #AB-210-NA) biotinylated at a 4:1 ratio. Plates were incubated for 40 min, washed and replenished with 100 µl/well of alkaline phosphatase-conjugated streptavidin (Jackson ImmunoResearch #016-050-084) at 0.02 µg/ml. Plates were incubated 30 min, washed and replenished with 200 µl/well of 1 mg/ml of p-nitrophenyl phosphate. After 30 min, plates were read at 405 nm on a $V_{max}$ plate reader.

Data analysis

Standard curve data were fit to a second order polynomial and unknown TNF-α concentrations determined from their OD by solving this equation for concentration. TNF concentrations were then plotted vs. test compound concentration using a second order polynomial. This equation was then used to calculate the concentration of test compounds causing a 50% reduction in TNF production.

The following compounds had an $IC_{50}$ of less than 15 µM:
2-cyclohexyloxy-5-(2-chlorophenylcarbonylamino) pyridine;
2-cyclohexyloxy-5-(2-methylphenylcarbonylamino) pyridine;
2-cyclohexyloxy-5-(2,6-dichlorophenylcarbonylamino) pyridine;
2-cyclohexyloxy-5-(2,6-dimethylphenylcarbonylamino) pyridine;
2-(2,4-dimethylphenoxy)-5-(2-methylphenylcarbonylamino) pyridine;
2-(2-methyl-4-fluorophenoxy)-5-(2-methylphenylcarbonylamino)pyridine;
2-(2-methyl-4-chlorophenoxy)-5-(2-chlorophenylcarbonylamino)pyridine;
2-(2-methyl-4-chlorophenoxy)-5-(2,6-dichlorophenylcarbonylamino)pyridine;
2-(2-methyl-4-chlorophenoxy)-5-(2,6-dimethylphenylcarbonylamino)pyridine;
2-(4-chlorophenoxy)-5-(2,6-dimethylphenylcarbonylamino) pyridine;
2-(2-methyl-4-fluorophenoxy)-5-(2,6-dichlorophenylcarbonylamino)pyridine;
2-(2-methyl-4-fluorophenoxy)-5-(2,6-dimethylphenylcarbonylamino)pyridine;
2-(2-methyl-4-fluorophenoxy)-5-(2-fluorophenylcarbonylamino)pyridine;
2-(2,4-dimethylphenoxy)-5-(2,6-dimethylphenylcarbonylamino)pyridine;
2-(l-naphthyloxy)-5-(2-methylphenylcarbonylamino) pyridine;
2-(1-naphthyloxy)-5-(2,6-dichlorophenylcarbonylamino) pyridine;
2-(2-methyl-3-pyridyloxy)-5-(2,6-dichlorophenylcarbonylamino)pyridine;
2-(2-methyl-4-chlorophenoxy)-5-((3,5-dimethyl-4-isoxazolyl)carbonylamino)pyridine;
2-cyclohexylamino-5-(2,6-dichlorophenylcarbonylamino) pyridine;
2-cyclohexylamino-5-(2,6-dimethylphenylcarbonylamino) pyridine;
2-(2-methylcyclohexylamino)-5-(2,6-dichlorophenylcarbonylamino)pyridine;
2-(2-methylcyclohexylamino)-5-(2-methylphenylcarbonylamino)pyridine;
2-(2-methylphenylamino)-5-(2-methylphenylcarbonylamino)pyridine;
2-(2-methylphenylamino)-5-(2,6-dimethylphenylcarbonylamino)pyridine;
2-(2-methyl-4-chlorophenylamino)-5-(2-methylphenylcarbonylamino)pyridine; and
2-(2-methyl-4-chlorophenylamino)-5-(2-methylphenylaminocarbonyl)pyridine.

Compounds of the invention can also be shown to inhibit LPS-induced release of IL-1β, IL-6 and/or IL-8 from monocytes by measuring concentrations of IL-1β, IL-6 and/or IL-8 by methods well known to those skilled in the art. In a similar manner to the above described assay involving the LPS induced release of TNF-α from monocytes, compounds of this invention can also be shown to inhibit LPS induced release of IL-1β, IL-6 and/or IL-8 from monocytes by measuring concentrations of IL-1β, IL-6 and/or IL-8 by methods well known to those skilled in the art. Thus, the compounds of the invention may lower elevated levels of TNF-α, IL-1, IL-6, and IL-8 levels. Reducing elevated levels of these inflammatory cytokines to basal levels or below is favorable in controlling, slowing progression, and alleviating many disease states. All of the compounds are useful in the methods of treating disease states in which TNF-A, IL-1β, IL-6, and IL-8 play a role to the full extent of the definition of TNF-α-mediated diseases described herein.

Inhibition of LPS-Induced TNF-α production in mice

Male DBA/1LACJ mice are dosed with vehicle or test compounds in a vehicle (the vehicle consisting of 0.5% tragacanth in 0.03 N HCl) 30 minutes prior to lipopolysaccharide (2 mg/kg, I.V.) injection. Ninety minutes after LPS injection, blood are collected and the serum is analyzed by ELISA for TNF levels.

Selected compounds from the class have shown in vivo activity in a LPS mouse model in which serum levels of TNF-α were reduced in the presence of compounds of this invention.

Compounds of the invention may be shown to have anti-inflammatory properties in animal models of inflammation, including carageenan paw edema, collagen induced arthritis and adjuvant arthritis, such as the carageenan paw edema model (C. A. Winter et al Proc. Soc. Exp. Biol. Med. (1962) vol 111, p 544; K. F. Swingle, in R. A. Scherrer and M. W. Whitehouse, Eds., Antiinflammatory Agents, Chemistry and Pharmacology, Vol. 13-II, Academic, New York, 1974, p. 33) and collagen induced arthritis (D. E. Trentham et al J. Exp. Med. (1977) vol. 146, p 857; J. S. Courtenay, Nature (New Biol.) (1980), Vol 283, p 666).

$^{125}$I-Glucagon Binding Screen with CHO/hGLUR Cells

The assay is described in WO 97/16442, which is incorporated herein by reference in its entirety.

Reagents

The reagents can be prepared as follows: (a) prepare fresh 1M o-Phenanthroline (Aldrich) (198.2 mg/ml ethanol); (b) prepare fresh 0.5M DTT (Sigma); (c) Protease Inhibitor Mix (1000×): 5 mg leupeptin, 10 mg benzamidine, 40 mg bacitracin and 5 mg soybean trypsin inhibitor per ml DMSO and store aliquots at −20° C.; (d) 250 μm human glucagon (Peninsula): solubilize 0.5 mg vial in 575 μl 0.1N acetic acid (1 μl yields 1 μM final concentration in assay for non-specific binding) and store in aliquots at −20° C.; (e) Assay Buffer: 20 mM Tris (pH 7.8), 1 mM DTT and 3 mM o-phenanthroline; (f) Assay Buffer with 0.1% BSA (for dilution of label only; 0.01% final in assay): 10 μl 10% BSA (heat-inactivated) and 990 μl Assay Buffer; (g) $^{125}$I-Glucagon (NEN, receptor-grade, 2200 Ci/mmol): dilute to 50,000 cpm/25 μl in assay buffer with BSA (about 50 pM final concentration in assay).

Harvesting of CHO/hGLUR Cells for Assay

1. Remove media from confluent flask then rinse once each with PBS (Ca, Mg-free) and Enzyme-free Dissociation Fluid (Specialty Media, Inc.).
2. Add 10 ml Enzyme-free Dissoc. Fluid and hold for about 4 min. at 37° C.
3. Gently tap cells free, triturate, take aliquot for counting and centrifuge remainder for 5 min. at 1000 rpm.
4. Resuspend pellet in Assay Buffer at 75000 cells per 100 μl.

Membrane preparations of CHO/hGLUR cells can be used in place of whole cells at the same assay volume. Final protein concentration of a membrane preparation is determined on a per batch basis.

Assay

The determination of inhibition of glucagon binding can be carried out by measuring the reduction of I$^{125}$-glucagon binding in the presence of compounds of Formula I. The reagents are combined in 120 μL of assay buffer as follows:

|  | Compound/Vehicle | 250 μM Glucagon | $^{125}$I-Glucagon | CHO/hGLUR Cells |
|---|---|---|---|---|
| Total Binding | —/5 μl | — | 25 μl | 100 μl |
| + Compound | 5 μl/— | — | 25 μl | 100 μl |
| Nonspecific Binding | —/5 μl | 1 μl | 25 μl | 100 μl |

The mixture is incubated for 60 min. at 22° C. on a shaker at 275 rpm. The mixture is filtered over pre-soaked (0.5% polyethylimine (PEI)) GF/C filtermat using an Innotech Harvester or Tomtec Harvester with four washes of ice-cold 20 mM Tris buffer (pH 7.8). The radioactivity in the filters is determined by a gamma-scintillation counter.

Thus, compounds of the invention may also be shown to inhibit the binding of glucagon to glucagon receptors.

Cyclooxygenase Enzyme Activity Assay

The human monocytic leukemia cell line, THP-1, differentiated by exposure to phorbol esters expresses only COX-1; the human osteosarcoma cell line 143B expresses predominantly COX-2. THP-1 cells are routinely cultured in RPMI complete media supplemented with 10% FBS and human osteosarcoma cells (HOSC) are cultured in minimal essential media supplemented with 10% fetal bovine serum (MEM-10%FBS); all cell incubations are at 37° C. in a humidified environment containing 5% $CO_2$.

COX-1 Assay

In preparation for the COX-1 assay, THP-1 cells are grown to confluency, split 1:3 into RPMI containing 2% FBS and 10 mM phorbol 12-myristate 13-acetate (TPA), and incubated for 48 hours on a shaker to prevent attachment. Cells are pelleted and resuspended in Hank's Buffered Saline (HBS) at a concentration of $2.5 \times 10^6$ cells/mL and plated in 96-well culture plates at a density of $5 \times 10^5$ cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at $3 \times 10^6$ cells/mL in MEM-FBS containing 1 ng human IL-1b/mL, plated in 96-well tissue culture plates at a density of $3 \times 10^4$ cells per well, incubated on a shaker for 1 hour to evenly distribute cells, followed by an additional 2 hour static incubation to allow attachment. The media is then replaced with MEM containing 2% FBS (MEM-2%FBS) and 1 ng human IL-1b/mL, and the cells incubated for 18–22 hours. Following replacement of media with 190 mL MEM, 10 mL of test compound diluted in HBS is added to achieve the desired concentration and the cells incubated for 4 hours. The supernatants are removed and replaced with MEM containing 30 mM arachidonic acid, the cells incubated for 20 minutes at 37° C., and enzyme activity determined as described below.

COX Activity Determined

After incubation with arachidonic acid, the reactions are stopped by the addition of 1 N HCl, followed by neutralization with 1 N NaOH and centrifugation to pellet cell debris. Cyclooxygenase enzyme activity in both HOSC and THP-1 cell supernatants is determined by measuring the concentration of $PGE_2$ using a commercially available ELISA (Neogen #404110). A standard curve of $PGE_2$ is used for calibration, and commercially available COX-1 and COX-2 inhibitors are included as standard controls.

The following compound exhibits activities in the Cyclooxygenase assay with $IC_{50}$ values of 10 μM or less: 2-(2,4-dimethylphenylamino)-5-(2,6-dichlorophenylcarbonyl amino)pyridine.

Raf Kinase assay

In vitro Raf kinase activity is measured by the extent of phosphorylation of the substrate MEK (Map kinase/ERK kinase) by activated Raf kinase. Phosphorylated MEK is trapped on a filter and incorporation of radiolabeled phosphate is quantified by scintillation counting.

MATERIALS:

Activated Raf is produced by triple transfection of Sf9 cells with baculoviruses expressing "Glu-Glu"-epitope tagged Raf,val$^{12}$-H-Ras, and Lck. The "Glu-Glu"-epitope, Glu-Try-Met-Pro-Met-Glu, was fused to the carboxy-terminus of full length c-Raf.

Catalytically inactive MEK (K97A mutation) is produced in Sf9 cells transfected with a baculovirus expressing c-terminus "Glu-Glu" epitope-tagged K97A MEK1.

Anti "Glu-Glu" antibody was purified from cells grown as described in: Grussenmeyer, et al., Proceedings of the National Academy of Science, U.S.A. pp 7952–7954, 1985.

Column buffer: 20 mM Tris pH=8, 100 mM NaCl, 1 mM EDTA, 2.5 mM EGTA, 10 mM $MgCl_2$, 2 mM DTT, 0.4 mM AEBSF, 0.1% n-octylglucopyranoside, 1 nM okadeic acid, and 10 μg/mL each of benzamidine, leupeptin, pepstatin, and aprotinin.

5× Reaction buffer: 125 mM HEPES pH=:8, 25 mM $MgCl_2$, 5 mM EDTA, 5 mM $Na_3VO_4$, 100 μg/mL BSA.

Enzyme dilution buffer: 25 mM HEPES pH=8, 1 mM EDTA, 1 mM $Na_3VO_4$, 400 μg/mL BSA.

Stop solution: 100 mM EDTA, 80 mM sodium pyrophosphate.

Filter plates: Milipore multiscreen # SE3MO78E3, Immobilon-P (PVDF).

METHODS:

Protein purification: Sf9 cells were infected with baculovirus and grown as described in Williams, et al., Proceedings of the National Academy of Science, U.S.A. pp 2922–2926, 1992. All subsequent steps were preformed on ice or at 4° C. Cells were pelleted and lysed by sonication in column buffer. Lysates were spun at 17,000×g for 20 min, followed by 0.22 μM filtration. Epitope tagged proteins were purified by chromatography over GammaBind Plus affinity column to which the "Glu-Glu" antibody was coupled. Proteins were loaded on the column followed by sequential washes with two column volumes of column buffer, and eluted with 50 μg/mL Glu-Tyr-Met-Pro-Met-Glu in column buffer.

Raf kinase assay: Test compounds were evaluated using ten 3-fold serial dilutions starting at 10–100 μM. 10 μL of the test inhibitor or control, dissolved in 10% DMSO, was added to the assay plate followed by the addition of 30 μL of the a mixture containing 10 μL 5× reaction buffer, 1 mM $^{33}P$-γ-ATP (20 μCi/mL), 0.5 μL MEK (2.5 mg/mL), 1 μL 50 mM β-mercaptoethanol. The reaction was started by the addition of 10 μL of enzyme dilution buffer containing 1 mM DTT and an amount of activated Raf that produces linear kinetics over the reaction time course. The reaction was mixed and incubated at room temperature for 90 min. and stopped by the addition of 50 μL stop solution. 90 μL aliquots of this stopped solution were transferred onto GFP-30 cellulose microtiter filter plates (Polyfiltronics), the filter plates washed in four well volumes of 5% phosphoric acid, allowed to dry, and then replenished with 25 μl scintillation cocktail. The plates were counted for $^{33}P$ gamma emission using a TopCount Scintillation Reader.

Accordingly, the compounds of the invention or a pharmaceutical composition thereof are useful for prophylaxis and treatment of rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexiel; Reiter's syndrome; type I and type II diabetes; bone resorption diseases; graft vs. host reaction; ischemia reperfusion injury; atherosclerosis; brain trauma; Alzheimer's disease; stroke; myocardial infarction; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster, all of which are sensitive to TNF-α and/or IL-1 inhibition or glucagon antagonism, will also be positively effected by the compounds and methods of the invention.

The compounds of the present invention may also possess oncolytic characteristics and may be useful for the treatment of cancer. The compounds of the present invention may also block signal transduction by extracellular mitogenic stimuli and oncoproteins through inhibition of Raf kinase.

The compounds of the present invention also may possess analgesic properties and may be useful for the treatment of pain disorders, such as hyperalgesia due to excessive IL-1. The compounds of the present invention may also prevent the production of prostaglandins by inhibition of enzymes in the human arachidonic acid/prostaglandin pathway, including cyclooxygenase (WO 96/03387, incorporated herein by reference in its entirety).

Because of their ability to lower TNF-α and IL-1 concentrations or inhibit glucagon binding to its receptor, the compounds of the invention are also useful research tools for studying the physiology associated with blocking these effects.

The methods of the invention comprise administering an effective dose of a compound of the invention, a pharmaceutical salt thereof, or a pharmaceutical composition of either, to a subject i.e., an animal, preferably a mammal, most preferably a human) in need of a reduction in the level of TNF-α, IL-1, IL-6, and/or IL-8 levels and/or reduction in plasma glucose levels and/or which subject may be suffering from rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; cancer; bone resorption diseases; graft vs. host reaction; Alzheimer's disease; stroke; myocardial infarction; ischemia reperfusion injury; atherosclerosis; brain trauma; multiple sclerosis; cerebral malaria; sepsis; septic shock; toxic shock syndrome; fever, and myalgias due to infection, or which subject is infected by HIV-1, HIV-2, HIV-3, cytomegalovirus (CMV), influenza, adenovirus, the herpes viruses (including HSV-1, HSV-2), or herpes zoster.

In another aspect, this invention comprises the use of a compound of the invention, or pharmaceutically acceptable salts thereof, in the manufacture of a medicament for the treatment either acutely or chronically of a TNF-α, IL-1β, IL-6, and/or IL-8 mediated disease state, including those described previously. The compounds of the present are also useful in the manufacture of an anti-cancer medicament. The compounds of the present invention are also useful in the manufacture of a medicant to attenuate or prevent signal transduction by extracellular mitogenic stimuli and oncoproteins through inhibition of Raf kinase. Also, the compounds of this invention are useful in the manufacture of a analgesic medicament and a medicament for treating pain disorders, such as hyperalgesia. The compounds of the present invention also are useful in the manufacture of a medicament to prevent the production of prostaglandins by inhibition of enzymes in the human arachidonic acid/prostaglandin pathway.

In still another aspect, this invention provides a pharmaceutical composition comprising an effective TNF-α, IL-1β, IL-6, and/or IL-8 lowering amount and/or effective plasma glucose level lowering amount, and/or effective tumor supressing amount of a compound of the invention and a pharmaceutically acceptable carrier or diluent, and if desired other active ingredients. The compounds of the invention are administered by any suitable route, preferably in the form of a pharmaceutical composition adapted to such a route, and in a dose effective for the treatment intended. Therapeutically effective doses of the compounds of the present invention required to arrest the progress or prevent tissue damage associated with the disease are readily ascertained by one of ordinary skill in the art using standard methods.

For the treatment of TNF-α, IL-1β, IL-6, and IL-8 mediated diseases, cancer, and/or hyperglycemia, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

The dosage regimen for treating a TNF-α, IL-1, IL-6, and IL-8 mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or Liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hyroxy-ethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

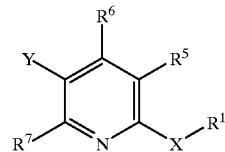

or a pharmaceutically acceptable salt thereof, wherein

X is O, S, S(O), S(O)$_2$ or NR$^2$;

Y is —C(O)—NR$^3$R$^4$ or —NR$^4$—C(O)—R$^3$;

R$^1$ is a cycloalkyl or aryl radical which is optionally substituted by 1–4 radicals of alkyl, halo, haloalkyl, cyano, azido, nitro, amidino, R$^{18}$—Z$^-$ or R$^{18}$—Z$^{18}$-alkyl; provided that the total number of aryl, heteroaryl, cycloalkyl and heterocyclyl radicals in R$^1$ is 1–3; and provided when Y is —NR$^4$—C(O)—

R$^2$ is a hydrogen or alkyl radical;

R$^3$ is a heteroaryl radical which is optionally substituted by 1–5 radicals of alkyl, halo, haloalkyl, cyano, azido, nitro, amidino, R$^{19}$—Z$^{19}$— or R$^{19}$—Z$^{19}$-alkyl; provided that the total number of aryl and heteroaryl radicals in R$^3$ is 1–3;

R$^4$ is a hydrogen, alkyl, alkenyl, haloalkyl, haloalkenyl, aryl, heteroaryl, arylalkyl, heteroarylalkyl or R$^{20}$—Z$^{20}$-alkyl radical; wherein neither R$^3$ or R$^4$ is 3-(2,6-dihalophenyl)-5-methylisoxazol-4yl or 5-methoxy-6-trifluoromethylindol-1-yl;

wherein R$^{18}$, R$^{19}$ and R$^{20}$ are each independently a hydrogen, alkyl, haloalkyl, aryl, heteroalkyl, arylalkyl or heteroarylalkyl radical; wherein the aryl and heteroaryl radicals of R$^4$, R$^{18}$, R$^{19}$ and R$^{20}$ are optionally substituted by 1–3 radicals of hydroxy, alkoxy, alkylthiol, amino, alkylamino, dialkylamino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy; and Z$^{18}$, Z$^{19}$ and Z$^{20}$ are each independently —O—, —S—, —S(O)—, —S(O)$_2$—, —CO$_2$—, —C(O)—, —NR$^{21}$—, —NR$^{21}$—C(O)—, —C(O)—NR$^{21}$—, —NR$^{21}$—S(O)$_2$— or —S(O)$_2$—NR$^{21}$—; wherein each R$^{21}$ is independently a hydrogen or alkyl radical;

R$^5$ and R$^6$ are each independently a hydrogen, alkyl, halo, haloalkyl, haloalkoxy, aminoalkyl, alkylaminoalkyl, dialkylaminoalkyl, amino, alkylamino, dialkylamino, alkanoylamino, alkylsulfonylamino, aminosulfonyl, alkylaminosulfonyl, dialkylaminosulfonyl, hydroxy, hydroxyalkyl, thiol, alkylthiol, alkylsulfinyl, alkylsulfonyl, alkoxy, alkoxyalkyl, cyano, azido, nitro, carboxy, alkoxycarbonyl, aminocarbonyl, alkylaminocarbonyl or dialkylaminocarbonyl radical; and R$^7$ is a hydrogen, alkyl, halo, haloalkyl, haloalkoxy, aminoalkyl, alkylaminoalkyl, dialkylaminoalkyl, aminosulfonyl, alkylaminosulfonyl, dialkylaminosulfonyl, hydroxy, hydroxyalkyl, thiol, alkylthiol, alkylsulfinyl, alkylsulfonyl, alkoxy, alkoxyalkyl, cyano, azido, nitro, carboxy, alkoxycarbonyl, aminocarbonyl, alkylaminocarbonyl or dialkylaminocarbonyl radical.

2. The compound of claim 1 or a pharmaceutically acceptable salt thereof, wherein $R^1$ is a cycloalkyl or aryl radical which is optionally substituted by 1–4 radicals of $C_1$–$C_6$ alkyl, halo, $C_1$–$C_6$ haloalkyl of 1–3 halo radicals, cyano, azido, nitro, amidino, $R^{18}$—$Z^{18}$— or $R^{18}$—$Z^{18}$—$C_1$–$C_6$ alkyl; provided that the total number of aryl, heteroaryl, cycloalkyl and heterocyclyl radicals in $R^1$ is 1–3;

$R^2$ is a hydrogen or $C_1$–$C_4$ alkyl radical;

$R^3$ is a heteroaryl radical which is optionally substituted by 1–5 radicals of $C_1$–$C_6$ alkyl, halo, $C_1$–$C_6$ haloalkyl of 1–3 halo radicals, cyano, azido, nitro, amidino, $R^{19}$—$Z^{19}$— or $R^{19}$—$Z^{19}$—$C_1$–$C_6$ alkyl; provided that the total number of aryl and heteroaryl radicals in $R^3$ is 1–3;

$R^4$ is a radical of hydrogen, $C_1$–$C_6$ alkyl, $C_2$–$C_6$ alkenyl, $C_1$–$C_6$ haloalkyl of 1–3 halo radicals, $C_2$–$C_6$ haloalkenyl of 1–3 halo radicals, aryl, heteroaryl, aryl-$C_1$–$C_4$ alkyl, heteroaryl-$C_1$–$C_4$ alkyl or $R^{20}$—$Z^{20}$—$C_1$–$C_6$ alkyl radical; wherein neither $R^3$ or $R^4$ is 3-(2,6-dihalophenyl)-5-methylisoxazol-4yl or 5-methoxy-6-trifluoromethylindol-1-yl; and wherein $R^{18}$, $R^{19}$ and $R^{20}$ are each independently a hydrogen, $C_1$–$C_4$ alkyl, $C_1$–$C_4$ haloalkyl of 1–3 halo radicals, aryl, heteroaryl, aryl-$C_1$–$C_4$ alkyl or heteroaryl-$C_1$–$C_4$ alkyl radical; wherein the aryl and heteroaryl radicals of $R^4$, $R^{18}$, $R^{19}$ and $R^{20}$ are optionally substituted by 1–3 radicals of hydroxy, $C_1$–$C_4$ alkoxy, $C_1$–$C_4$ alkylthiol, amino, $C_1$–$C_4$ alkylamino, di($C_1$–$C_4$ alkyl)amino, $C_1$–$c_5$ alkanoylamino, $C_1$–$C_4$ alkylsulfonylamino, $C_1$–$C_4$ alkylsulfinyl, $C_1$–$C_4$ alkylsulfonyl, ($C_1$–$C_4$ alkoxy)carbonylamino, ($C_1$–$C_4$ alkoxy)carbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals; and each $R^{21}$ is independently a hydrogen or $C_1$–$C_4$ alkyl radical;

$R^5$ and $R^6$ are each independently a hydrogen, $C_1$–$C_4$ alkyl, halo, $C_1$–$C_4$ haloalkyl of 1–3 halo radicals, $C_1$–$C_4$ haloalkoxy of 1–3 halo radicals, $C_1$–$C_4$ aminoalkyl, ($C_1$–$C_4$alkyl)amino-$C_1$–$C_4$ alkyl, di($C_1$–$C_4$ alkyl)amino-$C_1$–$C_4$ alkyl, amino, $C_1$–$C_4$ alkylamino, di($C_1$–$C_4$ alkyl)amino, $C_1$–$C_5$ alkanoylamino, $C_1$–$C_4$ alkylsulfonylamino, aminosulfonyl, $C_1$–$C_4$ alkylaminosulfonyl, di($C_1$–$C_4$ alkyl)aminosulfonyl, hydroxy, $C_1$–$C_4$ hydroxyalkyl, thiol, $C_1$–$C_4$ alkylthiol, $C_1$–$C_4$ alkylsulfinyl, $C_1$–$C_4$ alkylsulfonyl, $C_1$–$C_4$ alkoxy, ($C_1$–$C_4$ alkoxy)$C_1$–$C_4$ alkyl, cyano, azido, nitro, carboxy, ($C_1$–$C_4$ alkoxy)carbonyl, aminocarbonyl, ($C_1$–$C_4$ alkyl)aminocarbonyl or di($C_1$–$C_4$ alkyl)aminocarbonyl radical; and $R^7$ is a hydrogen, $C_1$–$C_4$ alkyl, halo, $C_1$–$C_4$ haloalkyl of 1–3 halo radicals, $C_1$–$C_4$ haloalkoxy of 1–3 halo radicals, $C_1$–$C_4$ aminoalkyl, ($C_1$–$C_4$ alkyl)amino-$C_1$–$C_4$ alkyl, di($C_1$–$C_4$ alkyl)amino-$C_1$–$C_4$ alkyl, aminosulfonyl, $C_1$–$C_4$ alkylaminosulfonyl, di($C_1$–$C_4$ alkyl)aminosulfonyl, hydroxy, $C_1$–$C_4$ hydroxyalkyl, thiol, $C_1$–$C_4$ alkylthiol, $C_1$–$C_4$ alkylsulfinyl, $C_1$–$C_4$ alkylsulfonyl, $C_1$–$C_4$ alkoxy, ($C_1$–$C_4$ alkoxy)$C_1$–$C_4$ alkyl, cyano, azido, nitro, carboxy, ($C_1$–$C_4$ alkoxy)carbonyl, aminocarbonyl, ($C_1$–$C_4$ alkyl)aminocarbonyl or di($C_1$–$C_4$ alkyl)aminocarbonyl radical; and wherein cycloalkyl is a monocyclic, bicyclic or tricyclic carbocyclic alkyl radical of 5–12 ring members, which is optionally partially unsaturated, benzo fused or heterocyclo fused; aryl is a phenyl or biphenyl radical which is optionally benzo fused or heterocyclo fused; heterocyclyl is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals; and heteroaryl is a monocyclic or bicyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused.

3. The compound of claim 2 or a pharmaceutically acceptable salt thereof, wherein Y is —$NR^4$—C(O)—$R^3$.

4. The compound of claim 3 or a pharmaceutically acceptable salt thereof, wherein X is O or $NR^2$;

$R^1$ is a cycloalkyl or aryl radical which is optionally substituted by 1–4 radicals of $C_1$–$C_4$ alkyl, halo, $C_1$–$C_4$ haloalkyl of 1–3 halo radicals, cyano, azido, nitro, amidino, $R^{18}$—$Z^{18}$— or $R^{18}$—$Z^{18}$—$C_1$–$C_4$ alkyl; provided that the total number of aryl, heteroaryl, cycloalkyl and heterocyclyl radicals in $R^1$ is 1–2;

wherein each $R^{18}$ is independently a hydrogen, $C_1$–$C_4$ alkyl, trifluoromethyl, aryl, heteroaryl, aryl-$C_1$–$C_2$ alkyl or heteroaryl-$C_1$–$C_2$ alkyl radical; wherein the aryl and heteroaryl radicals are optionally substituted by 1–2 radicals of hydroxy, $C_1$–$C_4$ alkoxy, $C_1$–$C_4$ alkylthiol, amino, $C_1$–$C_4$ alkylamino, di($C_1$–$C_4$ alkyl) amino, acetylamino, cyano, halo, azido, $C_1$–$C_4$ alkyl, trifluoromethyl or trifluoromethoxy; and $R^2$ is a hydrogen or $C_1$–$C_2$ alkyl radical;

$R^3$ is an aryl or heteroaryl radical which is optionally substituted by 1–5 radicals of $C_1$–$C_6$ alkyl, halo, $C_1$–$C_4$ haloalkyl of 1–3 halo radicals, cyano, azido, nitro, amidino, $R^{19}$—$Z^{19}$— or $R^{19}$—$Z^{19}$—$C_1$–$C_4$ alkyl; provided that the total number of aryl and heteroaryl radicals in $R^3$ is 1–2; and wherein each $R^{19}$ is independently a hydrogen, $C_1$–$C_4$ alkyl, trifluoromethyl, aryl, heteroaryl, aryl-$C_1$–$C_4$ alkyl or heteroaryl-$C_1$–$C_4$ alkyl radical; wherein the aryl and heteroaryl radicals are optionally substituted by 1–2 radicals of hydroxy, $C_1$–$C_4$ alkoxy, $C_1$–$C_4$ alkylthiol, amino, $C_1$–$C_4$ alkylamino, di($C_1$–$C_4$ alkyl) amino, acetylamino, cyano, halo, $C_1$–$C_4$ alkyl, trifluoromethyl or trifluoromethoxy; and $R^4$ is a radical of hydrogen, $C_1$–$C_6$ alkyl, aryl, heteroaryl, aryl-$C_1$–$C_4$ alkyl, heteroaryl-$C_1$–$C_4$ alkyl or $R^{20}$—$Z^{20}$—$C_2$–$C_4$ alkyl radical; wherein neither $R^3$ or $R^4$ is 3-(2,6-dihalophenyl)-5-methylisoxazol-4-yl or 5-methoxy-6-trifluoromethylindol-1-yl; and wherein $R^{20}$ is a hydrogen, $C_1$–$C_4$ alkyl, aryl, heteroaryl, aryl-$C_1$–$C_2$ alkyl or heteroaryl-$C_1$–$C_2$ alkyl radical; wherein the aryl and heteroaryl radicals of $R^4$ and $R^{20}$ are optionally substituted by 1–2 radicals of hydroxy, $C_1$–$C_4$ alkoxy, $C_1$–$C_4$ alkylthiol, amino, $C_1$–$C_4$ alkylamino, di($C_1$–$C_4$ alkyl)amino, acetylamino, halo, $C_1$–$C_4$ alkyl, trifluoromethyl or trifluoromethoxy; and $Z^{20}$ is —O— or —$NR^{21}$—; wherein each $R^{21}$ is independently a hydrogen or methyl radical;

$R^5$ and $R^6$ are each independently a hydrogen, $C_1$–$C_4$ alkyl, halo, trifluoromethyl, trifluoromethoxy, amino, $C_1$–$C_4$ alkylamino, di($C_1$–$C_4$ alkyl)amino, $C_1$–$C_5$ alkanoylamino, hydroxy, $C_1$–$C_4$ hydroxyalkyl, $C_1$–$C_4$ alkoxy, cyano, azido, nitro, carboxy, ($C_1$–$C_4$ alkoxy) carbonyl, aminocarbonyl, ($C_1$–$C_4$ alkyl)aminocarbonyl or di($C_1$–C4alkyl)aminocarbonyl radical; and $R^7$ is a hydrogen, $C_1$–$C_4$ alkyl, halo, trifluoromethyl, trifluoromethoxy, hydroxy, $C_1$–$C_4$ hydroxyalkyl, $C_1$–$C_4$ alkoxy, carboxy, ($C_1$–$C_4$ alkoxy)carbonyl, aminocarbonyl, ($C_1$–$C_4$ alkyl)aminocarbonyl or di($C_1$–$C_4$ alkyl)aminocarbonyl radical; and wherein cycloalkyl is a monocyclic or bicyclic carbocyclic alkyl radical of 5–12 ring members, which is optionally partially unsaturated, benzo fused or heterocyclo fused; aryl is a phenyl or biphenyl radical which is optionally benzo fused or heterocyclo fused; heterocyclyl is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals; and heteroaryl is a monocyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused.

5. The compound of claim 4 or a pharmaceutically acceptable salt thereof, wherein
$R^3$ is a radical of the formula

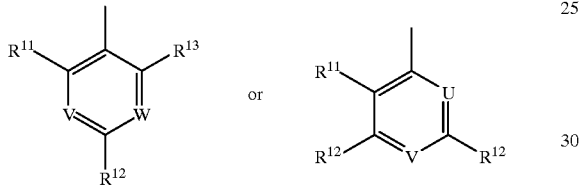

wherein
U is C—$R^{13}$ or N;
V and W are each independently C—$R^{12}$ or N; wherein at least one of U, V and W is N;
$R^{11}$ and $R^{13}$ are each independently a radical of hydrogen, $C_1$–$C_4$ alkyl, halo, trifluoromethyl, cyano, azido, nitro, amidino or $R^{19}$—$Z^{19}$—; and each $R^{12}$ is independently a radical of hydrogen, $C_1$–$C_6$ alkyl, halo, $C_1$–$C_4$ haloalkyl of 1–3 halo radicals, $R^{31}$—$Z^{31}$— or $R^{31}$—$Z^{31}$—$C_1$–$C_4$ alkyl; provided that the combined total number of aryl and heteroaryl radicals in $R^{11}$, $R^{12}$ and $R^{13}$ is 0–1;
wherein each $R^{19}$ is independently a hydrogen, $C_1$–$C_4$ alkyl, trifluoromethyl, aryl, heteroaryl, aryl-$C_1$–$C_4$ alkyl or heteroaryl-$C_1$–$C_4$ alkyl radical; wherein the aryl and heteroaryl radicals are optionally substituted by 1–2 radicals of hydroxy, methoxy, ethoxy, amino, methylamino, dimethylamino, acetylamino, cyano, halo, methyl, ethyl, trifluoromethyl or trifluoromethoxy; and
each $Z^{19}$ is independently —O—, —S(O)$_2$—, —CO$_2$—, —C(O)—, —NR$^{21}$—C(O)—, —C(O)—NR$^{21}$—, —NR$^{21}$—S(O)$_2$— or —S(O)$_2$—NR$^{21}$—;
wherein each $R^{31}$ is independently a hydrogen, $C_1$–$C_4$ alkyl, trifluoromethyl, aryl, heteroaryl, aryl-$C_1$–$C_4$ alkyl or heteroaryl-$C_1$–$C_4$ alkyl radical; wherein the aryl and heteroaryl radicals are optionally substituted by 1–2 radicals of hydroxy, methoxy, ethoxy, amino, methylamino, dimethylamino, acetylamino, cyano, halo, methyl, ethyl, trifluoromethyl or trifluoromethoxy; and
each $Z^{31}$ is independently —O—, —NR$^{21}$—, —NR$^{21}$—C(O)—, —C(O)—NR$^{21}$—, —NR$^{21}$—S(O)$_2$— or —S(O)$_2$—NR$^{21}$—;

wherein $R^4$ is a radical of hydrogen, $C_1$–$C_6$ alkyl, aryl, heteroaryl, aryl-$C_1$–$C_4$ alkyl, heteroaryl-$C_1$–$C_4$ alkyl or $R^{20}$—$Z^{20}$—$C_2$–$C_4$ alkyl radical;
wherein $R^{20}$ is a hydrogen, $C_1$–$C_4$ alkyl, aryl, heteroaryl, aryl-$C_1$–$C_2$ alkyl or heteroaryl-$C_1$–$C_2$ alkyl radical; wherein the aryl and heteroaryl radicals of $R^4$ and $R^{20}$ are optionally substituted by 1–2 radicals of hydroxy, methoxy, ethoxy, methylthiol, ethylthiol, amino, methylamino, dimethylamino, ethylamino, diethylamino, acetylamino, halo, methyl, ethyl, trifluoromethyl or trifluoromethoxy; and
$R^5$ and $R^6$ are each independently a hydrogen, methyl, ethyl, halo, trifluoromethyl, trifluoromethoxy, amino, $C_1$–$C_2$ alkylamino, di($C_1$–$C_2$ alkyl)amino, hydroxy, methoxy or ethoxy radical; and
$R^7$ is a hydrogen, methyl, ethyl, halo, trifluoromethyl, trifluoromethoxy, hydroxy, methoxy or ethoxy radical; and
wherein cycloalkyl is a monocyclic or bicyclic carbocyclic alkyl radical of 5–10 ring members, which is optionally partially unsaturated with one double bond, benzo fused or heterocyclo fused; aryl is a phenyl or biphenyl radical which is optionally benzo fused or heterocyclo fused; heterocyclyl is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals; and heteroaryl is a monocyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused.

6. The compound of claim 5 or a pharmaceutically acceptable salt thereof, wherein
$R^1$ is a radical of the formula

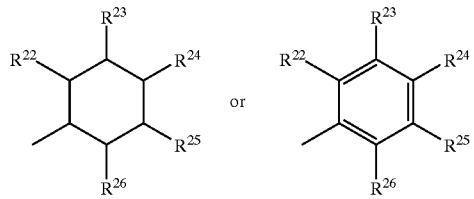

wherein
$R^{22}$, $R^{23}$, $R^{24}$, $R^{25}$ and $R^{26}$ are each independently a radical of hydrogen, $C_1$–$C_4$ alkyl, halo, trifluoromethyl, cyano, azido, nitro, amidino, $R^{18}$—$Z^{18}$— or $R^{18}$—$Z^{18}$—$C_1$–$C_4$ alkyl; provided at least one of $R^{21}$, $R^{22}$, $R^{23}$, $R^{24}$ and $R^{25}$ is hydrogen; and provided that the combined total number of aryl and heteroaryl radicals in $R^{22}$, $R^{23}$, $R^{24}$, $R^{25}$ and $R^{26}$ is 0–1;
wherein each $Z^{18}$ is independently —O—, —S—, —S(O)$_2$—, —CO$_2$—, —NR$^{21}$—, —NR$^{21}$—C(O)—, —C(O)—NR$^{21}$—, —NR$^{21}$—S(O)$_2$— or —S(O)$_2$—NR$^{21}$—; and
wherein aryl is a phenyl or biphenyl radical which is optionally benzo fused or heterocyclo fused; and heteroaryl is a monocyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused.

7. The compound of claim 6 or a pharmaceutically acceptable salt thereof, wherein X is $NR^2$;

$R^2$ is a hydrogen or methyl radical;

$R^4$ is a radical of hydrogen, methyl or ethyl radical; and $R^5$, $R^6$ and $R^7$ are each independently a hydrogen radical; and wherein aryl is a phenyl, biphenyl or naphthyl radical; and heteroaryl is a monocyclic aromatic heterocyclic ring system having 5–6 ring members per ring, wherein 1–3 ring members are oxygen, sulfur or nitrogen heteroatoms.

8. The compound of claim 7 or a pharmaceutically acceptable salt thereof, wherein $R^{11}$ and $R^{13}$ are each independently a radical of hydrogen, methyl, ethyl, fluoro, chloro, trifluoromethyl, cyano, azido, nitro, amidino, $R^{19}$—O—, $R^{19}$—$S(O)_2$—, $R^{19}$—O—C(O)—, $R^{19}$—C(O)—, $R^{19}$—$NR^{12}$—C(O)— or $R^{19}$—$NR^{21}$—$S(O)_2$—; and each $R^{12}$ is independently a radical of hydrogen, methyl, ethyl, fluoro, chloro, trifluoromethyl, trifluoromethoxy, methoxy, ethoxy, amino, methylamino, dimethylamino, acetylamino, aminocarbonyl, methylaminocarbonyl, dimethylaminocarbonyl, aminomethyl, (methylamino)methyl or (dimethylamino)methyl; provided that the combined total number of aryl and heteroaryl radicals in $R^{11}$, $R^{12}$ and $R^{13}$ is 0–1; and wherein each $R^{19}$ is independently a hydrogen, methyl, ethyl, trifluoromethyl, phenyl, heteroaryl, phenylmethyl or heteroaryl-methyl radical; wherein the phenyl and heteroaryl radicals are optionally substituted by 1–2 radicals of hydroxy, methoxy, ethoxy, amino, methylamino, dimethylamino, acetylamino, cyano, fluoro, chloro, methyl, ethyl, trifluoromethyl or trifluoromethoxy.

9. The compound of claim 2 or a pharmaceutically acceptable salt thereof, wherein Y is —C(O)—$NR^3R^4$.

10. The compound of claim 9 or a pharmaceutically acceptable salt thereof, wherein X is O or $NR^2$;

$R^1$ is a cycloalkyl or aryl radical which is optionally substituted by 1–4 radicals of $C_1$–$C_4$ alkyl, halo, $C_1$–$C_4$ haloalkyl of 1–3 halo radicals, cyano, azido, nitro, amidino, $R^{18}$—$Z^{18}$— or $R^{18}$—$Z^{18}$—$C_1$–$C_4$ alkyl; provided that the total number of aryl, heteroaryl, cycloalkyl and heterocyclyl radicals in $R^1$ is 1–2;

wherein each $R^{18}$ is independently a hydrogen, $C_1$–$C_4$ alkyl, trifluoromethyl, aryl, heteroaryl, aryl-$C_1$–$C_2$ alkyl or heteroaryl-$C_1$–$C_2$ alkyl radical; wherein the aryl and heteroaryl radicals are optionally substituted by 1–2 radicals of hydroxy, $C_1$–$C_4$ alkoxy, $C_1$–$C_4$ alkylthiol, amino, $C_1$–$C_4$ alkylamino, di($C_1$–$C_4$ alkyl)amino, acetylamino, cyano, halo, azido, $C_1$–$C_4$ alkyl, trifluoromethyl or trifluoromethoxy; and each $Z^{18}$ is independently —O—, —S—, —S(O)—, —$S(O)_2$—, —$CO_2$—, —C(O)—, —$NR^{21}$—, —$NR^{21}$—C(O)—, —C(O)—$NR^{21}$—, —$NR^{21}$—$S(O)_2$— or —$S(O)_2$—$NR^{21}$—; wherein each $R^{21}$ is independently a hydrogen or $C_1$–$C_4$ alkyl radical;

$R^2$ is a hydrogen or $C_1$–$C_2$ alkyl radical;

$R^3$ is a heteroaryl radical which is optionally substituted by 1–5 radicals of $C_1$–$C_6$ alkyl, halo, $C_1$–$C_4$ haloalkyl of 1–3 halo radicals, cyano, azido, nitro, amidino, $R^{19}$—$Z^{19}$— or $R^{19}$—$Z^{19}$—$C_1$–$C_4$ alkyl; provided that the total number of aryl and heteroaryl radicals in $R^3$ is 1–2;

wherein each $R^{19}$ is independently a hydrogen, $C_1$–$C_4$ alkyl, trifluoromethyl, aryl, heteroaryl, aryl-$C_1$–$C_4$ alkyl or heteroaryl-$C_1$–$C_4$ alkyl radical; wherein the aryl and heteroaryl radicals are optionally substituted by 1–2 radicals of hydroxy, $C_1$–$C_4$ alkoxy, $C_1$–$C_4$ alkylthiol, amino, $C_1$–$C_4$ alkylamino, di($C_1$–$C_4$ alkyl)amino, acetylamino, cyano, halo, $C_1$–$C_4$ alkyl, trifluoromethyl or trifluoromethoxy; and $R^4$ is a radical of hydrogen, $C_1$–$C_6$ alkyl, aryl, heteroaryl, aryl-C1–$C_4$ alkyl, heteroaryl-C1–$C_4$ alkyl or $R^{20}$—$Z^{20}$—$C_2$–$C_4$ alkyl radical; wherein neither $R^3$ or $R^4$ is 3-(2,6-dihalophenyl)-5-methylisoxazol-4-yl or 5-methoxy-6-trifluoromethylindol-1-yl; and wherein $R^{20}$ is a hydrogen, $C_1$–$C_4$ alkyl, aryl, heteroaryl, aryl-$C_1$–$C_2$ alkyl or heteroaryl-$C_1$–$C_2$ alkyl radical; wherein the aryl and heteroaryl radicals of $R^4$ and $R^{20}$ are optionally substituted by 1–2 radicals of hydroxy, $C_1$–$C_4$ alkoxy, $C_1$–$C_4$ alkylthiol, amino, $C_1$–$C_4$ alkylamino, di($C_1$–$C_4$ alkyl)amino, acetylamino, halo, $C_1$–$C_4$ alkyl, trifluoromethyl or trifluoromethoxy; and $Z^{20}$ is —O— or —$NR^{21}$—; wherein each $R^{21}$ is independently a hydrogen or methyl radical;

$R^5$ and $R^6$ are each independently a hydrogen, $C_1$–$C_4$ alkyl, halo, trifluoromethyl, trifluoromethoxy, amino, $C_1$–$C_4$ alkylamino, di($C_1$–$C_4$ alkyl)amino, $C_1$–$C_5$ alkanoylamino, hydroxy, $C_1$–$C_4$ hydroxyalkyl, $C_1$–$C_4$ alkoxy, cyano, azido, nitro, carboxy, ($C_1$–$C_4$ alkoxy)carbonyl, aminocarbonyl, ($C_1$–$C_4$ alkyl)aminocarbonyl or di($C_1$–$C_4$ alkyl)aminocarbonyl radical; and $R^7$ is a hydrogen, $C_1$–$C_4$ alkyl, halo, trifluoromethyl, trifluoromethoxy, hydroxy, $C_1$–$C_4$ hydroxyalkyl, $C_1$–$C_4$ alkoxy, carboxy, ($C_1$–$C_4$ alkoxy)carbonyl, aminocarbonyl, ($C_1$–$C_4$ alkyl)aminocarbonyl or di($C_1$–$C_4$ alkyl)aminocarbonyl radical; and wherein cycloalkyl is a monocyclic or bicyclic carbocyclic alkyl radical of 5–12 ring members, which is optionally partially unsaturated, benzo fused or heterocyclo fused; aryl is a phenyl or biphenyl radical which is optionally benzo fused or heterocyclo fused; heterocyclyl is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals; and heteroaryl is a monocyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused.

11. The compound of claim 10 or a pharmaceutically acceptable salt thereof, wherein $R^3$ is a radical of the formula

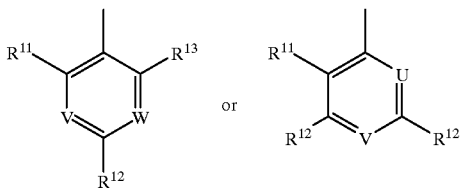

wherein

U is C—$R^{13}$ or N;

V and W are each independently C—$R^{12}$ or N;

107

$R^{11}$ and $R^{13}$ are each independently a radical of hydrogen, $C_1$–$C_4$ alkyl, halo, trifluoromethyl, cyano, azido, nitro, amidino or $R^{19}$—$Z^{19}$—; and each $R^{12}$ is independently a radical of hydrogen, $C_1$–$C_6$ alkyl, halo, $C_1$–$C_4$ haloalkyl of 1–3 halo radicals, $R^{31}$—$Z^{31}$— or $R^{31}$—$Z^{31}$—$C_1$–$C_4$ alkyl; provided that the combined total number of aryl and heteroaryl radicals in $R^{11}$, $R^{12}$ and $R^{13}$ is 0–1; provided when U is C—$R^{13}$ and V and W are each C—$R^{12}$, $R^{11}$ and $R^{13}$ are each other than a nitro, cyano, carboxy or alkoxycarbonyl radical;

wherein each $R^{19}$ is independently a hydrogen, $C_1$–$C_4$ alkyl, trifluoromethyl, aryl, heteroaryl, aryl-$C_1$–$C_4$ alkyl or heteroaryl-$C_1$–$C_4$ alkyl radical; wherein the aryl and heteroaryl radicals are optionally substituted by 1–2 radicals of hydroxy, methoxy, ethoxy, amino, methylamino, dimethylamino, acetylamino, cyano, halo, methyl, ethyl, trifluoromethyl or trifluoromethoxy; and each $Z^{19}$ is independently —O—, —S(O)$_2$—, —CO$_2$—, —C(O)—, —NR$^{21}$—C(O)—, —C(O)—NR$^{21}$—, —NR$^{21}$—S(O)$_2$— or —S(O)$_2$—NR$^{21}$—; wherein each $R^{21}$ is independently a hydrogen or methyl radical;

wherein each $R^{31}$ is independently a hydrogen, $C_1$–$C_4$ alkyl, trifluoromethyl, aryl, heteroaryl, aryl-$C_1$–$C_4$ alkyl or heteroaryl-$C_1$–$C_4$ alkyl radical; wherein the aryl and heteroaryl radicals are optionally substituted by 1–2 radicals of hydroxy, methoxy, ethoxy, amino, methylamino, dimethylamino, acetylamino, cyano, halo, methyl, ethyl, trifluoromethyl or trifluoromethoxy; and each $Z^{31}$ is independently —O—, —NR$^{21}$—, —NR$^{21}$—C(O)—, —C(O)—NR$^{21}$—, —NR$^{21}$—S(O)$_2$— or —S(O)$_2$—NR$^{21}$—;

$R^4$ is a radical of hydrogen, C1–C6 alkyl, aryl, heteroaryl, aryl-$C_1$–$C_4$ alkyl, heteroaryl-$C_1$–$C_4$ alkyl or $R^{20}$—$Z^{20}$—$C_2$–$C_4$ alkyl radical; and wherein $R^{20}$ is a hydrogen, C1–C4 alkyl, aryl, heteroaryl, aryl-$C_1$–$C_2$ alkyl or heteroaryl-$C_1$–$C_2$ alkyl radical; wherein the aryl and heteroaryl radicals of $R^4$ and $R^{20}$ are optionally substituted by 1–2 radicals of hydroxy, methoxy, ethoxy, methylthio, ethylthiol, amino, methylamino, dimethylamino, ethylamino, diethylamino, acetylamino, halo, methyl, ethyl, trifluoromethyl or trifluoromethoxy; and $R^5$ and $R^6$ are each independently a hydrogen, methyl, ethyl, halo, trifluoromethyl, trifluoromethoxy, amino, $C_1$–$C_2$ alkylamino, di($C_1$–$C_2$ alkyl)amino, hydroxy, methoxy or ethoxy radical; and $R^7$ is a hydrogen, methyl, ethyl, halo, trifluoromethyl, trifluoromethoxy, hydroxy, methoxy or ethoxy radical; and wherein cycloalkyl is a monocyclic or bicyclic carbocyclic alkyl radical of 5–10 ring members, which is optionally partially unsaturated with one double bond, benzo fused or heterocyclo fused; aryl is a phenyl or biphenyl radical which is optionally benzo fused or heterocyclo fused; heterocyclyl is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals; and heteroaryl is a monocyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused.

108

12. The compound of claim 11 or a pharmaceutically acceptable salt thereof, wherein $R^1$ is a radical of the formula wherein $R^{22}$, $R^{23}$, $R^{24}$, $R^{25}$ and $R^{26}$ are each independently a radical of hydrogen, $C_1$–$C_4$ alkyl, halo, trifluoromethyl, cyano, azido, nitro, amidino, $R^{18}$—$Z^{18}$— or $R^{18}$—$Z^{18}$—$C_1$–$C_4$ alkyl; provided at least one of $R^{21}$, $R^{22}$, $R^{23}$, $R^{24}$ and $R^{25}$ is hydrogen; and provided that the combined total number of aryl and heteroaryl radicals in $R^{22}$, $R^{23}$, $R^{24}$, $R^{25}$ and $R^{26}$ is 0–1;

each $Z^{18}$ is independently —O—, —S—, —S(O)$_2$—, —CO$_2$—, —NR$^{21}$—, —NR$^{21}$—C(O)—, —C(O)—NR$^{21}$—, —NR$^{21}$—S(O)$_2$— or —S(O)$_2$—NR$^{21}$—; and wherein aryl is a phenyl or biphenyl radical which is optionally benzo fused or heterocyclo fused; and heteroaryl is a monocyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused.

13. The compound of claim 12 or a pharmaceutically acceptable salt thereof, wherein X is NR$^2$;

$R^2$ is a hydrogen or methyl radical;

$R^4$ is a radical of hydrogen, methyl or ethyl radical; and $R^5$, $R^6$ and $R^7$ are each independently a hydrogen radical; and wherein aryl is a phenyl, biphenyl or naphthyl radical; and heteroaryl is a monocyclic aromatic heterocyclic ring system having 5–6 ring members per ring, wherein 1–3 ring members are oxygen, sulfur or nitrogen heteroatoms.

14. The compound of claim 13 or a pharmaceutically acceptable salt thereof, wherein $R^{11}$ and $R^{13}$ are each independently a radical of hydrogen, methyl, ethyl, fluoro, chloro, trifluoromethyl, cyano, azido, nitro, amidino, $R^{19}$—O—, $R^{19}$—S(O)$_2$—, $R^{19}$—O—C(O)—, $R^{19}$—C(O)—, $R^{19}$—NR$^{21}$—C(O)— or $R^{19}$—NR$^{21}$—S(O)$_2$—; provided when U is C—$R^{13}$ and V and W are each C—$R^{12}$, $R^{11}$ and $R^{13}$ are each other than a nitro, cyano, carboxy or alkoxycarbonyl radical; and provided that the combined total number of aryl and heteroaryl radicals in $R^{11}$ and $R^{13}$ is 0–1;

each $R^{12}$ is independently a radical of hydrogen, methyl, ethyl, fluoro, chloro, trifluoromethyl, trifluoromethoxy, methoxy, ethoxy, amino, methylamino, dimethylamino, acetylamino, aminocarbonyl, methylaminocarbonyl, dimethylaminocarbonyl, aminomethyl, (methylamino)methyl or (dimethylamino)methyl; and wherein each $R^{19}$ is independently a hydrogen, methyl, ethyl, trifluoromethyl, phenyl, heteroaryl, phenylm ethyl or heteroaryl-methyl radical; wherein the phenyl and heteroaryl radicals are optionally substituted by 1–2 radicals of hydroxy, methoxy, ethoxy, amino, methylamino, dimethylamino, acetylamino, cyano, fluoro, chloro, methyl, ethyl, trifluoromethyl or trifluoromethoxy.

15. A pharmaceutical composition comprising a compound of claim 1 and a pharmaceutically acceptable carrier.

16. A method for prophylaxis or treatment of inflammation comprising administering an effective amount of a compound of claim 1.

17. A method for prophylaxis or treatment of inflammation comprising administering an effective amount of a composition of claim 15.

* * * * *

UNITED STATES PATENT AND TRADEMARK OFFICE
CERTIFICATE OF CORRECTION

PATENT NO.    : 6,458,813 B1
DATED         : October 1, 2002
INVENTOR(S)   : Mantlo et al.

It is certified that error appears in the above-identified patent and that said Letters Patent is hereby corrected as shown below:

Column 1,
Line 30, change "osteophorosis" to -- osteoporosis --.
Line 57, add -- (1994) -- after "1481".

Column 6,
Line 43, change "—NR—S(O)$_2$—" to -- —NR$^{21}$—S(O)$_2$— --.
Line 57, change "aryl-C$_1$-C4 alkyl," to -- aryl-C$_1$-C$_4$ alkyl, --.

Column 8,
Line 40, change "Z" to -- Z$^{19}$ --.

Column 12,
Line 21, change "" R—O—C(O)—C(O)—"" to -- R—O—C(O)— --.
Line 38, change "S(O)$_2$" to -- S(O) --.

Column 17,
Line 45, change "(R—X—H)" to -- (R$^1$—X—H) --.

Column 18,
Line 54, delete "15" before "according".

Column 20,
Line 31, change "approriate" to -- appropriate --.

Column 21,
Line 5, change "prescence" to -- presence --.

Column 29,
Line 26, change "C$_{19}$H$_{21}$N$_3$OC;" to -- C$_{19}$H$_{21}$N$_3$OCl--.

Column 55,
Line 34, change "chlorophenoxyl" to -- chlorophenoxy) --.

Column 69,
Line 53, change "(trifluorophenyl)phenyl" to -- (trifluoromethyl)phenyl --.

Column 70,
Line 61, change "[bi" to -- [b] --.

Column 74,
Lines 38-39, change "3-4-yl" to -- 3-yl --.

UNITED STATES PATENT AND TRADEMARK OFFICE
CERTIFICATE OF CORRECTION

PATENT NO. : 6,458,813 B1
DATED : October 1, 2002
INVENTOR(S) : Mantlo et al.

It is certified that error appears in the above-identified patent and that said Letters Patent is hereby corrected as shown below:

Column 83,
Line 14, change "$C_{18}H_{13}ClN_2O_1$" to -- $C_{18}H_{13}Cl_1N_2O_1$ --.
Line 16, change "$C_{12}H_8ClN_2O_1$" to -- $C_{12}H_8Cl_1N_2O_1$ --.
Line 18, change "2:68.6." to -- 268.6. --.

Column 85,
Line 26, change "2-cyclohexyl" to -- 2-dicyclohexyl --.

Column 90,
Line 12, change "cyclohexyl" to -- cycloheptyl --.

Column 92,
Line 54, change "TNF-A," to -- TNF-α, --.

Column 93,
Line 21, change "250 $\mu$m" to -- 250 $\mu$M --.

Column 95,
Line 27, change "0.22 $\mu$M" to -- 0.22 $\mu$m --.
Line 55, change "osteophorosis" to -- osteoporosis --.

Column 96,
Line 31, change "osteophorosis" to -- osteoporosis --.

Column 99,
Line 30, change "hyroxy" to -- hydroxy --.
Line 43, change "from" to -- form --.

Column 100,
Line 19, change "—Z⁻ " to -- —$Z^{18}$ --.
Lines 21-22, delete "and provided when Y is —$NR^4$—C(O) —".

Column 102,
Line 32, delete "an aryl or".
Line 32, add -- a -- before "heteroaryl".

Column 105,
Line 18, change "$R^{19}$—$NR^{12}$—C(O)—" to -- $R^{19}$—$NR^{21}$—C(O)— --.

UNITED STATES PATENT AND TRADEMARK OFFICE
CERTIFICATE OF CORRECTION

PATENT NO. : 6,458,813 B1
DATED : October 1, 2002
INVENTOR(S) : Mantlo et al.

It is certified that error appears in the above-identified patent and that said Letters Patent is hereby corrected as shown below:

Column 106,
Line 67, add -- wherein at least one of U, V and W are N; -- after "N;".

Column 108,
Line 16, change "$^{R24}$," to -- $R^{24}$, --.

Signed and Sealed this

Twenty-ninth Day of April, 2003

JAMES E. ROGAN
*Director of the United States Patent and Trademark Office*